United States Patent [19]
Takezawa et al.

[11] Patent Number: 5,234,946
[45] Date of Patent: Aug. 10, 1993

[54] SUBSTITUTED ALKYLAMINE DERIVATIVES

[75] Inventors: Hiroshi Takezawa, Hachioji; Masahiro Hayashi, Ichikawa; Yoshikazu Iwasawa, Oiso; Masaaki Hosoi, Kawasaki; Yoshiaki Iida, Yokohama; Yoshimi Tsuchiya, Funabashi; Masahiro Horie, Tokyo; Toshio Kamei, Tachikawa, all of Japan

[73] Assignee: Banyu Pharmaceutical Co., Ltd., Tokyo, Japan

[21] Appl. No.: 753,611

[22] Filed: Aug. 30, 1991

Related U.S. Application Data

[63] Continuation-in-part of Ser. No. 533,532, Jun. 5, 1990, abandoned, which is a continuation-in-part of Ser. No. 465,209, Mar. 8, 1990, abandoned, which is a continuation-in-part of Ser. No. 274,972, Nov. 22, 1988, abandoned.

[30] Foreign Application Priority Data

Nov. 27, 1987 [JP] Japan ............... 62-299584
Apr. 19, 1988 [JP] Japan ................ 63-96286
May 10, 1988 [JP] Japan ............... 63-113310
Nov. 11, 1988 [JP] Japan ............... 63-285381

[51] Int. Cl.$^5$ ............... A61K 31/38; C07D 333/32
[52] U.S. Cl. .................... 514/444; 514/513; 514/532; 514/538; 514/613; 514/617; 514/627; 514/336; 514/340; 514/342; 514/824; 514/127; 514/397; 514/471; 514/438; 514/374; 514/378; 514/365; 514/372; 514/397; 514/406; 514/364; 514/362; 514/363; 514/385; 514/247; 514/256; 514/255; 514/382; 514/422; 514/428; 514/655; 558/257; 546/284; 546/213; 544/238; 544/333; 544/405; 548/235; 548/247; 548/205; 548/214; 548/373.1; 548/143; 548/127; 548/128; 548/131; 548/134; 548/136; 548/255; 548/517; 548/518; 548/531; 548/561; 548/374.1; 548/375.1; 548/376.1; 548/316.4; 548/315.1; 548/314.7; 548/315.4; 548/315.7; 548/311.1; 548/325.1; 548/332.5; 548/331.5; 548/326.5; 548/333.5; 548/334.1; 548/335.1; 548/335.5; 548/342.1; 548/341.1; 548/365.7; 548/364.1; 548/370.7; 548/366.1; 548/372.1; 549/59; 549/60; 549/74; 549/75; 549/76; 549/491; 549/496; 549/438; 549/61; 549/65; 549/72; 549/493; 549/494; 549/495; 549/488; 549/479; 564/123; 564/164; 564/185; 564/196; 564/388; 564/383; 564/384; 564/389; 560/37; 560/42; 560/109; 560/142

[58] Field of Search ............. 549/59, 60, 74, 75, 549/77, 76, 491, 496, 438; 558/257; 560/37, 42, 109, 142; 548/327, 336, 235, 247, 205, 214, 336, 374, 143, 127, 128, 131, 134, 136, 255, 266.2, 252; 546/284, 213; 514/513, 532, 538, 613, 617, 627, 620, 336, 340, 342, 444, 824, 427, 397, 471, 438; 544/238, 333, 405

[56] References Cited

U.S. PATENT DOCUMENTS

| | | |
|---|---|---|
| 3,375,256 | 3/1968 | Bach et al. |
| 3,455,918 | 7/1969 | Marxer et al. |
| 4,305,959 | 12/1981 | Shepherd ............... 564/422 |
| 4,382,951 | 5/1983 | Grassberger et al. .......... 549/23 |
| 4,609,732 | 9/1986 | Plummer ............... 546/297 |
| 4,680,291 | 7/1987 | Hamberger et al. .......... 564/387 |
| 4,751,245 | 6/1988 | Bisacchi et al. ............. 564/300 |
| 4,755,534 | 7/1988 | Stuetz .................... 564/387 |

FOREIGN PATENT DOCUMENTS

| | | |
|---|---|---|
| 0051196 | 10/1981 | European Pat. Off. |
| 0066628 | 12/1981 | European Pat. Off. |
| 2185980 | 1/1987 | United Kingdom |

OTHER PUBLICATIONS

Stuetz, A. Chem. Abs., No. 85436c, (1983), 100.
Stuetz, A. Chem. Abs., No. 169006d, (1981), 95.
Stuetz, A. Chem. Abs., No. 217260, (1987), 107.
Maeda, et al., Chem. Abs., No. 6950, (1981), 107.

*Primary Examiner*—Richard L. Raymond
*Assistant Examiner*—Mark W. Russell
*Attorney, Agent, or Firm*—Sherman and Shalloway

[57] ABSTRACT

The substituted alkylamine derivatives represented by formula (I)

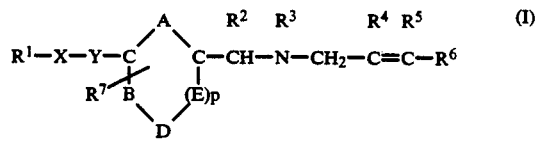

(Abstract continued on next page.)

wherein

R$^1$ represents (a) substituted or unsubstituted C$_{2-6}$ alkenyl group, (b) substituted or unsubstituted C$_{3-6}$ cycloalkenyl group, (c) substituted or unsubstituted C$_{2-6}$ alkynyl group, (d) substituted or unsubstituted aryl group, (e) substituted or unsubstituted heterocyclic group, (f) fused heterocyclic group which may be substituted, or (g) group represented by the formula R$^{11}$-Ar wherein R$^{11}$ is a heterocyclic group and Ar is a 5- or 6-membered aromatic ring which may contain a hetero N, O or S atom, and which may be substituted;

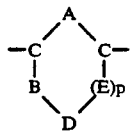

represents a 5- or 6-membered aromatic ring which may contain a hetero N, O or S atom, and may be substituted by R$^7$, X and Y are linking groups, R$^2$ is H or lower alkyl, R$^3$ is hydrogen, lower alkyl, lower alkenyl, lower alkynyl or lower cycloalkyl, R$^4$ and R$^5$ are independently hydrogen or halogen atoms, R$^6$ represents (a) substituted or unsubstituted acyclic hydrocarbon group which may be unsaturated, (b) substituted or unsubstituted cycloalkyl group, or (c) substituted or unsubstituted phenyl group, or non-toxic salts thereof. (E)-N-(6-6-dimethyl-2-hepten-4-ynyl)-N-ethyl-3-[4-(3-thienyl)-2-thienylmethyloxy]benzylamine hydrochloride is a representative example. The substituted alkylamine derivatives are useful as pharmaceuticals, particularly for the treatment and prevention of hypercholesterolemia, hyperlipemia and arteriosclerosis.

19 Claims, No Drawings

SUBSTITUTED ALKYLAMINE DERIVATIVES

This application is a continuation-in-part of copending applications Ser. No. 533,532, filed Jun. 5, 1990 which is CIP of Ser. No. 465,209, filed Mar. 8, 1990; and a CIP of Ser. No. 274,972 filed Nov. 22, 1988; all abandoned, and priority is claimed therefrom.

The disclosure of each of these application Ser. No. 533,532, Ser. No. 465,209, and Ser. No. 274,972, are incorporated herein, in their entirety, by reference thereto.

This invention relates to novel substituted alkylamine derivatives. More specifically, it relates to substituted alkylamine derivatives and their salts which are useful as pharmaceuticals, particularly for the treatment and prevention of hypercholesterolemia, hyperlipemia and arteriosclerosis, processes for production thereof, and their use.

Arteriosclerosis is a degenerative arterial disease which has closely to do with aging and diet, and is regarded as the cause of coronary and cerebral arterial diseases, the principal cause of death in the present day. Arteriosclerosis begins in early ages as deposition of lipid on the endothelia of large vessels, and with age, its degree increases. It will finally show clinical symptoms as ischemic heart diseases such as myocardial infarction and angina pectoris, cerebral arteriosclerosis such as cerebral infarction, and aneurism. It is known that the increase of various blood lipids is involved in this lipid deposition. In particular, the increase of blood cholesterol is the most prominent risk factor, and decreasing the blood cholesterol level to a normal value is the most effective therapeutic and prophylactic means against arteriosclerosis. It is said that in humans, more than 50% of cholesterol is derived from de novo biosynthesis. Nowadays, lovastatin and eptastatin which are inhibitors of enzymes in the process of de novo biosynthesis are clinically used as hypocholesterolemic agents (see, for example, A. W. Alberts et al., Proc. Natl. Acad. Sci., vol. 77, page 3957 (1980); and Tsujita et al., Biochim Biophs. Acta, vol. 877, page 50, 1986). However, since 3-hydroxy-3-methyl glutaryl-coenzyme A reductase, a target enzyme of these inhibitors, is positioned in the early stage of the cholesterol biosynthesis pathway, the administration of these drugs will also inhibit formation of dolichol and ubiquinone which are other biologically important metabolites. Furthermore, it was reported that triparanol, an inhibitor of the later stage of the cholesterol biosynthesis pathway, becomes the cause of cataract due to the accumulation of desmosterol. Since squalene epoxidase is positioned in the middle stage of the cholesterol biosynthesis pathway, an inhibitor of this enzyme is expected to solve these problems and serve as a hypocholesterolemic agent with high safety.

Some compounds have already been known as inhibitors of squalene epoxidase [see G. Petranyi et al., Science, vol. 224, page 1239 (1984)]. All of these, however, were developed as antimycotic agents which inhibit fungal squalene epoxidase selectively. No inhibitor has been known which inhibits mammalian enzyme and has utility as an hypocholesterolemic agent.

It is a primary object of this invention to provide an hypolipemic agent, and a therapeutic and prophylactic agent for arteriosclerosis which is safer and better than conventional hypolipemic agents.

The present inventors investigated squalene epoxidase inhibitors having hypocholesterolemic activity in order to develop a novel antiarteriosclerotic agent, and have found that substituted alkylamine derivatives of general formula [I] given below selectively inhibit squalene epoxidase of mammals, and have strong hypocholesterolemic activity.

Thus, the present invention provides substituted alkylamine derivatives represented by the general formula

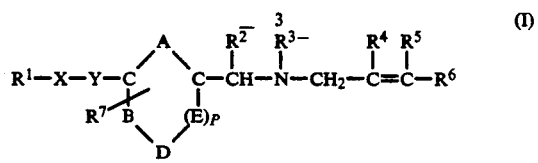

Wherein
$R^1$ is selected from the group consisting of
a) a $C_{2-6}$ alkenyl group, or a $C_{2-6}$ alkenyl group substituted by a hydroxyl group, a halogen atom, a cyano group, a $C_{1-4}$ alkoxy group, an aryl group, a furyl group, an oxazolyl group or a thiazolyl group, b) a $C_{5-7}$ cycloalkenyl group, or a $C_{5-7}$ cycloalkenyl group substituted by a hydroxyl group, a halogen atom, a cyano group, a $C_{1-4}$ alkoxy group, an aryl group, a furyl group, an oxazolyl group or a thiazolyl group, c) a $C_{2-6}$ alkynyl group, or a $C_{2-6}$ alkynyl group substituted by a hydroxyl group, a halogen atom, a cyano group, a $C_{1-4}$ alkoxy group, an aryl group, a furyl group, an oxazolyl group or a thiazolyl group, d) an aryl group, or an aryl group substituted by a hydroxy group, a halogen atom, a cyano group, a formyl group, a $C_{1-6}$ alkyl group, a $C_{1-6}$ halogenoalkyl group, a $C_{1-6}$ hydroxyalkyl group, a $C_{2-6}$ alkenyl group, a $C_{1-4}$ alkoxy group, or a $C_{3-5}$ alkenyloxy group, e) a heterocyclic group selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl group, said heterocyclic group being optionally substituted by a hydroxy group, a halogen atom, a cyano group, a formyl group, a $C_{1-6}$ alkyl group, a $C_{1-6}$ halogenoalkyl group, a $C_{1-6}$ hydroxyalkyl group, a $C_{2-6}$ alkenyl group, a $C_{1-4}$ alkoxy group, or a $C_{3-5}$ alkenyloxy group, f) a fused heterocyclic group selected from the group consisting of a benzo [b] furanyl, a benzo [b] thienyl group, a benzoxazolyl group, a benzothiazolyl group, a quinolyl group and an isoquinolyl group, said fused heterocyclic group being optionally substituted by a hydroxy group, a halogen atom, a cyano group, a formyl group, a $C_{1-6}$ alkyl group, a $C_{1-6}$ halogenoalkyl group, a $C_{1-6}$ hydroxyalkyl group, a $C_{2-6}$ alkenyl group, a $C_{1-4}$ alkoxy group, or a $C_{3-5}$ alkenyloxy group, and g) a group represented by the formula

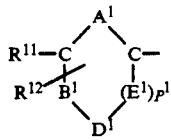

wherein

R$^{11}$ is a heterocyclic group selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl group;

R$^{12}$ is a hydrogen atom, a halogen atom, a hydroxyl group, a cyano group, a C$_{1-6}$ alkyl group or a C$_{1-4}$ alkoxy group;

p$^1$ is 0 or 1;
A$^1$ is CH, N, O or S;
B$^1$ is CH, N, O or S;
D$^1$ is CH, N, O or S;
E$^1$ is CH, N, O or S;
provided that no more than 2 of B$^1$, D$^1$ and E$^1$ can be simultaneously N, O or S;

R$^2$ is a hydrogen atom or a C$_{1-6}$ alkyl group;

R$^3$ is a hydrogen atom, a C$_{1-6}$ alkyl group, C$_{2-6}$ alkenyl group, a C$_{2-6}$ alkynyl group, or a C$_{3-6}$ cycloalkyl group;

R$^4$ and R$^5$ may be the same or different and each is a hydrogen atom, or a halogen atom;

R$^6$ is selected from the group consisting of a) a C$_{1-17}$ acyclic hydrocarbon group, or a C$_{1-17}$ acyclic hydrocarbon group substituted by a hydroxy group, a halogen atom, a C$_{3-6}$ cycloalkyl group, a C$_{1-4}$ alkoxy group, a phenyl group, or a phenyl group substituted by a halogen atom, a C$_{1-6}$ alkyl group or a C$_{1-4}$ alkoxy group, in which said acyclic hydrocarbon group may contain 1 or 2 unsaturated bonds selected from the group consisting of double and triple bonds, b) a C$_{3-6}$ cycloalkyl group, or a C$_{3-6}$ cycloalkyl group substituted by a hydroxy group, a halogen atom, a C$_{1-4}$ alkoxy group, a phenyl group, or a phenyl group substituted by a halogen atom, a C$_{1-6}$ alkyl group or a C$_{1-4}$ alkoxy group, and c) a phenyl group, or a phenyl group substituted by a hydroxyl group, a halogen atom, a C$_{1-6}$ alkyl group or a C$_{1-4}$ alkoxy group;

R$^7$ is a hydrogen atom, a halogen atom, a hydroxyl group, a cyano group, a C$_{1-6}$ alkyl group or a C$_{1-4}$ alkoxy group;

p is 0 or 1;
A is CH, N, O or S;
B is CH, N, O or S;
D is CH, N, O or S;
E is CH, N, O or S;
provided that no more than 2 of B, D and E can be simultaneously N, O or S; and X and Y are independently O, S, CO, CHR$^a$ or NR$^b$, or X-Y is —CH=CH— or —C≡C—, in which R$^a$ is a hydrogen atom or a C$_{1-6}$ alkyl group; and R$^b$ is a hydrogen atom or a C$_{1-6}$ alkyl group;

provided that, when one of X and Y is O, S or NR$^b$, the other is CO or CHR$^a$; and, further, provided that the rings

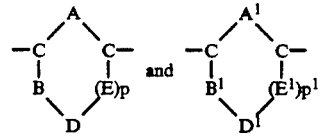

are aromatic rings, nontoxic salts of these, processes for production thereof, and the use thereof in the treatment of hypercholesterolemia, hyperlipemia and arteriosclerosis.

The invention will be described below in more detail.

It has previously been known that allylamine derivatives typified by naftifine and terbinafine represented by the following structural formulae

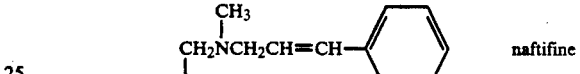

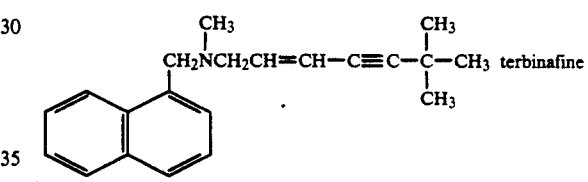

show strong inhibiting activity on the fungal squalene epoxidase, and therefore are useful as an antifungal agent (see G. Petranyi et al., Science, vol. 224, page 1239 (1984). However, these compounds hardly show an inhibitory action on the mammalian squalene epoxidase including human squalene epoxidase, and cannot be inhibitors of cholesterol biosynthesis (see N. S. Ryder et al., Biochem J., vol. 230, page 765 (1985).

The present inventors extensively made investigations in order to develop a drug which selectively acts on the mammalian squalene epoxidase and shows anticholesterol activity, and have found that if a 1,3-substituted 5- or 6-membered aromatic ring of the formula

wherein A, B, D, E, R$^7$ and p are as defined above, in which its 3-position is substituted by a group of the formula R$^1$-X-Y- (R$^1$, X and Y are as defined above) is substituted for the naphthalene ring moiety of the naftifine and terbinafine, a compound showing strong inhibitory activity on the mammalian squalene epoxidase can be obtained.

The inventors have also found that the squalene epoxidase inhibitory activity of the compounds of general formula [I] is very selective, and these compounds show little activity on the enzymes of fungi and are very valuable as drugs for treatment or prevention of hypercholesterolemia, hyperlipemia and arteriosclerosis.

Now, the definitions and specific examples of the various terms mentioned in the description of this specification will be explained.

The $C_{1-6}$ alkyl group may be, for example, a linear or branched alkyl group having 1 to 6 carbon atoms, such as methyl, ethyl, propyl, isopropyl, butyl, isobutyl, sec-butyl, tert-butyl, pentyl, isopentyl, neopentyl and hexyl groups. The $C_{2-6}$ alkenyl group may be, for example, a linear or branched alkenyl group of 2 to 6 carbons containing 1 or 2 double bonds in the carbon chain, such as vinyl, 1-propenyl, isopropenyl, allyl, 1-methyl-1-propenyl, 2-methyl-1-propenyl, 1-methyl-2-propenyl, 2-methyl-2-propenyl, 1-butenyl, 2-butenyl, 3-butenyl, 1,3-butadienyl, 2-methyl-1-butenyl, 3-methyl-1,3-butadienyl, 2-ethyl-1-butenyl, 3-methyl-2-butenyl, 1-pentenyl, 2-pentenyl, 1,3-pentadienyl, 2,4-pentadienyl, 3-methyl-2-pentenyl, 1-hexenyl and 2-hexenyl groups. The $C_{2-6}$ alkynyl group may be, for example, a linear or branched alkynyl group of 2 to 6 carbon atoms containing 1 or 2 triple bonds in the carbon chain, such as ethynyl, 1-propynyl, propargyl, 1-butynyl, 2-butynyl, 3-butynyl, 3-methyl-1-butynyl, 3,3-dimethyl-1-butynyl, 1-pentynyl, 2-pentynyl, 3-pentynyl, 1,3-pentadiynyl, 1-ethynyl-2-propynyl, 4-methyl-2-pentynyl and 2-hexynyl groups.

The $C_{1-4}$ alkoxy group may be, for example, a linear or branched alkoxy group having 1 to 4 carbon atoms such as methoxy, ethoxy, propoxy, isopropoxy, butoxy, isobutoxy, sec-butoxy and tert-butoxy groups. The lower alkenyloxy group includes linear or branched alkenyloxy groups having 3 to 6 carbon atoms such as 2-propenyloxy, 2-methyl-2-propenyloxy, 2-methyl-2-butenyloxy and 3-methyl-2-butenyloxy groups. Examples of the $C_{3-6}$ cycloalkyl groups are cycloalkyl groups having 3 to 6 carbon atoms such as cyclopropyl, cyclobutyl, cyclopentyl and cyclohexyl groups. Examples of the cycloalkenyl groups are cycloalkenyl groups of 5 to 7 carbon atoms containing 1 or 2 double bonds in the ring, such as 1-cyclopentenyl, 2-cyclopentenyl, 3-cyclopentenyl, 2,4-cyclopentadienyl, 1-cyclohexenyl, 1,3-cyclohexadienyl, 1,4-cyclohexadienyl, and 1-cycloheptenyl groups.

Examples of the aryl group include monocyclic or polycyclic aromatic groups such as phenyl, naphthyl and tetrahydronaphthyl groups.

The halogen atoms may be, for example, fluorine, chlorine, bromine or iodine.

The $C_{1-6}$ halogenoalkyl group may be, for example, a linear or branched halogenoalkyl group such as chloromethyl, 2-chloroethyl, 3-chloropropyl, trifluoromethyl, 2,2,2-trifluoroethyl, 1-chlorobutyl, 2-chloropentyl and 3-chlorohexyl. The $C_{1-6}$ hydroxyalkyl group may be, for example, a linear or branched hydroxyalkyl group such as hydroxymethyl, 2-hydroxyethyl, 3-hydroxypropyl, 4-hydroxybutyl, 5-hydroxypentyl, 6-hydroxyhexyl, 2-hydroxy-1-methyl propyl and 2-hydroxy-1-methylethyl.

The $C_{1-17}$ acyclic hydrocarbon group which may contain 1 or 2 unsaturated bond selected from double and triple bonds may be, for example, a $C_1-C_{17}$, preferably $C_3-C_{12}$, linear or branched saturated hydrocarbon group, or a $C_1-C_{17}$, preferably $C_3-C_{12}$, linear or branched unsaturated hydrocarbon group having 1 or 2 double bonds and/or triple bonds. Specific examples include methyl, ethyl, propyl, isopropyl, butyl, isobutyl, sec-butyl, tert-butyl, pentyl, isopentyl, tert-pentyl, neopentyl, hexyl, 1,2,2-trimethylpropyl, 1,1-dimethylbutyl, 2,2-dimethylbutyl, 3,3-dimethylbutyl, 1,1-dimethylpentyl, 3,3-dimethylpentyl, 4,4-dimethylpentyl, 2,4,4-trimethylpentyl, heptyl, octyl, nonyl, decanyl, undecyl, dodecyl, tridecyl, tetradecyl, pentadecyl, hexadecyl, heptadecyl, vinyl, ethynyl, allyl, isopentenyl, 1-pentenyl, propargyl, 1-propynyl, 1-butenyl, 2-butenyl, 3-butenyl, 1-butynyl, 2-butynyl, 3-butynyl, 1-methyl-1-propenyl, 2-methyl-1-propenyl, 1-methyl-2-propenyl, 2-methyl-2-propenyl, 1,2-dimethyl-1-propenyl, 1,2-dimethyl-2-propenyl, 2-methyl-1-butenyl, 2-methyl-2-butenyl, 3-methyl-1-butenyl, 3-methyl-1-butynyl, 3,3-dimethyl-1-butenyl, 3,3-dimethyl-1-butynyl, 4,4-dimethyl-1-pentenyl, 4,4-dimethyl-1-pentynyl, 3-ethyl-1-pentenyl, 3-ethyl-1-pentenyl, 4-ethyl-1-hexenyl, 4-ethyl-1-hexynyl, 1,1-dimethyl-2-hexenyl, 1,1,4,4-tetramethyl-2-pentenyl, 1,1,4,4-tetramethyl-2-pentynyl, 1,3-butadienyl, 2-methyl-1,3-butadienyl, 1,3-pentadienyl, 4-penten-2-ynyl, 3-penten-2-ynyl, 3-methyl-3-buten-1-ynyl, 5,5-dimethyl-1,3-hexadienyl and 5,5-dimethyl-3-hexen-1-ynyl groups.

The $C_{3-6}$ cycloalkane may be, for example, cyclopropane, cyclobutane, cyclopentane and cyclohexane.

In order to disclose the compounds of the invention represented by general formula [I] more specifically, the various symbols used in formula [I] will be explained in detail by citing preferred examples.

The $C_{2-6}$ alkenyl group $R^1$ which may be substituted is a linear or branched lower alkenyl group which may be substituted, for example, by a hydroxyl group, a halogen atom, a cyano group, a $C_{1-4}$ alkoxy group, an aryl group, a furyl group, an oxazolyl group or a thiazolyl group. Preferably, it may be an unsubstituted lower alkenyl group such as vinyl, allyl, 1-propenyl, isopropenyl, 1-methyl-1-propenyl, 2-methyl-1-propenyl, 1-methyl-2-propenyl, 2-methyl-2-propenyl, 1-butenyl, 2-butenyl, 3-butenyl, 2-methyl-1-butenyl, 2-ethyl-1-butenyl, 3-methyl-2-butenyl, 1-pentenyl, 2-pentenyl, 3-methyl-2-pentenyl, 1-hexenyl and 2-hexenyl groups; or a substituted lower alkenyl group such as 2-fluoro-2-propenyl, 2-chloro-2-propenyl, 2-bromo-2-propenyl, 2,3-dichloro-2-propenyl, 1,1-difluoro-2-propenyl, 3-fluoro-2-butenyl, 3-chloro-2-butenyl, 3-hydroxy-1-propenyl, 2-cyanoethenyl, 3-cyano-2-propenyl, 3-methoxy-1-propenyl, 3-methoxy-1-butenyl, 4-methoxy-2-butenyl, 4-methoxy-3-methyl-2-butenyl, 3-methoxy-1-vinyl-1-butenyl, 3-methoxy-2-methyl-1-vinyl-1-butenyl, styryl, cinnamyl, 2-(2-furyl)ethenyl, 2-(3-furyl)ethenyl, 3-(2-furyl)-2-propenyl, 4-phenyl-1,3-butadienyl, alpha-methylenecinnamyl, alpha-ethylidenecinnamyl, 1,1-dimethyl-3-phenyl2-propenyl, beta-methyl-alpha-methylenecinnamyl, 4-(2-furyl)- 1,2-butadienyl, 4-(3-furyl)-1,3-butadienyl, 3-(2-furyl)-1-methylene-2-propenyl, 3-(3-furyl)-1-methylene-2-propenyl, 2-(2-oxazolyl)ethenyl, 2-(5-oxazolyl)ethenyl, 2-(2-thiazolyl)ethenyl, 2-(4-thiazolyl)ethenyl and 2-(5-thiazolyl)ethenyl groups.

Examples of especially preferred lower substituted alkenyl groups $R^1$ include unsubstituted alkenyl groups of 3 to 5 carbon atoms, such as 1-propenyl, isopropenyl, 1-methyl-1-propenyl, 2-methylpropenyl, 1-methyl-2-propenyl, 2-methyl-2-propenyl, 1-butenyl and 2-methyl-1-butenyl groups.

The $C_{5-7}$ cycloalkenyl group $R^1$ which may be substituted is a cycloalkenyl group which may be substituted by, for example, a hydroxyl group, a halogen atom, a cyano group, a lower alkoxy group, an aryl group, a furyl group, an oxazolyl group or a thiazolyl group. Specific examples include 1-cyclopentenyl, 2-cyclohexenyl, 1,4-cyclohexadienyl, 2-methyl-1-cyclopentenyl, 2-methyl-1-cyclohexenyl, 3-hydroxy-1-cyclohexenyl, 3-methoxy-1-cyclohexenyl, 2-fluoro-1-cyclopentenyl, 2-chloro-1-cyclopentenyl, 2-fluoro-1-cyclohexenyl, 2-chloro-1-cyclohexenyl, 2-cyano-1-cyclohexenyl, 4-methoxy-1,3-cyclohexadienyl, 2-(2-furyl)-1-cyclohexenyl, 2-phenyl-1-cyclohexenyl, 3-(2-furyl)-2-cyclohexenyl, 3-phenyl-1-cyclohexenyl, 2-(5-oxazolyl)-1-cyclohexenyl, 2-(2-thiazolyl)-1-cyclohexenyl, and 2-(5-thiazolyl)-1-cyclohexenyl groups.

The $C_{2-6}$ alkynyl group $R^1$ which may be substituted may be a lower alkynyl group which may be substituted, for example, by a hydroxyl group, a halogen atom, a cyano group, a lower alkyl group, a lower alkoxy group, an aryl group, a furyl group, an oxazolyl group or a thiazolyl group. Specific preferred examples include substituted or unsubstituted lower alkynyl groups such as ethynyl, 1-propynyl, propargyl, 1-butynyl, 2-butynyl, 3-methyl-1-butynyl, 3,3-dimethyl-1-butynyl, 1-pentynyl, 2-pentynyl, 2-phenylethynyl, 2-(2-furyl)ethynyl, 2-(5-oxazolyl)ethynyl, 2-(5-thiazolyl)ethynyl and 3-methoxy-3-methyl-1-butynyl.

The aryl group $R^1$ which may be substituted may be an aryl group which may be substituted, for example, by a hydroxyl group, a halogen atom, a cyano group, a formyl group, a $C_{1-6}$ alkyl group, a halogenoalkyl group having 1 or 2 carbon atoms such as a trifluoromethyl or 2,2,2-trifluoroethyl group, a hydroxyalkyl group having 1 or 2 carbon atoms such as a hydroxymethyl or 1-hydroxyethyl group, a $C_{2-6}$ alkenyl group, a $C_{1-4}$ alkoxy group, a linear or branched $C_{3-5}$ alkenyloxy group having 3 to 5 carbon atoms such as a 2-propenyloxy, 2-methyl-2-propenyloxy or 3-methyl-2-butenyloxy group. Examples of preferred aryl groups $R^1$ include unsubstituted aryl groups such as phenyl, 1-naphthyl and 2-naphthyl groups; and substituted phenyl groups such as 2-hydroxyphenyl, 3-hydroxyphenyl, 2-fluorophenyl, 3-fluorophenyl, 4-fluorophenyl, 2-chlorophenyl, 3-chlorophenyl, 2,6-difluorophenyl, 2-cyanophenyl, 3-cyanophenyl, 2-formylphenyl, 3-formylphenyl, 2-methylphenyl, 3-methylphenyl, 4-methylphenyl, 2-ethylphenyl, 2-propylphenyl, 2,3-dimethylphenyl, 2,6-dimethylphenyl, 2-methoxyphenyl, 3-methoxyphenyl, 2-ethoxyphenyl, 2-propoxyphenyl, 3-propoxyphenyl, 3-isopropoxyphenyl, 3-butoxyphenyl, 3-isobutoxyphenyl, 2-hydroxymethylphenyl, 3-hydroxymethylphenyl, 2-trifluoromethylphenyl, 3-trifluoromethylphenyl, 2-vinylphenyl, 3-vinylphenyl, 3-allylphenyl, 3-isopropenylphenyl, 3-(1-propenyl)phenyl, 3-(2-methyl-1-propenyl)phenyl, 3-(2-methyl-2-propenyl)phenyl, 3-(1-butenyl)phenyl, 3-(2-butenyl)phenyl, 3-(2-methyl-1-butenyl)phenyl, 3-(3-methyl-1-butenyl)phenyl, 3-(1-pentenyl)phenyl, 3-(2-pentenyl)phenyl, 3-(1,3-butadienyl)phenyl, 3-(1-vinyl-1-propenyl)phenyl, 2-allyloxyphenyl, 3-allyloxyphenyl, 3-(2-methyl-2-propenyloxy)phenyl, 3-(3-methyl-2-butenyloxy)phenyl.

The heterocyclic group $R^1$ is a heterocyclic group selected from the group consisting of a pyrrolyl, furyl, thienyl, oxazoly, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl group, said heterocyclic group being optionally substituted by a hydroxy group, a halogen atom, a cyano group, a formyl group, a $C_{1-6}$ alkyl group, a $C_{1-6}$ halogenoalkyl group, a $C_{1-6}$ hydroxyalkyl group, a $C_{2-6}$ alkenyl group, a $C_{1-4}$ alkoxy group or a $C_{3-5}$ alkenyloxy group.

Examples of preferred heterocyclic groups include 2-furyl, 3-furyl, 2-thienyl, 3-thienyl, 2-oxazoly, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 2-pyridyl, 3-pyridyl, 4-pyridyl, 2-pyrimidinyl, 4-pyrimidinyl, 3-methyl-2-furyl, 2-methyl-3-furyl, 4-methyl-3-furyl, 5-methyl-2-furyl, 3-chloro-2-furyl, 2-chloro-3-furyl, 3-fluoro-2-furyl, 5-chloro-2-furyl, 4-cyano-2-furyl, 5-cyano-2-furyl, 3-methyl-2-thienyl, 2-methyl-3-thienyl, 5-methyl-2-thienyl, 5-chloro-2-thienyl, 4-cyano-2thienyl, 5-cyano-2-thienyl, 4-methyl-2-oxazolyl, 5-methyl-2-oxazolyl, 5-methyl-4-oxazolyl, 4-methyl-5-oxazolyl, 5-cyano-2-oxazolyl, 2-cyano-5-oxazolyl, 4-methyl-2-thiazolyl, 5-methyl-2-thiazolyl, 5-cyano-2-thiazolyl, 2-cyano-5-thazolyl, 5-methyl-3-isoxazolyl, 3-methyl-5-isoxazolyl, 5-cyano-3-isoxazolyl, 3-cyano-5-isoxazolyl, 3-methyl-2-pyridyl, 4-methyl-2-pyridyl, 2-methyl-3-pyridyl, 4-methyl-3-pyridyl, 2-chloro-3-pyridyl, 4-chloro-3-pyridyl, 2-methyl-4-pyridyl, 3-methyl-4-pyridyl, 2-chloro-4-pyridyl, 6-methoxy-2pyridyl, 2-methoxy-3-pyridyl, 4-methoxy-3-pyridyl, 2-methoxy-4-pyridyl, 4-cyano-2-pyridyl, 6-cyano-2-pyridyl, 2-cyano-4-pyridyl. Preferred among them are 2-furyl, 3-furyl, 2-thienyl, 3-thienyl, 2-oxazolyl, 4-oxazolyl, 5-oxazolyl, 2-thiazolyl, 4-thiazolyl, 5-thiazolyl, 3- Cisoxazolyl, 4-isoxazolyl, 5-isoxazolyl, 3-isothiazolyl, 4-isothiazolyl, 5-isothiazolyl, 2-pyridyl, 3-pyridyl, 4-pyridyl, 2-pyrimidinyl and 4-pyrimidinyl groups; and 5-membered substituted aromatic heterocyclic groups such as 5-chloro-2-furyl, 2-chloro-3-furyl, 3-methyl-2-furyl, 2-methyl-3-furyl, 4-methyl-3-furyl, 5-methyl-2-furyl, 5-cyano-2-furyl, 4-cyano-2-furyl, 3-methyl-2-thienyl, 2-methyl-3-thienyl, 5-methyl-2-thienyl, 4-cyano-2-thienyl, 5-cyano-2-thienyl, 2-chloro-4-oxazolyl, 2-chloro-5-oxazolyl, 4-methyl-2-oxazolyl, 5-methyl-2-oxazolyl, 2-methyl-4-oxazolyl, 5-methyl-4-oxazolyl, 2-methyl-5-oxazolyl, 4-methyl-5-oxazolyl, 5-cyano-2-oxazolyl, 2-cyano-5-oxazolyl, 2-chloro-4-thiazolyl, 2-chloro-5-thiazolyl, 4-methyl-2-thiazolyl, 5-methyl-2-thiazolyl, 2-methyl-4-thiazolyl, 2-methyl-5-thiazolyl, 5-cyano-2-thiazolyl, 2-cyano-5-thiazolyl, 5-methyl-3isoxazolyl, 3-methyl-5-isoxazolyl, 5-cyano-3-isoxazolyl and 3-cyano-5-isoxazolyl.

The fused heterocyclic group $R^1$ is a fused heterocyclic group selected from the group consisting of a benzo [b] furanyl group, a benzo [b] thienyl group, a benzoxazolyl group, a benzothiazolyl group, a quinolyl group and an isoquinolyl group, said fused heterocyclic group being optionally substituted by a hydroxy group, a halogen atom, a cyano group, a formyl group, a $C_{1-6}$ alkyl group, a $C_{1-6}$ halogenoalkyl group a $C_{1-6}$ hydroxyalkyl group, a $C_{2-6}$ alkenyl group, a $C_{1-4}$ alkoxy group, or a $C_{3-5}$ alkenyloxy group.

Examples of preferred fused heterocyclic group include 2-benzo [b] furanyl, 3-benzo [b] furanyl, 4-benzo [b] furanyl, 2-benzo [b] thienyl, 4-benzo [b] thienyl, 2-benzoxazolyl, 4-benzoxazolyl, 7-benzoxazolyl, 2-benzothiazolyl, 4-benzothiazolyl, 7-benzothiazolyl, 2-quinolyl, 8-quinolyl and 3-isoquinolyl groups.

The group represented by the formula

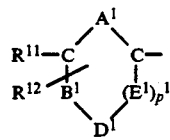

is an aromatic group substituted by heterocyclic group $R^{11}$, i.e., pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl or thiomorpholinyl group, in which said aromatic group is optionally substituted by $R^{12}$, i.e., a halogen atom, a hydroxyl group, a cyano group, $C_{1-6}$ alkyl group or a $C_{1-4}$ alkoxy group.

Examples of the substituted aromatic group include 3-(2-furyl)phenyl, 3-(3-furyl)phenyl, 3-(2-furyl)-2-methylphenyl, 3-(3-furyl)-2-methylphenyl, 3-(2-furyl)-6methylphenyl, 3-(3-furyl)-6-methylphenyl, 3-(2-thienyl)phenyl, 3-(3-thienyl)phenyl, 2-methyl-3-(2-thienyl)phenyl, 6-methyl-3-(3-thienyl)phenyl, 3-(2-oxazolyl)phenyl, 3-(4-oxazolyl)phenyl, 3-(5-oxazolyl)phenyl, 3-(2-thiazolyl)phenyl, 3-(4-thiazolyl)phenyl, 3-(5-thiazolyl)phenyl, 3-(3-isoxazolyl)phenyl, 3-(4-isoxazolyl)phenyl, 3-(5-isoxazolyl)phenyl, 3-(3-isothiazolyl)phenyl, 3-(4-isothiazolyl)phenyl, 3-(5-isothiazolyl)phenyl, 3-(1-pyrrolyl)phenyl, 3-(2-pyrrolyl)phenyl, 3-(3-pyrrolyl)phenyl, 3-(1-imidazolyl)phenyl, 3-(2-imidazolyl)phenyl, 3-(4-imidazolyl)phenyl, 3-(3-furazanyl)phenyl, 3-(2-pyridyl)phenyl, 3-(3-pyridyl)phenyl, 3-(4-pyridyl)phenyl, 3-(2-pyrimidinyl)phenyl, 3-(4-pyrimidinyl)phenyl, 3-(2-pyrazinyl)phenyl, 3-(3-pyridazinyl)phenyl, 3-(4-pyridazinyl)phenyl, 3-(1-pyrazolyl)phenyl, 3-[2-(1,3,5-triazinyl)]phenyl, 3-[2-(1,3,4-oxadiazolyl)]phenyl, 3-[2-(1,3,4-thiadiazolyl)]-phenyl, 4-(2-furyl)-2-furyl, 5-(2-furyl)-2-furyl, 5-(3-furyl)-2-furyl, 4-(2-thienyl)-2-thienyl, 4-(3-thienyl)-2-thienyl, 5-(3-thienyl)-2-thienyl, 5-(3-thienyl)-3-thienyl, 5-(2-oxazolyl)-2-furyl, 5-(2-thiazolyl)-2-furyl, 4-(2-oxazolyl)-2-thienyl, 4-(4-oxazolyl)-2-thienyl, 5-phenyl-2-furyl, 2-(2-furyl)-4-oxazolyl, 2-(2-furyl)-5-oxazolyl, 4-(2-furyl)-2-oxazolyl, 5-(2-furyl)-2-oxazolyl, 4-(2-oxazolyl)-2-oxazolyl, 5-(2-oxazolyl)-2-oxazolyl, 2-(2-oxazolyl)-4-oxazolyl, 2-(5-oxazolyl)-4-oxazolyl, 2-(5-oxazolyl)-5-oxazolyl, 2-(2-oxazolyl)-5-oxazolyl, 4-phenyl-2-oxazolyl, 5-phenyl-2-oxazolyl, 2-phenyl-4-oxazolyl, 2-phenyl-5-oxazolyl, 5-phenyl-3-isoxazolyl, 3-phenyl- 5-isoxazolyl, 2-(2-furyl)-4-thiazolyl, 2-(2-furyl)-5-thiazolyl, 4-(2-furyl)-2-thiazolyl, 5-(2-furyl)-2-thiazolyl, 5-phenyl-2-thiazolyl, 2-phenyl-4-thiazolyl, 2-phenyl-5-thiazolyl, 2-(3-thienyl)-4-thiazolyl, 2-(5-oxazolyl)-4-thiazolyl, 2-(3-thienyl)-5-thiazolyl, 2-(5-oxazolyl)-5-thiazolyl, 2-(4-thiazolyl)-4-thiazolyl, 2-(4-thiazolyl)-5-thiazolyl, 2-(5-thiazolyl)-4-thiazolyl, 2-(5-thiazolyl)-5-thiazolyl, 4-(5-thiazolyl)-2-thiazolyl, 5-(5-thiazolyl)-2-thiazolyl, 4-(2-thiazolyl)-2-thiazolyl, 2-(2-thiazolyl)-5-thiazolyl, 5-phenyl-2-thienyl, 2-(3-thienyl)-4-pyridyl, 4-(3-thienyl)-2-pyridyl, 5-(3-thienyl)-3-pyridyl, 4-phenyl-2-pyridyl, 2-phenyl-4-pyridyl, 4-phenyl-2-pyrimidyl and 2-phenyl-4-pyrimidyl groups. Preferred among them are 3-(2-furyl)phenyl, 3-(3-furyl)phenyl, 3-(2-thienyl)-phenyl, 3-(3-thienyl)-phenyl, 3-(1-pyrrolyl)-phenyl, 3-(1-imidazolyl)phenyl, 3-(2-oxazolyl)phenyl, 3-(4-oxazolyl)-phenyl, 3-(5-oxazolyl)phenyl, 3-(2-thiazolyl)phenyl, 3-(4-thiazolyl)phenyl, 3-(5-thiazolyl)-phenyl, 3-(3-isoxazolyl)phenyl, 3-(4-isoxazolyl)phenyl, 3-(5-isoxazolyl)phenyl, and 3-(1-pyrazolyl)phenyl groups. The 2-methylphenyl, 2-(2-furyl)phenyl, 3-(3-furyl)phenyl, 3-(1-pyrrolyl)phenyl, 3-(4-oxazolyl)-phenyl, 3-(5-oxazolyl)phenyl, 3-(1-imidazolyl)phenyl, 3-(4-thiazolyl)phenyl, 3-(5-thiazolyl)phenyl, 5-(2-furyl)-2-furyl, 4-phenyl-2-furyl, 5-phenyl-2-furyl, 4-phenyl-2-thienyl, 5-phenyl-2-thienyl, 2-phenyl-5-oxazolyl, 4-phenyl-2-oxazolyl, 5-phenyl-2-oxazolyl, 2-(2-furyl)-4-oxazolyl, 2-(2-furyl)-5-oxazolyl, 2-(2-thienyl)-4-oxazolyl, 2-(2-thienyl)-5-oxazolyl, 2-(5-oxazolyl)-4-oxazolyl, 2-(5-oxazolyl)-5-oxazolyl, 2-phenyl-5-thiazolyl, 4-phenyl-2-thiazolyl, 5-phenyl-2-thiazolyl, 2-(2-furyl)-4-thiazolyl, 2-(2-furyl)-5-thiazolyl, 2-(4-thiazolyl)-4-thiazolyl, 2-(5-thiazolyl)-4-thiazolyl, 2-(4-thiazolyl)-5-thiazolyl and 2-(5-thiazolyl)-5-thiazolyl groups are especially preferred.

X and Y are identical or different and each represents an oxygen atom, a sulfur atom, a carbonyl group, a group of the formula —$CHR^a$— in which $R^a$ represents a hydrogen atom or a lower alkyl group, or a group of the formula —$NR^b$— in which $R^b$ represents a hydrogen atom or a lower alkyl group; or taken together, X and Y represent a vinylene or ethynylene group. If either one of X and Y represents an oxygen atom, a sulfur atom or the group —$NR^b$—, the other represents a carbonyl group or the group —$CHR^a$—. Examples of groups represented by the formula —X—Y— include —$(CHR^a)_2$—, —$CHR^aO$—, —$OCHR^a$—, —$CHR^aS$, —$SCHR^a$—, —$CHR^aNR^b$—, —$NR^bCHR^a$—, —$CHR^aCO$—, —$COCHR^a$—, —$COO$—, —$OCO$—, —$COS$—, —$SCO$—, —$CONR^b$, —$NR^bCO$—, —CH═CH—, and —C≡C— (in these formulae, $R^a$ and $R^b$ are as defined hereinabove). Of these, the ethylene group, (E)-vinylene group, the group —$CH_2O$—, and the group —$CH_2NH$— are preferred.

$R^2$ is preferably a hydrogen atom or a linear or branched lower alkyl group having 1 to 4 carbon atoms such as a methyl, ethyl, propyl or isopropyl group. The hydrogen atom is preferred.

$R^3$ represents a hydrogen atom, a $C_{1-6}$ alkyl group, a $C_{2-6}$ alkenyl group, a $C_{2-6}$ alkyl group or a $C_{3-6}$ cycloalkyl group, for example linear or branched lower alkyl groups having 1 to 5 carbon atoms such as methyl, ethyl, propyl, isopropyl, butyl, isobutyl and pentyl groups, linear or branched lower alkenyl groups having 3 to 5 carbon atoms such as allyl, 2-butenyl, 2-pentenyl, 2-methyl-2-propenyl and 3-methyl-2-butenyl groups, linear or branched lower alkynyl groups having 3 to 5 carbon atoms such as propargyl, 2-butynyl and 2-pentynyl groups, and cycloalkyl groups having 3 to 5 carbon atoms such as cyclopropyl, cyclobutyl and cyclopentyl groups. Methyl, ethyl, propyl, allyl, propargyl and cyclopropyl groups are preferred, and the methyl, ethyl and propyl groups are most preferred.

$R^4$ and $R^5$ represent a hydrogen atom or a halogen atom, preferably a hydrogen atom, a fluorine atom or a chlorine atom. The hydrogen atom is especially preferred.

A trans-form (E-form) geometric isomer and a cis-form (Z-form) geometric isomer exist at the double bond formed by the two carbon atoms to which $R^4$ and $R^5$ are bonded respectively. The trans-form geometric isomer is preferred.

The acyclic hydrocarbon group $R^6$ which may be substituted (the acyclic hydrocarbon groups may contain 1 or 2 unsaturated bonds selected from the group consisting of double and triple bonds) means a linear or branched acyclic hydrocarbon group having 1 to 17, preferably 3 to 12, carbon atoms which may be substituted, for example, by a hydroxyl group, a halogen atom, a $C_{3-6}$ cycloalkyl group, a $C_{1-4}$ alkoxy group, or a phenyl group which may be substituted by a halogen atom, a $C_{1-6}$ alkyl group or a $C_{1-4}$ alkoxy group and in which the carbon chain may contain 1 or 2 unsaturated bonds selected from the group consisting of double and triple bonds Examples of preferred acyclic hydrocarbon groups include substituted or unsubstituted saturated hydrocarbons such as isopropyl, tert-butyl, isopentyl, tert-pentyl, neopentyl, isopropoxymethyl, tert-butoxymethyl, 2-(isopropoxy)ethyl, 2-(tert-butoxy)ethyl, 2-methoxy-2-methylpropyl, p-(tert-butyl)benzyl, phenethyl, alpha-methylbenzyl, alpha,-alpha-dimethylbenzyl, 3-phenylpropyl, 2-(p-fluorophenyl)ethyl, 2-[p-(tert-butyl)phenyl]ethyl, alpha,alpha-dimethyl-p-fluorobenzyl and alpha,alpha-dimethyl-p-(tert-butyl)benzyl group; groups represented by the formula —CH=CH—$R^g$ (in which $R^g$ represents a lower alkyl group which may be substituted, a lower alkenyl group which may be substituted, a cycloalkyl group which may be substituted, or a phenyl group which may be substituted), such as 2-cyclopropylvinyl, 2-(1-methylcyclopropyl)vinyl, 1-propenyl, 1-butenyl, 3-methyl-1-butenyl, 3,3-dimethyl-1-butenyl, 3-methoxy-3-methyl-1-butenyl, 1-pentenyl, 3-methyl-1pentenyl, 3,3-dimethyl-1-pentenyl, 3-ethyl-1-pentenyl, 1-hexenyl, 1-heptenyl, 1-octenyl, styryl, 2-(p-fluorophenyl)vinyl, 2-[p-(tert-butyl)phenyl]vinyl, 3-methyl-3-phenyl-1-butenyl, 3-methyl-3-(p-fluorophenyl)-1-butenyl, 3-methyl-3-[p-(tert-butyl)phenyl]-1-butenyl, 1,3-butadienyl, 3-methyl-1,3-butadienyl, 1,3-pentadienyl, 3-methyl-1,3-pentadienyl, 4-methyl-1,3-pentadienyl, 3,4-dimethyl-1,3-pentadienyl, 1,3-hexadienyl and 5,5-dimethyl-1,3-hexadienyl groups; and groups represented by the formula —C≡—C—$R^g$ in which $R^g$ is as defined hereinabove, such as 2-cyclopropylethynyl, 2-(1-methylcyclopropyl)ethynyl, 1-propynyl, 1-butynyl, 3-methyl-1-butynyl, 3,3-dimethyl-1-butynyl, 3-methoxy-3-methyl-1-butynyl, 1-pentynyl, 3-methyl-1-pentynyl, 3,3-dimethyl-1-pentynyl, 3-ethyl-1-pentynyl, 1-hexynyl, 1-heptynyl, 1-octynyl, 2-phenylethynyl, 2-(p-fluorophenyl)ethynyl, 2-p-(tert-butyl)phenyl)ethynyl, 3-methyl-3-phenyl-1-butynyl, 3-methyl-3-(p-fluorophenyl)-1-butynyl, 3-methyl-3-p-(tert-butyl)phenyl]-1-butynyl, 3-buten-1-ynyl, 3-methyl-3-buten-1-ynyl, 3-penten-1-ynyl, 3-methyl-3-penten-1-ynyl, 4-methyl-3-penten-1-ynyl, 3,4-dimethyl-3-penten-1-ynyl, 3-hexen-1-ynyl and 5,5-dimethyl-3-hexen-1-ynyl groups. Preferred among them are groups of the formula —CH=CH—$R^c$ (in which $R^c$ represents an alkyl or alkenyl group having 3 to 6 carbon atoms which may be substituted by one lower alkoxy group having 1 to 4 carbon atoms, or a cycloalkyl group having 3 to 6 carbon atoms which may be substituted by an alkyl group having 1 to 4 carbon atoms, such as 3,3-dimethyl-1-butenyl, 3-methoxy-3-methyl-1-butenyl, 1-pentenyl, 3,3-dimethyl-1-pentenyl, 3-ethyl-1-pentenyl, 1-hexenyl, 3,3-dimethyl-1-hexenyl, 1-heptenyl, 1-octenyl, 3-methyl-1,3-butadienyl, 1,3-pentadienyl, 4-methyl-1,3-pentadienyl, 1,3-hexadienyl, 5,5-dimethyl-1,3-hexadienyl, 2-cyclopropylvinyl, 2-(1-methylcyclopropyl)vinyl, 2-cyclopentylvinyl and 2-cyclohexylvinyl groups; and groups of the formula —C≡C—$R^c$ in which $R^c$ is as defined above, such as 3,3-dimethyl-1-butynyl, 3-methoxy-3-methyl-1-butynyl, 1-pentynyl, 3,3-dimethyl-1-pentynyl, 3-ethyl-1-pentynyl, 1-hexynyl, 3,3-dimethyl-1-hexynyl, 1-heptynyl, 1-octynyl, 3-methyl-3-butyn-1-ynyl, 3-penten-1-ynyl, 4-methyl-3-penten-1-ynyl, 3-hexen-1-ynyl, 5,5-dimethyl-3-hexen-1-ynyl, 2-cyclopropylethynyl, 2-(1-methylcyclopropyl)ethynyl, 2-cyclopentylethynyl and 2-cyclohexylethynyl groups. More preferred are groups of the following formula

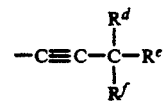

in which $R^d$ represents a hydrogen atom, an alkyl group having 1 to 4 carbon atoms, or an alkoxy group having 1 to 4 carbon atoms, and $R^e$ and $R^f$ are identical or different and each represents a methyl group or an ethyl group or taken together represents a cyclopropyl group, such as 3-methyl-1-butynyl, 3,3-dimethyl-1-butynyl, 3-methoxy-3-methyl-1-butynyl, 3-methyl-1-pentynyl, 3-ethyl-1-pentynyl, 3-methyl-1-hexynyl, 2-cyclopropylethynyl and 2-(1-methylcyclopropyl)ethynyl groups. Of these, the 3,3-dimethyl-1-butynyl and 3-methoxy-3-methyl-1-butynyl groups are most preferred.

The $C_{3-6}$ cycloalkyl group $R^6$ which may be substituted may be, for example, a cycloalkyl group which may be substituted by, for example, a hydroxyl group, a halogen atom, a $C_{1-4}$ alkoxy group or a phenyl group which may be substituted by a halogen atom, a $C_{1-6}$ alkyl group, or a $C_{1-4}$ alkoxy group. Examples of preferred cycloalkyl groups include 1-cyclopropyl, 1-methyl-cyclopropyl, 1-ethylcyclopropyl, 1-methoxycyclopropyl, cyclobutyl, 1-methylcyclobutyl, cyclopentyl, 1-methylcyclopentyl, 1-methoxycyclopentyl, 1-cyclohexyl and 1-methoxycyclohexyl, groups. The phenyl group $R^6$ which may be substituted may be, for example, a phenyl group which may be substituted by a hydroxyl group, a halogen atom, a $C_{1-6}$ alkyl group or a $C_{1-4}$ alkoxy group. Examples of preferred phenyl groups include phenyl, 4-hydroxyphenyl, 4-fluorophenyl, 4-chlorophenyl, 4-methylphenyl, 4-ethylphenyl, 4-propylphenyl, 4-isopropylphenyl, 4-butylphenyl, 4-isobutylphenyl, 4-(tert-butyl)phenyl, 2-methoxyphenyl, 3-methoxyphenyl, 4-methoxyphenyl, 3,4-dimethoxyphenyl and 2,6-dichlorophenyl.

Examples of preferred 5- or 6-membered aromatic rings represented by the formula

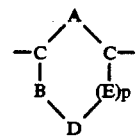

in which A, B, D, E and p are as defined, include benzene, pyrrole, furan, thiophene, oxazole, isoxazole, thiazole, imidazole, pyridine, pyrimidine, pyrazine, pyridazine and triazine rings The benzene, furan, thiophene, oxazole, isoxazole, thiazole, pyridine and pyrimidine rings are preferred, and the benzene ring is most preferred.

Most preferably, the aromatic ring is unsubstituted. As required, it may have one substituent, or two identical or different substituents, selected from the group consisting of halogen atoms, a hydroxyl group, cyano group, $C_{1-6}$ alkyl groups and $C_{1-4}$ alkoxy groups. Of these, the hydroxyl group, fluorine and chlorine atoms, the methyl group and the ethyl group are preferred.

A preferred group of the compounds provided by this invention are substituted alkylamines of general formula [I] in which $R^1$ represents an aryl or heterocyclic group which may be substituted by a hydroxy group, a halogen atom, a cyano group, a formyl group, a $C_{1-6}$ alkyl group, a $C_{1-6}$ halogenoalkyl group, a $C_{1-2}$ hydroxyalkyl group, a $C_{2-6}$ alkenyl group, a $C_{1-4}$ alkoxy group or a $C_{2-5}$ alkenyl group, or a group represented by the formula

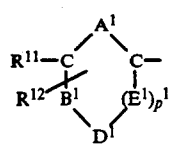

wherein $R^{11}$ is a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl or thiomorpholinyl group, and the ring of the formula

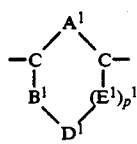

is a benzene, pyrrole, furan, thiophene, oxazole, isoxazole, thiazole, isothiazole, imidazole, 1,3,4-oxadiazole, 1,3,4-thiadiazole, pyridine, pyridazine, pyrimidine, pyrazine or triazine ring; X represents a methylene group and Y represents an oxygen atom or an imino group, or X and Y, taken together, represent an ethylene group or an (E)-vinylene group; the aromatic ring of the formula

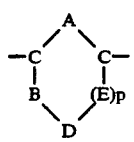

is a benzene, furan, thiophene, oxazole, isoxazole, thiazole, pyridine, isothiazole, imidazole, 1,3,4-oxadiazole, 1,3,4-thiadiazole, pyridazine, triazole or pyrimidine ring; $R^2$ represents a hydrogen atom; $R^3$ represents an alkyl group having 1 to 5 carbon atoms, an alkenyl group having 3 to 5 carbon atoms, an alkynyl group having 3 to 5 carbon atoms, or a cycloalkyl group having 3 to 5 carbon atoms; $R^4$ and $R^5$ each represent a hydrogen atom, and the double bond formed by the two carbon atoms to which they are bonded is of a transform (E-form); and $R^6$ is a group of the formula —CH=CH—$R^c$ in which $R^c$ represents an alkyl or alkenyl group having 3 to 6 carbon atoms which may be substituted by one alkoxy group having 1 to 4 carbon atoms, or a cycloalkyl group having 3 to 6 carbon atoms which may be substituted by 1 or 2 alkyl groups having 1 to 4 carbon atoms, or a group of the formula —C≡C—$R^c$ in which $R^c$ is as defined. In this group, more preferably, $R^1$ is a phenyl, naphthyl, furyl, thienyl, pyridyl, oxazolyl, thiazolyl, isoxazolyl, isothiazolyl, pyrazinyl, pyrimidyl, pyridazinyl, 1,3,5-triazinyl, benzofuranyl, benzothienyl, benzoxazolyl, benzothiazolyl or benzofurazanyl group which may have one substituent, or two identical or different substituents, selected from the class consisting of halogen atoms and hydroxyl, cyano, formyl, hydroxymethyl, $C_1$-$C_3$ alkyl, $C_3$-$C_5$ alkenyl, $C_3$-$C_5$ alkynyl, $C_1$-$C_3$ alkoxy and $C_3$-$C_5$ alkenyloxy groups, or a group represented by the formula

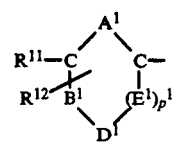

wherein $R^{11}$ is a furyl, pyrrolyl, thienyl, oxazolyl, isoxazolyl, thiazolyl, isothiazolyl, imidazolyl, phenyl, pyridyl, tetrahydrothienyl or dihydrothienyl group, and the ring of the formula

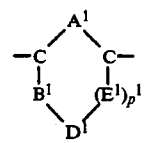

is a benzene, pyrrole, furan, thiophene, oxazole, isoxazole, thiazole, isothiazole, imidazole, 1,3,4-oxadiazole, 1,3,4-thiadiazole, pyridine, pyridazine, pyrimidine, pyrazine or triazine ring.

Especially preferred substituted alkylamines of general formula [I] are those in which $R^1$ is a 2-methylphenyl, 2-fluorophenyl or 3-cyanophenyl group, and those in which $R^1$ is the aromatic ring of the formula

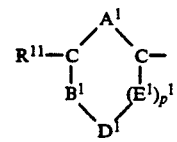

wherein $R^{11}$ is a thienyl, pyrrolyl, oxazolyl, isoxazolyl, thiazolyl, isothiazolyl, imidazolyl, pyridyl, tetrahydrothienyl or dihydrothienyl group, and the ring of the formula

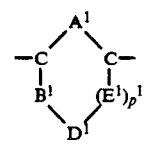

is a benzene or thiophene ring.

A further preferred group of the formula

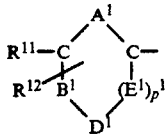

is those in which $R^{11}$ is a 3-thienyl, 1-pyrrolyl, 5-oxazolyl, 4-isoxazolyl, 5-isoxazolyl, 4-thiazolyl, 5-thiazolyl, 3-isothiazolyl, 4-isothiazolyl, 5-isothiazolyl, 3-pyridyl, tetrahydrothienyl, 2,3-dihydro-4-thienyl or 2,5-dihydro-3-thienyl group; the aromatic ring represented by the formula

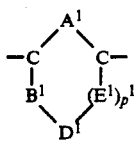

is a benzene or thiophene ring.

On the other hand, in the preferred groups of compounds of general formula [I], $R^3$ desirably represents an alkyl group having 1 to 3 carbon atoms, an allyl group, a propargyl group or a cyclopropyl group; and $R^6$ represents a group of the formula

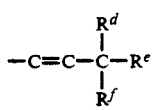

in which $R^d$ represents a hydrogen atom, an alkyl group having 1 to 4 carbon atoms or an alkoxy group having 1 to 4 carbon atoms; $R^e$ and $R^f$ may be identical or different and each represents a methyl or ethyl group, or taken together, may represent a cyclopropyl group. Particularly, $R^3$ is preferably a methyl, ethyl or propyl group.

The above substituted alkylamine derivatives may exist in the form of an acid addition salt. Examples of the acid addition salts are inorganic acid salts such as hydrochlorides, hydrobromides, hydroiodides, sulfates, nitrates, perchlorates and phosphates; and organic acid salts such as p-toluenesulfonates, benzenesulfonates, methanesulfonates, oxalates, succinates, tartarates, citrates, fumarates and maleates. Preferably, they are nontoxic salts which are pharmaceutically acceptable. Furthermore, depending upon the embodiments of the substituents, the compounds of formula [I] provided by this invention may contain stereoisomers such as geometric isomers and optical isomers. The compounds [I] of this invention include all of these stereoisomers and their mixtures.

General processes for producing the compounds of this invention will now be described.

The compounds [I] of this invention may be produced by any one of the following processes A, B, C, D and E.

Reaction Scheme 1

[Process A]

-continued
Reaction Scheme 1

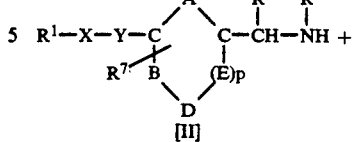

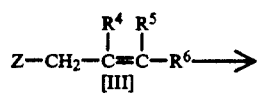

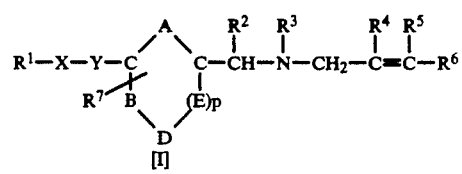

[Process B]

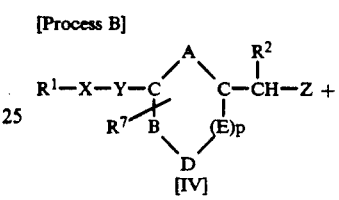

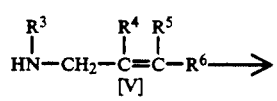

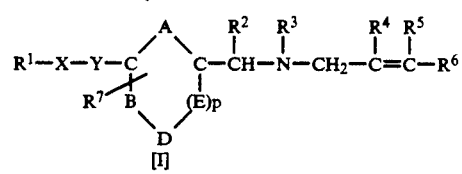

[Process C]

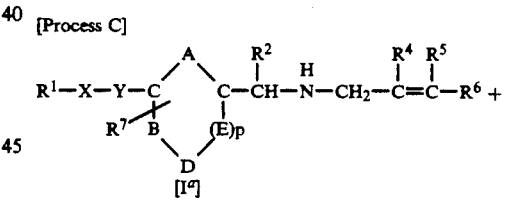

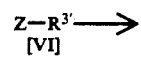

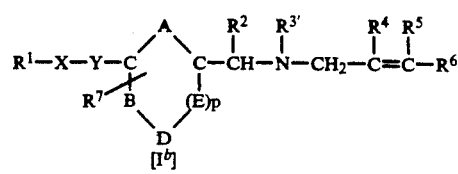

[Process D]

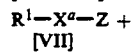

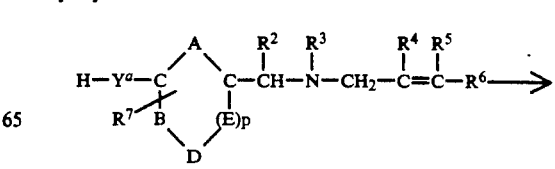

-continued
Reaction Scheme 1

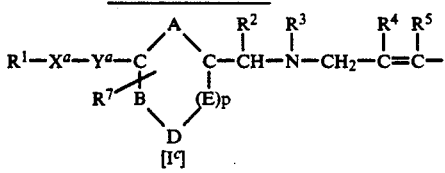

[I$^c$]

[Process E]
R$^1$—X$^b$—H +
[IX]

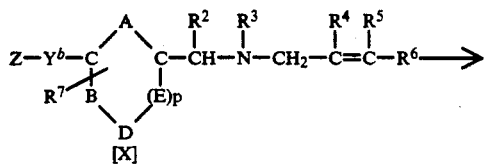

[Process F]
R$^1$—CHO +
[XI]

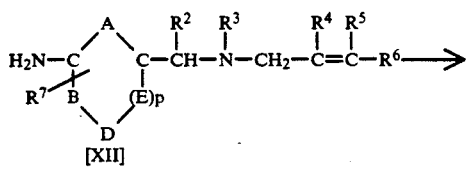

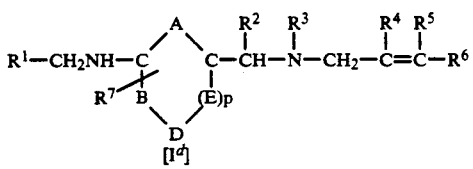

[I$^d$]

In the above formulae, Z represents a leaving group; R$^{3'}$ represents a C$_1$-C$_6$ alkyl group, a C$_2$-C$_6$ alkenyl group, a C$_2$-C$_6$ alkynyl group or a C$_3$-C$_6$ cycloalkyl group, X$^a$ and Y$^b$ represent a carbonyl group or a group of the formula —CHR$^a$— in which R$^a$ is as defined above; X$^b$ and Y$^a$ represent an oxygen atom, a sulfur atom or a group of the formula —NR$^b$—in which R$^b$is as defined above; and A, Q, R$^1$, R$^2$, R$^3$, R$^4$, R$^5$ and R$^6$ are as defined above.

The above processes A, B and C are alkylation of amines which are well known in the field of organic syntheses, and can therefore be carried out by using ordinary means known per se. These processes are carried out by using a solvent which does not adversely affect the reactions, and reacting compounds [II] and [III] in process A, compounds [IV] and [V] in process B and com( pounds [I$^a$] and [VI] in process C in nearly equimolar proportions or using one of them in a slightly excessive proportion. Examples of the solvent include aromatic hydrocarbons such as benzene, toluene and xylene; ethers such as ethyl ether, tetrahydrofuran and dioxane; halogenated hydrocarbons such as methylene chloride, chloroform and dichloroethane; alcohols such as ethanol and isopropanol; dimethylformamide, acetonitrile and dimethyl sulfoxides; and mixtures of these.

The reaction temperature is generally −20° C. to 150° C., preferably from room temperature to the boiling point of the solvent used. The reaction time may be usually 5 minutes to 10 days, preferably 1 to 24 hours. Advantageously, the reactions are carrried out in the presence of a base in order to carry them out smoothly. Examples of the base are alkali metal hydrides such as sodium hydride, lithium hydride and potassium hydride; alkali metal or alkaline earth metal hydroxides such as sodium hydroxide, potassium hydroxide and calcium hydroxide; alkali metal carbonates such as sodium carbonate, potassium carbonate and sodium hydrogen carbonate; and organic amines such as triethylamine and pyridine. The amount of the base used is not critical, and can be varied over a broad range. Generally, it is nearly 1 mole, or slightly more, preferably 1 to 2 moles, per mole of the starting materials.

Processes D and E are for the production of compounds [I$^c$] or [I$^d$] corresponding to the compounds of general formula [I] in which the group of the formula —X—Y—is —COO—, —OCO—, —CONR$^b$—, —NR$^b$CO—, —CHR$^a$O—, —OCHR$^a$—, —CHR$^a$S—, or —S—CHR$^a$—(in which R$^a$ and R$^b$ are as defined). Processes D and E are usually carried out in a solvent which does not adversely affect the reaction (such as tetrahydrofuran, dioxane, chloroform, benzene, acetone, dimethylformamide or dimethyl sulfoxide) by reacting compounds [VII] and [VIII] in process D and compounds [IX] and [X] in process E in nearly equimolar proportions or using one of them in a slightly excessive molar proportion. The reaction conditions used at this time vary depending upon the starting compounds used. Generally, the reaction temperature is in the range of −70° C. to 100° C., preferably −20° C. to 50° C., and the reaction time is 1 minute to 24 hours, preferably 30 minutes to 5 hours. Preferably, the reaction is carried out in the presence of a base so as to perform the action smoothly. Examples of the base used at this time are inorganic bases such as sodium hydride, lithium hydride, sodium hydroxide, potassium hydroxide, sodium carbonate, potassium carbonate, sodium hydrogen carbonate and potassium hydrogen carbonate and organic bases such as pyridine, triethylamine and dimethylaminopyridine. The amount of the base used is not critical, and can be varied over a broad range. Generally, it is nearly 1 mole, or slightly more, preferably 1 to 2 moles, per mole of the starting materials.

Process F is for the production of compounds of formula [I$^e$] corresponding to compounds of formula [I] in which the group —X—Y— is —CH$_2$NH—.

Process F can be carried out by condensing compound [XI] with compound [XII] in benzene or alcohol to form an imine and thereafter, reducing the product. The reagent used in the reduction may be, for example, sodium borohydride, sodium cyanoborohydride or lithium aluminium hydride. The reaction is carried out, for example, in methanol, ethanol or tetrahydrofuran at 0° C. to room temperature for 1 to 6 hours.

If the starting compounds [I$^a$], [II], [III], [IV], [V], [VII], [VIII], [IX], [X], [XI] and [XII] contain reactive functional groups such as a hydroxyl or amino group in addition to the amino groups which are involved in the reaction, these reactive functional groups may, as required, be protected prior to the reaction, and the protected groups may be removed after the reaction. Protective groups which can be easily eliminated by hydrolysis under acidic or alkaline conditions may be used for this purpose. Examples of the protective groups are methoxymethyl, tetrahydropyranyl, trityl, dimethyl-(tert-butyl)silyl, formyl, acetyl, methoxycarbonyl, ethoxycarbonyl and tert-butoxycarbonyl groups.

The desired compound of formula [I] obtained by the above processes in accordance with this invention can be isolated and purified by, for example, column chromatography, solvent extraction, precipitation and recrystallization, either alone or in combination. As required, the compound [I] of the invention as a free base may be converted to its acid addition salt, or vice versa. The step of converting the free base of the compound [I] into its acid addition salt or the step of converting the acid addition salt to its free base can be carried out easily by ordinary methods using the corresponding acids or bases.

The leaving group represented by Z may be, for example, a halogen atom such as a chlorine, bromine or iodine atom, or an organic sulfonyloxy group such as a methanesulfonyloxy or p-toluenesulfonyloxy group.

The starting compounds [I$^a$] to [XII] used in processes A to F can be purchased as commercial goods, or may be produced and obtained by the methods described in the literature (see, for example, J. Med. Chem., vol. 27, page 1539, 1984; J. Med. Chem., vol. 29, page 112, 1086; and Japanese Laid-Open Patent Publications Nos. 32440/-1981, 123177/1982, 208252/1983, 45/1986, 201850/1987 and 5059/1988), the general processes shown below, or processes substantially in accordance with them.

For example, the starting compounds used in this invention may be produced by the following synthesizing methods.

Reaction Scheme 2

Production Route (a)

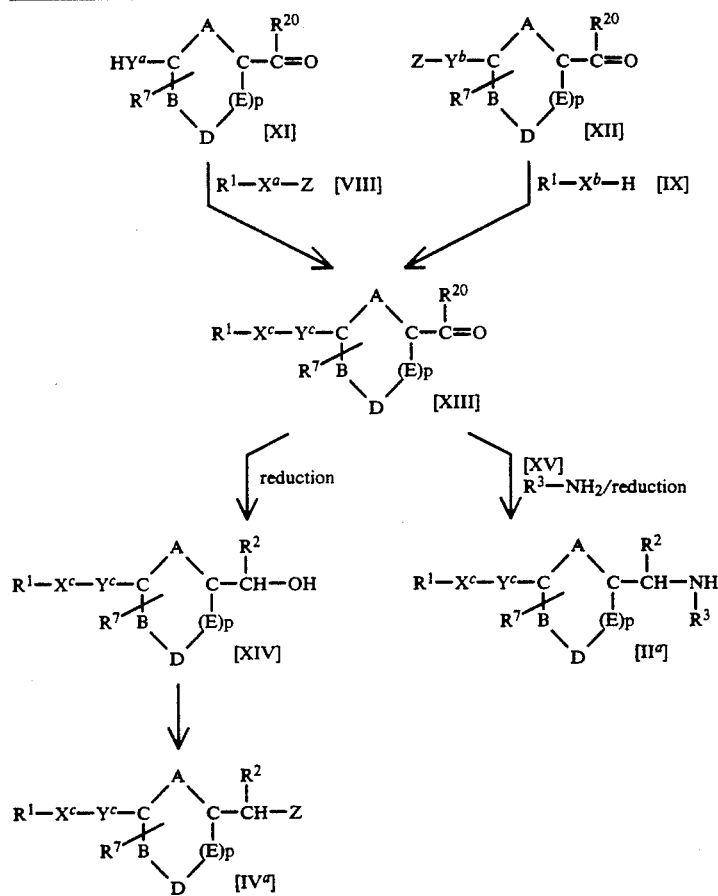

Production Route (b)

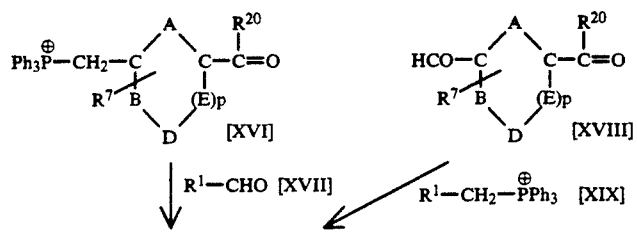

-continued
Reaction Scheme 2
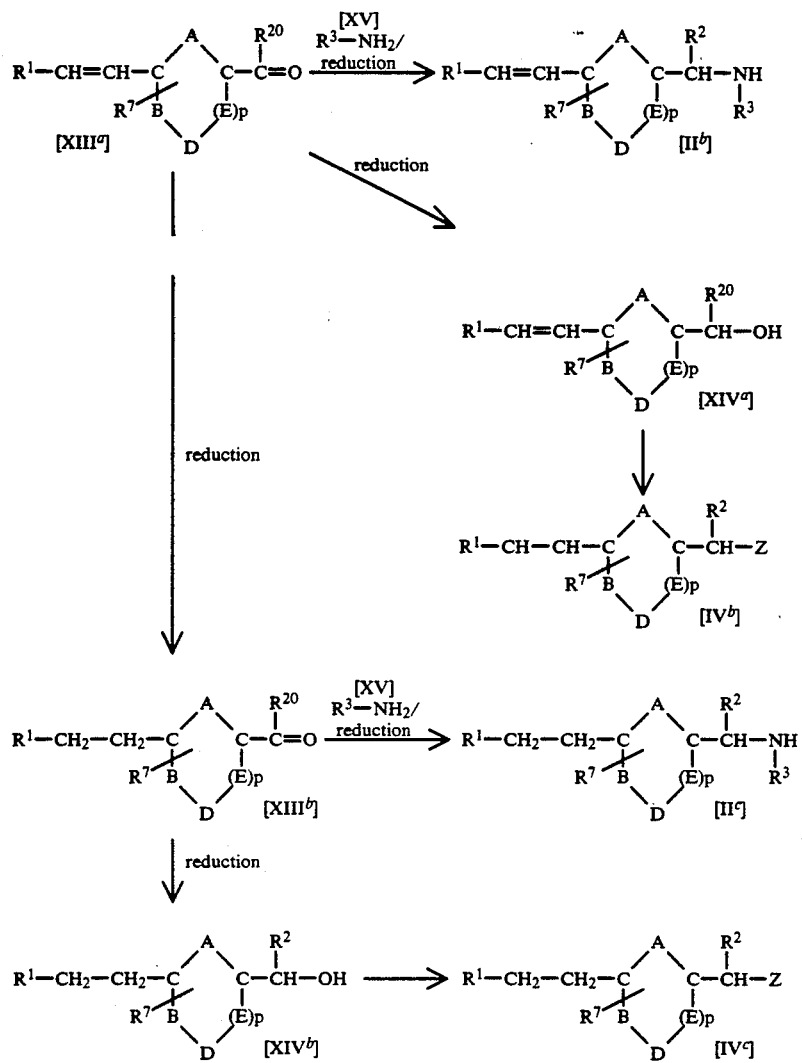
Production Route (c)
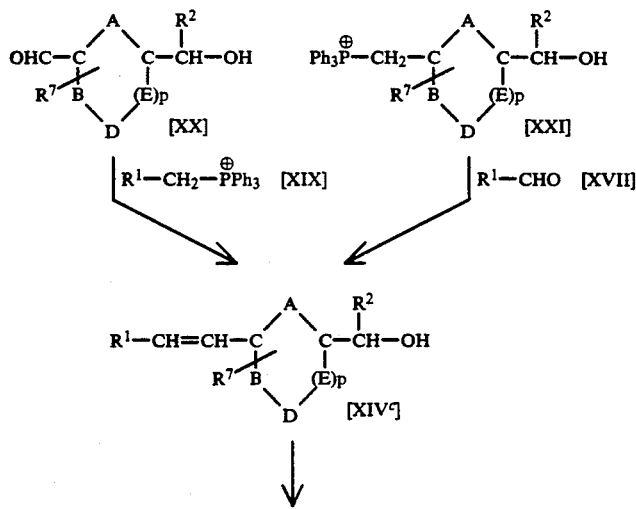

Reaction Scheme 2
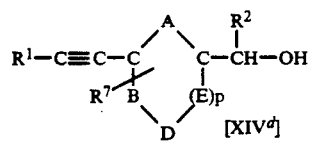
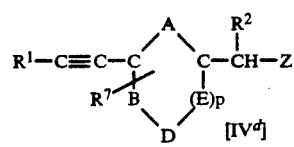
Production Route (d)
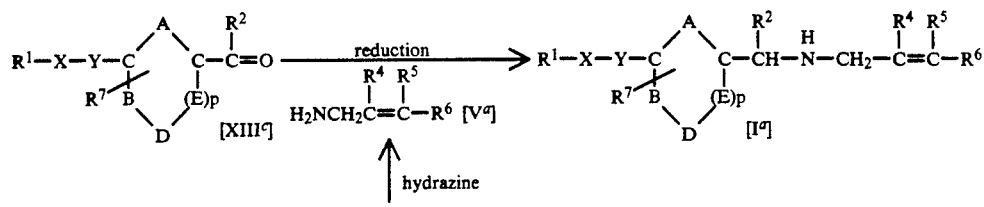
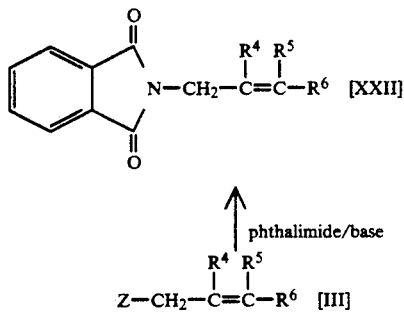
Production Route (e)
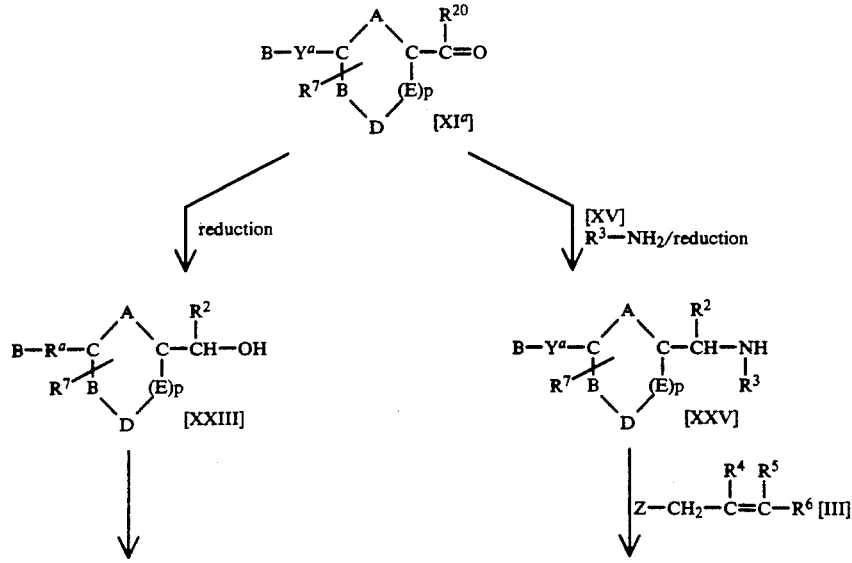

-continued
Reaction Scheme 2
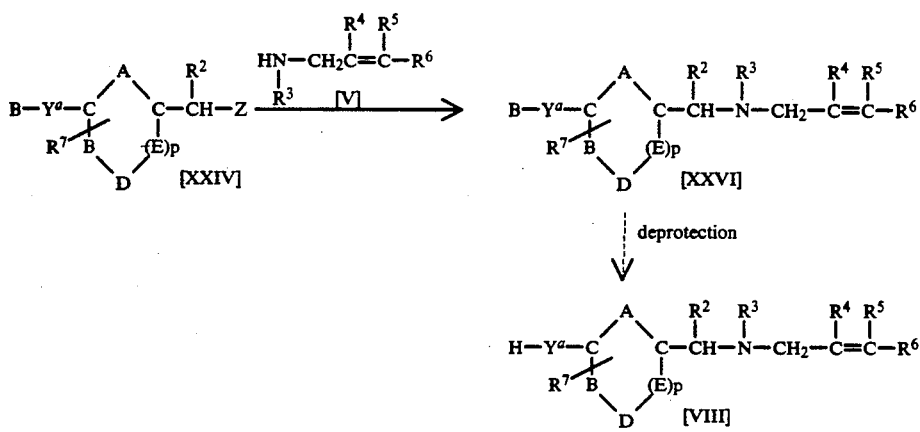
Production Route (f)
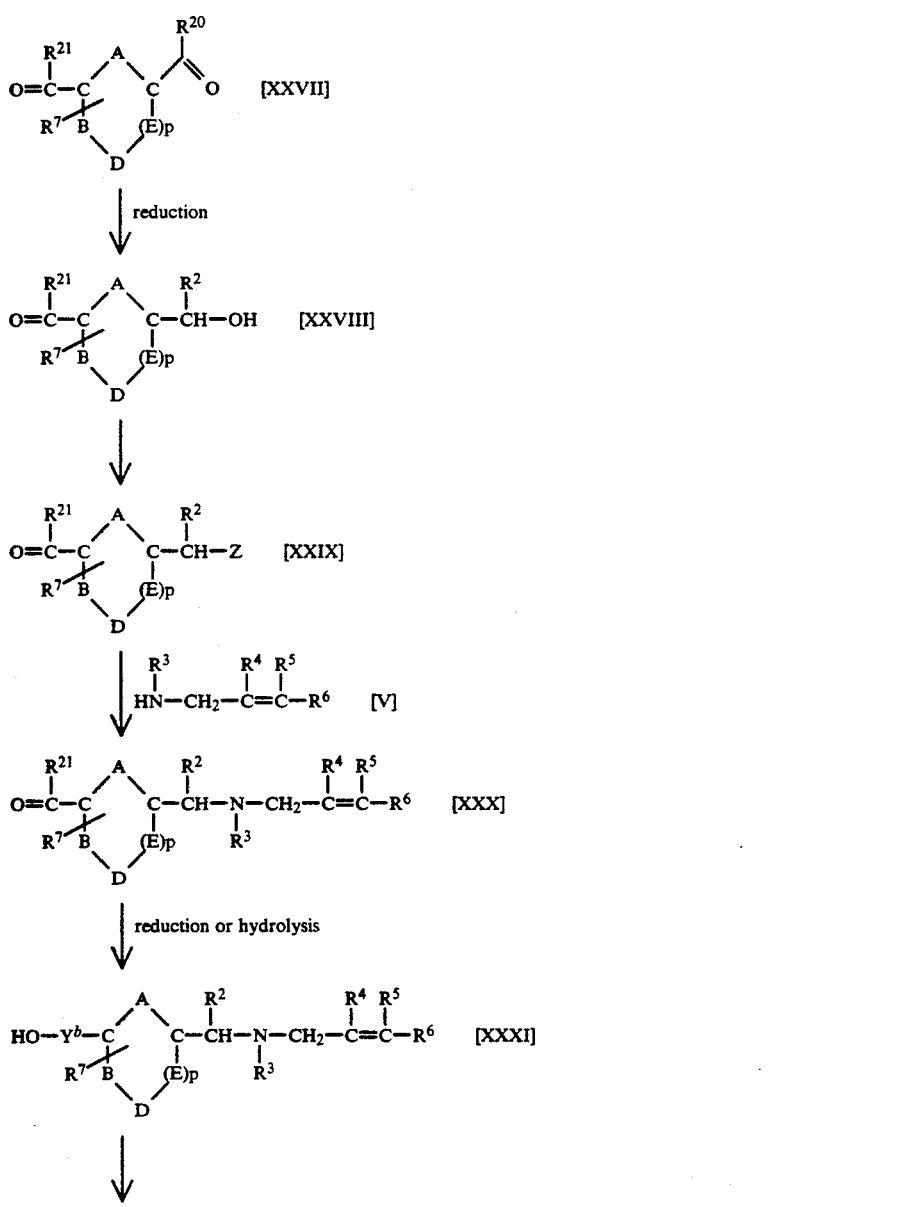

-continued
Reaction Scheme 2

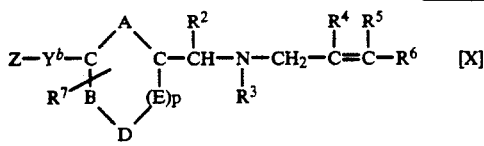

In the above formulae, $X^c$ and $Y^c$ are identical or different, and each represents an oxygen atom, a sulfur atom, a carbonyl group, a group of the formula —CHR$^a$— in which R$^a$ is as defined above or a group of the formula —NR$^b$— in which R$^b$ is as defined above; each of R$^{20}$ and R$^{21}$ represents a hydrogen atom, a lower alkyl group or a lower alkoxy group; B represents a hydrogen atom or a protective group; and A, Q, X, Y, X$^a$, X$^b$, Y$^a$, Y$^b$, Z, R$^1$, R$^2$, R$^3$, R$^4$, R$^5$ and R$^6$ are as defined above. When either one of X$^c$ and Y$^c$ represents an oxygen atom, a sulfur atom or the group —NR$^b$—, the other represents a carbonyl group or the group —CHR$^a$—.

Production Route (a)

The step of reacting compound [XI] with compound [VII] to produce compound [XIII] is carried out in the presence of a base such as sodium hydride, sodium hydroxide or potassium carbonate in a solvent, for example tetrahydrofuran, ethanol or dimethylformamide, at a temperature of −20° C. to 100° C. for 2 to 3 hours using the compounds [XI] and [VII] in nearly equimolar proportions. The step of reacting compound [XII] with compound [IX] to produce compound [XIII] can be performed in the same way as the step of reacting compound [XI] with compound [VII].

The step of reacting compound [XIII] with compound [XV] to produce compound [II$^a$] can be performed by condensing compound [XIII] with compound [XV] in benzene or an alcohol to form an imine or amide and reducing it, or by reacting an excessive amount of compound [XV] with compound [XIII] and simultaneously performing reduction. Reagents used for reduction at this time are, for example, sodium borohydride, sodium cyanoborohydride and aluminum lithium hydride. The reaction may be carried out, for example, in methanol, etanol or tetrahydrofuran at 0° C. to room temperature for 1 to 6 hours.

The step of reducing compound [XIII] to produce compound [XIV] may be performed by, for example, treating the compound [XIII] with sodium borohydride, sodium cyanoborohydride or lithium aluminum hydride in a solvent such as methanol, ethanol or tetrahydrofuran at 0° C. to room temperature for 1 to 5 hours.

The step of converting compound [XIV] to compound [IV$^a$] may be performed by, for example, treating the compound [XIV] with halogenation reagents such as thionyl chloride or phosphorus tribromide or with sulfonation reagents such as methane sulfonyl chloride in the presence of triethylamine in a solvent such as chloroform or methylene chloride at −20° C. to room temperature for 1 to 5 hours.

Production Route (b)

The step of reacting compound [XVI] with compound [XVII] to produce compound [XIII$^a$] may be performed, for example, by treating the compounds with a base such as butyl lithium or sodium hydride in a solvent such as tetrahydrofuran at 0° C. to room temperature for 1 to 6 hours.

The step of reacting compound [XVIII] with compound [XIX] may be carried out in the same way as the step of reacting compound [XVI] with compound [XVII].

The step of producing compound [XIII$^b$] by reducing compound [XIII$^a$] may be carried out, for example, by catalytically reducing compound [XIII$^a$] in a solvent such as methanol or ethanol, at room temperature and atmospheric pressure for 1 to 10 hours in the presence of a catalyst such as palladium-carbon.

The step of producing compounds [II$^b$] or compound [II$^c$] by reacting compound [XIII$^a$] or compound [XIII$^b$] with compound [XV] may be carried out in the same way as in the above step of reacting compound [XIII] with compound [XV] to produce compound [II$^a$]. Furthermore, the step of reducing compound [XIII$^a$] or compound [XIII$^b$] to form compound [XIV$^a$] or compound [XIV$^b$], and then converting the compound [XIV$^a$] or compound [XIV$^b$] into compound [IV$^b$] or compound [IV$^c$] may be carried out in the same way as a series of steps of producing compound [IV$^a$] from compound [XIII] via compound [XIV] described above.

Production Route (c)

The step of producing compound [XIV$^c$] by reacting compound [XX] with compound [XIX] or reacting compound [XXI] with compound [XVII] may be carried out in the same way as in the above-described step of producing compound [XIII$^a$] by reacting compound [XVI] with compound [XVII].

The step of converting compound [XIV$^c$] into compound [XIV$^d$] may be performed by reacting compound [XIV$^c$], either as such or after protection by a suitable protecting group, with bromine in an organic solvent such as methylene chloride, chloroform or ethyl ether at 0° to 60° C. for 0.5 to 3 hours, concentrating the reaction mixture to dryness, and then treating the residue in the presence of a base such as sodium hydroxide or potassium hydroxide in an alcohol solution such as methanol, ethanol or isopropanol at the boiling point of the solvent for 1 to 10 hours.

The step of converting compound [XIV$^d$] into compound [IV$^d$] may be carried out in the same way as in the step of converting compound [XIV] into compound [IV$^a$].

Production Route (d)

the step of producing compound [I$^a$] by reacting compound [XIII$^c$] with compound [V$^a$] may be performed in the same way as in the production of compound [II$^a$] by reacting compound [XIII] with compound [XV].

The compound [V$^a$] used at this time can be produced by the so-called Gabriel method which comprises reacting compound [III] with phthalimide at 10° to 100° C. in the presence of a base such as sodium hydroxide or potassium carbonate in a solvent such as tetrahydrofuran or dimethylformamide to produce compound [XXII] and then reacting this compound with hydrazine in ethanol or dimethylformamide to produce compound [V$^a$].

Production Route (e)

The step of producing compound [XXV] by reacting compound [XI$^a$] with compound [XV] may be performed in the same way as in the step of producing compound [II$^a$] by reacting compound [XIII] with compound [XV], the step of reducing compound [XI$^a$] to produce compound [XXIII] and then converting it into compound [XXIV] may be performed in the same way as the step of reducing compound [XIII] to produce compound [XIV] and converting it into compound [IV$^a$]. The step of reacting compound [XXIV] with compound V or reacting compound [XXV] with compound [III] to produce compound [XXVI], and then, as required, deprotecting this compound to obtain compound [VIII] may be carried out by the same method as in process A or B described above.

In the starting compound of formula [XI$^a$] in Production Route (e), the protecting group B may be any of various protective groups normally used in organic syntheses as protective groups for the hydroxyl group, mercapto group or amino group. Specific examples are methoxymethyl, tetrahydropyranyl, trityl, tert-butoxycarbonyl and dimethyl-tert-butylsilyl groups.

Production Route (f)

The step of producing compound [XXVIII] by reducing compound [XXVII] is the partial reduction utilizing the difference in reactivity in the reduction of the coexisting carbonyl groups, and can be carried out, for example, by reducing compound [XXVII] with 1 to 2 equivalents, based on compound [XXVII], of a reducing agent such as sodium borohydride at −20° C. to room temperature for 1 to 5 hours in a solvent such as ethanol or tetrahydrofuran, or catalytically reducing compound [XXVII] in the presence of a catalyst such as palladium-carbon for 1 to 5 hours. The step of producing compound [XXX] by converting compound [XXVIII] into compound [XXIX], and then reacting it with compound [V] may be carried out in the same way as in the step of producing compound [XXVI] by converting compound [XXIII] into compound [XXIV] and reacting the resulting compound with compound [V].

The step of producing compound [XXXI] by converting compound [XXX] may be carried out by reduction when the product is an alcohol product in which Y$^b$ is a group of the formula —CHR$^a$— in which R$^a$ is as defined above, or by hydrolysis when the product is a carboxylic acid product in which Y$^b$ is a carbonyl group.

The step of producing the corresponding alcohol [XXXI] by reducing the compound [XXX] can be carried out in the same way as in the step of producing compound [XIV] by reducing the compound [XIII]. The step of hydrolyzing compound [XXX] to produce the corresponding carboxylic acid compound [XXXI] can be carried out, for example, by dissolving the compound [XXX] in a solvent such as hydrous ethanol or hydrous tetrahydrofuran in which an equimolar proportion or an excessive molar proportion of a base such as sodium hydroxide is present, and hydrolyzing it at room temperature to 100° C. for 1 to 10 hours.

The step of producing compound [X] by converting compound [XXXI] can be performed, for example, by treating it with a halogenation reagent such as thionyl chloride or phosphorus tribromide in the absence of a solvent or in a solvent such as chloroform or methylene chloride at −20° C. to room temperature for 1 to 5 hours.

The products obtained by the above steps may, as required, be purified or isolated by known purifying methods such as chromatography, recrystallization, solvent extraction, precipitation and distillation either singly or in combination.

Starting compounds for these starting intermediates can be purchased as commercial goods or can be easily obtained by the known methods of organic syntheses described in the literature (see, for example, J. Med. Chem., vol. 27, page 1539, 1984; J. Med. Chem., vol. 29, page 112, 1086; and Japanese Laid-Open Patent Publications Nos. 32440/1981, 123177/1982, 208252/1983, 45/1986, 01850/1987 and 5059/1988).

The compounds of this invention represented by general formula I] inhibit the mammalian squalene epoxidase very selectively and strongly, and are expected to be useful as an hypolipemic agent or an antiarterio sclerotic agent.

The following Pharmacological Test Examples, Antimycotic Test Example, and Acute Toxicity Test Example given below demonstrate this fact.

PHARMACOLOGICAL TEST EXAMPLE 1

Squalene Epoxidase Inhibiting Activity (1) Preparation of Squalene Epoxidase

The rat squalene epoxidase was prepared by the method described in J. Biol. Chem., vol. 245, page 1670, 1970; ibid., vol. 250, page 1572, 1975).

SD-strain female rats were killed by exsanguination. Livers were extracted and homogenized with in the presence of 2 volumes of 0.1M Tris-HCl buffer (pH 7.5). The homogenate was centrifuged at 9750 Xg for 10 minutes. The supernatant fraction was further centrifuged at 105000 Xg for 1 hour. The sediment was washed with 0.1M Tris-HCl buffer (pH 7.5), and then centrifuged at 105000 Xg for 1 hour. The microsomes obtained were suspended in 0.1M Tris-HCl buffer (pH 7.5) so that the amount of proteins was 40 mg/ml, and under ice cooling, the suspension was stirred in the presence of 2% Triton X-100 to solubilize the enzyme. After the solubilization, the solution was diluted to a Triton X-100 concentration of 0.5% with 1 mM EDTA and 1 mM dithiothreitol, and centrifuged at 105000 Xg for 1 hour. The resulting supernatant fraction was used in the following test as a squalene epoxidase fraction.

(2) Method of Assaying the Squalene Epoxidase Activity

The squalene epoxidase activity was assayed in accordance with the method described in J. Biol. Chem., vol. 245, page 1670, 1970.

Three microliters of a dimethyl sulfoxide solution of a test drug was added to a solution composed of 0.2 ml of the squalene epoxidase fraction prepared in (1) [proteins 0.4 mg, 0.5% Triton X-100, 20 M Tris-HCl buffer (pH 7.5)], 100 M FAD, 1 mM NADPH, 1 mM EDTA and 8 M $^3$H-squalene-Tween 80 emulsion to adjust the total amount of the solution to 0.3 ml. The solution was incubated at 37° C. for 30 minutes with shaking. Then, 0.3 ml of a 10% methanolic potassium hydroxide was added to stop the reaction, and the reaction mixture was left to stand at room temperature for 1 hour. The nonsaponified material was extracted with petroleum ether, and the solvent was evaporated under a nitrogen stream. The resulting residue was dissolved in a small amount of ethyl ether and spotted on pre-coated silica gel TLC plate, followed by developing with benzene/ethyl acetate (99.5:0.5). The position of the resulting $^3$H-squalene-2,3-epoxide on TLC was determined using ergosterol acetate as a marker, and the $^3$H-squalene-2,3-epoxide portion on the TLC was cut off. The TLC strip was immersed in a toluene-type scintillator, and measured by a liquid scintillation counter. As a result, the 50% inhibitory concentrations (IC$_{50}$ values) of the compounds of this invention on squalene epoxidase were determined. The results are shown in Table 1.

The numbers designating the compounds correspond to the numbers given in Examples given hereinafter. The same applies to Tables 2 to 4.

TABLE 1

| Drug | 50% inhibitory concentration (IC$_{50}$, μM) |
|---|---|
| Compound | |
| 1 | 6.80 |
| 2 | 1.40 |
| 6 | 0.56 |
| 8 | 2.90 |
| 10 | 4.70 |
| 12 | 6.00 |
| 16 | 1.40 |
| 18 | 0.25 |
| 19 | 3.10 |
| 28 | 5.60 |
| 34 | 1.70 |
| 36 | 0.30 |
| 37 | 0.27 |
| 41 | 2.10 |
| 42 | 9.60 |
| 43 | 3.90 |
| 44 | 0.16 |
| 45 | 0.12 |
| 46 | 0.15 |
| 47 | 0.15 |
| 48 | 5.10 |
| 49 | 4.90 |
| 50 | 2.10 |
| 51 | 1.10 |
| 52 | 1.40 |
| 53 | 0.66 |
| 54 | 1.80 |
| 55 | 0.60 |
| 56 | 2.10 |
| 57 | 3.10 |
| 58 | 7.90 |
| 61 | 6.10 |
| 62 | 0.36 |
| 63 | 5.40 |
| 64 | 0.51 |
| 65 | 4.60 |
| 66 | 1.20 |
| 67 | 2.40 |
| 68 | 1.20 |
| 69 | 0.51 |
| 70 | 3.10 |
| 71 | 0.54 |
| 72 | 9.70 |
| 73 | 2.30 |
| 74 | 0.57 |
| 75 | 0.87 |
| 76 | 1.90 |
| 79 | 3.30 |
| 80 | 3.50 |
| 83 | 5.50 |
| 85 | 3.30 |
| 88 | 6.80 |
| 89 | 0.84 |
| 90 | 0.32 |
| 92 | 2.00 |
| 93 | 0.12 |
| 94 | 2.10 |
| 95 | 2.10 |
| 96 | 0.36 |
| 97 | 7.70 |
| 100 | 3.60 |

TABLE 1-continued

| Drug | 50% inhibitory concentration (IC$_{50}$, μM) |
|---|---|
| 101 | 0.45 |
| 103 | 1.50 |
| 105 | 0.69 |
| 108 | 0.27 |
| 110 | 0.52 |
| 111 | 0.29 |
| 114 | 2.20 |
| 115 | 1.00 |
| 120 | 5.40 |
| 123 | 0.007 |
| 124 | 0.004 |
| 129 | 0.011 |
| 130 | 0.006 |
| 136 | 0.060 |
| 140 | 0.027 |
| 146 | 0.033 |
| 147 | 0.031 |
| 152 | 0.026 |
| 154 | 0.026 |
| 168 | 0.026 |
| 169 | 0.023 |
| 172 | 0.034 |
| 174 | 0.021 |
| 176 | 0.034 |
| 191 | 0.011 |
| 198 | 0.022 |
| 199 | 0.033 |
| terbinafine | >100 |
| naftifine | >100 |

PHARMACOLOGICAL TEST EXAMPLE 2

Inhibitory Activity on Cholesterol Biosynthesis in Cultured Cells

Human hepatoma (Hep-G2) cells were cultured in 10 cm$^2$ dishes until they formed a monolayer. One milliliter of the culture medium was replaced, and 1 Ci of [$^{14}$C] sodium acetate and 1 microliter of a dimethyl sulfoxide solution of a test drug were added, and the cells were cultured at 37° C. in air containing 5% of carbon dioxide for 6 hours.

After the cultivation, the medium was aspirated, and the cells were cooled with ice, and washed with Dulbecco's phosphate buffered saline solution. The resulting cells were scraped by a rubber policeman, and collected by centrifugation. The cells collected were dissolved in 400 microliters of 0.3N sodium hydroxide. A 200 microliters aliquot of the solution was used for extraction, and the remainder, for protein determination.

To 200 microliters of the extracted cells, 15% ethanolic potassium hydroxide was added, and saponification was carried out at 75° C. for 1 hour. Water (1 ml) was then added, and the mixture was extracted with 2 ml of petroleum ether twice to remove non-saponified materials. The petroleum ether extracts were washed with 1 ml of water, and evaporated to dryness under a nitrogen stream. The residue was spotted on a pre-coated silica gel TLC plate using a small amount of chloroform, and developed with hexane/ethyl ether/acetic acid (85:15:4). Cholesterol and squalene portions on the TLC were detected with iodine, and the corresponding TLC portions were cut out. The TLC strips were immersed in a toluene-type scintillator, and radioactivity was counted by a liquid scintillation counter. The results were corrected by the amount of proteins measured by the method described in J. Biol. Chem., vol. 193, page 265, 1951. The 50% inhibitory concentration (IC$_{50}$ value) of the compound of the invention on cholesterol biosynthesis in the cultured Hep-G2 cells was calculated. The results are shown in Table 2.

TABLE 2

| Compound | 50% inhibitory concentration (IC$_{50}$, µM) |
|---|---|
| 2 | 1.50 |
| 6 | 0.34 |
| 36 | 0.064 |
| 37 | 0.085 |
| 44 | 0.050 |
| 45 | 0.083 |
| 46 | 0.11 |
| 47 | 0.090 |
| 64 | 0.12 |
| 78 | 0.020 |
| 79 | 0.023 |
| 96 | 0.45 |
| 123 | 0.053 |
| 124 | 0.011 |
| 129 | 0.012 |
| 130 | 0.011 |
| 136 | 0.054 |
| 140 | 0.009 |
| 146 | 0.006 |
| 147 | 0.005 |
| 152 | 0.022 |
| 154 | 0.025 |
| 163 | 0.030 |
| 168 | 0.010 |
| 169 | 0.010 |
| 172 | 0.033 |
| 195 | 0.029 |
| 199 | 0.017 |
| 201 | 0.052 |

PHARMACOLOGICAL TEST EXAMPLE 3

Test on Inhibition of Cholesterol Biosynthesis in Vivo

Female SD rats, 5 weeks of age, were used in the in vivo test. The rats were kept for 9 days in an environment of reversed light cycle (i.e., dark between 6:00 am and 6:00 pm). The rats were allowed to take a solid diet and water freely. The test drug was orally administered two hours before dark sixth hour when the cholesterol synthesis reached a maximum. Compounds 123–188 were dissolved in water containing 5% of dimethyl sulfoxide and 2% Tween 80 and administered orally at the dose of 3 mg/kg (1 ml/100 g of body weight).

An equal volume of 0.5% methyl cellulose was administered to a control group. One hour after administration of the test drug, [$^{14}$C] sodium acetate (56 mCi/mmole) was intraperitoneally administered to the rats in a dose of 20 Ci/100 g of body weight. At dark sixth hour, a blood sample was obtained from the abdominal artery under ether anesthesia, and the plasma was separated by centrifugation.

Two milliliters of plasma was mixed with a 15% methanolic potassium hydroxide and saponified by heating at 75° C. for 3 hours. The resulting sample was extracted with 2 ml of petroleum ether twice. The extracts were washed with 2 ml of distilled water, and finally evaporated under a nitrogen stream. The resulting residue was dissolved in a small amount of ethyl ether, and all the solution was spotted on a pre-coated silica gel TLC plate. The plate was developed with a solvent system composed of hexane/ethyl ether/acetic acid (85:15:4). Color formation was carried out by iodine, and the radioactivity of the cholesterol portion was measured by a liquid scintillation counter.

The results were expressed in dpm of the resulting $^{14}$C-cholesterol present in 1 ml of the plasma. The inhibition of cholesterol biosynthesis was calculated by comparing the amounts of $^{14}$C-cholesterol biosynthesized in the test group and that in the control group. The results are shown in Table 3.

TABLE 3

Cholesterol biosynthesis inhibiting test in rats (n = 5)

| Test drug | $^{14}$C-cholesterol, dpm (control group) | Inhibition of cholesterol biosynthesis |
|---|---|---|
| Compound 123 | 471 (2196) | 79% |
| Compound 124 | 530 (2456) | 78% |
| Compound 131 | 402 (1456) | 72% |
| Compound 132 (3 mg/kg) | 503 (2196) | 77% |
| Compound 133 | 340 (2098) | 84% |
| Compound 152 | 650 (2454) | 74% |
| Compound 172 | 83 (2104) | 96% |
| Compound 173 | 125 (2454) | 95% |
| Compound 174 | 94 (2394) | 96% |
| Compound 175 | 355 (2649) | 87% |
| Compound 177 | 316 (2394) | 87% |
| Compound 180 | 194 (1456) | 87% |
| Compound 188 | 115 (2394) | 95% |

ANTIMYCOTIC ACTIVITY TEST EXAMPLE

Each of the test fungi was cultured (*Candida albicans* was cultured overnight in Sabouraud broth; Trichophyton was introduced in Sabouraud's agar and cultured for 2 days, after which the spores were harvested). Thereafter, one platinum loopful of *Candida albicans* or Trichophyton ($10^6$ cells/ml for *C. albicans*; $10^6$ spores/ml for Trichophyton) was inoculated in Sabouraud's agar containing the test drug in various concentrations, and cultured (at 37° C. for 2 days for *C. albicans*; at 28° C. for 5 days for Trichophyton). Then, the minimum growth inhibition concentration (MIC) was measured. The results given in Table 4 show that the test drugs had very weak antimycotic activity and did not inhibit growth of the test fungi even in a concentration of as high as 100 micrograms/ml.

TABLE 4

| Test drug | MIC (µg/ml) | |
|---|---|---|
| | *C. albicans* | Trichophyton |
| Compound 2 | >100 | >100 |
| Compound 18 | >100 | >100 |
| Compound 45 | >100 | >100 |
| Compound 61 | >100 | >100 |
| Compound 64 | >100 | >100 |
| Compound 90 | >100 | >100 |
| Compound 100 | >100 | >100 |
| Compound 103 | >100 | >100 |
| terbinafine | 0.3 | <0.01 |

ACUTE TOXICITY TEST EXAMPLE

Each of test drugs (compounds 2, 6, 44, 45, 75, 90, 96, 124, 130, 140, 141, 146 and 172) was suspended or dissolved in 0.5% methyl cellulose, olive oil or middle chain triglyceride (MCT), and orally administered to mice (ddy, male, body weight 28±2 g, two or five per group). The acute toxicity value (LD$_{50}$) was calculated from the mortality determined one week after administration.

The test drug had very low toxicity, and even in a high dose of 1000 mg/kg, no case of death was caused.

As can be seen from the results of the foregoing tests, the compounds of this invention strongly inhibit squalene epoxidase and thus the biosynthesis of cholesterol. Accordingly, they are effective for the treatment and prevention of various diseases induced by the increase of the biosynthesis of cholesterol, for example obesity, hyperlipemia and arteriosclerosis. Furthermore, the squalene epoxidase inhibiting activity of the compounds of this invention is not observed on fungi, and is specific for mammals. The compounds of this invention also have low toxicity. Accordingly, they are very useful as pharmaceuticals.

The compound of formula [I] provided by this invention is formulated into a form suitable for oral or parenteral administration, and can be used in the treatment and remedy of hypercholesterolemia, hyperlipemia and arteriosclerosis. In using the compounds of the invention clinically, they can be formulated together with pharmaceutically acceptable adjuvants suitable for dosage forms, and then administered. Various adjuvants usually used in the pharmaceutical field can be used. Examples of the adjuvants include gelatin, lactose, sucrose, titanium dioxide, starch, crystalline cellulose, hydroxypropylmethyl cellulose, carboxymethyl cellulose, corn starch, microcrystalline wax, white Vaseline, magnesium melasilicate aluminate, anhydrous calcium phosphate, citric acid, trisodium citrate, hydroxypropyl cellulose, sorbitol, sorbitan fatty acid esters, polyvinylpyrrolidone, magnesium stearate, light anhydrous silicic acid, talc, vegetable oil, benzyl alcohol, gum arabic, propylene glycol or polyalkylene glycols.

Formulations prepared as mixtures with these adjuvants include, for example, solid preparations such as tablets, capsules, granules, powders and suppositories and liquid preparations such as syrups, elixirs and injectable preparations. These preparations can be formed by ordinary methods known in the field of pharmaceutical preparation. The liquid preparations may be in the form of a solution or suspension in water or another suitable medium. As required, the injectable preparations may be dissolved in physiological saline or glucose solution, or a buffer or a preservative may be added.

These formulations may contain 1.0 to 100% by weight, preferably 1.0 to 60% by weight, of the compound of this invention based on the total drugs. They may also contain other therapeutically effective compounds.

When the compound of this invention is used as an hypolipemic agent, an antiarteriosclerotic agent or an hypocholesterolemic agent, its dosage and the number of administration differ depending upon the sex, age, body weight and the severity of symptom of a patient and the type and range of the intended therapeutic effect. Generally, in oral administration, it is administered preferably in a dose of 0.01 to 20 mg/kg once or in several divided portions. In parenteral administration, it is preferably administered in a dose of 0.001 to 20 mg/kg once or in several divided portions.

The following Examples and Referential Examples illustrate the present invention more specifically. It should be understood that the present invention is not limited to these examples alone.

EXAMPLE 1

Production of (E)-N-(6,6-dimethyl-2-hepten-4-ynyl)-3-benzyloxybenzylamine (compound 1)

3-Benzyloxybenzylamine hydrochloride (110 mg) was dissolved in 3 ml of dimethylformamide, and 89 mg of 1-bromo-6,6-dimethyl-2-hepten-4-yne (a 3:1 E/Z form mixture; the same in the following examples) and 61 mg of potassium carbonate were added, and the mixture was stirred at room temperature for 2 hours. Water (15 ml) was added to the reaction mixture to dilute it, and the diluted reaction mixture was extracted with 10 ml of ethyl ether twice. The extracts were combined, washed with 10 ml of a saturated aqueous sodium chloride solution, and dried over anhydrous magnesium sulfate. The solvent was then evaporated. The residue was purified by preparative thin-layer chromatography [thin layer plate: Kieselgel 60F$_{254}$, ART. 5744 (E. Merck Co.); developing solvent: chloroform/methanol=5/1] to give 16 mg (yield 11%) of the captioned compound as a colorless oil.

IR $v_{max}^{neat}$ cm$^{-1}$:2968, 1599, 1491, 1458, 1263, 1155, 1029, 738, 696.

NMR(CDCl$_3$)δ:1.24(9H, s), 2.30(1H, br), 3.28(2H, dd, J=6.4Hz, 1.5Hz), 3.77(2H, s), 5.06(2H, s), 5.64(1H, dt, J=15.9Hz, 1.5Hz), 6.09(1H, dt, J=15.9Hz, 6.4Hz), 6.84–6.92(2H, m), 6.97–6.98(1H, m), 7.20–7.25(1H, m), 7.31–7.45(5H, m).

As an alternative method of synthesizing the above compound, phthalimide and 1-bromo-6,6-dimethyl-2-hepten-4-yne (a mixture of E and Z forms in a ratio of about 3:1) are reacted in dimethylformamide. The resulting (E)-N-(6,6-dimethyl-2-hepten-4-ynyl)phthalimide (by recrystallization from hexane, it is separated into an E form and a Z form, m.p. 106°-108° C.) is reacted with hydrazine to produce (E)-6,6-dimethyl-2-hepten-4-ynylamine. This compound is reductively alkylated by using equimolar proportions of 3-benzyloxybenzaldehyde and sodium borohydride in methanol to give the captioned compound.

EXAMPLE 2

Production of (E)- and (Z)-N-(6,6-dimethyl-2-hepten-4-ynyl)-N-methyl-3-benzyloxybenzylamine hydrochloride N-methyl-3-benzyloxybenzylamine hydrochloride (1.72 g) was dissolved in 20 ml of dimethylformamide, and 1.31 g of 1-bromo-6,6-dimethyl-2-hepten-4-yne and 0.76 g of sodium carbonate were added. The mixture was stirred overnight at room temperature. The reaction mixture was diluted with 80 ml of water, and extracted with 50 ml of ethyl ether twice. The extracts were combined, washed with 20 ml of a saturated aqueous sodium chloride solution, and then dried over anhydrous magnesium sulfate.

The desiccant was removed by filtration, and the solvent was evaporated. The residue was purified by medium-pressure liquid chromatography [column: Lobar column, size B, Lichroprep Si 60F (made by E. Merck Co.); eluting solvent: hexane/ethyl acetate=6/1] to give a fraction containing the captioned (E)-form and a fraction containing the captioned (Z)-form. These fractions were separately evaporated under reduced pressure, dissolved in methanol containing hydrogen chloride, again concentrated under reduced pressure, and recrystallized from a mixture of tetrahydrofuran and ethyl ether. The amounts of the products obtained and their properties are shown below.

(E)-N-(6,6-dimethyl-2-hepten-4-ynyl)-N-methyl-3-benzyloxybenzylamine hydrochloride (compound 2)

Amount:1.09 g (yield 44%).
Melting point: 142°–143° C.
IR$\nu_{max}^{KBr}$ cm$^{-1}$:2968, 2482, 1458, 1266, 696.
NMR(CDCl$_3$)δ:1.23(9H, s), 2.57(3H, s), 3.55(2H, d, J=7.6Hz), 4.04(2H, s), 5.14(2H, s), 5.80(1H, d, J=15.7Hz), 6.22(1H, dt, J=15.7Hz, 7.6Hz), 7.00–7.04(1H, m), 7.05–7.08(1H, m), 7.28–7.39(5H, m), 7.43–7.46(2H, m).

(Z)-N-(6,6-dimethyl-2-hepten-4-ynyl)-N-methyl-3-benzyloxybenzylamine hydrochloride (compound 3)

Amount 0.46 g (yield 19%).
Melting point: 150°–152° C.
IR$\nu_{max}^{KBr}$ cm$^{-1}$:2506, 1452, 1263, 1182, 1020, 747.
NMR(CD$_3$OD)δ:1.21(9H, s), 2.76(3H, s), 3.88–3.90 (2H, m), 4.30(2H, s), 5.14(2H, s), 6.00–6.04(2H, m), 7.08–7.15(2H, m), 7.17–7.18(1H, m), 7.30–7.46(6H, m).

Compounds of Examples 3 to 11 were prepared by repeating Example 2 except that instead of the starting N-methyl-3-benzyloxybenzylamine hydrochloride, the corresponding amine hydrochlorides were used (when the reaction product was a free base, the hydrochloride producing step in the after-treatment was not included).

EXAMPLE 3

(E)-N-(6,6-dimethyl-2-hepten-4-ynyl)-N-isopropyl-3-benzyloxybenzylamine hydrochloride (compound 4)

Melting point: 167°–169° C.
IR$\nu_{max}^{KBr}$ cm$^{-1}$:2974, 1458, 1269, 696.
NMR(CDCl$_3$)δ:1.23(9H, s), 1.40(6H, br), 3.50 (3H, br), 4.00(2H, br), 5.17(2H, s), 5.74(1H, d, J=15.9Hz), 6.33–6.45 (1H, m), 6.98–7.02(1H, m), 7.11–7.14 (1H, m), 7.26–7.39(4H, m), 7.46–7.49 (2H, m), 7.50(1H, br).

(Z)-N-(6,6-dimethyl-2-hepten-4-ynyl)-N-isopropyl-3-benzyloxybenzylamine hydrochloride (compound 5)

IR$\nu_{max}^{neat}$ cm$^{-1}$:2968, 2932, 1602, 1491, 1458, 1266, 1167, 735.
NMR(CDCl$_3$)δ:1.04(6H, d, J=6.6Hz), 1.25(9H, s), 2.96(1H, sept, J=6.6Hz), 3.27(2H, dd, J=6.8Hz, 1.4Hz), 3.54(2H, s), 5.06 (2H, s), 5.49(1H, dt, J=10.7Hz, 1.4Hz), 5.82(1H, dt, J=10.7Hz, 6.8Hz), 6.81–6.84(1H, m), 6.92–6.96(1H, m), 7.04–7.05(1H, m), 7.16–7.22(1H, m), 7.30–7.45(5H, m).

EXAMPLE 4

(E)-N-(6,6-dimethyl-2-hepten-4-ynyl)-N-methyl-3-(2-methylbenzyloxy)benzylamine hydrochloride (compound 6)

Melting point:150°–152° C.
IR$\nu_{max}^{KBr}$ cm$^{-1}$:2974, 2680, 2626, 2506, 1602, 1497, 1458, 1263, 1164, 747.
NMR(CDCl$_3$)δ:1.25(9H, s), 2.40(3H, s), 2.62(3H, s), 3.45–3.58(1H, m), 3.65–3.75(1H, m), 3.95–4.07(1H, m), 4.12–4.25(1H, m), 5.14(2H, s), 5.82(1H, d, J=15.5Hz), 6.26(1H, dt, J=15.5Hz, 7.6Hz), 7.06 (1H, m), 7.11(1H, d, J=7.9Hz), 20 7.17–7.28(3H, m), 7.35(1H, t, J=7.9Hz), 7.40–7.45(2H, m).

(Z)-N-(6,6-dimethyl-2-hepten-4-ynyl)-N-methyl-3-(2-methylbenzyloxy)benzylamine hydrochloride (compound 7)

IR$\nu_{max}^{neat}$ cm$^{-1}$:2974, 1599, 1491, 1458, 1263, 1152, 1032, 747.
NMR(CDCl$_3$)δ:1.24(9H, s), 2.23(3H, s), 2.38(3H, s), 3.27(2H, dd, J=6.8Hz, 1.5Hz), 3.50 (2H, s), 5.03(2H, s), 5.61(1H, dt, J=10.7Hz, 1.5Hz), 5.95(1H, dt, J=10.7Hz, 6.8Hz), 6.85–6.89(1H, m), 6.91–6.94 (1H, m), 6.99–7.00(1H, m), 7.19–7.26 (4H, m), 7.39–7.43(1H, m).

EXAMPLE 5

(E)-N-(6,6-dimethyl-2-hepten-4-ynyl)-N-methyl-3-(3-chlorobenzyloxy)benzylamine (compound 8)

IR$\nu_{max}^{neat}$ cm$^{-}$:2974, 1602, 1458, 1266, 780.
NMR(CDCl$_3$)δ:1.24(9H, s), 2.18(3H, s), 3.03(2H, dd, J=6.5Hz, 1.5Hz), 3.46(2H, s), 5.03 (2H, s), 5.64(1H, dt, J=15.9Hz, 1.5Hz), 6.07(1H, dt, J=15.9Hz, 6.6Hz), 6.82–6.86(1H, m), 6.89–6.92(1H, m), 6.96–6.97(1H, m), 7.19–7.25(1H, m), 7.27–7.32(3H, m), 7.45(1H, br).

(Z)-N-(6,6-dimethyl-2-hepten-4-ynyl)-N-methyl-3-(3-chlorobenzyloxy)benzylamine (compound 9)

IR$\nu_{max}^{neat}$ cm$^{-1}$:2974, 1602, 1491, 1458, 1263, 1152, 1035, 780.
NMR(CDCl$_3$)δ:1.24(9H, s), 2.22(3H, s), 3.27(2H, dd, J=6.8Hz, 1.5Hz), 3.50(2H, s), 5.04 (2H, s), 5.62(1H, dt, J=10.7Hz, 1.5Hz), 5.94(1H, dt, J=10.7Hz, 6.8Hz), 6.82–6.86(1H, m), 6.91–6.94(1H, m), 6.97–6.98(1H, m), 7.20–7.26(1H, m), 7.27–7.32(3H, m), 7.43–7.44(1H, m).

EXAMPLE 6

(E)-N-(6,6-dimethyl-2-hepten-4-ynyl)-N-methyl-3-(4-fluorobenzyloxy)benzylamine (compound 10)

IR$\nu_{max}^{neat}$ cm$^{-1}$:2974, 1608, 1518, 1458, 1266, 1227, 1155.
NMR(CDCl$_3$)δ:1.20(9H, s), 2.18(3H, s), 3.03(2H, dd, J=6.6Hz, 1.4Hz), 3.48(2H, s), 5.02 (2H, s), 5.64(1H, dt, J=15.6Hz, 1.4Hz), 6.08(1H, dt, J=15.6Hz, 6.6Hz), 6.81–6.86(1H, m), 6.88–6.92(1H, m), 6.90–6.97(1H, m), 7.03–7.09(2H, m), 7.19–7.24(1H, m), 7.38–7.43(2H, m).

(Z)-N-(6,6-dimethyl-2-hepten-4-ynyl)-N-methyl-3-(4-fluorobenzyloxy)benzylamine (compound 11)

IR$\nu_{max}^{neat}$ cm$^{-1}$:2974, 1608, 1518, 1266, 1227, 1155.
NMR(CDCl$_3$)δ:1.24(9H, s), 2.21(3H, s), 3.26(2H, dd, J=6.8Hz, 1.5Hz), 3.49(2H, s), 5.01 (2H, s), 5.61(1H, dt, J=10.7Hz, 1.5Hz), 5.93(1H, dt, J=10.7Hz, 6.8Hz), 6.82–6.86(1H, m), 6.90–6.93(1H, m), 6.96–6.97(1H, m), 7.02–7.09(2H, m), 7.19–7.25(1H, m), 7.37–7.42(2H, m).

EXAMPLE 7

(E)-N-(6,6-dimethyl-2-hepten-4-ynyl)-N-methyl-3-(4-methoxybenzyloxy)benzylamine (compound 12)

Melting point: 35°–36° C.,
IR$\nu_{max}^{KBr}$ cm$^{-1}$:2968, 1611, 1587, 1518, 1458, 1251, 1173, 1032.
NMR(CDCl$_3$)δ:1.24(9H, s), 2.18(3H, s), 3.03(2H, dd, J=6.3Hz, 1.4Hz), 3.46(2H, s), 3.81 (3H, s), 4.98(2H, s), 5.64(1H, dt, J=15.9Hz, 1.4Hz), 6.08(1H, dt, J=15.9Hz, 6.3Hz), 6.83–6.94(4H, m), 6.95–6.96(1H, m), 7.18–7.23(1H, m), 7.34–7.38(2H, m).

(Z)-N-(6,6-dimethyl-2-hepten-4-ynyl)-N-methyl-3-(4-methoxybenzyloxy)benzylamine (compound 13)

IR$\nu_{max}^{neat}$ cm$^{-1}$:2968, 1614, 1518, 1458, 1251, 1173, 1032.

NMR(CDCl$_3$)δ:1.25(9H, s), 2.22(3H, s), 3.26(2H, dd, J=6.8Hz, 1.5Hz), 3.49(ZH, s), 3.81 (3H, s), 4.98(2H, s), 5.61(1H, dt, J=10.7Hz, 1.5Hz), 5.94(1H, dt, J=10.7Hz, 6.8Hz), 6.83–6.87(1H, m), 6.89–6.94(3H, m), 6.97–6.98(1H, m), 7.19–7.24(1H, m), 7.31–7.37(2H, m).

EXAMPLE 8

(E)-N-(6,6-dimethyl-2-hepten-4-ynyl)-N-methyl-3-(beta-phenethyloxy)benzylamine (compound 14)

IR$\nu_{max}^{neat}$ cm$^{-1}$:2974, 1605, 1458, 1266, 1029, 696.

NMR(CDCl$_3$)δ:1.24(9H, s), 2.17(3H, s), 3.03(2H, dd, J=6.6Hz, 1.4Hz), 3.10(2H, t, J=7.2Hz), 3.44(2H, s), 4.17(2H, t, J=7.4Hz), 5.64(1H, dt, J=15.9Hz, 1.4Hz), 6.08 (1H, dt, J=15.9Hz, 6.6Hz), 6.75–6.79 (1H, m), 6.85–6.89(2H, m), 7.16–7.35 (6H, m).

(Z)-N-(6,6-dimethyl-2-hepten-4-ynyl)-N-methyl-3-(beta-phenethyloxy)benzylamine (compound 15)

IR$\nu_{max}^{neat}$ cm$^{-1}$:2968, 1605, 1458, 1266, 1152, 1032, 696.

NMR(CDCl$_3$)δ:1.24(9H, s), 2.21(3H, s), 3.09(2H, t, J=7.0Hz), 3.26(2H, dd, J=6.8Hz, 1.5Hz), 3.47(2H, s), 4.17(2H, t, J=7.0Hz), 5.60 (1H, dt, J=10.7Hz, 1.5Hz), 5.94(1H, dt, J=10.7Hz, 6.8Hz), 6.76–6.80(1H, m), 6.87–6.90(2H, m), 7.17–7.35(6H, m).

EXAMPLE 9

(E)-N-(6,6-dimethyl-2-hepten-4-ynyl)-N-methyl-3-(alpha-phenethyloxy)benzylamine (compound 16)

IR$\nu_{max}^{neat}$ cm$^{-1}$:2974, 1584, 1491, 1455, 1152, 1071, 699.

NMR(CDCl$_3$)δ:1.25(9H, s), 1.63(3H, d, J=6.5Hz), 2.11 (3H, s), 2.96(2H, dd, J=6.7Hz, 1.4Hz), 3.99(2H, s), 5.33(1H, q, J=6.5Hz), 5.60 (1H, dt, J=15.9Hz, 1.4Hz), 6.03(1H, dt, J=15.9Hz, 6.7Hz), 6.70–7.40(1H, m), 6.78–6.81(1H, m), 6.84–6.86(1H, m), 7.08–7.13(1H, m), 7.21–7.59(5H, m).

(Z)-N-(6,6-dimethyl-2-hepten-4-ynyl)-N-methyl-3-(alpha-phenethyloxy)benzylamine (compound 17)

IR$\nu_{max}^{neat}$ cm$^{-1}$:2974, 1584, 1491, 1455, 1263, 1152, 1071, 699.

NMR(CDCl$_3$)δ:1.24(9H, s), 1.62(3H, d, J=6.3Hz), 2.15 (3H, s), 3.21(2H, dd, J=6.8Hz, 1.5Hz), 3.42(2H, s), 5.32(1H, q, J=6.3Hz), 5.58 (1H, dt, J=10.7Hz, 1.5Hz), 5.89(1H, dt, J=10.7Hz, 6.8Hz), 6.70–6.74(1H, m), 6.81–6.84(1H, m), 6.86–6.87(1H, m), 7.09–7.14(1H, m), 7.19–7.39(5H, m).

EXAMPLE 10

(E)-N-(6,6-dimethyl-2-hepten-4-ynyl)-N-methyl-3-(1-naphthylmethyloxy)benzylamine (compound 18)

IR$\nu_{max}^{neat}$ cm$^{-1}$:2974, 1599, 1458, 1263, 1020, 792, 777.

NMR(CDCl$_3$)δ:1.25(9H, s), 2.21(3H, s), 3.06(2H, dd, J=6.6Hz, 1.4Hz), 3.49(2H, s), 5.50 (2H, s), 5.66(1H, dt, J=15.9Hz, 1.4Hz), 6.10(1H, dt, J=15.9Hz, 6.6Hz), 6.92–6.96 (2H, m), 7.06–7.07(1H, m), 7.23–7.28 (1H, m), 7.44–7.58(3H, m), 7.60–7.63 (1H, m), 7.84–7.92(2H, m), 8.06–8.09 (1H, m).

(Z)-N-(6,6-dimethyl-2-hepten-4-ynyl)-N-methyl-3-(1-naphthylmethyloxy)benzylamine (compound 19)

IR$\nu_{max}^{neat}$ cm$^{-1}$:2968, 1602, 1458, 1263, 1026, 792, 777.

NMR(CDCl$_3$)δ:1.24(9H, s), 2.23(3H, s), 3.28(2H, dd, J=6.8Hz, 1.5Hz), 3.52(2H, s), 5.49 (2H, s), 5.62(1H, dt, J=10.7Hz, 1.5Hz), 5.95(1H, dt, J=10.7Hz, 6.8Hz), 6.92–6.97(2H, m), 7.06–7.07(1H, m), 7.23–7.28(1H, m), 7.43–7.56(3H, m), 7.59–7.62(1H, m), 7.83–7.91(2H, m), 8.04–8.08(1H, m).

EXAMPLE 11

(E)-N-(6,6-dimethyl-2-hepten-4-ynyl)-N-methyl-3-benzyloxy-alpha-phenethylamine (compound 20)

IR$\nu_{max}^{neat}$ cm$^{-1}$:2974, 1602, 1584, 1458, 1284, 1266, 696.

NMR(CDCl$_3$)δ:1.24(9H, s), 1.32(3H, d, J=6.5Hz), 2.16 (3H, s), 2.88(1H, ddd, J=14.4Hz, 6.9Hz, 1.3Hz), 3.07(1H, ddd, J=14.4Hz, 6.4Hz, 1.6Hz), 3.52(1H, q, J=6.5Hz), 5.06 (2H, s), 5.58(1H, ddd, J=15.9Hz, 1.6Hz, 1.3Hz), 6.02(1H, ddd, J=15.9Hz, 6.9Hz, 6.2Hz), 6.83–6.87(1H, m), 6.88–6.91(1H, m), 6.96–6.98(1H, m), 7.18–7.24(1H, m), 7.29–7.45(5H, m).

(Z)-N-(6,6-dimethyl-2-hepten-4-ynyl)-N-methyl-3-benzyloxy-alpha-phenethylamine (compound 21)

IR$\nu_{max}^{neat}$ cm$^{-1}$:2974, 1602, 1584, 1491, 1458, 1266, 1026, 735, 696.

NMR(CDCl$_3$)δ:1.21(9H, s), 1.37(3H, d, J=6.8Hz), 2.19 (3H, s), 3.18(1H, ddd, J=14.4Hz, 7.1Hz, 1.5Hz), 3.33(1H, ddd, J=14.4Hz, 6.8Hz, 1.5Hz), 3.54(1H, q, J=6.8Hz), 5.06 (2H, s), 5.57(1H, dt, J=10.7Hz, 1.5Hz), 5.90(1H, ddd, J=10.7Hz, 7.1Hz, 6.8Hz), 6.83–6.87(1H, m), 6.91–6.94(1H, m), 6.97–6.99(1H, m), 7.19–7.25(1H, m), 7.28–7.45(5H, m).

EXAMPLE 12

Production of (E) and (Z)-N-(6,6-dimethyl-2-hepten-4-ynyl)-N-methyl-3-benzoylaminobenzylamine N-methyl-3-benzoylaminobenzylamine hydrochloride (277 mg) was dissolved in 3 ml of dimethylformamide, and 221 mg of 1-bromo-6,6-dimethyl-2-hepten-4-yne and 552 mg of potassium carbonate were stirred overnight at room temperature. The reaction mixture was diluted with water, and extracted with ethyl ether. The extract was washed with a saturated aqueous sodium chloride solution, and dried over anhydrous sodium sulfate. The desiccant was separated by filtration, and then the solvent was evaporated. The residue was purified by preparative thin-layer chromatography [thin-layer plate: Kieselgel 60F$_{254}$, Art. 5744 (a product of E. Merck Co.); developing solvent: hexane/ethyl acetate=3/1] to give the following compounds as colorless oils.

(E)-N-(6,6-dimethyl-2-hepten-4-ynyl)-N-methyl-3-benzoylaminobenzylamine (compound 22)

Amount: 179 mg (yield 50.0%)

IR$\nu_{max}^{neat}$ cm$^{-1}$:3304, 2872, 1656, 1614, 1584, 1548, 1494, 1365, 1266, 966, 789.

NMR(CDCl$_3$)δ:1.24(9H, s), 2.20(3H, s), 3.06(2H, dd, J=6.6Hz, 1.5Hz), 3.49(2H, s), 5.66(1H, dt, J=15.9Hz, 1.5Hz), 6.10(1H, dt, J=15.9Hz, 6.6Hz), 7.09(1H, d, J=7.5Hz), 7.32(1H, t, J=7.5Hz), 7.45–7.58(4H, m), 7.64–7.67(1H, m), 7.85–7.88(2H, m).

(Z)-N-(6,6-dimethyl-2-hepten-4-ynyl)-N-methyl-3-benzoylaminobenzylamine (compound 23)

Amount:93 mg (yield 25.7%)

IR$\nu_{max}^{neat}$ cm$^{-1}$:3304, 2974, 2782, 1656, 1614, 1551, 1494, 1440, 1323, 1269, 1029, 792, 696.

NMR(CDCl$_3$)δ:1.24(9H, s), 2.23(3H, s), 3.29(2H, dd, J=6.8Hz, 1.5Hz), 3.52(2H, s), 5.62(1H, dt, J=10.7Hz, 1.5Hz), 5.96(1H, dt, J=10.7Hz, 6.8Hz), 7.10(1H, d, J=7.5Hz), 7.32(1H, t, J=7.5Hz), 7.45-7.57(4H, m), 7.65-7.68(1H, m), 7.84-7.88(2H, m).

Compounds of Examples 13 and 14 were obtained by repeating Example 12 except that instead of the starting N-methyl-3-benzoylaminobenzylamine hydrochloride, the corresponding amine hydrochlorides were used.

EXAMPLE 13

(E)-N-(6,6-dimethyl-2-hepten-4-ynyl)-N-methyl-3-(N-phenylcarbamoyl)benzylamine (compound 24)

Melting point: 120°-122° C.,

IR$\nu_{max}^{KBr}$ cm$^{-1}$:3382, 2968, 1656, 1599, 1533, 1449, 1323, 1269, 753, 696.

NMR(CDCl$_3$)δ:1.24(9H, s), 2.20(3H, s), 3.08(2H, dd, J=6.6Hz, 1.5Hz), 3.55(2H, s), 5.67 (1H, dt, J=15.9Hz, 1.5Hz), 6.10(1H, dt, J=15.9Hz, 6.6Hz), 7.15(1H, t, J=7.5Hz), 7.34-7.51(4H, m), 7.64-7.68 (2H, m), 7.51-7.76(4H, m), 7.76-7.90 (3H, m).

(Z)-N-(6,6-dimethyl-2-hepten-4-ynyl)-N-methyl-3-(N-phenylcarbamoyl)benzylamine (compound 25)

IR$\nu_{max}^{neat}$ cm$^{-1}$:3304, 2968, 1656, 1602, 1539, 1506, 1446, 1326, 1269, 753, 693.

NMR(CDCl$_3$)δ:1.23(9H, s), 2.26(3H, s), 3.30(2H, dt, J=6.8Hz, 1.6Hz), 3.60(2H, s), 5.66(1H, dt, J=10.7Hz, 1.6Hz), 5.97(1H, dt, J=10.7Hz, 6.8Hz), 7.15(1H, t, J=7.5Hz), 7.35-7.52(4H, m), 7.67(2H, d, J=7.5Hz), 7.65-7.92(3H, m).

EXAMPLE 14

(E)-N-(6,6-dimethyl-2-hepten-4-ynyl)-N-methyl-3-phenoxymethylbenzylamine (compound 26)

IR$\nu_{max}^{neat}$ cm$^{-1}$:2968, 2788, 1602, 1500, 1365, 1242, 753, 690.

NMR(CDCl$_3$)δ:1.21(9H, s), 2.19(3H, s), 3.04(2H, dd, J=6.6Hz, 1.5Hz), 3.50(2H, s), 5.05 (2H, s), 5.64(1H, dd, J=15.9Hz, 1.5Hz), 6.09(1H, dt, J=15.9Hz, 6.6Hz), 6.93-6.99 (3H, m), 7.25-7.38(6H, m).

(Z)-N-(6,6-dimethyl-2-hepten-4-ynyl)-N-methyl-3-henoxymethylbenzylamine (compound 27)

IR$\nu_{max}^{neat}$ cm$^{-1}$:2968, 1602, 1500, 1269, 1242, 1032, 753, 693.

NMR(CDCl$_3$)δ:1.24(9H, s), 2.21(3H, s), 3.28(2H, dd, J=5.7Hz, 1.5Hz), 3.53(2H, s), 5.05 (2H, s), 5.62(1H, dd, J=10.7Hz, 1.5Hz), 5.95(1H, dt, J=10.7Hz, 5.7Hz), 6.93-6.99 (3H, m), 7.25-7.39(6H, m).

EXAMPLE 15

Production of (E)- and (Z)-N-(6,6-dimethyl-2-hepten-4-ynyl)-N-methyl-3-benzyloxy-4-methylbenzylamine N-methyl-3-benzyloxy-4-methylbenzylamine hydrochloride (67 mg) was dissolved in 2 ml of dimethylformamide, and 48 mg of 1-bromo-6,6-dimethyl-2-hepten-4-yne and 51 mg of sodium carbonate were added. The mixture was stirred overnight at room temperature. The reaction mixture was concentrated under reduced pressure at below 40° C., and the residue was purified by preparative thin-layer chromatography [thin-layer plate: Kieselgel 60F$_{254}$, Art. 5744 (a product of E. Merck Co.); developing solvent:hexane/ethyl acetate=5/1)) to give the following compounds as colorless oily products.

(E)-(6,6-dimethyl-2-hepten-4-ynyl)-N-methyl-3-benzyloxy-4-methylbenzylamine (compound 28)

Amount:50 mg (yield 57%)

IR$\nu_{max}^{neat}$ cm$^{-1}$:2974, 2926, 1512, 1458, 1422, 1368, 1260, 1155, 1128, 1026, 735.

NMR(CDCl$_3$)δ:1.24(9H, s), 2.18(3H, s), 2.26(3H, s), 3.02(1H, dd, J=6.6Hz, 1.5Hz), 3.46 (2H, s), 5.09(2H, s), 5.63(1H, dt, J=15.7Hz, 1.5Hz), 6.07(1H, dt, J=15.7Hz, 6.6Hz), 6.78(1H, dd, J=7.6Hz, 1.2Hz), 6.91(1H, d, J=1.2Hz), 7.08(1H, d, J=7.6Hz), 7.28-7.42 (3H, m), 7.42-7.49(2H, m).

(Z)-(6,6-dimethyl-2-hepten-4-ynyl)-N-methyl-3-benzyloxy-4-methylbenzylamine (compound 29)

Amount:20 mg (yield 23%)

IR$\nu_{max}^{neat}$ cm$^{-1}$:2968, 2926, 1458, 1419, 1263, 1128, 1029, 735.

NMR(CDCl$_3$)δ:1.24(9H, s), 2.23(3H, s), 2.26(3H, s), 3.27(2H, d, J=6.9Hz), 3.50(2H, s), 5.09(2H, s), 5.62(1H, d, J=10.7Hz), 5.95(1H, dt, J=10.7Hz, 6.9Hz), 6.81 (1H, dd, J=7.6Hz, 1.2Hz), 6.93(1H, s), 7.09(1H, d, J=7.6Hz), 7.30-7.48(5H, m).

Compounds of Examples 16 to 18 were obtained by repeating Example 15 except that instead of the starting N-methyl-3-benzyloxy-4-methylbenzylamine hydrochloride, the corresponding amine hydrochlorides were used.

EXAMPLE 16

(E)-(6,6-dimethyl-2-hepten-4-ynyl)-N-methyl-5-benzyloxy-2-bromobenzylamine (compound 30)

IR$\nu_{max}^{neat}$ cm$^{-1}$:2974, 1485, 1458, 1419, 1365, 1281, 1260, 1041, 1026.

NMR(CDCl$_3$)δ:1.24(9H, s), 2.15(3H, s), 3.00(2H, dd, J=6.7Hz, 1.5Hz), 3.41(2H, s), 5.17 (2H, s), 5.62(1H, dt, J=15.9Hz, 1.5Hz), 6.03(1H, dt, J=15.9Hz, 6.7Hz), 6.77 (1H, dd, J=8.1Hz, 2.1Hz), 6.97(1H, d, J=2.1Hz), 7.30-7.52(6H, m).

(Z)-(6,6-dimethyl-2-hepten-4-ynyl)-N-methyl-5-benzyloxy-2-bromobenzylamine (compound 31)

IR$\nu_{max}^{neat}$ cm$^{-1}$:2968, 1485, 1458, 1419, 1284, 1266, 1041, 1029, 735.

NMR(CDCl$_3$)δ:1.24(9H, s), 2.19(3H, s), 3.23(2H, dd, J=6.8Hz, 1.3Hz), 3.45(2H, s), 5.16 (2H, s), 5.61(1H, dt, J=10.7Hz, 1.3Hz), 5.90(1H, dt, J=10.7Hz, 6.8Hz), 6.79 (1H, dd, J=8.1Hz, 1.9Hz), 6.98(1H, d, J=1.9Hz), 7.30-7.42(3H, m), 7.44-7.52 (3H, m).

EXAMPLE 17

(E)-(6,6-dimethyl-2-hepten-4-ynyl)-N-methyl-3-benzyloxy-2-methoxybenzylamine (compound 32)

IR$\nu_{max}^{neat}$ cm$^{-1}$:2972, 1482, 1458, 1270, 1014, 754.

NMR(CDCl$_3$)δ:1.24(9H, s), 2.20(3H, s), 3.07(2H, dd, J=6.5Hz, 1.7Hz), 3.45(2H, s), 3.86 (3H, s), 5.11(2H, s), 5.66(1H, dt, J=15.7Hz, 1.7Hz), 6.10(1H, dt, J=15.7Hz, 6.5Hz), 6.87(1H, dd, J=6.7Hz, 3.2Hz), 6.94-7.01(2H, m), 7.28-7.48(5H, m).

(Z)-(6,6-dimethyl-2-hepten-4-ynyl)-N-methyl-3-benzyloxy-2-methoxybenzylamine (compound 33)

IR$\nu_{max}^{neat}$ cm$^{-1}$:2968, 1518, 1461, 1266, 1137, 1029.
NMR(CDCl$_3$)δ:1.24(9H, s), 2.16(3H, s), 3.21(2H, dd, J=6.8Hz, 1.5Hz), 3.41(2H, s), 3.87 (3H, s), 5.15(2H, s), 5.60(1H, dt, J=10.7Hz, 1.5Hz), 5.90(1H, dt, J=10.7Hz, 6.8Hz), 6.82-6.92(3H, m), 7.26-7.39 (3H, m), 7.41-7.48(2H, m).

EXAMPLE 18

(E)-N-(6,6-dimethyl-2-hepten-4-ynyl)-N-methyl-3-furfuryloxybenzylamine (compound 34)

IR$\nu_{max}^{neat}$ cm$^{-1}$:2968, 1599, 1491, 1455, 1368, 1263, 1155, 1017, 741.
NMR(CDCl$_3$)δ:1.24(9H, s), 2.18(3H, s), 3.03(2H, dd, J=6.6Hz, 1.7Hz), 3.46(2H, s), 5.00 (2H, s), 5.65(1H, dt, J=15.9Hz, 1.7Hz), 6.08(1H, dt, J=15.9Hz, 6.6Hz), 6.38 (1H, dt, J=3.2Hz, 1.6Hz), 6.43(1H, dd, J=3.2Hz, 0.7Hz), 6.84-6.89(1H, m), 6.89-6.94(1H, m), 6.96-7.00(1H, m), 7.22(1H, t, J=7.8Hz), 7.45(1H, dd, J=1.6Hz, 0.7Hz).

(Z)-N-(6,6-dimethyl-2-hepten-4-ynyl)-N-methyl-3-furfuryloxybenzylamine (compound 35)

IR$\nu_{max}^{neat}$ cm-1 2968, 1605, 1458, 1260, 1155, 1017, 741.
NMR(CDCl$_3$)δ:1.25(9H, s), 2.22(3H, s), 3.26(2H, dd, J=6.8Hz, 1.5Hz), 3.49(2H, s), 5.00 (2H, s), 5.62(1H, dt, J=10.8Hz, 1.5Hz), 5.95(1H, dt, J=10.8Hz, 6.8Hz), 6.38 (1H, dd, J=3.2Hz, 2.0Hz), 6.43(1H, dd, J=3.2Hz, 0.8Hz), 6.84-6.90(1H, m), 6.91-6.96(1H, m), 6.96-7.00(1H, m), 7.23(1H, t, J=7.8Hz), 7.45(1H, dd, J=2.0Hz, 0.8Hz).

EXAMPLE 19

Production of
(E)-N-(6,6-dimethyl-2-hepten-4-ynyl)N-ethyl-3-bonzyloxybenzylamine hydrochloride (compound 36)

N-Ethyl-3-benzyloxybenzylamine hydrochloride (100 mg) was dissolved in 2 ml of dimethylformamide, and 73 mg of 1-bromo-6,6-dimethyl-2-hepten-4-yne and 69 mg of potassium carbonate were added. The mixture was stirred overnight at room temperature. The reaction mixture was concentrated under reduced pressure, and the residue was dissolved in 10 ml of ethyl ether. The insoluble material was separated by filtration, and the solvent was evaporated. The residue was subjected to silica gel column chromatography [Wakogel C-200, 10 g; eluting solvent: hexane/ethyl acetate=20/1→3/1] to isolate only the E-form. It was dissolved in HCl-methanol and again distilled under reduced pressure. Recrystallization of the residue from a mixture of tetrahydrofuran and hexane gave 58 mg (yield 40%) of the captioned compound as a colorless crystalline powder having a melting point of 116° to 119° C.

IR$\nu_{max}^{KBr}$ cm$^{-1}$:3460, 2974, 2926, 2494, 1458, 1266, 699.
NMR(CDCl$_3$)δ:1.25(9H, s), 1.43(3H, t, J=7.2Hz), 2.90-3.15(2H, m), 3.46-3.75(2H, m), 4.07(2H, s), 5.17(2H, s), 5.81(1H, d, J=15.9Hz), 6.22(1H, dt, J=15.9Hz, 7.7Hz), 7.02-7.07(1H, m), 7.12(1H, d, J=7.5Hz), 7.27-7.52(7H, m).

Compounds of Examples 20 to 30 were obtained by repeating Example 19 except that instead of the starting N-ethyl-3-benzyloxybenzylamine hydrochloride, the corresponding amines were used (when the product was a free base, the hydrochloride production step in the aftertreatment was not included).

EXAMPLE 20

(E)-N-(6,6-dimethyl-2-hepten-4-ynyl)-N-propyl-3-benzyloxybenzylamine (compound 37)

IR$\nu_{max}^{neat}$ cm$^{-1}$:2968, 2872, 1602, 1491, 1263, 1029, 783, 738.
NMR(CDCl$_3$)δ:0.86(3H, t, J=7.3Hz), 1.24(9H, s), 1.43-1.51(2H, m), 2.37(2H, t, J=7.4Hz), 3.06(2H, dd, J=6.3Hz, 1.5Hz), 3.52 (2H, s), 5.06(2H, s), 5.63(1H, dt, J=15.9Hz, 1.5Hz), 6.06(2H, dt, J=15.9Hz, 6.3Hz), 6.85(1H, ddd, J=8.2Hz, 2.8Hz, 0.6Hz), 6.91(1H, d, J=7.5Hz), 6.99-7.01(1H, m), 7.20 (1H, t, J=7.8Hz), 7.32-7.46(5H, m).

EXAMPLE 21

(E)-N-butyl-N-(6,6-dimethyl-2-hepten-4-ynyl)-3-benzyloxybenzylamine (compound 38)

IR$\nu_{max}^{neat}$ cm$^{-1}$:2968, 2932, 1599, 1458, 735.
NMR(CDCl$_3$)δ:0.87(3H, t, J=7.2Hz), 1.24(9H, s), 1.27-1.33(2H, m), 1.41-1.46(2H, m), 1.56(2H, s), 2.40(2H, t, J=7.2Hz), 3.06(2H, dd, J=6.3Hz, 1.4Hz), 3.52 (2H, s), 5.62(1H, dt, J=15.9Hz, 1.5Hz), 6.05(1H, dt, J=15.9Hz, 6.3Hz), 6.84 (1H, ddd, J=10.8Hz, 2.7Hz, 0.8Hz), 6.90(1H, d, J=7.8Hz), 6.99-7.10(1H, m), 7.20(1H, t, J=7.8Hz), 7.32-7.46(5H, m).

EXAMPLE 22

(E)-N-(6,6-dimethyl-2-hepten-4-ynyl)-N-isobutyl-3-benzyloxybenzylamine (compound 39)

IR$\nu_{max}^{neat}$ cm$^{-1}$:2968, 2872, 1599, 1458, 1263, 738, 693.
NMR(CDCl$_3$)δ:0.87(6H, d, J=6.6Hz), 1.24(9H, s), 1.76-1.79(1H, m), 2.15(1H, d, J=7.3Hz), 3.03(2H, dd, J=6.3Hz, 1.6Hz), 3.50 (2H, s), 5.06(2H, s), 5.61(1H, dt, J=15.9Hz, 1.6Hz), 6.05(1H, dt, J=15.9Hz, 6.3Hz), 6.84(1H, ddd, J=8.2Hz, 3.5Hz, 0.8Hz), 6.91(1H, dd, J=8.0Hz, 0.5Hz), 6.99-7.01(1H, m), 7.32-7 46(5H, m).

EXAMPLE 23

(E)-N-(6,6-dimethyl-2-hepten-4-ynyl)-N-pentyl-3-benzyloxybenzylamine (compound 40)

IR$\nu_{max}^{neat}$ cm$^{-1}$:2968, 2866, 1599, 1458, 1266, 735, 693.
NMR(CDCl$_3$)δ:0.87(3H, t, J=6.8Hz), 1.24(9H, s), 1.25-1.27(4H, m), 1.43-1.45(2H, m), 2.39(2H, t, J=7.0Hz), 3.06(2H, dd, J=6.4Hz, 1.6Hz), 3.52(2H, s), 5.06 (2H, s), 5.62(1H, dt, J=15.9Hz, 0.8Hz), 6.05(1H, dt, J=15.9Hz, 6.4Hz), 6.84(1H, ddd, J=8.2Hz, 2.6Hz, 0.9Hz), 6.90(1H, d, J=7.4Hz), 6.99-7.00(1H, m), 7.20(1H, t, J=7.8Hz), 7.32-7.46(5H, m).

EXAMPLE 24

(E)-N-allyl-N-(6,6-dimethyl-2-hepten-4-ynyl)-3-benzyloxybenzylamine (compound 41)

IR$\nu_{max}^{neat}$ cm-1 2974, 1599, 1491, 1458, 1263, 1152, 1029, 696.
NMR(CDCl$_3$)δ:1.25(9H, s), 3.05-3.10(4H, m), 3.50 (2H, s), 5.07(2H, s), 5.07-5.22(2H, m), 5.64(1H, dt; J=15.9Hz, 1.9Hz), 5.84 (1H, ddt, J=16.8Hz, J=10.8Hz, 6.3Hz), 6.06(1H, dt, J=15.9Hz, 6.7Hz), 6.84-7.46(9H, m).

EXAMPLE 25

(E)-N-(6,6-dimethyl-2-hepten-4-ynyl)-N-propargyl-3-benzyloxybenzylamine (compound 42)

IR$\nu_{max}^{neat}$ cm$^{-1}$:2974, 1602, 1491, 1458, 1365, 1263, 1155, 1029, 960, 738, 696.

NMR(CDCl$_3$)δ:1.24(9H, s), 2.22(1H, t, J=2.4Hz), 3.17(1H, dd, J=6.5Hz, 1.5Hz), 3.30(2H, d, J=2.4Hz), 5.06(2H, s), 5.71(1H, dt, J=15.9Hz, 1.5Hz), 6.02(1H, dt, J=15.9Hz,

EXAMPLE 26

(E)-N-cyclopropyl-N-(6,6-dimethyl-2-hepten-4-ynyl)-3-benzyloxybenzylamine (compound 43)

IR$\nu_{max}^{neat}$ cm-1 2974, 2926, 1590, 1491, 1458, 1365, 1263, 696.

NMR(CDCl$_3$)δ:0.38-0.44(4H, m), 1.29(9H, s), 1.80-1.87(1H, m), 3.14(2H, dd, J=6.8Hz, 1.6Hz), 3.67(2H, s), 5.06(2H, s), 5.55 (1H, dt, J=15.9Hz, 1.6Hz), 6.11(1H, dt, J=15.9Hz, 6.8Hz), 6.83-7.45(9H, m).

EXAMPLE 27

(E)-N-(6,6-dimethyl-2-hepten-4-ynyl)-N-ethyl-3-(2-methylbenzyloxy)benzylamine hydrochloride (compound 44)

Melting point: 125°-127° C.
IR$\nu_{max}^{KBr}$ cm$^{-1}$:2974, 2926, 2566, 2488, 1458, 1266, 750

NMR(CDCl$_3$)δ: 1.25(9H, s), 1.44(3H, t, J=7.2Hz), 2.40(3H, s), 2.90-3.16(2H, m), 3.48-3.60 (1H, m), 3.62-3.75(1H, m), 4.09(2H, s), 5.15(2H, s), 5.81(1H, d, J=15.8Hz), 6.23(1H, dt, J=15.8Hz, 7.6Hz), 7.05 (1H, dd, J=7.9Hz, 2.6Hz) 7.14(1H, d, J=7.9Hz), 7.16-7.28(3H, m), 7.34(1H, t, J=7.9Hz), 7.41-7.45(1H, m), 7.52 (1H, br).

EXAMPLE 28

(E)-N-(6,6-dimethyl-2-hepten-4-ynyl)-N-propyl-3-(2-methylbenzyloxy)benzylamine hydrochloride (compound 45)

Melting point: 138°-140° C.
IR$\nu_{max}^{KBr}$ cm$^{-1}$:2968, 2872, 1599, 1491, 1458, 1263, 1152, 747.

NMR(CDCl$_3$):0.93(3H, t, J=7.3Hz), 1.25(9H, s), 1.80(2H, br), 2.40(3H, s), 2.75(2H, br), 3.48(2H, br), 3.97(2H, br), 5.12(2H, s), 5.70(1H, d, J=15.6Hz), 6.18(1H, dt, J=15.6Hz, 7.0Hz) 7.11(1H, dd, J=7.2Hz, 1.2Hz), 7.08(1H, d, J=7.2Hz), 7.18-7.45 (6H, m).

EXAMPLE 29

(E)-N-(6,6-dimethyl-2-hepten-4-ynyl)-N-ethyl-3-(3-cyanobenzyloxy)benzylamine (compound 46)

IR$\nu_{max}^{neat}$ cm$^{-1}$:2974, 1491, 1458, 1263, 1155, 1044, 789, 687.

NMR(CDCl$_3$)δ:1.03(3H, t, J=7.1Hz), 1.24(9H, s), 2.50(2H, q, J=7.1Hz), 3.08(2H, dd, J=6.4Hz, 1.5Hz), 3.54(2H, s), 5.09 (2H, s), 5.64(1H, dt, J=15.9Hz, 1.5Hz), 6.06(1H, dt, J=15.9Hz, 6.4Hz), 6.80-6.86(1H, m), 6.94(1H, d, J=7.6Hz), 6.97-7.02(1H, m), 7.23(1H, t, J=7.9Hz), 7.50(1H, t, J=7.6Hz), 7.59-7.64(1H, m), 7.65-7.71(1H, m), 7.75-7.78(1H, m).

EXAMPLE 30

(E)-N-(6,6-dimethyl-2-hepten-4-ynyl)-N-propyl-3-(3-cyanobenzyloxy)benzylamine hydrochloride (compound 47)

Melting point: 136°-138° C.
IR$\nu_{max}^{KBr}$ cm$^{-1}$:2974, 2500, 1605, 1455, 1266, 1182.

NMR(CDCl$_3$)δ:0.95(3H, t, J=7.3Hz), 1.26(9H, s), 1.82-2.02(2H, m), 2.76-2.99(2H, m), 3.51-3.78(2H, m), 4.08(2H, br), 5.26 (2H, s), 5.83(1H, d, J=15.7Hz), 6.19 (2H, dt, J=15.7Hz, 5.8Hz), 6.99-7.08 (2H, m), 7.33(1H, t, J=7.9Hz), 7.49 (1H, t, J=7.7Hz), 7.60(1H, d, J=7.7Hz), 7.74-7.84(3H, m).

EXAMPLE 31

Production of (E)-N-(6,6-dimethyl-2-hepten-4-ynyl)-N-methyl-3-benzyloxy-5-methylbenzylamine hydrochloride (compound 48)

3-Benzyloxy-5-methylbenzyl bromide (118 mg) and 76 mg of (E)-N-methyl-6,6-dimethyl-2-hepten-4-ynylamine hydrochloride were dissolved in 25 ml of dimethylformamide, and 67 mg of potassium carbonate was added. The mixture was stirred overnight at room temperature. The reaction mixture was evaporated under reduced pressure, and the residue was purified by preparative thin-layer chromatography [thin layer plate: Kieselgel 60F$_{254}$, Art. 5715 (a product of E. Merck Co.); developing solvent: hexane/ethyl acetate=4/1]. The purified compound was then converted into a hydrochloride using HCl methanol solution. Treatment with a mixture of tetrahydrofuran and hexane gave 102 mg (yield 60.9%) of the captioned compound as a colorless crystalline powder having a melting point of 180° to 186° C.

IR$\nu_{max}^{KBr}$ cm$^{-1}$:3450, 2968, 2500, 1599, 1461, 1326, 1299, 1161, 1062, 969, 729.

NMR(CDCl$_3$)δ:1.25(9H, s), 2.35(3H, s), 2.58 (3H, s), 3.41-3.70(2H, m), 3.91-4.13 (2H, m), 5.14(2H, s), 5.80(1H, d, J=15.9Hz), 6.25(1H, dt, J=15.9Hz, 6.6Hz), 6.87-6.91(2H, m), 7.17-7.20 (1H, m), 7.29-7.47(5H, m).

Compounds of Examples 32 and 33 were obtained by repeating Example 31 except that instead of the starting 3-benzyloxy-5-methylbenzyl bromide, the corresponding benzyl bromide derivatives were used (when the product was a free base, the hydrochloride producing step was not included in the after-treatment).

EXAMPLE 32

(E)-N-(6,6-dimethyl-2-hepten-4-ynyl)-N-methyl-3-benzyloxy-4-fluorobenzylamine (compound 49)

IR$\nu_{max}^{neat}$ cm$^1$:2974, 1518, 1461, 1431, 1269, 1116, 1023.

NMR(CDCl$_3$)δ:1.25(9H, s), 2.14(3H, s), 2.99(2H, dd, J=6.2Hz, 1.5Hz), 3.40(2H, s), 5.14 (2H, s), 5.62(1H, dt, J=15.9Hz, 1.5Hz), 6.04(1H, dt, J=15.9Hz, 6.2Hz), 6.77-6.83(1H, m), 6.97-7.05(2H, m), 7.28-7.48(5H, m).

EXAMPLE 33

(E)-N-(6,6-dimethyl-2-hepten-4-ynyl)-N-methyl-3-benzyloxy-4-hydroxybenzylamine hydrochloride (compound 50)

Melting point:98° C. (colorless crystalline powder containing 0.3 mole of hexane)

IR$\nu_{max}^{KBr}$ cm$^{-1}$:2968, 2626, 1527, 1461, 1446, 1368, 1284, 1263, 1164, 1131.

NMR(CDCl$_3$)δ:1.25(9H, s), 2.59(3H, s), 3.40-3.52 (1H, m), 3.61-3.73(1H, m), 3.87-3.97 (1H, m), 4.07-4.18(1H, m), 5.27(1H, s), 5.82(1H, d, J=15.6Hz), 5.89(1H, s), 6.23(1H, dt, J=15.6Hz, 7.6Hz), 6.81 (1H, dd, J=7.9Hz, 1.8Hz), 6.91(1H, d, J=7.9Hz), 7.46-7.52(2H, m), 7.74 (1H, br).

EXAMPLE 34

Production of (E)-N-(6,6-dimethyl-2-hepten-4-ynyl)-N-methyl-3-(2-methoxybenzyloxy)benzylamine hydrochloride (compound 51)

0.33 g of 3-(2-methoxybenzyloxy)benzyl methanesulfonate was dissolved in 4 ml of dimethylformamide, and 0.19 g of (E)-N-methyl-6,6-dimethyl-2-hepten-4-ynylamine hydrochloride and 0.17 g of potassium carbonate were added, and the mixture was stirred overnight at room temperature. The reaction mixture was concentrated under reduced pressure. The residue was dissolved in ethyl ether, and then the insoluble salts were removed by filtration. The filtrate was concentrated under reduced pressure, and the residue was purified by silica gel column chromatography Wakogel C-200, 6 g; eluting solvent: hexane/ethyl acetate=2/1) to give 0.40 g of the free base of the captioned compound as a pale yellow oil. The product was dissolved in 5 ml of methanol, and 0.9 ml of 30% HCl/methanol solution was added, and the mixture was evaporated under reduced pressure. Recrystallization from a mixture of tetrahydrofuran and hexane gave 0.19 g (yield 47%) of the captioned compound as colorless needles.

Melting point:138°-140° C.

IR$\nu_{max}^{KBr}$ cm$^{-1}$:3448, 2968, 2494, 1608, 1500, 1464, 1266, 1248, 1047, 1029, 756.

NMR(CDCl$_3$)δ:1.24(9H, s), 2.59(3H, s), 3.56 (2H, br), 3.86(3H, s), 4.09(2H, br), 5.15(2H, s), 5.80(1H, d, J=15.0Hz), 6.26(1H, br), 6.89-6.98(2H, m), 7.05 (1H, d, J=7.7Hz), 7.16-7.19(2H, m), 7.26-7.40(2H, m), 7.41(1H, dd, J=6.7Hz, 1.2Hz).

Compounds of Examples 35 to 46 were obtained by repeating Example 34 except that instead of the starting 3-(2-methoxybenzyloxy)benzyl methanesulfonate, the corresponding benzyl methanesulfonates were used (when the product was a free base, the hydrochloride producing step was not included in the after-treatment).

EXAMPLE 35

(E)-N-(6,6-dimethyl-2-hepten-4-ynyl)-N-methyl-3-(3-methoxybenzyloxy)benzylamine hydrochloride (compound 52)

Melting point:118°-120° C.

IR$\nu_{max}^{KBr}$ cm$^{-1}$:3450, 2968, 2488, 1590, 1497, 1461, 1266, 1155, 1041, 783.

NMR(CDCl$_3$)δ:1.24(9H, s), 2.60(3H, s), 3.57 (2H, br), 3.82(3H, s), 4.08(2H, br), 5.13(2H, s), 5.82(1H, d, J=15.4Hz), 6.25(1H, br), 6.85(1H, dd, J=7.2Hz, 2.1Hz), 7.00-7.11(4H, m), 7.26-7.36 (2H, m), 7.39(1H, s).

EXAMPLE 36

(E)-N-(6,6-dimethyl-2-hepten-4-ynyl)-N-methyl-3-(3-methylbenzyloxy)benzylamine (compound 53)

IR$\nu_{max}^{neat}$ cm$^{-1}$:2968, 2788, 1596, 1491, 1458, 1365, 1266, 1026, 777.

NMR(CDCl$_3$)δ:1.24(9H, s), 2.18(3H, s), 2.37(3H, s), 3.03(2H, dd, J=6.5Hz, 1.5Hz), 3.46 (2H, s), 5.02(2H, s), 5.64(1H, dt, J=15.7Hz, 1.5Hz), 6.08(1H, dt, J=15.7Hz, 6.6Hz), 6.83-6.91(2H, m), 6.97-6.98(1H, m), 7.11-7.14(1H, m), 7.18-7.30(4H, m).

EXAMPLE 37

(E)-N-(6,6-dimethyl-2-hepten-4-ynyl)-N-methyl-3-(4-methylbenzyloxy)benzylamine (compound 54)

IR$\nu_{max}^{neat}$ cm$^{-1}$:2968, 1602, 1587, 1491, 1458, 1263, 1152, 1032.

NMR(CDCl$_3$)δ:1.24(9H, s), 2.18(3H, s), 2.36(3H, s), 3.03(2H, dd, J=6.5Hz, 1.4Hz), 3.45 (2H, s), 5.01(2H, s), 5.64(1H, dt, J=15.9Hz, 1.4Hz), 6.08(1H, dt, J=15.9Hz, 6.6Hz), 6.82-6.90(2H, m), 6.95-6.96(1H, m), 7.15-7.25(3H, m), 7.32(2H, d, J=8.0Hz).

EXAMPLE 38

(E)-N-(6,6-dimethyl-2-hepten-4-ynyl)-N-methyl-3-(2,3-dimethylbenzyloxy)benzylamine hydrochloride (compound 55)

Melting point:182°-184° C.,

IR$\nu_{max}^{KBr}$ cm$^{-1}$:3448, 2968, 2482, 1587, 1497, 1461, 1263, 1167, 1032, 783.

NMR(CDCl$_3$)δ:1.24(9H, s), 2.28(3H, s), 2.31 (3H, s), 2.61(3H, s), 3.60(2H, br), 4.08(2H, br), 5.13(2H, s), 5.82(1H, d, J=15.5Hz), 6.26(1H, dt, J=15.5Hz, 7.6Hz), 7.03-7.16(4H, m), 7.25-7.28 (1H, m), 7.34(1H, t, J=7.4Hz), 7.40 (1H, d, J=1.7Hz).

EXAMPLE 39

(E)-N-(6,6-dimethyl-2-hepten-4-ynyl)-N-methyl-3-(2-chlorobenzyloxy)benzylamine (compound 56)

IR$\nu_{max}^{neat}$ cm$^{-1}$:2974, 1590, 1491, 1452, 1365, 1266, 1152, 1038, 753.

NMR(CDCl$_3$)δ:1.24(9H, s), 2.18(3H, s), 3,03(2H, dd, J=6.6Hz, 1.4Hz), 3.47(2H, s), 5.17 (2H, s), 5.64(1H, dt, J=15.9Hz, 1.4Hz), 6.08(1H, dt, J=15.9Hz, 6.6Hz), 6.87 (1H, dd, J=7.0Hz, 2.8Hz), 6.92(1H, d, J=7.5Hz), 6.98(1H, d, J=1.8Hz), 7.22 (1H, d, J=7.7Hz), 7.24-7.31(2H, m), 7.38-7.41(1H, m), 7.55-7.59(1H, m).

EXAMPLE 40

(E)-N-(6,6-dimethyl-2-hepten-4-ynyl)-N-methyl-3-(3-trifluoromethylbenzyloxy)benzylamine hydrochloride (compound 57)

Melting point:145°-146° C.

IR$\nu_{max}^{KBr}$ cm$^{-1}$:3460, 2974, 2626, 2506, 1458, 1335, 1266, 1197, 1164, 1125, 1074.

NMR(CDCl$_3$)δ:1.25(9H, s), 2.63(3H, s), 3.62 (2H, br), 4.10(2H, br), 5.22(2H, s), 5.85(1H, d, J=15.5Hz), 6.25(1H, dt, J=15.5Hz, 7.6Hz), 7.03-7.09(2H, m), 7.34(1H, t, J=7.7Hz), 7.50(1H, t, J=7.7Hz), 7.57-7.63(2H, m), 7.68(1H, d, J=7.6Hz), 7.74(1H, s).

EXAMPLE 41

(E)-N-(6,6-dimethyl-2-hepten-4-ynyl)-N-methyl-3-(3-phenylpropoxy)benzylamine hydrochloride (compound 58)

Melting point:100° C. (amorphous powder)

IR$\nu_{max}^{KBr}$ cm$^{-1}$:3454, 2968, 2548, 2488, 1605, 1587, 1497, 1458, 1266, 699.

NMR(CDCl$_3$)67 :1.24(9H, s), 2.06-2.16(2H, m), 2.62 (3H, s), 2.82(2H, t, J=7.5Hz), 3.62 (2H, d, J=7.3Hz), 4.06(2H, t, J=6.0Hz), 4.07(2H, s), 5.84(1H, d, J=15.9Hz), 6.29(1H, dt, J=15.9Hz, 7.5Hz), 6.95 (1H, dd, J=3.8Hz, 2.5Hz), 7.07(1H, d, J=7.6Hz), 7.16-7.35(7H, m).

EXAMPLE 42

(E)-N-(6,6-dimethyl-2-hepten-4-ynyl)-N-methyl-3-(2-methyl-2-propenyloxy)benzylamine (compound 59)

IR$\nu_{max}^{neat}$ cm$^{-1}$:2974, 2788, 1602, 1587, 1491, 1455, 1365, 1266, 1152, 1026.

NMR(CDCl$_3$)δ:1.24(9H, s), 1.84(3H, s), 2.19(3H, s), 3.03(2H, dd, J=6.6Hz, 1.5Hz), 3.45 (3H, s), 4.43(2H, s), 4.98(1H, m), 5.10(1H, m), 5.65(1H, dt, J=15.8Hz, 1.5Hz), 6.09(1H, dt, J=15.8Hz, 6.6Hz), 6.78–6.82(1H, m), 6.86–6.91(2H, m), 7.20(1H, t, J=7.8Hz).

EXAMPLE 43

N-(E)-6,6-dimethyl-2-hepten-4-ynyl)-N-methyl-3-[(E)-3,7-dimethyl-2,6-octadienyloxy] benzylamine (compound 60)

IR$\nu_{max}^{neat}$ cm$^{-1}$:2968, 2926, 2584, 2488, 1602, 1458, 1266, 1188, 963.

NMR(CDCl$_3$)δ:1.24(9H, s), 1.61(3H, s), 1.68(3H, s), 1.74(3H, s), 2.06-2.16(4H, m), 2.24 (3H, s), 3.10(2H, d, J=6.5Hz), 3.52 (2H, s), 4.54(2H, d, J=6.6Hz), 5.07–5.13(1H, m), 5.47–5.51(1H, m), 5.67(1H, dt, J=15.9Hz, 1.6Hz), 6.11 (1H, dt, J=15.9Hz, 6.5Hz) 6.82(1H, dd, J=8.1Hz, 1.8Hz), 6.88–6.94(2H, m), 7.22(1H, t, J=8.1Hz).

EXAMPLE 44

(E)-N-(6,6-dimethyl-2-hepten-4-ynyl)-N-methyl-3-(3-methyl-2-butenyloxy)benzylamine (compound 61)

IR$\nu_{max}^{neat}$ cm$^{-1}$:2968, 2866, 2788, 1602, 1491, 1458, 1365, 1266, 1020.

NMR(CDCl$_3$)δ:1.24(9H, s), 1.73(3H, s), 1.80 2.19(3H, s), 3.03(2H, dd, J=6.2Hz, 1.4Hz), 3.45(2H, s), 4.51(2H, d, J=6.8Hz), 5.50(1H, t.sept., J=6.8Hz, 1.4Hz), 5.65(1H, dt, J=15.9Hz, 1.4Hz), 6.08(1H, dt, J=15.9Hz, 6.2Hz), 6.79 (1H, ddd, J=8.2Hz, 2.9Hz, 1.4Hz), 6.86–6.90(2H, m), 7.20(1H, t, J=7.8Hz).

EXAMPLE 45

(E)-N-(6,6-dimethyl-2-hepten-4-ynyl)-N-methyl-3-(2-ethylbenzyloxy)benzylamine hydrochloride (compound 62)

Melting point:146°–148° C.

IR$\nu_{max}^{KBr}$ cm$^{-1}$:3440, 2968, 2872, 2488, 1602, 1497, 1455, 1263, 1176, 1023, 969, 777, 759.

NMR(CDCl$_3$)δ:1.24(9H, s), 1.27(3H, t, J=7.6Hz), 2.62(3H, s), 2.74(2H, q, J=7.6Hz), 3.60 (2H, br), 4.07(2H, br), 5.15(2H, s), 5.82(1H, d, J=15.6Hz), 6.27(1H, dt, J=15.6Hz, 7.6Hz), 7.03–7.07(1H, m), 7.11–7.15(1H, m), 7.18–7.45(6H, m).

EXAMPLE 46

N-(E)-6,6-dimethyl-2-hepten-4-ynyl]-N-methyl-3-[(E)-3-phenyl-2-propenyloxy)benzylamine hydrochloride (compound 63)

Melting point: 128°–130° C.

IR$\nu_{max}^{KBr}$ cm$^{-1}$:3448, 2968, 2482, 1602, 1494, 1458, 1263, 969, 693.

NMR(CDCl$_3$)δ:1.25(9H, s), 2.61(3H, s), 3.59 (3H, br), 4.07(2H, br), 4.80(2H, dd, J=6.9Hz, 1.2Hz), 5.82(1H, d, J=15.6Hz), 6.25(1H, dt, J=15.6Hz, 7.2Hz), 6.41 (1H, dt, J=15.8Hz, 6.9Hz), 6.79(1H, dt, J=15.8Hz, 1.2Hz), 7.02–7.08 (2H, m), 7.22–7.37(4H, m), 7.39–7.45 (3H, m).

EXAMPLE 47

Production of (E)-N-(6,6-dimethyl-2-hepten-4-ynyl)N-methyl-3-(3-cyanobenzyloxy)benzylamine hydrochloride (compound 64)

100 mg of (E)-N-(6,6-dimethyl-2-hepten-4-ynyl)N-methyl-3-hydroxybenzylamine was dissolved in 2 ml of anhydrous tetrahydrofuran, and with stirring under ice cooling, 19 mg of 60% oily sodium hydride was added. The mixture was stirred for 10 minutes. A dimethylformamide solution (1 ml) of 88 microliters of 3-cyanobenzyl bromide was added to the resulting solution, and the mixture was stirred at room temperature for 2 hours. Water (10 ml) was then added to dilute the mixture. The mixture was extracted with 10 ml of ethyl ether twice. The extracts were combined, washed with a saturated aqueous sodium chloride solution and dried over anhydrous sodium sulfate. The solvent was then evaporated. The residue was purified by silica gel column chromatography (Wakogel C-200, 5 g; eluting solvent:hexane/ethyl acetate=4/1) to give 120 mg (yield 77%) of the free base of the captioned compound as a colorless oil. The product was treated with HCl-methanol, and the solvent was evaporated. Recrystallization of the residue from ethyl ether/hexane gave the captioned compound as colorless needles.

Melting point: 131°–133° C.;

IR$\nu_{max}^{KBr}$ cm$^{-1}$:2972, 2624, 2232, 1458, 1268, 1166, 688.

NMR(CDCl$_3$)δ:1.25(9H, s), 2.61(3H, s), 3.48-3.80 (2H, m), 3.85-4.25(2H, m), 5.24(2H, s), 5.83(1H, d, J=15.9Hz), 6.23(1H, dt, J=15.9Hz, 7.1Hz), 7.00–7.06(2H, m), 7.33(1H, t, J=7.8Hz), 7.50(1H, t, J=7.8Hz), 7.59–7.64(1H, m), 7.75(1H d, J=8.1Hz), 7.79(1H, s).

Compounds of Examples 48 to 71 were obtained by repeating Example 47 except that instead of the starting 3-cyanobenzyl bromide, the corresponding benzyl halogen derivatives or benzyl methanesulfonate derivatives were used (when the product was a free base, the hydrochloride producing step was not included in the after-treatment).

EXAMPLE 48

(E)-N-(6,6-dimethyl 2-hepten-4-ynyl)-N-methyl-3-(3-hydroxybenzyloxy)-benzylamine (compound 65)

IR $_{max}^{neat}$ cm$^{-1}$: 2968, 1596, 1491, 1458, 1368, 1266, 1155, 780.

NMR(CDCl$_3$)δ: 1.24(9H, s), 2.19(3H, s), 3.04(2H, d, J=5.8Hz), 3.48(2H, s), 5.02(2H, s), 5.65(1H, dt, J=15.9Hz, 2.1 Hz), 6.08(1H, dt, J=15.9Hz, 6.6Hz), 6.78(1H, dd, J=7.8Hz, 2.2Hz), 6.85(1H, dd, J=7.8Hz, 2.2Hz), 6.87–6.93(2H, m), 6.95–6.98 (2H, m), 7.18–7.24(2H, m).

EXAMPLE 49

(E)-N-(6,6-dimethyl-2-hepten-4-ynyl)-N-methyl-3-(2-fluorobenzyloxy)benzylamine hydrochloride (compound 66)

Melting point: 154°–155° C.

IR$\nu_{max}^{KBr}$ cm$^{-1}$: 2968, 2626, 2560, 2506, 1587, 1497, 1458, 1272, 1248, 762.

NMR(CDCl$_3$)δ: 1.24(9H, s), 2.62(3H, s), 3.60(2H, d, J=6.4Hz), 4.10(2H, s), 5.19(2H, s), 5.83(1H, d,

J=16.0Hz), 6.26(1H, dt, J=16.0Hz, 6.4Hz), 7.02-7.20(4H, m), 7.27-7.38(3H, m), 7.51(1H, dt, J=7.4Hz, 1.7Hz).

EXAMPLE 50

(E)-N-(6,6-dimethyl-2-hepten-4-ynyl)-N-methyl-3-(2-cyanobenzyloxy)benzylamine hydrochloride (compound 67)

Melting point: 161°-163° C.

IR$\nu_{max}^{KBr}$ cm$^{-1}$: 2974, 2620, 2230, 1590, 1497, 1458, 1263, 1167, 771.

NMR(CDCl$_3$)δ: 1.25(9H, s), 2.63(3H, s), 3.62(2H, d, J=7.6Hz, 4.10(2H, s), 5.31(2H, s), 5.85(1H, d, J=15.8Hz), 6.30(1H, dt, J=15.8Hz, 7.6Hz), 7.04-7.08(1H, m), 7.36(1H, t, J=7.9Hz), 7.45(1H, dt, J=7.6Hz, 1.2Hz), 7.50(1H, t, J=1.9Hz), 7.63(1H, dt, J=7.6Hz, 1.2Hz), 7.69-7.73 (2H, m).

EXAMPLE |

(E)-N-(6,6-dimethyl-2-hepten-4-ynyl)-N-methyl-3-(2-trifluoromethylbenzyloxy)benzylamine hydrochloride (compound 68)

Melting point: 204°-206° C.

IR$\nu_{max}^{KBr}$ cm$^{-1}$: 2974, 1458, 1317, 1254, 1167, 1119, 777.

NMR(CDCl$_3$)δ: 1.25(9H, s), 2.60(3H, s), 3.58(2H, d, J=7.2Hz), 4.07(2H, s), 5.31(2H, s), 5.82(1H, d, J=15.7Hz), 6.25(1H, dt, J=15.7Hz, 7.2Hz), 7.00-7.04(1H, m), 7.21(1H, d, J=7.5Hz), 7.26-7.27 (1H, m), 7.36(1H, t, J=7.9Hz), 7.44 (1H, t, J=7.7Hz), 7.58(1H, t, J=7.6Hz) 7.69-7.75(2H, m).

EXAMPLE 52

(E)-N-(6,6-dimethyl-2-hepten-4-ynyl)-N-methyl-3-(3-isopropenylbenzyloxy)benzylamine (compound 69)

IR$\nu_{max}^{neat}$ cm$^{-1}$: 2974, 1602, 1 497, 1458, 1320, 1266, 1179, 966.

NMR(CDCl$_3$)δ: 1.25(9H, s), 2.18(3H, s), 2.19(3H, s), 3.03(2H, dd, J=6.5Hz, 1.5Hz), 3.46 (2H), s), 5.06(2H, s), 5.10(1H, dt, J=3.0Hz, 1.5Hz), 5.39(1H, dt, J=1.5Hz, 0.9Hz), 5.64(1H, dt, J=15.9Hz, 1.5Hz), 6.08(1H, dt, J=15.98Hz, 6.5Hz), 6.85-6.92(2H, m), 6.99(1H, t, J=1.7Hz), 7.22(1H, t, J=8.1Hz), 7.33-7.45(3H, m), 7.53-7.54(1H, m).

EXAMPLE 53

(E)-N-(6,6-dimethyl-2-hepten-4ynyl)-N-methyl-3-[3-(2-methyl-1-propenyl)benzyloxy]benzylamine (compound 70)

IR$\nu_{max}^{neat}$ cm$^{-1}$: 2968, 1602, 1491, 1458, 1365, 1266, 1152, 1023, 780, 696.

NMR(CDCl$_3$)δ: 1.24(9H, s), 1.85(3H, d, J=1.4Hz), 1.90(3H, d, J=1.4Hz, 2.18(3H, s), 3.03(2H, dd, J=6.6Hz, 1.4Hz), 3.56 (2H, s), 5.05(2H, s), 5.64(1H, dt, J=15.7Hz, 1.4Hz), 6.08(1H, dt, J=15.7Hz, 6.6Hz), 6.26-6.29(1H, m), 6.83-6.91(2H, m), 6.97(1H, dd, J=2.2Hz, 2.0Hz), 7.16-7.35(5H, m).

EXAMPLE 54

(E)-N-(6,6-dimethyl-2-hepten-4ynyl)-N-methyl-3-[3-(2-methyl-2-propenyl)benzyloxy]benzylamine (compound 71)

IR$\nu_{max}^{neat}$ cm$^{-1}$: 2974, 1599, 1491, 1458, 1368, 1266, 1155, 1026, 888, 780, 696.

NMR(CDCl$_3$)δ: 1.24(9H, s), 1.67(3H, s), 2.18 (3H, s), 3.03(2H, dd, J=6.6Hz, 1.5Hz), 3.34(2H, s), 3.46(2H, s), 4.74(1H, m), 4.81(1H, m), 5.04(2H, s), 5.64(1H, dt, J=15.9Hz, 1.5Hz), 6.08(1H, dt, J=15.9Hz, 6.6Hz), 6.84-6.91(1H, m), 6.96-6.98(1H, m), 7.13-7.16(1H, m), 7.21(1H, t, J=7.7Hz), 7.25-7.33 (3H, m).

EXAMPLE 55

(E)-N-(6,6-dimethyl-2-hepten-4-ynyl)-N-methyl-3-3-(3-methyl-2-butenyl)benzyloxy)benzylamine (compound 72)

IR$\nu_{max}^{neat}$ cm$^{-1}$: 2974, 2920, 1602, 1491, 1455, 1365, 1266, 1155, 1026, 783.

NMR(CDCl$_3$)δ: 1.24(9H, s), 1.61(3H, s), 1.72(3H, d, J=1.5Hz), 1.75(3H, d, J=1.5Hz), 2.18(3H, s), 3.03(2H, dd, J=6.6Hz, 1.5Hz), 3.36(2H, d, J=7.3Hz), 3.46 (2H, s), 5.03(2H, s), 5.33(1H, t.sept., J=7.3Hz, 1.5Hz), 5.64(1H, dt, J=15.9Hz, 1.5Hz), 6.08(1H, dt, J=15.9Hz, 6.6Hz), 6.84-6.91(2H, m), 6.96-6.98(1H, m), 7.11-7.33(5H,m).

EXAMPLE 56

(E)-N-(6,6-dimethyl-2-hepten-4-ynyl)-N-methyl-3-[3-(3-methyl-2-butenyloxy)benzyloxy]benzylamine (compound 73)

IR$\nu_{max}^{neat}$ cm$^{-1}$: 2974, 1602, 1494, 1452, 1266, 1152, 1023.

NMR(CDCl$_3$)δ: 1.24(9H, s), 1.74(3H, s), 1.79(3H, s), 2.18(3H, s), 3.03(2H, dd, J=6.6Hz, 1.5Hz), 3.46(2H, s), 4.51(1H, d, J=6.5Hz), 5.03(2H, s), 5.47-5.52 (1H, m), 5.64(1H, dt, J=15.6Hz, 1.4Hz), 6.08(1H, dt, J=15.6Hz, 6.5Hz), 6.83-6.91(2H, m), 6.96-7.01(3H, m), 7.21(1H, t, J=8.0Hz), 7.23(1H, dd, J=8.3Hz, 8.2Hz),

EXAMPLE 57

(E)-N-(6,6-dimethyl-2-hepten-4-ynyl)-N-methyl-3-(3-phenylbenzyloxy)benzylamine hydrochloride (compound 74)

Melting point: 147°-148° C.,

IR$\nu_{max}^{KBr}$ cm$^{-1}$: 2974, 2486, 1458, 1263, 1164, 1035, 756, 699.

NMR(CDCl$_3$)δ: 1.25(9H, s), 2.59(3H, s), 3.47-3.53 (2H, m), 3.99-4.12(2H, m), 5.23(2H, s), 5.81(1H, d, J=15.8Hz), 6.24(1H, dt, J=15.8Hz, 7.2Hz), 7.05-7.10(2H, m), 7.32-7.69(11H, m).

EXAMPLE 58

(E)-N-(6,6-dimethyl-2-hepten-4-ynyl)-N-methyl-(3-methyl-2-furylmethyloxy)benzylamine (compound 75)

IR$\nu_{max}^{neat}$ cm$^{-1}$:2974, 1602, 1491, 1458, 1368, 1263, 1158, 1017.

NMR(CDCl$_3$)δ: 1.24(9H, s), 2.09(3H, s), 2.19(3H, s), 3.04(2H, d, J=6.6Hz), 3.47(2H, s), 4.95 (2H, s), 5.65(1H, dt, J=15.9Hz, 1.5Hz), 6.09(1H, dt, J=15.9Hz, 6.6Hz), 6.24 (1H, d, J=1.9Hz), 6.85-6.98(3H, m), 7.22(1H, t, J=7.8Hz), 7.35(1H, d, J=1.9Hz).

EXAMPLE 59

(E)-N-(6,6-dimethyl-2-hepten-4-ynyl)-N-methyl-3-(2-methyl-3-furylmethyloxy)benzylamine (compound 76)

IR$\nu_{max}^{neat}$ cm$^{-1}$:2968, 2926, 1599, 1458, 1365, 1265, 1143, 1028.

NMR(CDCl$_3$)δ:1.26(9H,s), 2.19(3H,s), 2.32(3H,s), 3.05(2H, dd, J=6.6Hz, 1.5Hz), 3.46 (2H, s), 4.84(2H, s), 5.65(1H, dt, J=15.9Hz, 1.5Hz), 6.08(1H, dt, J=15.9Hz, 6.6Hz), 6.48(1H, d, J=2.0Hz), 6.84(1H, dd, J=6.8Hz, 2.7Hz), 6.90(1H, d, J=6.8Hz), 6.95-6.96(1H, m), 7.22(1H, t, J=6.8Hz), 7.86(1H, d, J=2.0Hz).

EXAMPLE 60

(E)-N-(6,6-dimethyl-2-hepten-4-ynyl)-N-methyl-3-(5-isoxazolylmethyloxy)benzylamine (compound 77)

Melting point: 55°-56° C.
IR$\nu_{max}^{KBr}$ cm$^{-1}$:2972, 1600, 1382, 1258, 1164, 1026, 776.
NMR(CDCl$_3$)δ: 1.24(9H, s), 2.18(3H, s), 3.04(2H, dd, J=6.5Hz, 1.5Hz), 3.46(2H, s), 5.19 (2H, s), 5.65(1H, dt, J=15.9Hz, 1.5Hz), 6.08(1H, dt, J=15.9Hz, 6.5Hz), 6.33-6.36 (1H, m), 6.81-6.87(1H, m), 6.92-6.99 (2H, m), 7.24(1H, t, J=8.0Hz), 8.24 (1H, d, J=1.8Hz).

EXAMPLE 61

(E)-N-(6,6-dimethyl-2-hepten-4-ynyl)-N-methyl-3-(4-pyridylmethyloxy)benzylamine hydrochloride (compound 78)

IR$\nu_{max}^{KBr}$ cm$^{-1}$:3442, 2974, 2626, 1644, 1611, 1266, 792.

NMR(CDCl$_3$)δ: 1.25(9H, s), 2.65(3H, s), 3.45-3.77 (2H, m), 3.96-4.31(2H, m), 5.63(2H, s), 5.87(1H, d, J=14.8Hz), 6.10-6.26(1H, m), 6.97(1H, d, J=7.5Hz), 7.15(1H, d, J=7.8Hz), 7.37(1H, t, J=7.5Hz), 8.00-8.20(3H, m), 8.60-8.80(2H, m).

EXAMPLE 62

(E)-N-(6,6-dimethyl-2-hepten-4-ynyl)-N-methyl-3-(2-thienylmethyloxy)benzylamine (compound 79)

IR$\nu_{max}^{neat}$ cm$^{-1}$:2974, 1587, 1491, 1458, 1365, 1263, 1023, 699.

NMR(CDCl$_3$)δ: 1.24(9H, s), 2.18(3H, s), 3.03(2H, dd, J=6.6Hz, 1.5Hz), 3.46(2H, s), 5.22(2H, s), 5.64(1H, dt, J=15.8Hz, 1.5Hz), 6.08(1H, dt, J=15.8Hz, 6.5Hz), 6.87(1H, ddd, J=8.2Hz, 2.6Hz, 0.8Hz), 6.91(1H, d, J=7.6Hz), 6.97-7.02(2H, m), 7.10-7.12 (1H, m), 7.22(1H, t, J=7.8Hz), 7.32 (1H, dd, J=5.0Hz, 1.2Hz).

EXAMPLE 63

(E)-N-(6,6-dimethyl-2-hepten-4-ynyl)-N-methyl-3-(8-quinolylmethyloxy)benzylamine hydrochloride (compound 80)

Melting point: 99°-101° C.
IR$\nu_{max}^{KBr}$ cm$^{-1}$:2968, 1599, 1506, 1491, 1365, 1269, 1152, 1020, 822, 789.
NMR(CDCl$_3$)δ: 1.24(9H, s), 2.17(3H, s), 3.03(1H, dd, J=6.7Hz, 1.5Hz), 3.46(2H, s), 5.64(1H, dd, J=16.0Hz, 1.5Hz), 5.84 (2H, s), 6.08(1H, dd, J=16.0Hz, 6.7Hz), 6.91(1H, d, J=7.7Hz), 6.98(1H, dd, J=6.8Hz, 1.6Hz), 7.23(1H, dd, J=7.7Hz, 6.8Hz), 7.45(1H, dd, J=8.3Hz, 4.2Hz), 7.57(1H, dd, J=8.5Hz, 7.0Hz), 7.83(1H, d, J=8.5Hz), 7.95(1H, dd, J=7.0Hz, 0.9Hz), 8.19(1H, dd, J=8.3Hz, 1.6Hz), 8.96(1H, dd, J=4.2Hz, 1.6Hz).

EXAMPLE 64

(E)-N-(6,6-dimethyl-2-hepten-4-ynyl)-N-methyl-3-(2-benzofuranylmethyloxy)benzylamine (compound 81)

Melting point: 66°-67° C.
IR$\nu_{max}^{KBr}$ cm$^{-1}$: 2968, 1602, 1458, 1260, 1014, 966, 792, 753.
NMR(CDCl$_3$)δ: 1.24(9H, s), 2.18(3H, s), 3.03(2H, dd, J=6.6Hz, 1.5Hz), 3.47(2H, s), 5.17(2H, s), 5.65(1H, dt, J=15.9Hz, 1.5Hz), 6.08(1H, dt, J=15.9Hz, 6.6Hz), 6.79(1H, d, J=0.6Hz), 6.88-6.94(2H, m), 7.01-7.03 (1H, m).

EXAMPLE 65

N-(E)-6,6-dimethyl-2-hepten-4-ynyl]-N-methyl-3-(Z)2-methyl-2-butenyloxy)benzylamine hydrochloride (compound 82)

Melting point: 141°-142° C.
IR$\nu_{max}^{KBr}$ cm$^{-1}$:2974, 2626, 2494, 1458, 1266, 1164, 1026, 975.
NMR(CDCl$_3$)δ: 1.25(9H, s), 1.72(3H, dd, J=6.8Hz, 1.0Hz), 1.80-1.84(3H, m), 2.62(3H, s), 3.43-3.58(1H, m), 3.62-3.77(1H, m), 3.94-4.06(1H, m), 4.10-4.23(1H, m), 4.59(2H, s), 5.49-5.59(1H, m), 5.84 (1H, d, J=15.6Hz), 6.27(1H, dt, J=15.6Hz, 7.6Hz), 7.00(1H, dd, J=8.3Hz, 2.1Hz), 7.12(1H, d, J=6.8Hz), 7.29(1H, br), 7.34(1H, dd, J=8.3Hz, 6.8Hz).

EXAMPLE 66

N-[(E)-6,6-dimethyl-2-hepten-4-ynyl]-N-methyl-3-(E)-2-methyl-2-butenyloxy)benzylamine hydrochloride (compound 83)

Melting point: 119°-121° C.
IR$\nu_{max}^{KBr}$ cm$^{-1}$: 2974, 2920, 2626, 2560, 2506, 1458, 1266, 1251, 1164.
NMR(CDCl$_3$)δ: 1.25(9H, s), 1.66(3H, dd, J=6.5Hz, 1.0Hz), 1.73-1.76(3H, m), 2.62(3H, s), 3.44-3.78(2H, m), 3.93-4.24(2H, m), 4.46(2H, s), 5.62-5.72(1H, m), 5.83 (1H, d, J=15.6Hz), 6.26(1H, dt, J=15.6Hz, 7.3Hz), 6.98(1H, dd, J=8.2Hz, 2.0Hz), 7.08(1H, d, J=7.6Hz), 7.27 (1H, m), 7.32(1H, dd, J=8.2Hz, 7.6Hz).

EXAMPLE 67

(E)-N-(6,6-dimethyl-2-hepten-4-ynyl]-N-methyl-3-(2-ethyl-2-propenyloxy)benzylamine (compound 84)

IR$\nu_{max}^{neat}$ cm$^{-1}$:2968, 1458, 1365, 1266, 1152, 1024.
NMR(CDCl$_3$)δ: 1.11(3H, t, J=7.4Hz), 1.24(9H, s), 2.13-2.22(5H, m), 3.04(2H, dd, J=6.6Hz 1.4Hz), 3.45(2H, s), 4.47(2H, s), 4.98 (1H, s), 5.12(1H, s), 5.65(1H, dt, J=15.9Hz, 1.4Hz), 6.09(1H, dt, J=15.9Hz, 6.6Hz), 6.78-6.83(1H, m), 6.86-6.91 (2H, m), 7.20(1H, t, J=7.8Hz).

EXAMPLE 68

(E)-N-(6,6-dimethyl-2-hepten-4-ynyl)-N-methyl-3-(2,3-dimethyl-2-butenyloxy)benzylamine (compound 85)

IR$\nu_{max}^{neat}$ cm$^{-1}$:2974, 2926, 1458, 1266, 1149, 1017.

NMR(CDCl$_3$)δ:1.24(9H, s), 1.74(3H, s), 1.79(6H, s), 2.19(3H, s), 3.04(2H, dd, J=6.6Hz, 1.7Hz), 3.46(2H, s), 4.49(2H, s), 5.65 (1H, dt, J=15.9Hz, 1.7Hz), 6.09(1H, dt, J=15.9Hz, 6.7Hz), 6.78-6.84(1H, m), 6.85-6.93(2H, m), 7.20(1H, t, J=7.8Hz).

EXAMPLE 69

(E)-N-(6,6-dimethyl-2-hepten-4-ynyl)-N-methyl-3-(4-phenylbutoxy)benzylamine (compound 86)

IR$\nu_{max}^{neat}$ cm$^{-1}$:2968, 1602, 1458, 1266, 1152, 696.

NMR(CDCl$_3$)δ: 1.24(9H, s), 1.75-1.90(4H, m), 2.18 (3H, s), 2.62-2.76(2H, m), 3.03(2H, dd, J=6.6Hz, 1.6Hz), 3.45(2H, s), 3.92-4.04 (2H, m), 5.64(1H, dt, J=15.9Hz, 1.5Hz), 6.09(1H, dt, J=15.9Hz, 6.6Hz), 6.74–6.79(1H, m), 6.84–6.89(2H, m), 7.15–7.24(4H, m), 7.25–7.32(2H, m).

EXAMPLE 70

(E)-N-(6,6-dimethyl-2-hepten-4-ynyl)-N-methyl-3-(5-phenylpentoxy)benzylamine (compound 87)

IR$\nu_{max}^{neat}$ cm$^{-1}$:2938, 2866, 2788, 1605, 1458, 1266, 696.

NMR(CDCl$_3$)δ:1.24(9H, s), 1.44–1.58(2H, m), 1.64–1.76(2H, m), 1.76–1.87(2H, m), 2.18(3H, s), 2.65(2H, t, J=7.7Hz), 3.04(2H, dd, J=6.6Hz, 1.5Hz), 3.45 (2H, s), 3.95(2H, t, J=6.5Hz), 5.64 (1H, dt, J=15.9Hz, 1.5Hz), 6.09 (1H, dt, J=15.9Hz, 6.6Hz), 6.74–6.79 (1H, m), 6.84–6.89(2H, m), 7.14–7.23 (4H, m), 7.24–7.31(2H, m).

EXAMPLE 71

(E)-N-(6,6-dimethyl-2-hepten-4-ynyl)-N-methyl-3-(3-formylbenzyloxy)benzylamine (compound 88)

IR$\nu_{max}^{neat}$ cm$^{-1}$:2974, 1707, 1590, 1455, 1266, 1155, 783, 756.

NMR(CDCl$_3$)ν: 2.19(3H, s), 3.04(2H, dd, J=6.6Hz, 1.2Hz), 3.47(2H, s), 5.15(2H, s), 5.64(1H, dt, J=15.9Hz, 1.5Hz), 6.08 (1H, dt, J=15.9Hz, 6.5Hz), 6.86(1H, dd, J=8.2Hz, 2.5Hz), 6.92(1H, d, J=7.6Hz), 6.99–7.00(1H, m), 7.22(1H, t, J=7.9Hz), 7.57(1H, t, J=7.6Hz), 7.72(1H, dt, J=8.0Hz, 0.8Hz), 7.85 (1H, dt, J=7.6Hz, 1.3Hz), 7.96–7.99 (1H, m), 10.05(1H, s).

EXAMPLE 72

Production of (E)-N-(6,6-dimethyl-2-hepten-4-ynyl)-N-methyl-3-(3-hydroxymethylbenzyloxy)benzylamine (compound 89)

85 mg of the (E)-N-(6,6-dimethyl-2-hepten-4-ynyl)-N-methyl-3-(3-formylbenzyloxy)benzylamine obtained as above was dissolved in 2 ml of ethanol, and under ice cooling, 8.6 mg of sodium borohydride was added with stirring for 30 minutes. The solvent was evaporated under reduced pressure. The residue was dissolved in a mixture of ethyl acetate and water. The organic layer was separated, and dried over anhydrous magnesium sulfate. The desiccant was removed by filtration, and the solvent was evaporated. The residue was purified by silica gel column chromatography (Wakogel C-200, 15 g; eluting solvent: hexane/ethyl acetate=10/1→5/1) to give 40 mg (yield 39%) of the captioned compound as a colorless oil.

IR$\nu_{max}^{neat}$ cm$^{-1}$:2972, 1588, 1492, 1458, 1366, 1266, 1158, 1028, 784.

NMR(CDCl$_3$)δ: 1.24(9H, s), 2.18(3H, s), 3.03(2H, dd, J=6.6Hz, 1.5Hz), 3.46(2H, s), 4.73(2H, s), 5.07(2H, s), 5.64(1H, dt, J=15.8Hz, 1.5Hz), 6.07(1H, dt, J=15.8Hz, 6.5Hz), 6.84–6.91(2H, m), 6.97–6.99(1H, m), 7.22(1H, t, J=7.8Hz), 7.31–7.39(3H, m), 7.46–7.47(1H, m).

EXAMPLE 73

Production of N-[(E)-6,6-dimethyl-2-hepten-4-ynyl]-N-methyl-3-[(E)-styryl]benzylamine hydrochloride (compound 90)

133 mg of (E)-3-bromomethylstilbene was dissolved in 5 ml of dimethylformamide, and 86 mg of (E)-N-methyl-6,6-dimethyl-2-hepten-4-ynylamine hydrochloride and 200 mg of potassium carbonate were added. The mixture was stirred overnight at room temperature. The reaction mixture was diluted with water, and extracted with isopropyl ether. The extract was washed with water, and dried over anhydrous sodium sulfate. The desiccant was removed by filtration, and then the solvent was evaporated. The residue was purified by preparative thin-layer chromatography thin-layer plate: Kieselgel 60F$_{254}$, Art. 5744 (a product of E. Merck Co.); developing solvent: hexane/ethyl acetate=5/1]to give 150 mg (yield 89.7%) of the captioned compound as a colorless oil.

IR$\nu_{max}^{KBr}$ cm$^{-1}$:3020, 2866, 2788, 1500, 1455, 1266, 1134, 963, 768, 696.

NMR(CDCl$_3$)δ: 1.24(9H, s), 2.21(3H, s), 3.07(2H, dd, J=6.6Hz, 1.5Hz), 3.51(2H, s), 5.68 (1H, dt, J=15.9Hz, 1.5Hz), 6.12(1H, dt, J=15.9Hz, 6.6Hz), 7.11(2H, s), 7.19–7.53(9H, m).

Compounds of Examples 74 to 77 were obtained by repeating Example 73 except that instead of the starting (E)-3-bromomethylstilbene, the corresponding brominated derivatives were used.

EXAMPLE 74

N-(E)-6,6-dimethyl-2-hepten-4-ynyl)-N-methyl-3-[(Z)-styryl]benzylamine (compound 91)

IR$\nu_{max}^{neat}$ cm$^{-1}$:3022, 2866, 2788, 1497, 1455, 1308, 1200, 1026, 837, 774.

NMR(CDCl$_3$)δ:1.24(9H, s), 2.11(3H, s), 2.97(1H, dd, J=6.6Hz, 1.5Hz), 3.37(2H, s), 5.59(1H, dt, J=15.9Hz, 1.5Hz), 6.02(1H, dt, J=15.9Hz, 6.6Hz), 6.59(2H, s), 7.11–7.21(9H, m).

EXAMPLE 75

N-[(E)-6,6-dimethyl-2-hepten-4-ynyl-N-methyl-3-(E)-o-methylstyryl)benzylamine (compound 92)

IR$\nu_{max}^{neat}$ cm$^{-1}$:3028, 2968, 2866, 2782, 1605, 1491, 1461, 1365, 1266, 1134, 1026, 963, 783, 714, 693.

NMR(CDCl$_3$)δ:1.25(9H, s), 2.23(3H, s), 2.45(3H, s), 3.08(2H, dd, J=6.7Hz, 1.5Hz), 3.52 (2H, s), 5.68(1H, dt, J=15.9Hz, 1.5Hz), 6.12(1H, dt, J=15.9Hz, 6.7Hz), 6.99 (1H, d, J=16.1Hz), 7.17–7.61(9H, m).

EXAMPLE 76

N-[(E)-6,6-dimethyl-2-hepten-4-ynyl]-N-methyl-3-(E)-2-(1-naphthylvinyl)]benzylamine (compound 93)

IR$\nu_{max}^{neat}$ cm$^{-1}$:3034, 2866, 2788, 1479, 1398, 1266, 1131, 963, 768.

NMR(CDCl$_3$)δ: 1.25(9H, s), 2.24(3H, s), 3.10(1H, dd, J=6.6Hz, 1.5Hz), 3.54(2H, s), 5.68 (1H, dt, J=15.9Hz, 1.5Hz), 6.14(1H, dt, J=15.9Hz, 6.6Hz), 7.15(1H, d, J=16.2Hz), 7.24–8.26(11H, m).

EXAMPLE 77

(E)-N-(6,6-dimethyl-2-hepten-4-ynyl)-N-methyl-3-(2-phenylethynyl)benzylamine (compound 94)

IR$\nu_{max}^{KBr}$ cm$^{-1}$:2968, 2788, 1605, 1497, 1365, 1026, 966, 756, 690.

NMR(CDCl$_3$)δ: 1.24(9H, s), 2.19(3H, s), 3.06(2H, dd, J=6.6Hz, 1.4Hz), 3.48(2H, s), 5.66 (1H, dt, J=15.9Hz, 1.4Hz), 6.10(1H, dt, J=15.9Hz, 6.6Hz), 7.26–7.44(6H, m), 7.50–7.55(3H, m).

EXAMPLE 78

Production of
(E)-N-(6,6-dimethyl-2-hepten-4-ynyl)-N-methyl-3-benzylaminobenzylamine (compound 95)

125 mg of 3-benzylaminobenzyl alcohol hydrochloride was suspended in 5 ml of chloroform, and 0.2 ml of thionyl chloride was added. The mixture was stirred at room temperature for 3 hours. The reaction mixture was concentrated under reduced pressure. The residue was washed with ethyl ether and then dissolved in dimethylformamide. 85 mg of (E)-N-methyl-6,6-dimethyl-2-hepten-4-ynylamine hydrochloride and 300 mg of potassium carbonate were added. The mixture was stirred overnight at room temperature. The reaction mixture was diluted with ethyl acetate. The extract was washed with a saturated aqueous sodium chloride solution and dried over anhydrous sodium sulfate. The desiccant was removed by filtration, and the solvent was evaporated under reduced pressure. The residue was purified by preparative thin-layer chromatography thin-layer plate: Kieselgel 60$F_{254}$, Art. 5744 (a product of E. Merck Co.); developing solvent: hexane/ethyl acetate=3/1] to give 100 mg (yield 57.5%) of the captioned compound as a pale yellow oil.

IR$\nu_{max}^{neat}$ cm$^{-1}$:3430, 2968, 2788, 1497, 1458, 1335, 1200, 1128, 966, 777, 696.

NMR(CDCl$_3$)δ: 1.24(9H, s), 2.17(3H, s), 3.01(2H, dt, J=6.7Hz, 1.5Hz), 3.40(2H, s), 4.32 (2H, s), 5.62(1H, dt, J=15.9Hz, 1.5Hz), 6.09(1H, dt, J=15.9Hz, 6.7Hz), 6.50–6.53(1H, m), 6.63–6.66(2H, m), 7.10(1H, t, J=7.5Hz), 7.25–7.39 (5H, m).

Compounds of Examples 79 and 80 were obtained by repeating Example 85 except that instead of the starting 3-benzylaminobenzyl alcohol hydrochloride, the corresponding benzyl alcohol hydrochlorides were used. (In Example 87, the resulting free base was treated in a customary manner with a HCl/methanol/ethyl ether solution to convert it to a hydrochloride.)

EXAMPLE 79

(E)-N-(6,6-dimethyl-2-hepten-4-ynyl)-N-methyl-3-(2-methylbenzylamino)benzylamine hydrochloride (compound 96)

IR$\nu_{max}^{neat}$ cm$^{-1}$:3432, 2972, 2778, 1608, 1364, 772, 746.

NMR(CDCl$_3$)δ: 1.24(9H, s), 2.19(3H, s), 2.38(3H, s), 3.03(2H, dd, J=6.6Hz, 1.5Hz), 3.42 (2H, s), 4.27(2H, s), 5.63(1H, dt, J=15.9Hz, 2.8Hz), 6.08(1H, dt, J=15.9Hz, 6.6Hz), 6.52(1H, ddd, J=8.2Hz, 2.5Hz, 1.2Hz), 6.63–6.67(2H, m), 7.09–7.19 (4H, m), 7.31–7.34(1H, m).

EXAMPLE 80

(E)-N-(6,6-dimethyl-2-hepten-4-ynyl)-N-methyl-3-anilinomethylbenzylamine hydrochloride (compound 97)

Melting point: 120°–122° C.

IR$\nu_{max}^{KBr}$ cm$^{-1}$:3418, 2632, 1635, 1602, 1461, 1365, 1263, 756, 549.

NMR(CDCl$_3$)δ: 1.25(9H, s), 2.62(3H, s), 3.65–3.78 (2H, m), 4.05(1H, br), 4.31(1H, br), 4.42(2H, s), 5.92(1H, d, J=15.9Hz), 6.10–6.30(1H, m), 7.20–8.00(9H, m).

EXAMPLE 81

Production of
(E)-N-(6,6-dimethyl-2-hepten-4-ynyl)-N-methyl-3-(N-methylbenzylamino)benzylamine (compound 98)

250 mg of N-benzyl-N-methyl-3-hydroxymethylaniline hydrochloride was dissolved in 10 ml of chloroform, and 1 ml of thionyl chloride was added. The mixture was stirred at room temperature for 3 hours. The reaction mixture was evaporated under reduced pressure, and the residue was dissolved in 3 ml of dimethylformamide. 163 mg of (E)-N-methyl-6,6-dimethyl-2-hepten-4-ynylamine hydrochloride and 120 mg of sodium carbonate were added, and the mixture was stirred overnight at room temperature. Water (15 ml) was added to the reaction mixture, and the mixture was extracted with 15 ml of ethyl ether twice. The extracts were combined, washed with 10 ml of a saturated aqueous sodium chloride solution, and then dried over anhydrous magnesium sulfate. The desiccant was removed by filtration, and the solvent was evaporated. The residue was purified by preparative thin-layer chromatography thin-layer plate: Kieselgel 60$F_{254}$, Art. 5744 (a product of E. Merck Co.); developing solvent: chloroform/ethyl acetate=10/1]. Recrystallization from hexane gave 183 mg (yield 58.5%) of the captioned compound as colorless needles having a melting point of 62° to 63° C.

IR$\nu_{max}^{KBr}$ cm$^{-1}$:2974, 1602, 1458, 1383, 1365.

NMR(CDCl$_3$)δ: 1.24(9H, s), 3.00(3H, s), 3.43 (3H, s), 3.43–3.47(2H, m), 4.53 (2H, s), 5.61(1H, dt, J=15.9Hz, 1.4Hz), 6.05(1H, dt, J=15.9Hz, 6.6Hz), 6.61–6.67(2H, m), 6.72–6.73(1H, m), 7.15–7.17(1H, m), 7.21–7.34(5H, m).

EXAMPLE 82

(E)-N-(6,6-dimethyl-2-hepten-4-ynyl)-N-methyl-3-benzylthiobenzylamine (compound 99)

Methyl 3-benzylthiobenzoate (120 mg) was dissolved in 5 ml of anhydrous tetrahydrofuran, and with stirring under ice cooling, 10 mg of lithium aluminum hydride was added by portions over the course of 5 minutes. The mixture was stirred at this temperature for 10 minutes. Twenty milliliters of a 5% aqueous solution of ammonium chloride was added to decompose the excess of the reducing agent. The mixture was then extracted with 20 ml of ethyl ether twice. The extracts were combined, and dried over anhydrous magnesium sulfate. The solvent was evaporated to give 100 ml (yield 93%) of 3-benzylthiobenzyl alcohol as a colorless oil.

One hundred milligrams of the alcohol obtained above was dissolved in 10 ml of chloroform, and 0.3 ml of thionyl chloride was added. The mixture was reacted at room temperature for 2 hours. The reaction mixture was concentrated under reduced pressure, and the residue was dissolved in 20 ml of water and 20 ml of ethyl ether. The ether layer was separated, and the solvent was evaporated. The residue was purified by medium-pressure liquid chromatography column: Lobar column, size A, Lichroprep Si 60F (a product of E. Merck Co.); eluting solvent: hexane] to give 55 mg (yield 51%) of 3-benzylthiobenzyl chloride as a colorless oil.

The resulting chloride (55 mg) was dissolved in 3 ml of dimethylformamide, and 50 mg of (E)-N-methyl-6,6-dimethyl-2-hepten-4-ynylamine hydrochloride and 50 mg of potassium carbonate were added. The mixture was stirred overnight at room temperature. Water (20 ml) and 20 ml of ethyl ether were added to the reaction mixture, and the organic layer was separated, washed with a saturated aqueous sodium chloride solution and then dried over anhydrous magnesium sulfate. The desiccant was removed by filtration, and the solvent was evaporated. The residue was purified by medium-pressure liquid chromatography column: Lobar column, size A, Lichroprep Si 60F (a product of E. Merck Co.); eluting solvent: hexane/ethyl acetate=20/11 to give 37 mg (yield 46%) of the captioned compound as a colorless oil.

IR$\nu_{max}^{neat}$ cm$^{-1}$: 2974, 2788, 1458, 1365, 966, 777, 696.

NMR(CDCl$_3$)$\delta$: 1.24(9H, s), 2.13(3H, s), 2.99(2H, dd, J=6.6Hz, 1.5Hz), 3.40(2H, s), 4.11 (2H, s), 5.63(1H, dt, J=15.9Hz, 1.5Hz), 6.06(1H, dt, J=15.9Hz, 6.6Hz), 7.09–7.30(9H, m).

EXAMPLE 83

(E)-N-(6,6-dimethyl-2-hepten-4-ynyl)-N-methyl-3-(beta-phenethyl)benzylamine (compound 100)

Ethyl 3-phenethylbenzoate (180 mg) was dissolved in 2 ml of anhydrous tetrahydrofuran, and under ice cooling, 42 mg of lithium aluminum hydride was added by portions over 5 minutes. The mixture was stirred for one hour under ice cooling. Water (10 ml) was added to the reaction mixture to decompose the excess of the reducing agent. The mixture was then extracted with 20 ml of ethyl ether. The extract was separated, washed with a saturated aqueous sodium chloride solution, and dried over anhydrous sodium sulfate. The solvent was evaporated to give 140 mg (yield 93%) of 3-phenethylbenzyl alcohol.

The resulting alcohol (140 mg) was dissolved in 1 ml of chloroform, and 0.3 ml of thionyl chloride was added. The mixture was reacted at room temperature for 30 minutes. The reaction mixture was evaporated under reduced pressure to give 150 mg (yield 99%) of 3-phenethylbenzyl chloride as a pale yellow oil.

The resulting chloride (150 mg) was dissolved in 1 ml of dimethylformamide, and 124 mg of (E)-N-methyl-6,6-dimethyl-2-hepten-4-ynylamine hydrochloride and 300 mg of potassium carbonate were added, and the mixture was stirred overnight at room temperature. Water (10 ml) and 20 ml of ethyl acetate were added to the reaction mixture. The organic layer was separated, washed with a saturated aqueous sodium chloride solution and dried over anhydrous sodium sulfate. The desiccant was removed by filtration, and the solvent was evaporated. The residue was purified by silica gel column chromatography [Wakogel C-200, 20 g; eluting solvent: hexane/ethyl acetate=10/1) to give 150 mg (yield 58%) of the captioned compound as a colorless oil.

IR$\nu_{max}^{neat}$ cm$^{-1}$:3028, 2866, 1608, 1458, 1365, 1269, 1206, 786, 699.

NMR(CDCl$_3$)$\delta$: 1.24(9H, s), 2.16(3H, s), 2.91(4H, s), 3.02(2H, dd, J=6.6Hz, 1.5 Hz), 3.45 (2H, s), 5.64(1H, d, J=15.9Hz), 6.08 (1H, dt, J=15.9Hz, 6.6Hz), 7.05–7.30 (9H, m).

EXAMPLE 84

Production of (E)-N-(6,6-dimethyl-2-hepten-4-ynyl)-N-methyl-3-[(E)-2-(2-pyridyl)vinyl]benzylamine (compound 101)

3.9 g of (2-pyridyl)methyltriphenylphosphonium chloride was suspended in 20 ml of tetrahydrofuran, and with stirring, 5.3 ml of a 20% aqueous solution of potassium carbonate and 0.13 g of isophthalaldehyde were added. The mixture was stirred overnight at room temperature. Hexane was added, and the resulting aqueous layer was discarded, and concentrated under reduced pressure. Hexane was added to the residue. The insoluble matter was removed by filtration, and the filtrate was evaporated under reduced pressure. The residue was purified by medium-pressure liquid chromatography [column: Lobar column, size B, Lichroprep Si 60 (a product of E. Merck Co.); eluting solvent: hexane/ethyl acetate=7/1→4/1]to give 0.76 g (yield 36%) of (E)-2-[2-(3-formylphenyl)vinyl]pyridine.

The resulting vinyl pyridine (573 mg) was dissolved in 5 ml of methanol, and under ice cooling, 104 mg of sodium borohydride was added. The mixture was stirred at room temperature for 30 minutes. The reaction mixture was concentrated under reduced pressure, and water and ethyl acetate were added to the residue. The organic layer was separated and evaporated under reduced pressure. The residue was dissolved in 5 ml of chloroform and under ice cooling, 0.17 ml of thionyl chloride was added. The mixture was stirred at room temperature for 1 hour. The reaction mixture was evaporated under reduced pressure, and the residue was treated with ethyl ether to give 412 mg (yield 57%) of (E)-2-2-(3-chloromethylphenyl)vinyl]pyridine hydrochloride as colorless needles having a melting point of 159° to 160° C. The resulting hydrochloride was dissolved in 5 ml of dimethylformamide, and 219 mg of (E)-N-methyl-6,6-di-methyl-2-hepten-4-ynylamine hydrochloride and 166 mg of potassium carbonate were added, and the mixture was stirred overnight at room temperature. The reaction mixture was diluted with water and benzene. The organic layer was separated and evaporated, then the residue was purified by medium-pressure liquid chromatography [column: Lobar column, size B, Lichroprep Si 60 (a product of E. Merck Co.); eluting solvent: hexane/ethyl acetate=6/1→3/1] to give 277 mg (yield 67%) of the captioned compound as a colorless oil.

IR$\nu_{max}^{neat}$ cm$^{-1}$:2968, 2788, 1587, 1473, 1440, 1365, 1266, 966, 792, 756, 696, 552.

NMR(CDCl$_3$)$\delta$: 1.25(9H, s), 2.21(3H, s), 3.07(2H, dd, J=6.6Hz, 1.5Hz), 3.51(2H, s), 5.67 (1H, d, J=15.8Hz), 6.11(1H, dt, J=15.9Hz, 6.6Hz), 7.12–7.69(9H, m), 8.60(1H, dd, J=5.0Hz, 1.1Hz).

EXAMPLE 85

Production of (E)-N-(6,6-dimethyl-2-hepten-4-ynyl)-2-benzyloxy-6-pyridylmethylamine dihydrochloride (compound 102)

91 mg of 2-benzyloxy-6-chloromethylpyridine was dissolved in 1.2 ml of dimethylformamide, and 110 mg of (E)-N-methyl-6,6-dimethyl-2-hepten-4-ynylamine hydrochloride and 96 mg of potassium carbonate were added. The mixture was stirred overnight at room temperature. The reaction mixture was concentrated under reduced pressure, and the residue was dissolved in chloroform. The inorganic salts were removed by filtration and the filtrate was evaporated and purified by thin-layer chromatography [thin layer plate: Kieselgel 60F$_{254}$, Art. 5715 (a product of E. Merck Co.); developing solvent: hexane/ethyl acetate=3/1] to give 115 mg of the free base of the captioned compound as a pale yellow oil. The product was dissolved in 3 ml of methanol, and 0.26 ml of a 30% hydrogen chloride/methanol solution was added. The mixture was concentrated under reduced pressure. Recrystallization of the residue from a mixture of ethyl ether and hexane gave 108 mg (yield 68%) of the captioned compound as a colorless crystalline powder having a melting point of 103° to 106° C.

IR$\nu_{max}^{KBr}$cm$^{-1}$: 3448, 2968, 2866, 2596, 1635, 1608, 1578, 1458, 1368, 1320, 1266, 969.

NMR(CDCl$_3$)δ: 1.24(9H, s), 2.67(3H, s), 3.54–3.64 (1H, m), 3.71–3.80(1H, m), 4.37(2H, s), 5.49(2H, s), 5.80(1H, d, J=15.5Hz), 6.25(1H, dt, J=15.5Hz, 7.5Hz), 6.98 (1H, d, J=7.9Hz), 7.30–7.44(5H, m), 7.49(1H, d, J=7.9Hz), 7.82(1H, t, J=7.9Hz).

Compounds of Examples 86 to 88 were obtained by repeating Example 85 except that instead of the starting 2-benzyloxy-6-chloromethylpyridine, the corresponding chloromethylpyridines were used.

EXAMPLE 86

(E)-N-(6,6-dimethyl-2-hepten-4-ynyl)-N-methyl-4-benzyloxy-2-pyridylmethylamine dihydrochloride (compound 103)

Melting point: 126°–128° C.,

IR$\nu_{max}^{KBr}$ cm$^{-1}$:3454, 2968, 2596, 1635, 1500, 1461, 1332, 966.

NMR(CDCl$_3$)δ: 1.24(9H, s), 2.85(3H, s), 3.72–3.77 (1H, m), 3.86(1H, d, J=7.6Hz), 4.90 (2H, s), 5.52(2H, s), 5.96(1H, d, J=15.6Hz), 6.27(1H, dt, J=15.6Hz, 7.6Hz), 7.26–7.54(1H, m), 8.41(1H, d, J=6.5Hz), 8.82–8.84(1H, m).

EXAMPLE 87

(E)-N-(6,6-dimethyl-2-hepten-4-ynyl)-N-methyl-2-(2-methylbenzyloxy)-6-pyridylmethylamine (compound 104)

IR$\nu_{max}^{neat}$ cm$^{-1}$:2968, 1599, 1581, 1455, 1311, 1266, 1005.

NMR(CDCl$_3$)δ: 1.24(9H, s), 2.28(3H, s), 2.41(3H, s), 3.14(2H, dd, J=6.4Hz, 1.4Hz), 3.59 (2H, s), 5.35(2H, s), 5.68(1H, dd, J=15.9Hz, 1.4Hz), 6.11(1H, dt, J=15.9Hz, 6.4Hz), 6.64(1H, d, J=7.9Hz), 6.98 (1H, d, J=7.1Hz), 7.19–7.45(4H, m), 7.54(1H, dd, J=7.9Hz, 7.1Hz).

EXAMPLE 88

(E)-N-(6,6-dimethyl-2-hepten-4-ynyl)-N-methyl-4-(2-methylbenzyloxy)-2-pyridylmethylamine (compound 105)

IR$\nu_{max}^{neat}$ cm$^{-1}$:2968, 1596, 1566, 1461, 1365, 1308, 1014, 747.

NMR(CDCl$_3$)δ: 1.24(9H, s), 2.25(3H, s), 2.38(3H, s), 3.61(2H, s), 5.09(2H, s), 5.66(1H, dt, J=15.9Hz, 3.4Hz), 6.09(1H, dt, J=15.9Hz, 6.6Hz), 6.77(1H, dd, J=6.4Hz, 2.7Hz), 7.08(1H, d, J=2.4Hz), 7.20–7.31(3H, m), 7.37–7.40(1H, m), 8.35(1H, d, J=5.6Hz).

EXAMPLE 89

Production of N-[(E)-6,6-dimethyl-2-hepten-4-ynyl]-N-methyl-5-[(E)-styryl)-3-pyrazolylmethylamine dihydrochloride (compound 106)

The same reaction as in Example 85 was repeated except that (E)-3-chloromethyl-5-styrylpyrazole was used instead of 2-benzyloxy-6-chloromethylpyridine. The product was recrystallized from a mixture of acetone and ethyl acetate to give the captioned compound as colorless needles having a melting point of 198° to 200° C.

IR$\nu_{max}^{KBr}$ cm$^{-1}$:3130, 2968, 2482, 1464, 966, 750, 696.

NMR(CDCl$_3$)δ: 1.24(9H, s), 2.72(3H, s), 3.72(2H, br), 4.23(2H, s), 5.94(1H, d, J=15.6Hz), 6.14–6.24(1H, m), 6.78(1H, s), 6.97(1H, d, J=16.6Hz), 7.15(1H, d, J=16.6Hz), 7.28–7.40(3H, m), 7.49(2H, d, J=7.2Hz).

EXAMPLE 90

N-(E)-6,6-dimethyl-2-hepten-4-ynyl]-N-methyl-5-(Z)-styryl)furfurylamine (compound 107)

Fifty milligrams of (Z)-2-hydroxymethyl-5-styrylfuran and 24.3 microliters of anhydrous pyridine were dissolved in 1.5 ml of anhydrous ethyl ether, and at −30° C., 0.5 ml of an anhydrous ethyl ether solution of 18.2 microliters of thionyl chloride was added dropwise with stirring in an atmosphere of nitrogen. After the addition, the mixture was stirred for 2 days at 10° C. Then, 75 mg of (E)-N-methyl-6,6-dimethyl-2-hepten-4-ynylamine hydrochloride, 111 mg of potassium carbonate and 1 ml of dimethylformamide were added to the resulting solution, and the mixture was stirred overnight at room temperature. The reaction mixture was concentrated under reduced pressure, and the residue was purified by silica gel column chromatography Wakogel C-200 5 g; eluting solvent: hexane/ethyl acetate=5/1) to give 45 mg (yield 54%) of the captioned compound as a pale yellow oil.

IR$\nu_{max}^{neat}$ cm$^{-1}$:2968, 1455, 1365, 1266, 1020, 966, 795, 696.

NMR(CDCl$_3$)δ:1.25(9H, s), 2.20(3H, s), 3.01(2H, dd, J=6.7Hz, 1.4Hz), 3.48(2H, s), 5.60(1H, dt, J=15.7Hz, 1.4Hz), 6.03(1H, dt, J=15.7Hz, 6.7Hz), 6.10(1H, d, J=3.4Hz), 6.17(1H, d, J=3.4Hz), 7.22–7.36(3H, m), 7.42–7.48(2H, m).

EXAMPLE 91

Production of N-[(E)-6,6-dimethyl-2-hepten-4-ynyl)-N-methyl-5-[(E)-styryl]furfurylamine (compound 108)

Example 90 was repeated except that (E)-2-hydroxymethyl-5-styrylfuran was used instead of (Z)-2-hydroxymethyl-5-styrylfuran. The captioned compound was obtained as a pale yellow oil.

IR$\nu_{max}^{neat}$ cm$^{-1}$:2968, 1662, 1608, 1266, 756.

NMR(CDCl$_3$)δ: 1.25(9H, s), 2.29(3H, s), 3.10(2H, dd, J=6.8Hz, 1.5Hz), 3.59(2H, s), 5.67(1H, dt, J=15.9Hz, 1.5Hz), 6.10(1H, dt, J=15.9Hz, 6.8Hz), 6.22(1H, d, J=16.2Hz), 7.01(1H, d, J=16.2Hz), 7.19–7.24(1H, m), 7.29–7.37(2H, m), 7.42–7.48(2H, m).

EXAMPLE 92

The same reaction as in Example 90 was carried out except that a mixture of (E)- and (Z)-2-hydroxymethyl-4-styrylthiazoles was used instead of (Z)-2-hydroxymethyl-5-styrylfuran. The product containing a mixture of the (E)-form and (Z)-form were separated and purified by preparative thin-layer chromatography [thin-layer plate: Kieselgel 60F$_{254}$, Art. 5744 (a product of E. Merck Co.); developing solvent: toluene/ethyl acetate/aqueous 20% ammonia=240/100/1] to give the following compounds as pale yellow oils.

N-(E)-6,6-dimethyl-2-hepten-4-ynyl]-N-methyl-2-(Z)-styryl)-4-thiazolylmethylamine (compound 109)

IR$\nu_{max}^{KBr}$ cm$^{-1}$:2968, 1458, 1365, 1266, 963, 750, 696.

NMR(CDCl$_3$)δ: 1.23(9H, s), 2.24(3H, s), 3.09(2H, dd, J=6.6Hz, 1.5Hz), 3.62(2H, s), 5.63(1H, dt, J=15.9Hz, 1.5Hz), 6.09(1H, dt, J=15.9Hz, 6.6Hz), 6.88(1H, dd, J=11.9Hz, 1.3Hz), 6.91(1H, s), 6.95(1H, d, J=11.9Hz), 7.36-7.40(5H, m).

N-[(E)-6,6-dimethyl-2-hepten-4-ynyl)-N-methyl-2-(E)-styryl]-4-thiazolylmethylamine (compound 110)

IR$\nu_{max}^{neat}$ cm$^{-1}$:2968, 2926, 1458, 1365, 1266, 960, 750, 690.

NMR(CDCl$_3$)δ:1.24(9H, s), 2.29(3H, s), 3.13(2H, dd, J=6.7Hz, 1.6Hz), 3.67(2H, s), 5.67(1H, dt, J=15.9Hz, 1.6Hz), 6.19(1H, dt, J=15.9Hz, 6.7Hz), 7.05(1H, s), 7.30 (1H, d, J=16.2Hz), 7.38(1H, d, J=16.2Hz), 7.26-7.40(3H, m), 7.51-7.53 (2H, m).

EXAMPLE 93

N-[(E)-6,6-dimethyl-2-hepten-4-ynyl]-N-methyl-2-(E)-styryl]-4-oxazolylmethylamine (compound 111)

Example 90 was repeated except that (E)-2-hydroxymethyl-5-styryloxazole was used instead of (Z)--hydroxymethyl-5-styrylfuran. The captioned compound was obtained as a colorless oil.

IR$\nu_{max}^{neat}$ cm$^{-1}$:2968, 1716, 1455, 960, 750, 693.

NMR(CDCl$_3$)δ: 1.24(9H, s), 2.35(3H, s), 3.18(2H, dd, J=6.7Hz, 1.4Hz), 3.74(2H, s), 5.70(1H, dt, J=15.7Hz, 1.4Hz), 6.09(1H, dt, J=15.7Hz, 6.7Hz), 6.87(1H, d, J=16.4Hz), 6.99(1H, s), 7.08(1H, d, J=16.4Hz), 7.25-7.40(3H, m), 7.45-7.51(2H, m).

EXAMPLE 94

Production of (E)- and (Z)-N-methyl-N-(2-nonen-4-ynyl)-3-benzyloxybenzylamine

Two hundred milligrams of N-methyl-3-benzyloxybenzylamine hydrochloride was dissolved in 3 ml of dimethylformamide, and 152 mg of 1-bromo-2-nonen-4-yne (a mixture of the E- and Z-forms) and 80 mg of sodium carbonate were added. The mixture was stirred overnight at room temperature. Water (15 ml) was added to the reaction mixture to dilute it. The mixture was extracted with 10 ml of ethyl ether twice. The extracts were combined, washed with 10 ml of a saturated aqueous sodium chloride solution, and dried over anhydrous magnesium sulfate. The solvent was evaporated, and the residue was purified by preparative chromatography [thin-layer plate: Kieselgel 60F$_{254}$, Art. 5744 (a product of E. Merck Co.1; developing solvent: chloroform/ethyl acetate=10/1] to give the following compounds as colorless oils.

(E)-N-methyl-N-(2-nonen-4-ynyl)-3-benzyloxybenzyl amine (compound 112)

Amount: 112 mg (yield: 42%),
IR$\nu_{max}^{neat}$ cm$^{-1}$:2932, 1587, 1491, 1458, 1263, 1026.

NMR(CDCl$_3$)δ: 0.91(3H, t, J=7.2Hz), 1.37-1.54 (4H, m), 2.18(3H, s), 2.30(2H, dt, J=6.8Hz, 2.0Hz) 3.04(2H, dd, J=6.6Hz, 1.5Hz), 3.46(2H, s), 5.06(2H, s), 5.63 (1H, dm, J=15.9Hz), 6.09(1H, dt, J=15.9Hz, 6.6Hz), 6.84-6.91(2H, m), 6.96-6.97(1H, m), 7.18-7.24(1H, m), 7.26-7.46(5H, m).

(Z)-N-methyl-N-(2-nonen-4-ynyl)-3-benzyloxybenzyl amine (compound 113)

Amount: 36 mg (yield: 14%).

IR$\nu_{max}^{neat}$ cm$^{-1}$:2932, 1587, 1458, 1263, 1152, 1026, 738, 696.

NMR(CDCl$_3$)δ: 0.92(3H, t, J=7.0Hz), 1.38-1.54 (4H, m), 2.22(3H, s), 2.33(2H, dt, J=6.8Hz, 1.9Hz), 3.28(2H, dd, J=6.8Hz, 1.5Hz), 3.50(2H, s), 5.06(2H, s), 5.61 (1H, dm, J=11.0Hz), 5.95(1H, dt, J=11.0Hz, 6.8Hz), 6.85-6.88(1H, m), 6.91-6.93(1H, m), 6.98-6.99(1H, m), 7.19-7.25(1H, m), 7.31-7.46(5H, m).

Compounds of Examples 95 and 96 were obtained by repeating Example 94 except that instead of the starting 1-bromo-2-nonen-4-yne, the corresponding brominated alkene derivatives were used.

EXAMPLE 95

(E)-N-(6-methoxy-6-methyl-2-hepten-4-ynyl)-N-methyl-3-benzyloxybenzylamine (compound 114)

IR$\nu_{max}^{neat}$ cm$^{-1}$:1458, 1260, 1170, 1152, 1077, 1026.
NMR(CDCl$_3$)δ: 1.47(6H, s), 2.19(3H, s), 3.05(2H, dd, J=6.5Hz, 1.6Hz), 3.36(3H, s), 3.47 (2H, s), 5.06(2H, s), 5.68(1H, dt, J=15.8Hz, 1.6Hz), 6.17(1H, dt, J=15.8Hz, 6.5Hz), 6.85-6.91(2H, m), 6.97-6.98(1H, m), 7.19-7.26(1H, m), 7.31-7.46(5H, m).

(Z)-N-(6-methoxy-6-methyl-2-hepten-4-ynyl)-N-methylbenzyloxybenzylamine (compound 115)

IR$\nu_{max}^{neat}$ cm$^{-1}$:1458, 1254, 1170, 1152, 1077, 1029.
NMR(CDCl$_3$)δ: 1.47(6H, s), 2.22(3H, s), 3.28(2H, dd, J=6.8Hz, 1.5Hz) 3.35(3H, s), 3.50 (2H, s), 5.06(2H, s), 5.65(1H, dt, J=10.6Hz, 1.5Hz), 6.04(1H, dt, J=10.6Hz, 6.8Hz), 6.85-6.92(2H, m), 6.97-6.99(1H, m), 7.20-7.26(1H, m), 7.31-7.46(5H, m).

EXAMPLE 96

(E)-N-(5-phenyl-2-penten-4-ynyl)-N-methyl-3-benzyloxybenzylamine (compound 116)

IR$\nu_{max}^{neat}$ cm$^{-1}$:1599, 1491, 1458, 1263, 1026, 756, 693.

NMR(CDCl$_3$)δ: 2.22(3H, s), 3.12(2H, dd, J=6.7Hz 1.4Hz) 3.50(3H, s), 5.07(2H, s), 5.88 (1H, dt, J=15.9Hz, 1.4Hz), 6.28(1H, dt, J=15.9Hz, 6.7Hz), 6.85-6.93(2H, m), 6.98-6.99(1H, m), 7.20-7.26(1H, m), 7.28-7.46(10H, m).

(Z)-N-(5-phenyl-2-penten-4-ynyl)-N-methyl-3-benzyloxybenzylamine (compound 117)

IR$\nu_{max}^{neat}$ cm$^{-1}$:1599, 1491, 1458, 1263, 1026, 756, 738, 693.

NMR(CDCl$_3$)δ: 2.27(3H, s), 3.39(2H, dd, J=6.8Hz, 1.5Hz), 3.54(2H, s), 5.05(2H, s), 5.84 (1H, dt, J=10.7Hz, 1.5Hz), 6.10(1H, dt, J=10.7Hz, 6.8Hz), 6.84-6.88(1H, m), 6.92-6.95(1H, m), 6.99-7.00(1H, m), 7.19-7.25(1H, m), 7.28-7.42(10H, m).

EXAMPLE 97

Production of (E)-N-(3-phenyl-2-propenyl)-N-methyl-3-benzyloxybenzylamine (compound 118)

Ninety milligrams of 3-benzyloxybenzyl chloride was dissolved in 2 ml of dimethylformamide, and 71 mg of (E)-N-methylcinnamylamine hydrochloride and 45 mg of sodium carbonate were added. The mixture was stirred overnight at room temperature. Water (15 ml) was added to the reaction mixture, and the mixture was extracted with 10 ml of ethyl ether twice. The extracts were combined, washed with 10 ml of a saturated aqueous sodium chloride solution, and dried over anhydrous magnesium sulfate. The desiccant was removed by filtration, and the solvent was evaporated. The residue was purified by preparative thin-layer chromatography [thin-layer plate: Kieselgel 60F$_{254}$, Art. 5744 (a product of E. Merck Co.); developing solvent: chloroform/ethyl acetate=10/1)] to give 108 mg (yield 81.3%) of the captioned compound as a colorless oil.

IR$\nu_{max}^{neat}$cm$^{-1}$: 1599, 1491, 1455, 1266, 1152, 1026, 741, 693.

NMR(CDCl$_3$)δ2.24(3H, s), 3.18(2H, dd, J=6.6Hz, 1.2Hz) 3.53(2H, s), 5.07(2H, s), 6.30 (1H, dt, J=15.9Hz, 6.6Hz), 6.53(1H, dt, J=15.8Hz, 1.2Hz), 6.85–6.89(1H, m), 6.92–6.95(1H, m), 7.00–7.01(1H, m), 7.20–7.46(6H, m).

EXAMPLE 98

(E)-N-methyl-N-[5-(1-methylcyclopropyl)-2-penten-4-ynyl]-3-(2-methylbenzyloxy)benzylamine (compound 119)

Carbon tetrabromide (18.3 g) and 28.9 g of triphenylphosphine were added to 350 ml of methylene chloride, and the mixture was stirred at room temperature for 10 minutes. Then, 4.62 g of 1-methylcyclopropanaldehyde [J. Am. Chem., Soc., 97, 2778 (1975)] was added, and the mixture was stirred for 10 minutes. The reaction mixture was washed with water and concentrated under reduced pressure. Hexane was added to the residue, and the mixture was filtered. The filtrate was concentrated, and distilled under reduced pressure to give 5.62 g of 1-(2,2-dibromoethenyl)-1-methylcyclopropane. The dibromo compound obtained above (720 mg) was dissolved in 10 ml of tetrahydrofuran, and under cooling at −80° C., 4.0 ml of a 1.57M hexane solution of butyl lithium was added. The mixture was stirred at this temperature for 1 hour and then at room temperature for 1 hour. The solution was again cooled to −10° C., and a tetrahydrofuran solution (4.5 ml) of 168 mg of acrolein was added. The mixture was stirred at room temperature for 30 minutes. An aqueous solution of ammonium chloride and ethyl ether were added to the reaction mixture. The organic layer was separated and the solvent was evaporated. The residue was distilled at 100° C. under a reduced pressure of 5 mmHg to give 205 mg of a fraction containing 1-(1-methylcyclopropyl)-4-penten-1-yn-3-ol as a main component.

Two hundred milligrams of the above fraction was dissolved in 5 ml of methylene chloride, and with stirring under ice cooling, 0.42 ml of triethylamine and 0.14 ml of methanesulfonyl chloride was added. The mixture was stirred for 30 minutes, and then 450 mg of N-methyl-3-(2-methylbenzyloxy)benzylamine was added. The mixture was stirred at room temperature for 2 hours. The reaction mixture was diluted with methylene chloride and then washed with water. The solvent was evaporated, and the residue was purified by medium-pressure liquid chromatography (column: Lobar column, size A, Lichroprep Si 60F (a product of E. Merck Co.; eluting solvent: hexane/ethyl acetate=10/1→7/1] to give the captioned compound as a colorless oil.

IR$\nu_{max}^{neat}$ cm$^{-1}$:2962, 2926, 2788, 2224, 1599, 1458, 1266, 1152, 1020, 747.

NMR(CDCl$_3$)δ:0.58–0.63(2H, m), 0.89–0.93(2H, m), 1.26(3H, s), 2.19(3H, s), 2.38(3H, s), 3.04(2H, dd, J=6.5Hz, 1.4Hz), 3.47 (2H, s), 5.03(2H, s), 5.62(1H, dt, J=15.8Hz, 1.4Hz), 6.08(1H, dt, J=15.8Hz, 6.5Hz), 6.85–6.92(2H, m), 6.97(1H, d, J=1.7Hz), 7.20–7.26(5H, m), 7.40–7.43(1H, m).

EXAMPLE 99

(E)-N-(6,6-dimethyl-2,4-heptadienyl)-N-methyl-3-(2-methylbenzyloxy)benzylamine compound (120)

Using 200 mg of (E), (E)-6,6-dimethyl-2,4-heptadienol, 0.43 ml of triethylamine, 180 mg of methanesulfonyl chloride and 350 mg of N-methyl-3-(2-methylbenzyloxy)benzylamine, the same reaction as in Example 110 above was carried out. There was obtained 131 mg (yield 25%) of the captioned compound as a colorless oil.

IR$\nu_{max}^{neat}$ cm$^{-1}$:2962, 1599, 1491, 1461, 1263, 1020, 990, 747.

NMR(CDCl$_3$)δ: 1.03(9H, s), 2.19(3H, s), 2.38(3H, s), 3.04(2H, dd, J=6.6Hz, 1.5Hz) 3.47(2H, s), 5.03(2H, s), 5.68(1H, d, J=14.9Hz), 5.68(1H, dt, J=14.6Hz, 6.6Hz), 5.98(1H, dd, J=14.9Hz, 10.1Hz), 6.13(1H, ddt, J=14.6Hz, 10.1Hz, 1.5Hz), 6.87(1H, ddd, J=8.4Hz, 2.8Hz, 1.4Hz), 6.90–6.94 (1H, m), 6.98–7.00(1H, m), 7.19–7.26 (4H, m), 7.40–7.44(1H, m).

EXAMPLE 100

(E),(E)-N-(3,7-dimethyl-2,6-octadienyl)-N-methyl-3-benzyloxybenzylamine (compound 121)

Geranyl bromide (313 mg), 290 mg of N-methyl-3-benzyloxybenzylamine hydrochloride and 200 mg of potassium carbonate were added to 3 ml of dimethylformamide, and the mixture was stirred overnight at room temperature. Ethyl ether and water were added to the reaction mixture. The organic layer was separated, and washed with a saturated aqueous sodium chloride solution. The organic layer was dried over anhydrous magnesium sulfate and the solvent was evaporated. The residue was purified by medium-pressure liquid chromatography [column: Lobar column, size B, Lichroprep Si 60F (a product of E. Merck Co.); eluting solvent: hexane/ethyl acetate=10/1→7/1] to give the captioned compound as a colorless oil.

IR$\delta_{max}^{neat}$ cm$^{-1}$:2920, 1596, 1491, 1455, 1263, 1152, 1026, 696.

NMR(CDCl$_3$)δ: 1.60(3H, s), 1.62(3H, s), 1.66(3H, s), 2.01–2.15 (4H, m), 2.18(3H, s), 2.98 (2H, d, J=6.8Hz) 3.45(2H, s), 5.06 (2H, s), 5.07–5.12(1H, m), 5.27–5.33 (1H, m), 6.86(1H, dd, J=7.8Hz, 2.4Hz), 6.91(1H, d, J=7.6Hz), 7.19–7.46(6H, m).

EXAMPLE 101

Production of (E)-N-(6,6-dimethyl-2-hepten-4-ynyl)-N-methyl-3-3-(2-furyl)benzyloxy]benzylamine hydrochloride (compound 122)

190 mg of (E)-N-(6,6-dimethyl-2-hepten-4-ynyl)-N-methyl-3-hydroxybenzylamine was dissolved in 3 ml of anhydrous tetrahydrofuran, and 31 mg of 60% oily sodium hydride was added with ice cooling and stirring. The solution was stirred for 10 minutes. To the resulting solution were added an ether solution of 3-(2-furyl)-benzyl chloride (prepared in advance by reacting 160 mg of 3-(2-furyl)benzyl alcohol and 73 microliters of thionyl chloride in anhydrous ethyl ether with ice cooling and stirring for 3 hours, and thereafter washing the resulting solution with a saturated aqueous solution of sodium chloride and a 5% aqueous solution of sodium hydrogen carbonate) and 1 ml of dimethylformamide. The mixture was stirred overnight at room temperature. 30 ml of water and 30 ml of ethyl ether were added to the reaction solution, and the mixture was separated. The organic layer was separated, washed with a saturated aqueous solution of sodium chloride, and dried over anhydrous sodium sulfate. The solvent was then evaporated. The residue was purified by medium-pressure liquid chromatography column: Lobar column, size B, Lichroprep Si 60F (E. Merck Co.; eluting solvent: hexane/ethyl acetate=10/1→8/1] to give 63 mg (yield 21%) of a free base of the captioned compound as a colorless oil. The free base was treated with a solution of methanol and hydrogen chloride and recrystallized from a mixture of ethyl acetate/ethyl ether to give the captioned hydrochloride, m.p. 115°–116° C.

IR$\nu_{max}^{KBr}$ cm$^{-1}$:2968, 2488, 1605, 1497, 1461, 1266, 789.

NMR (CDCl$_3$)δ: 1.25(9H, s), 2.60(3H, s), 3.50–3.64 (2H, m), 4.00–4.13(2H, m), 5.20(2H, s), 5.78–5.84(1H, m), 6.18–6.32(1H, m), 6.47 (1H, dd, J=3.5Hz, 2.0Hz), 6.70(1H, d, J=3.5Hz), 7.05–7.11(2H, m), 7.30–7.47(5H, m), 7.62(1H, d, J=7.1Hz), 7.78(1H, s).

EXAMPLE 102

Production of
(E)-N-(6,6-dimethyl-2-hepten-4-ynyl)-N-ethyl-3-[3-(1-pyrrolyl)benzyloxy)benzylamine (compound 123)

100 mg of (E)-N-(6,6-dimethyl-2-hepten-4-ynyl)-N-ethyl-3-hydroxybenzylamine was dissolved in 1 ml of anhydrous tetrahydrofuran, and 20 mg of 60% oily sodium hydride was added to the solution with ice cooling and stirring, and the mixture was stirred for 10 minutes. To the resulting solution was added 1 ml of a dimethylformamide solution of 100 mg of 3-(1-pyrrolyl)benzyl methanesulfonate, and the mixture was stirred overnight at room temperature. The solution was extracted by adding 20 ml of water and 30 ml of ethyl ether. The organic layer was separated, washed with a saturated aqueous solution of sodium chloride, and dried over anhydrous sodium sulfate. The solvent was evaporated. The residue was purified by silica gel column chromatography [Wakogel C-200, 20 g, eluting solvent: hexane/ethyl acetate=10/1→5/1) to give 110 mg (yield 70%) of the captioned compound as a colorless oil.

IR$\nu_{max}^{neat}$ cm$^{-1}$:2968, 1596, 1506, 1488, 1455, 1341, 1263, 1071, 786, 726.

NMR (CDCl$_3$)δ: 0.98(3H, t, J=7.0Hz), 1.19(9H, s), 2.45(2H, q, J=7.0Hz), 3.03(2H, dd, J=6.4Hz, 1.6Hz), 3.49(2H, s), 5.06(2H, s), 5.59(1H, dt, J=15.9Hz, 1.6Hz), 6.01(1H, dt, J=15.9Hz, 6.4Hz), 6.30(2H, t, J=2.1Hz), 6.80(1H, ddd, J=8.3Hz, 2.6Hz, 0.8Hz), 6.88(1H, d, J=7.6Hz), 6.96–6.98(1H, m), 7.06(2H, t, J=2.1Hz), 7.17 (1H, t, J=7.8Hz), 7.25–7.32(2H, m), 7.39(1H, t, J=7.8Hz), 7.44–7.45(1H, m).

EXAMPLE 103

Production of
(E)-N-ethyl-N-(6-methoxy-6-methyl-2-hepten-4-ynyl)-3-3-(3-thienyl)benzyloxy]-benzylamine hydrochloride (compound 124)

57.5 mg of (E)-N-ethyl-N-(6-methoxy-6-methyl-2-hepten-4-ynyl)-3-hydroxybenzylamine was dissolved in 0.5 ml of anhydrous tetrahydrofuran, and under a nitrogen atmosphere, 8.1 mg of 60% oily sodium hydride was added. The mixture was stirred at room temperature for 10 minutes, and to this solution was added 1 ml of a dimethylformamide solution of 53.7 mg of 3-(3-thienyl)benzyl methanesulfonate. The mixture was stirred overnight at room temperature, and the solvent was evaporated under reduced pressure. The residue was purified by medium-pressure liquid chromatography [column: Lobar column, size A, Lichroprep Si 60 (E. Merck Co.); eluting solvent: hexane/ethyl acetate=6/1→1/1]] to give 81.6 mg (yield 89%) of a free base of the captioned compound as a colorless oil. The free base was treated with a solution of hydrogen chloride and methanol and recrystallized from a mixture of ethyl acetate and ethyl ether to give the captioned hydrochloride, m.p. 153°–155° C.

IR$\nu_{max}^{KBr}$ cm$^{-1}$:3340, 2986, 2932, 1605, 1455, 1266, 1173, 1071, 777.

NMR (CDCl$_3$)δ: 1.41(3H, t, J=7.2Hz), 1.47(6H, s), 2.90–3.20(2H, m), 3.34(3H, s), 3.40–3.80 (2H, m), 4.08(2H, br.s), 5.22(2H, s), 5.84 (1H, d, J=15.9Hz), 6.36(1H, dt, J=15.9Hz, 7.9Hz), 7.00–7.20(2H, m), 7.33(1H, t, J=7.9Hz), 7.40–7.70(7H, m), 7.73(1H, s).

EXAMPLE 104

Production of
(E)-N-(6,6-dimethyl-2-hepten-4-ynyl)-N-methyl-3-[3-(5-isoxazolyl)benzyloxy]benzylamine (compound 125)

106 mg of 5-(3-methylphenyl)isoxazole, 119 mg of N-bromosuccinimide and 2 mg of benzoyl peroxide were dissolved in 10 ml of carbon tetrachloride, and the solution was refluxed for 3 hours with stirring. After cooling, the precipitate was separated by filtration, and concentrated under reduced pressure to give 5-(3-bromomethylphenyl)isoxazole as a pale yellow oily product.

The resulting bromomethyl compound was dissolved in 5 ml of dimethylformamide. The solution was added to 10 ml of a tetrahydrofuran solution of phenolate prepared in advance from 171 mg of (E)-N-(6,6-dimethyl-2-hepten-4-ynyl)-N-methyl-3-hydroxybenzylamine and 30 mg of 60% oily sodium hydride, and under ice cooling, the mixture was stirred for 1 hour. Water and ethyl ether were added to the reaction solution to dilute it. The organic layer was separated and then dried over anhydrous magnesium sulfate. The desiccant was separated by filtration, and the solvent was evaporated. The residue was purified by medium-pressure liquid chromatography [column: Lobar column, size A, Lichroprep Si 60 (E. Merck Co.); eluting solvent: hexane/ethyl acetate=10/1→5/1) and preparative thin-layer chromatography [thin layer plate: Kieselgel 60F$_{254}$, Art. 5744 (E. Merck Co.); developing solvent: hexane/ethyl acetate=3/1] to give 19 mg (yield 11%) of the captioned compound as a colorless oil.

IR$\nu_{max}^{neat}$ cm$^{-1}$:2974, 2788, 1584, 1491, 1470, 1266, 786.

NMR (CDCl$_3$)δ: 1.24(9H, s), 2.19(3H, s), 3.04(2H, dd, J=6.5Hz, 1.4Hz), 3.47(2H, s), 5.13(2H, s), 5.65(1H, dt, J=15.8Hz, 1.4Hz), 6.08(2H, dt, J=15.8Hz, 6.5Hz), 6.55(1H, d, J=1.9Hz), 6.88 (1H, ddd, J=8.1Hz, 2.6Hz, 0.9Hz), 6.70–6.75 (1H, m), 7.00–7.03(1H, m), 7.24(1H, t, J=8.1Hz), 7.50–7.55(2H, m), 7.77(1H, dt, J=6.7Hz, 1.9Hz), 7.88–7.91(1H, m), 8.30(1H, d, J=1.9Hz).

EXAMPLE 105

Production of
(E)-N-(6,6-dimethyl-2-hepten-4-ynyl)-N-methyl-3-[3-(1-imidazolyl)benzyloxy]benzylamine (compound 126)

90 mg of 1-(3-hydroxymethylphenyl)imidazole was dissolved in 10 ml of chloroform, and 100 microliters of thionyl chloride was added. The mixture was stirred at room temperature for 3 hours. The solvent was evaporated under reduced pressure. The residue was dissolved in a mixture of ethyl ether and water. The organic layer was separated, washed successively with a 5% aqueous solution of sodium hydrogen carbonate and then with water, and dried over anhydrous magnesium sulfate. The desiccant was separated by filtration and then ethyl ether was evaporated to give 1-(3-chloromethylphenyl)imidazole as a pale yellow oily product.

The resulting chloromethyl compound was dissolved in 1.5 ml of dimethylformamide, and a tetrahydrofuran solution (1.5 ml) of phenolate prepared from 140 mg of (E)-N-(6,6-dimethyl-2-hepten-4-ynyl)-N-methyl-3-hydroxybenzylamine and 22 mg of 60% oily sodium hydride was added. The mixture was reacted as in Examples 1 to 4 to give 110 mg (yield 57%) of the captioned compound as a colorless oil.

IR$\nu_{max}^{neat}$ cm$^{-1}$:1599, 1506, 1491, 1455, 1311, 1263, 1056, 1026, 786.

NMR (CDCl$_3$)δ: 1.24(9H, s), 2.18(3H, s), 3.36(2H, dd, J=6.5Hz, 1.4Hz), 3.47(2H, s), 5.13(2H, s), 5.65(1H, dt, J=15.8Hz, 1.4Hz), 6.07(1H, dt, J=15.8Hz, 6.5Hz), 6.87(1H, ddd, J=8.3Hz, 2.7Hz, 1.0Hz), 6.92(1H, d, J=8.3Hz), 6.99-7.10(1H, m), 7.22(1H, t, J=1.4Hz), 7.24(1H, t, J=7.7Hz), 7.31(1H, t, J=1.4Hz), 7.34-7.45(2H, m), 7.50(1H, t, J=7.7Hz), 7.51(1H, s), 7.88(1H, t, J=1.4Hz).

Compounds of Examples 106 to 144 below were obtained by performing the same reaction as in Examples 1 to 5 except that instead of the various starting compounds in Examples 1 to 5, the corresponding 3-hydroxybenzylamine derivatives and 3-heterocyclylbenzyl halogen derivatives or methanesulfonyl derivatives or starting materials therefor were used.

EXAMPLE 106

(E)-N-(6,6-dimethyl-2-hepten-4-ynyl)-N-ethyl-3-[3-(3-furyl)benzyloxy]benzylamine (compound 127)

IR$\nu_{max}^{neat}$ cm$^{-1}$:2968, 1458, 1263, 1161, 1059, 1038, 1020, 873, 777.

NMR (CDCl$_3$)δ: 1.03(3H, t, J=7.1Hz), 1.24(9H, s), 2.50(2H, q, J=7.1Hz), 3.09(2H, d, J=6.4Hz), 3.54(2H, s), 5.08(2H, s), 5.64(1H, dt, J=15.9 Hz, 1.5 Hz), 6.07(1H, dt, J=15.9 Hz, 6.4 Hz), 6.71(1H, dd, J=1.8 Hz, 0.9 Hz), 6.87 (1H, dd, J=7.8 Hz, 2.0 Hz), 6.92(1H, d, J=7.6 Hz), 7.02(1H, br.s), 7.22(1H, t, J=7.8 Hz), 7.34 (1H, dt, J=7.4 Hz, 1.7 Hz), 7.39(1H, t, J=7.1 Hz), 7.45(1H, dt, J=7.4 Hz, 1.7 Hz), 7.48(1H, t, J=1.7 Hz), 7.57(1H, br.s), 7.75(1H, t, J=1.4 Hz).

EXAMPLE 107

(E)-N-(6,6-dimethyl-2-hepten-4-ynyl)-N-methyl-3-[3-(2-thienyl)benzyloxy]benzylamine (compound 128)

IR$\nu_{max}^{neat}$ cm$^{-1}$: 2968, 1599, 1491, 1455, 1365, 1266, 1152, 1026, 786, 696.

NMR (CDCl$_3$) δ: 1.24(9H, s), 2.18(3H, s), 3.04 (2H, dd, J=6.6 Hz, 1.5 Hz), 3.47(2H, s), 5.10 (2H, s), 5.65(1H, dt, J=15.8 Hz, 1.5 Hz), 6.08 (1H, dt, J=15.8 Hz, 6.6 Hz), 6.86-6.93(2H, m), 7.00(1H, br.s), 7.23(1H, t, J=7.8 Hz), 7.29 (1H, dd, J=5.1 Hz, 1.1 Hz), 7.33(1H, dd, J=3.6 Hz, 1.1 Hz), 7.36-7.39(1H, m), 7.40(1H, t, J=7.6 Hz), 7.57(1H, dt, J=7.6 Hz, 1.8 Hz), 7.68-7.71(1H, m).

EXAMPLE 108

(E)-N-(6,6-dimethyl-2-hepten-4-ynyl)-N-methyl-3-[3-(3-thienyl)benzyloxy]benzylamine (compound 129)

IR$\nu_{max}^{neat}$ cm$^{-1}$: 2968, 1599, 1491, 1455, 1365, 1263, 1026, 774.

NMR (CDCl$_3$) δ: 1.24(9H, s), 2.18(3H, s), 3.03 (2H, dd, J=6.6 Hz, 1.5 Hz), 3.47(2H, s), 5.10 (2H, s), 5.64(1H, dt, J=15.8 Hz, 1.5 Hz), 6.08 (1H, dt, J=15.8 Hz, 6.6 Hz), 6.86-6.92(2H, m), 7.00(1H, br.s), 7.23(1H, t, J=8.0 Hz), 7.36 (1H, dt, J=7.6 Hz, 1.6 Hz), 7.39-7.40(2H, m), 7.41(1H, t, J=7.6 Hz), 7.46-7.48(1H, m), 7.55 (1H, dt, J=7.6 Hz, 1.7 Hz), 7.67(1H, br.s).

EXAMPLE 109

(E)-N-(6,6-dimethyl-2-hepten-4-ynyl)-N-ethyl-3-[3-(3-thienyl)benzyloxy)benzylamine hydrochloride (compound 130)

m.p. 168°-169° C.

IR$\nu_{max}^{KBr}$ cm$^{-1}$: 2974, 2500, 1602, 1461, 1266, 1173, 777, 759, 747.

NMR (CDCl$_3$) δ: 1.25(9H, s), 1.42(3H, t, J=7.3 Hz), 2.95-3.06(2H, m), 3.50-3.67(2H, m), 4.08(2H, d, J=5.3 Hz), 5.23(2H, s), 5.80(1H, d, J=15.7 Hz), 6.22(1H, dt, J=15.7 Hz, 7.5 Hz), 7.06(1H, ddd, J=8.3 Hz, 2.5 Hz, 0.8 Hz), 7.09(1H, d, J=8.3 Hz), 7.33(1H, t, J=8.1 Hz), 7.37-7.43(4H, m), 7.51 (1H, dd, J=2.8 Hz, 1.5 Hz), 7.53-7.58(2H, m), 7.73(1H, br.s).

EXAMPLE 110

(E)-N-(6,6-dimethyl-2-hepten-4-ynyl)-N-propyl-3-[3-(3-thienyl)benzyloxy)benzylamine hydrochloride (compound 131)

m.p. 164°-166° C.

IR$\nu_{max}^{KBr}$ cm$^{-1}$: 2968, 1605, 1458, 1266, 777.

NMR (CDCl$_3$) δ: 0.92(3H, t, J=7.3 Hz), 1.25(9H, s), 1.82-1.98(2H, m), 2.73-2.92(2H, m), 3.44-3.78 (2H, m), 4.09(2H, br.s), 5.23(2H, s), 5.78(1H, d, J=15.6 Hz), 6.21(1H, dt, J=15.6 Hz, 7.8 Hz), 7.04-7.09(2H, m), 7.33(1H, t, J=8.1 Hz), 7.35-7.43(4H, m), 7.50(1H, dd, J=2.5 Hz, 1.5 Hz), 7.53-7.57(2H, m), 7.74(1H, s).

EXAMPLE 111

(E)-N-(6,6-dimethyl-2-hepten-4-ynyl)-N-methyl-3-[3-(1-pyrrolyl)benzyloxy)benzylamine (compound 132)

IR$\nu_{max}^{neat}$ cm$^{-1}$: 1596, 1506, 1488, 1458, 1341, 1266, 1029, 786, 726.

NMR (CDCl$_3$) δ: 1.24(9H, s), 2.18(3H, s), 3.03(2H, dd, J=6.6 Hz, 1.5 Hz), 3.47(2H, s), 5.11(2H, s), 5.64(1H, dt, J=15.8 Hz, 1.5 Hz), 6.07(1H, dt, J=15.8 Hz, 6.6 Hz), 6.35(2H, t, J=2.2 Hz), 6.86 (1H, ddd, J=10.8 Hz, 2.3 Hz, 0.8 Hz), 6.91(1H, d, J=7.8 Hz), 6.98-6.99(1H, m), 7.10(2H, t, ( J=2.2 Hz), 7.22(1H, t, J=7.8 Hz), 7.25-7.50 (4H, m).

EXAMPLE 112

(E)-N-(6,6-dimethyl-2-hepten-4-ynyl)-N-propyl-3-[3-(1-pyrrolyl)benzyloxy)benzylamine (compound 133)

IR$\nu_{max}^{neat}$ cm$^{-1}$: 2968, 1596, 1506, 1488, 1455, 1341, 1263, 1071, 723.

NMR (CDCl$_3$) δ: 0.85(3H, t, J=7.4 Hz), 1.24(9H, s), 1.47(2H, sex., J=7.4 Hz), 2.36(2H, t, J=7.4 Hz), 3.06(2H, dd, J=6.4 Hz, 1.6 Hz), 3.53(2H, s), 5.11(2H, s), 5.63(1H, dt, J=15.9 Hz, 1.6 Hz), 6.05(1H, dt, J=15.9 Hz, 6.4 Hz), 6.35(2H, t, J=2.2 Hz), 6.85(1H, ddd, J=8.2 Hz, 2.6 Hz, 0.9 Hz), 6.92(1H, d, J=7.6 Hz), 7.00–7.03(1H, m), 7.11 (2H, t, J=2.2 Hz), 7.21(1H, t, J=7.8 Hz), 7.28–7.37(2H, m), 7.44(1H, t, J=7.8 Hz), 7.49 (1H, t, J=1.5 Hz).

EXAMPLE 113

(E)-N-(6,6-dimethyl-2-hepten-4-ynyl)-N-methyl-3-[3-(2-pyridyl)benzyloxy]benzylamine (compound 134)

IR$\nu_{max}^{neat}$ cm$^{-1}$: 2968, 1587, 1464, 1365, 1263, 1152, 1026, 768.

NMR (CDCl$_3$) δ: 1.24(9H, s), 2.18(3H, s), 3.03(1H, dd, J=6.5 Hz, 1.5 Hz), 3.47(2H, s), 5.15(2H, s), 5.64(1H, dt, J=15.9 Hz, 1.5 Hz), 6.08(1H, dt, J=15.9 Hz, 6.5 Hz), 6.86–6.92(2H, m), 7.00(1H, br.s), 7.22–7.27(3H, m), 7.49–7.51(2H, m), 7.75–7.77(2H, m), 7.93–7.96(1H, m), 8.08 (1H, br.s), 8.70(1H, dt, J=4.8 Hz, 1.5 Hz).

EXAMPLE 114

(E)-N-(6,6-dimethyl-2-hepten-4-ynyl)-N-methyl-3-[3-(3-pyridyl)benzyloxy]benzylamine (compound 135)

IR$\nu_{max}^{neat}$ cm$^{-1}$: 2968, 1599, 1491, 1458, 1365, 1263, 1152, 1023, 783.

NMR (CDCl$_3$) δ: 1.24(9H, s), 2.18(3H, s), 3.03(2H, dd, J=6.5 Hz, 1.5 Hz), 3.47(2H, s), 5.62(2H, s), 5.64(1H, dt, J=15.9 Hz, 1.5 Hz), 6.07(1H, dt, J=15.9 Hz, 6.6 Hz), 6.87–6.93(2H, m), 7.01(1H, br.s), 7.23(1H, t, J=7.9 Hz), 7.37(1H, ddd, J=6.8 Hz, 5.0 Hz, 0.9 Hz), 7.48–7.57(3H, m), 7.67 (1H, br.s), 7.87–7.91(1H, m), 8.60(1H, dd, J=4.8 Hz, 1.7 Hz), 8.86(1H, dd, J=2.4 Hz, 0.9 Hz).

EXAMPLE 115

(E)-N-(6,6-dimethyl-2-hepten-4-ynyl)-N-ethyl-3-[3-(3-pyridyl)benzyloxy)benzylamine (compound 136)

IR$\nu_{max}^{neat}$ cm$^{-1}$: 2968, 1596, 1458, 1263, 786, 711.

NMR (CDCl$_3$) δ: 1.02(3H, t, J=7.1 Hz), 1.23(9H, s), 2.50(2H, q, J=7.1 Hz), 3.09(2H, d, J=6.3 Hz), 3.54(2H, s), 5.14(2H, s), 5.63(1H, dd, J=15.9 Hz, 1.4 Hz), 6.06(1H, dt, J=15.9 Hz, 6.3 Hz), 6.87 (1H, dd, J=8.0 Hz, 2.7 Hz), 6.92(1H, d, J=7.6 Hz), 7.03(1H, br.s), 7.22(1H, t, J=7.8 Hz), 7.36 (1H, ddd, J=7.6 Hz, 4.9 Hz, 1.2 Hz), 7.48–7.57 (3H, m), 7.66(1H, d, J=1.2 Hz), 7.87–7.91 (1H, m), 8.60(1H, dd, J=5.1 Hz, 1.8 Hz), 8.85 (1H, dd, J=2.7 Hz, 1.2 Hz).

EXAMPLE 116

(E)-N-(6,6-dimethyl-2-hepten-4-ynyl)-N-methyl-3-[3-(4-pyridyl)benzyloxy)benzylamine (compound 137)

IR$\nu_{max}^{neat}$ cm$^{-1}$: 2972, 1596, 1490, 1458, 1364, 1266, 1152, 1026, 786.

NMR (CDCl$_3$) δ: 1.24(9H, s), 2.18(3H, s), 3.04(1H, dd, J=6.5 Hz, 1.5 Hz), 3.47(2H, s), 5.14(2H, s), 5.64(1H, dt, J=15.8 Hz, 1.5 Hz), 6.08(1H, dt, J=15.9 Hz, 1.5 Hz), 6.87–6.93(2H, m), 7.00(1H, br.s), 7.24(1H, t, J=8.0 Hz), 7.51–7.54(4H, m), 7.59–7.62(1H, m), 7.59–7.62(1H, m), 8.67(2H, dd, J=4.5 Hz, 1.7 Hz).

EXAMPLE 117

(E)-N-(6,6-dimethyl-2-hepten-4-ynyl)-N-methyl-3-[3-(2-oxazolyl)benzyloxy]benzylamine (compound 138)

IR$\nu_{max}^{neat}$ cm$^{-1}$: 2974, 1590, 1491, 1458, 1365, 1266, 1152, 1026, 798, 729.

NMR (CDCl$_3$) δ: 1.24(9H, s), 2.18(3H, s), 3.30(2H, dd, J=6.6 Hz, 1.5 Hz), 3.46(2H, s), 5.12(2H, s), 5.63(1H, dd, J=15.8 Hz, 1.5 Hz), 6.08(1H, dt, J=15.8 Hz, 6.6 Hz), 6.85–6.92(2H, m), 6.99–7.15 (1H, m), 7.22(1H, t, J=7.7 Hz), 7.24(1H, d, J=1.1 Hz), 7.48(1H, t, J=7.7 Hz), 7.54(1H, d, J=7.9 Hz), 7.72(1H, d, J=1.1 Hz), 8.01(1H, dt, J=7.9 Hz, 1.2 Hz), 8.13–8.16(1H, m).

EXAMPLE 118

(E)-N-(6,6-dimethyl-2-hepten-4-ynyl)-N-methyl-3-[3-(5-oxazolyl)benzyloxy]benzylamine (compound 139)

IR$\nu_{max}^{neat}$ cm$^{-1}$: 2968, 1596, 1458, 1263, 1152, 1026, 954, 789, 693.

NMR (CDCl$_3$) δ: 1.24(9H, s), 2.19(3H, s), 3.04(2H, dd, J=6.5 Hz, 1.4 Hz), 3.47(2H, s), 5.11(2H, s), 5.65(1H, dt, J=15.9 Hz, 1.4 Hz), 6.0B(1H, dt, J=15.9 Hz, 6.5 Hz), 6.86–6.93(2H, m), 7.00–7.02 (1H, m), 7.23(1H, t, J=7.9 Hz), 7.38(1H, s), 7.42–7.43(1H, m), 7.45(1H, t, J=7.6 Hz), 7.60–7.6 4(1H, m), 7.74–7.76(1H, m), 7.93 (1H. s).

EXAMPLE 119

(E)-N-(6,6-dimethyl-2-hepten-4-ynyl)-N-ethyl-3-[3-(5-oxazolyl)benzyloxy]benzylamine (compound 140)

IR$\nu_{max}^{neat}$ cm$^{-1}$: 2968, 1491, 1458, 1263, 1107, 954, 789.

NMR (CDCl$_3$) δ: 1.03(3H, t, J=7.1 Hz), 1.24(9H, s), 2.50(2H, q, J=7.1 Hz), 3.09(2H, dd, J=6.4 Hz, 1.5 Hz), 3.54(2H, s), 5.11(2H, s), 5.64(1H, dt, J=15.8 Hz, 1.5 Hz), 6.07(1H, dt, J=15.8 Hz, 6.4 Hz), 6.84–6.89(1H, m), 6.93(1H, d, J=7.7 Hz), 7.03(1H, br.s), 7.23(1H, t, J=7.7 Hz), 7.39 (1H, s), 7.40–7.49(2H, m), 7.62(1H, dt, J=6.6 Hz, 2.1 Hz), 7.75(1H, br.s), 7.93(1H, s).

Treatment of the free base with hydrogen chloride-methanol in a customary manner gave the hydrochloride, m.p. 160° C. (dec.).

EXAMPLE 120

(E)-N-(6,6-dimethyl-2-hepten-4-ynyl)-N-propyl-3-[3-(5-oxazolyl)benzyloxy)benzylamine (compound 141)

IR$\nu_{max}^{neat}$ cm$^{-1}$: 2968, 1596, 1491, 1455, 1263, 1107, 954, 789.

NMR (CDCl$_3$) δ: 0.85(3H, t, J=7.4 Hz), 1.47(2H, sex, J=7.4 Hz), 2.37(2H, t, J=7.4 Hz), 3.07(2H, dd, J=6.4 Hz, 1.5 Hz), 3.53(2H, s), 3.53(2H, s), 5.10(2H, s), 5.63(1H, dt, J=15.9 Hz, 1.5 Hz), 6.06(1H, dt, J=15.9 Hz, 6.4 Hz), 6.84–6.89 (1H, m), 6.92(1H, d, J=7.8 Hz), 7.02(1H, br.s), 7.22(1H, t, J=7.8 Hz), 7.38(1H, s), 7.40–7.49(2H, m), 7.62(1H, dt, J=6.6 Hz, 2.1 Hz), 7.75(1H, br.s), 7.93(1H, s).

EXAMPLE 121

(E)-N-(6,6-dimethyl-2-hepten-4-ynyl)-N-methyl-3-[3-(4-isoxazolyl)benzyloxy]benzylamine (compound 142)

IR$\nu_{max}^{neat}$ cm$^{-1}$: 2974, 1602, 1494, 1458, 1266, 756.

NMR (CDCl$_3$) δ: 1.24(9H, s), 2.19(3H, s), 3.04 (2H, dd, J=6.5 Hz, 1.4 Hz), 3.48(2H, s), 5.10 (2H, s), 5.65(1H, dt, J=15.9 Hz, 1.4 Hz), 6.08(2H, dt, J=15.9 Hz, 6.5 Hz), 6.85–6.95 (2H, m), 7.01(1H, br.s), 7.24(1H, t, J=8.0 Hz), 7.38–7.49(3H, m), 7.57(1H, br.s), 8.58(1H, s), 8.70(1H, s).

EXAMPLE 122

(E)-N-(6,6-dimethyl-2-hepten-4-ynyl)-N-methyl-3-[3-(2-thiazolyl)benzyloxy]benzylamine (compound 143)

IR$\nu_{max}^{neat}$ cm$^{-1}$: 2972, 1588, 1490, 1456, 1364, 1266, 1148, 1022, 788, 692.

NMR (CDCl$_3$) δ: 1.19(9H, s), 2.14(3H, s), 2.99 (2H, dd, J=6.6 Hz, 1.4 Hz), 3.42(2H, s), 5.08 (2H, s), 5.60(1H, dt, J=15.8 Hz, 1.4 Hz), 6.04 (1H, dt, J=15.8 Hz, 6.6 Hz), 6.83(1H, dd, J=8.1 Hz, 1.5 Hz), 6.87(1H, d, J=8.1 Hz), 6.95 (1H, d, J=1.5 Hz), 7.18(1H, t, J=7.8 Hz), 7.30 (1H, d, J=3.3 Hz), 7.42(1H, t, J=8.1 Hz), 7.47 (1H, d, J=7.6 Hz), 7.83(1H, d, J=3.3 Hz), 7.87 (1H, d, J=7.3 Hz), 8.01(1H, s).

EXAMPLE 123

(E)-N-(6,6-dimethyl-2-hepten-4-ynyl)-N-methyl-3-[3-(4-isothiazolyl)benzyloxy]benzylamine (compound 144)

IR$\nu_{max}^{neat}$ cm$^{-1}$: 2968, 1590, 1491, 1458, 1365, 1263, 1152, 1026, 780.

NMR (CDCl$_3$) δ: 1.24(9H, s), 2.18(3H, s), 3.03 (2H, dd, J=6.5 Hz, 1.5 Hz), 3.47(2H, s), 5.12 (2H, s), 5.64(1H, dt, J=15.9 Hz, 1.5 Hz), 6.07 (1H, dt, J=15.9 Hz, 6.5 Hz), 6.85–6.94(2H, m), 7.01(1H, t, J=2.1 Hz), 7.23(1H, t, J=7.9 Hz), 7.40–7.50(2H, m), 7.55(1H, dt, J=6.9 Hz, 1.9 Hz), 8.73(1H, s), 8.79(1H, s).

EXAMPLE 124

(E)-N-(6,6-dimethyl-2-hepten-4-ynyl)-N-methyl-3-[3-(5-isothiazolyl)benzyloxy]benzylamine (compound 145)

IR$\nu_{max}^{neat}$ cm$^{-1}$: 2968, 1590, 1491, 1458, 1419, 1368, 1266, 1152, 786, 756.

NMR (CDCl$_3$) δ: 1.24(9H, s), 2.19(3H, s), 3.04 (2H, dd, J=6.2 Hz, 1.5 Hz), 3.48(2H, s), 5.11 (2H, s), 5.65(1H, dt, J=15.6 Hz, 1.5 Hz), 6.08 (1H, dt, J=15.6 Hz, 6.2 Hz), 6.88(1H, ddd, J=8.2 Hz, 2.8 Hz, 1.0 Hz), 6.89–6.90(2H, m), 7.00–7.03(1H, m), 7.23(1H, t, J=7.8 Hz), 7.43 (1H, d, J=2.1 Hz), 7.45–7.50(2H, m), 7.54–7.59 (1H, m), 7.68–7.71(1H, m), 8.48(1H, d, J=2.1 Hz).

EXAMPLE 125

(E)-N-(6,6-dimethyl-2-hepten-4-ynyl)-N-ethyl-3-[3-(1-imidazolyl)benzyloxy]benzylamine (compound 146)

IR$\nu_{max}^{neat}$ cm$^{-1}$: 2968, 1506, 1491, 1458, 1308, 1263, 1056, 789.

NMR (CDCl$_3$) δ: 1.02(3H, t, J=7.1 Hz), 1.24(9H, s), 2.49(2H, q, J=7.1 Hz), 3.08(2H, dd, J=6.4 Hz, 1.5 Hz), 3.54(2H, s), 5.13(2H, s), 5.64(1H, dt, J=15.9 Hz, 1.5 Hz), 6.06(1H, dt, J=15.9 Hz, 6.4 Hz), 6.85(1H, ddd, J=8.0 Hz, 2.0 Hz, 0.9 Hz), 6.93(1H, d, J=7.5 Hz), 7.00–7.05(1H, m), 7.21 (1H, t, J=1.4 Hz), 7.23(1H, t, J=8.0 Hz), 7.31 (1H, t, J=1.4 Hz), 7.33–7.53(4H, m), 7.88(1H, t, J=1.4 Hz).

EXAMPLE 126

(E)-N-(6,6-dimethyl-2-hepten-4-ynyl)-N-propyl-3-[3-(1-imidazolyl)benzyloxy)benzylamine (compound 147)

IR$\nu_{max}^{neat}$ cm$^{-1}$: 2968, 1599, 1506, 1488, 1455, 1308, 1263, 1152, 1056, 786.

NMR (CDCl$_3$) δ: 0.85(3H, t, J=7.4 Hz), 1.24(9H, s), 1.47(2H, sex, J=7.4 Hz), 2.37(2H, t, J=7.4 Hz), 3.06(2H, dd, J=6.3 Hz, 1.5 Hz), 3.53(2H, s), 5.13(2H, s), 5.63(1H, dt, J=15.6 Hz, 1.5 Hz), 6.05(1H, dt, J=15.6 Hz, 6.3 Hz), 6.84(1H, ddd, J=8.2 Hz, 3.4 Hz, 0.8 Hz), 6.93(1H, d, J=7.6 Hz), 7.01(1H, br.s), 7.21(1H, t, J=1.4 Hz), 7.22 (1H, t, J=8.2 Hz), 7.31(1H, t, J=1.4 Hz), 7.33–7.53(4H, m), 7.88(1H, t, J=1.4 Hz).

EXAMPLE 127

(E)-N-(6,6-dimethyl-2-hepten-4-ynyl)-N-methyl-3-[3-(5-pyrimidinyl)benzyloxy]benzylamine (compound 148)

IR$\nu_{max}^{neat}$ cm$^{-1}$: 2974, 1584, 1455, 1419, 1266, 786, 756.

NMR (CDCl$_3$) δ: 1.24(9H, s), 2.19(3H, s), 3.04 (2H, d, J=6.2 Hz), 3.47(2H, s), 5.15(2H, s), 5.64(1H, d, J=15.9 Hz), 6.07(1H, dt, J=15.9 Hz, 6.2 Hz), 6.82–6.93(2H, m), 7.02(1H, br.s), 7.23(1H, t, J=7.5 Hz), 7.54–7.55(3H, m), 7.67 (1H, s), 8.96(2H, s), 9.22(1H, s).

EXAMPLE 128

(E)-N-(6,6-dimethyl-2-hepten-4-ynyl)-N-methyl-3-[3-(1,2,4-triazol-1-yl)benzyloxy)benzylamine (compound 149)

IR$\nu_{max}^{neat}$ cm$^{-1}$: 2974, 1599, 1512, 1458, 1266, 1215, 1146, 759.

NMR (CDCl$_3$) δ: 1.23(9H, s), 2.18(3H, s), 3.03 (2H, dd, J=6.6 Hz, 1.5 Hz), 3.46(2H, s), 5.14 (2H, s), 5.64(1H, dt, J=15.9 Hz, 1.5 Hz), 6.06 (1H, dt, J=15.9 Hz, 6.6 Hz), 6.85(1H, ddd, J=7.9 Hz, 2.7 Hz, 0.5 Hz), 6.92(1H, d, J=7.9 Hz), 6.98–7.05(1H, m), 7.23(1H, t, J=7.9 Hz), 7.45–7.49(1H, m), 7.53(1H, t, J=7.8 Hz), 7.64 (1H, dt, J=7.8 Hz, 1.8 Hz), 7.80(1H, br.s), 8.11(1H, s), 8.58(1H, s).

EXAMPLE 129

(E)-N-ethyl-N-(6-methoxy-6-methyl-2-hepten-4-ynyl)-3-[3-(1-pyrrolyl)benzyloxybenzylamine (compound 150)

IR$\nu_{max}^{neat}$ cm$^{-1}$: 1605, 1506, 1341, 1170, 1149, 1074, 960, 789, 723, 696.

NMR (CDCl$_3$) δ: 1.09(3H, t, J=6.9 Hz), 1.46(6H, s), 2.56(2H, q, J=6.9 Hz), 3.15(2H, dd, J=6.5 Hz, 1.5 Hz), 3.35(3H, s), 3.61(2H, s), 5.12(2H, s), 5.73(1H, dt, J=15.9 Hz, 1.5 Hz), 6.20(1H, dt, J=15.9 Hz, 6.5 Hz), 6.37(2H, t, J=2.1 Hz), 6.86 (1H, dd, J=7.8 Hz, 1.6 Hz), 6.93(1H, d, J=7.8 Hz), 6.99–7.05(1H, m), 7.10(2H, t, J=2.1 Hz), 7.23(1H, t, J=7.5 Hz), 7.29–7.46(3H, m), 7.48–7.50(1H, m).

EXAMPLE 130

(E)-N-(6,6-dimethyl-2-hepten-4-ynyl)-N-methyl-3-[3-(2,3-dihydro-4-thienyl)benzyloxy]benzylamine (compound 151)

IR$\nu_{max}^{neat}$ cm$^{-1}$: 2968, 2788, 1584, 1491, 1455, 1365, 1263, 1152, 1023, 783.

NMR (CDCl$_3$) δ: 1.24(9H, s), 2.18(3H, s), 3.03 (2H, dd, J=6.6 Hz, 1.4 Hz), 3.11–3.19(2H, m), 3.35–3.43(2H, m), 3.46(2H, s), 5.04(2H, s), 5.64(1H, dt, J=15.9 Hz, 1.4 Hz), 6.08(1H, dt, J=15.9 Hz, 6.6 Hz), 6.59(1H, t, J=2.1 Hz), 6.83–6.93(2H, m), 6.97–7.00(1H, m), 7.19–7.33(4H, m), 7.39–7.42(1H, m).

COMPOUND 131

(E)-N-(6,6-dimethyl-2-hepten-4-ynyl)-N-ethyl-3-[3-(2,3-dihydro-4-thienyl)benzyloxy]benzylamine (compound 152)

IR$\nu_{max}^{neat}$ cm$^{-1}$: 2968, 2926, 1587, 1491, 1455, 1365, 1263, 1149, 777.

NMR (CDCl$_3$) δ: 1.03(3H, t, J=7.1 Hz), 1.24(9H, s), 2.49(2H, q, J=7.1 Hz), 3.08(2H, dd, J=6.4 Hz, 1.5 Hz), 3.15(2H, dt, J=8.4 Hz, 1.8 Hz), 3.38 (2H, t, J=8.4 Hz), 3.53(2H, s), 5.04(2H, s), 5.64(1H, dt, J=15.8 Hz, 1.5 Hz), 6.07(1H, dt, J=15.8 Hz, 6.4 Hz), 6.59(1H, t, J=1.8 Hz), 6.82-6.87(1H, m), 6.89-6.94(1H, m), 6.98-7.02 (1H, m), 7.21(1H, t, J=7.8 Hz), 7.23-7.35 (3H, m), 7.39-7.42(1H, m).

EXAMPLE 132

(E)-N-ethyl-N-(6-methoxy-6-methyl-2-hepten-4-ynyl)-3-[3-(2,3-dihydro-4-thienyl)benzyloxy]benzyl amine (compound 153)

IR$\nu_{max}^{neat}$ cm$^{-1}$: 1452, 1380, 1365, 1254, 1173, 1149, 1077, 819, 777, 693.

NMR (CDCl$_3$) δ: 1.04(3H, t, J=7.0 Hz), 1.46(6H, s), 2.51(2H, q, J=7.0 Hz), 3.09-3.18(4H, m), 3.35(3H, s), 3.35-3.42(2H, m), 3.54(2H, s), 5.04(2H, s), 5.68(1H, dt, J=15.7 Hz, 1.8 Hz), 6.16(1H, dt, J=15.7 Hz, 6.6 Hz), 6.59(1H, t, J=1.6 Hz), 6.83-6.89(1H, m), 6.90-6.95(1H, m), 6.98-7.04(1H, m), 7.21(1H, t, J=7.5 Hz), 7.25-7.35(3H, m), 7.39-7.40(1H, m).

EXAMPLE 133

(E)-N-(6,6-dimethyl-2-hepten-4-ynyl)-N-ethyl-3-[3-(2,5-dihydro-3-thienyl)benzyloxy)benzylamine (compound 154)

IR$\nu_{max}^{neat}$ cm$^{-1}$: 2968, 2920, 1587, 1491, 1455, 1365, 1263, 1152, 777.

NMR (CDCl$_3$) δ: 1.02(3H, t, J=7.1 Hz), 1.24(9H, s), 2.49(2H, q, J=7.1 Hz), 3.08(2H, dd, J=6.4 Hz, 1.5 Hz), 3.53(2H, s), 3.91-3.96(2H, m), 4.11-4.15(2H, m), 5.06(2H, s), 5.64(1H, dt, J=15.8 Hz, 1.5 Hz), 6.05(1H, dt, J=15.8 Hz, 6.4 Hz), 6.26(1H, quint, J=2.0 Hz), 6.82-6.87 (1H, m), 6.89-6.94(1H, m), 6.99-7.01(1H, m), 7.21(1H, t, J=8.0 Hz), 7.34-7.37(3H, m), 7.47-7.49(1H, m).

EXAMPLE 134

(E)-N-(6,6-dimethyl-2-hepten-4-ynyl)-N-methyl-3-[3-(1-pyrrolidinyl)benzyloxy]benzylamine (compound 155)

IR$\nu_{max}^{neat}$ cm$^{-1}$: 2968, 1608, 1584, 1506, 1491, 1458, 1368, 1266, 1152, 768.

NMR (CDCl$_3$) δ: 1.24(9H, s), 1.97-2.02(4H, m), 2.18(3H, s), 3.03(2H, dd, J=6.6 Hz, 1.5 Hz), 3.29-3.31(4H, m), 3.46(2H, s), 5.01(2H, s), 5.64(1H, dt, J=15.9 Hz, 1.5 Hz), 6.08(1H, dt, J=15.9 Hz, 6.5 Hz), 6.51(1H, dd, J=8.3 Hz, 2.4 Hz), 6.62-6.64(1H, m), 6.72(1H, d, J=7.4 Hz), 6.85-6.90(2H, m), 6.98(1H, t, J=2.1 Hz), 7.20-7.22(2H, m).

EXAMPLE 135

(E)-N-(6,6-dimethyl-2-hepten-4-ynyl)-N-ethyl-3-[5-(3-thienyl)-2-thienylmethyloxy]benzylamine (compound 156)

IR$\nu_{max}^{neat}$ cm$^{-1}$: 2968, 2926, 1596, 1446, 1377, 1260, 1017, 852, 801, 771.

NMR (CDCl$_3$) δ: 1.04(3H, t, J=7.0 Hz), 1.24(9H, s), 2.50(2H, q, J=7.0 Hz), 3.10(1H, dd, J=6.3 Hz, 1.4 Hz), 3.54(2H, s), 5.18(2H, s), 5.64(1H, dt, J=15.9 Hz, 1.4 Hz), 6.08(1H, dt, J=15.9 Hz, 6.3 Hz), 6.86(1H, dd, J=8.0 Hz, 2.7 Hz), 6.93 (1H, d, J=7.6 Hz), 7.00-7.04(2H, m), 7.07(1H, d, J=3.6 Hz), 7.22(1H, t, J=8.0 Hz), 7.29(1H, dd, J=5.2 Hz, 1.2 Hz), 7.33(1H, dd, J=5.2 Hz, 4.5 Hz), 7.36(1H, dd, J=4.5 Hz, 1.2 Hz).

EXAMPLE 136

(E)-N-(6,6-dimethyl-2-hepten-4-ynyl)-N-methyl-3-[2-(5-oxazolyl)-4-pyridylmethyloxy]benzylamine (compound 157)

IR$\nu_{max}^{neat}$ cm$^{-1}$: 2968, 1620, 1491, 1455, 1365, 1266, 1113, 957, 831, 762.

NMR (CDCl$_3$) δ: 1.24(9H, s), 2.19(3H, s), 3.05 (2H, dd, J=6.5 Hz, 1.5 Hz), 3.48(2H, s), 5.14 (2H, s), 5.65(1H, dt, J=15.9 Hz, 1.5 Hz), 6.09 (1H, dt, J=15.9 Hz, 6.5 Hz), 6.86(1H, ddd, J=7.9 Hz, 2.7 Hz, 0.9 Hz), 6.94(1H, d, J=7.9 Hz), 7.00-7.01(1H, m), 7.25(1H, t, J=7.9 Hz), 7.32 (1H, dt, J=5.0 Hz, 0.8 Hz), 7.73(1H, s), 7.76-7.77(1H, m), 7.99(1H, s), 8.64(1H, dd, J=5.0 Hz, 0.8 Hz).

EXAMPLE 137

(E)-N-(6,6-dimethyl-2-hepten-4-ynyl)-N-methyl-3-[4-(5-oxazolyl)-2-pyridylmethyloxy]benzylamine (compound 158)

IR$\nu_{max}^{neat}$ cm$^{-1}$: 2968, 1617, 1584, 1494, 1455, 1263, 1155, 1113, 957.

NMR (CDCl$_3$) δ: 1.24(9H, s), 2.19(3H, s), 3.04 (2H, d, J=6.5 Hz), 3.48(2H, s), 5.24(2H, s), 5.64(1H, dt, J=15.9 Hz, 1.7 Hz), 6.08(1H, dt, J=15.9 Hz, 6.5 Hz), 6.88-6.95(2H, m), 7.04-7.05 (1H, m), 7.19-7.27(1H, m), 7.46(1H, dd, J=5.4 Hz, 1.5 Hz), 7.59(1H, s), 7.79(1H, m), 8.00(1H, s), 8.65(1H, d, J=6.2 Hz).

EXAMPLE 138

(E)-N-(6,6-dimethyl-2-hepten-4-ynyl)-N-methyl-3-[5-(5-oxazolyl)furfuryloxy]benzylamine (compound 159)

IR$\nu_{max}^{neat}$ cm$^{-1}$: 2968, 2926, 1458, 1263, 1107, 1020, 963, 789.

NMR (CDCl$_3$) δ: 1.24(9H, s), 2.19(3H, s), 3.04 (2H, dd, J=6.5 Hz, 1.5 Hz), 3.47(2H, s), 5.05 (2H, s), 5.65(1H, dt, J=15.9 Hz, 1.5 Hz), 6.09 (1H, dt, J=15.9 Hz, 6.5 Hz), 6.53(1H, d, J=3.4 Hz), 6.64(1H, d, J=3.4 Hz), 6.87(1H, ddd, J=8.1 Hz, 2.7 Hz, 0.8 Hz), 6.93(1H, d, J=8.1 Hz), 7.00(1H, m), 7.24(1H, t, J=8.1 Hz), 7.30 (1H, s), 7.86(1H, s).

EXAMPLE 139

(E)-N-(6,6-dimethyl-2-hepten-4-ynyl)-N-methyl-3-[3-(5-oxazolyl)-5-furylmethyloxy]benzylamine (compound 160)

IR$\nu_{max}^{neat}$ cm$^{-1}$: 2968, 1584, 1461, 1269, 1152, 1098, 1041, 1032, 891, 831.

NMR (CDCl$_3$) δ: 1.24(9H, s), 2.20(3H, s), 3.05 (2H, dd, J=6.5 Hz, 1.4 Hz), 3.48(2H, s), 4.97 (2H, s), 5.66(1H, dt, J=15.8 Hz, 1.4 Hz), 6.09 (1H, 15.8 Hz, 6.5 Hz), 6.75(1H, d, J=0.8 Hz), 6.82-6.88(1H, m), 6.92(1H, d, J=7.8 Hz), 6.98(1H, br.s), 7.23(1H, t, J=7.8 Hz), 7.28 (1H, s), 7.54(1H, d, J=0.8 Hz), 7.86(1H, s).

EXAMPLE 140

(E)-N-(6,6-dimethyl-2-hepten-4-ynyl)-N-methyl-3-[2-(5-oxazolyl)-4-thiazolylmethyloxy]benzylamine (compound 161)

IR$\nu_{max}^{neat}$ cm$^{-1}$: 2968, 1596, 1491, 1455, 1263, 1158, 1104, 1059, 1017, 966, 894.

NMR (CDCl$_3$) δ: 1.19(9H, s), 2.14(3H, s), 3.00 (2H, dd, J=6.6 Hz, 1.4 Hz), 3.43(2H, s), 5.22 (2H, d, J=0.96 Hz), 5.60(1H, dt, J=15.8 Hz, 1.4 Hz), 6.03(1H, dt, J=15.8 Hz, 6.6 Hz), 6.83 (1H, ddd, J=7.6 Hz, 2.6 Hz, 0.75 Hz), 6.89 (1H, d, J=7.6 Hz), 6.97(1H, m), 7.19(1H, t, J=7.6 Hz), 7.37(1H, t, J=0.96 Hz), 7.63(1H, s), 7.92(1H, s).

EXAMPLE 141

(E)-N-(6,6-dimethyl-2-hepten-4-ynyl)-N-methyl-3-[6-(5-oxazolyl)-2-pyridylmethyloxy)benzylamine (compound 162)

IR$\nu_{max}^{neat}$ cm$^{-1}$: 2968, 1596, 1452, 1365, 1260, 1158, 1107, 804, 786.

NMR (CDCl$_3$) δ: 1.24(9H, s), 2.18(3H, s), 3.03 (2H, dd, J=6.5 Hz, 1.4 Hz), 3.46(2H, s), 5.25 (2H, s), 5.64(1H, dt, J=15.8 Hz, 1.4 Hz), 6.07 (1H, dt, J=15.8 Hz, 6.5 Hz), 6.86–6.91(1H, m), 6.91–6.95(1H, m), 7.01–7.04(1H, m), 7.23(1H, t, J=8.0 Hz), 7.51(1H, dd, J=7.8 Hz, 0.9 Hz), 7.59(1H, dd, J=7.8 Hz, 0.9 Hz), 7.72(1H, s), 7.80(1H, t, J=7.8 Hz), 7.99(1H, s).

EXAMPLE 142

(E)-N-(6,6-dimethyl-2-hepten-4-ynyl)-N-methyl-3-[5-(5-oxazolyl)-3-pyridylmethyloxy]benzylamine (compound 163)

IR$\nu_{max}^{neat}$ cm$^{-1}$: 2968, 1590, 1491, 1455, 1266, 1152, 1107, 1026, 963, 759.

NMR (CDCl$_3$) δ: 1.24(9H, s), 2.19(3H, s), 3.05 (2H, dd, J=6.6 Hz, 1.4 Hz), 3.48(2H, s), 5.13 (2H, s), 5.65(1H, dt, J=15.9 Hz, 1.4 Hz), 6.09 (1H, dt, J=15.9 Hz, 6.6 Hz), 6.88(1H, dd, J=7.8 Hz, 2.6 Hz), 6.94(1H, d, J=7.8 Hz), 7.01–7.04(1H, m), 7.25(1H, t, J=7.8 Hz), 7.49 (1H, s), 8.00(1H, s), 8.05(1H, t, J=2.0 Hz), 8.65(1H, d, J=2.0 Hz), 8.90(1H, d, J=2.0 Hz).

EXAMPLE 143

(E)-N-(6,6-dimethyl-2-hepten-4-ynyl)-N-methyl-3-[2-methyl-3-(1-pyrrolyl)benzyloxy)benzylamine hydrochloride (compound 164)

m.p. 137°–139° C.

IR$\nu_{max}^{neat}$ cm$^{-1}$: 2968, 2500, 1599, 1497, 1458, 1332, 1263, 1038, 723.

NMR (CDCl$_3$) δ: 1.25(9H, s), 2.18(3H, s), 2.65 (3H, s), 3.48–3.61(1H, m), 3.65–3.78(1H, m), 3 95–4.08(1H, m), 4.16–4.29(1H, m), 5.21 (2H, s), 5.85(1H, d, J=15.6 Hz), 6.20–6.36 (1H, m), 6.32(2H, t, J=2.1 Hz), 6.79(2H, t, J=2.1 Hz), 7.04–7.11(1H, m), 7.24–7.30(2H, m), 7.35(1H, t, J=7.9 Hz), 7.51(1H, t, J=4.5 Hz), 7.63(1H, br.s).

EXAMPLE 144

(E)-N-(6,6-dimethyl-2-hepten-4-ynyl)-N-methyl-3-[6-methyl-3-(1-pyrrolyl)benzyloxybenzylamine (compound 165)

IR$\nu_{max}^{neat}$ cm$^{-1}$: 2968, 1590, 1518, 1488, 1455, 1341, 1266, 1026, 723.

NMR (CDCl$_3$) δ: 1.24(9H, s), 2.19(3H, s), 2.39 (3H, s), 3.04(2H, dd, J=6.5 Hz, 1.5 Hz), 3.48 (2H, s), 5.06(2H, s), 5.65(1H, dt, J=15.9 Hz, 1.5 Hz), 6.08(1H, dt, J=15.9 Hz, 6.5 Hz), 6.33 (2H, t, J=2.2 Hz), 6.86–6.95(2H, m), 6.99–7.02 (1H, m), 7.07(2H, t, J=2.2 Hz), 7.21–7.27 (3H, m), 7.50(1H, br.s).

EXAMPLE 145

Production of (E)-N-(6,6-dimethyl-2-hepten-4-ynyl)-N-methyl-3-3-(4-thiazolyl)benzyloxy]benzylamine (compound 166)

600 mg of 2-chloro-4-(3-tolyl)thiazole was dissolved in a mixture of 8 ml of carbon tetrachloride and 2 ml of 1,2-dichloroethane. N-bromosuccinimide (511 mg) and 3 mg of benzoyl peroxide were added, and the mixture refluxed with stirring for 3 hours. After cooling, the precipitate was separated from the reaction mixture by filtration. It was washed with an aqueous solution of sodium hydrogen carbonate, and the solvent was evaporated under reduced pressure to give 4-(3-bromomethylphenyl)-2-chlorothiazole as a pale yellow oil.

The resulting bromomethyl compound was dissolved in 2 ml of dimethylformamide, and the solution was added to 8 ml of a tetrahydrofuran solution of phenolate prepared in advance from 388 mg of (E)-N-(6,6-dimethyl-2-hepten-4-ynyl)-N-methyl-3-hydroxybenzylamine and 68 mg of 60% oily sodium hydride. The mixture was stirred for 1 hour under ice cooling and then for 2 hours at room temperature. Water and ethyl ether were added to the reaction solution. The organic layer was separated and dried over anhydrous sodium sulfate. The desiccant was separated by filtration, and the solvent was evaporated under reduced pressure. The residue was purified by silica gel column chromatography [Wakogel C-200, 80 g, eluting solvent: hexane/ethyl acetate=6/1→4/1] to give 396 mg (yield 57%) of (E)-N-(6,6-dimethyl-2-hepten-4-ynyl)-N-methyl-3-[3-(2-chloro-4-thiazolyl)benzyloxy]benzylamine as a pale yellow oil.

The resulting ether compound (92 mg) was dissolved in 0.8 ml of acetic acid. The solution was heated to 57° to 60° C. with stirring, and 40 mg of zinc powder was added at a time. The mixture was stirred for 30 minutes, and the reaction mixture was poured into ice water. Sodium carbonate was added to adjust the pH to 9.0. The solution was extracted with ethyl acetate. The extract was dried over anhydrous sodium sulfate, and the solvent was evaporated. The residue was purified by medium-pressure liquid chromatography column: Lobar column, size B, Lichroprep Si 60 (E. Merck Co.); eluting solvent: hexane/ethyl acetate=6/1→3/1) to give 52 mg (yield 60%) of the captioned compound as a colorless oil.

IR$\nu_{max}^{neat}$ cm$^{-1}$: 2968, 1587, 1491, 1455, 1365, 1266, 1026, 789.

NMR (CDCl$_3$) δ: 1.24(9H, s), 2.18(3H, s), 3.03 (2H, dd, J=6.5 Hz, 1.5 Hz), 3.47(2H, s), 5.13 (2H, s), 5.64(1H, dt, J=15.8 Hz, 1.5 Hz), 6.08(1H, dt, J=15.8 Hz, 6.5 Hz), 6.86–6.92 (2H, m), 7.00(1H, br.s), 7.22(1H, t, J=7.8 Hz), 7.44–7.45(1H, m), 7.57(1H, d, J=2.0 Hz), 7.64 (1H, t, J=7.7 Hz), 7.87–7.91(1H, m), 8.02(1H, br.s), 8.84(1H, d, J=2.0 Hz).

Compounds of Examples 146 to 148 were obtained by using 5-(3-bromomethylphenyl)-2-bromothiazole obtained from 5-(3-tolyl)thiazole [see J. Org. Chem., 51, 3375 (1986); Org. React., 6, 381; and Ann., 628 (1981)] instead of 4-(3-bromomethylphenyl)-2-chlorothiazole, condensing it with the corresponding 3-hydroxybenzylamine derivative, and performing the same dehalogenation reaction as in Example 145.

EXAMPLE 146

(E)-N-(6,6-dimethyl-2-hepten-4-ynyl)-N-methyl-3-[3-(5-thiazolyl)benzyloxy]benzylamine (compound 167)

IR$\nu_{max}^{neat}$ cm$^{-1}$: 2974, 1590, 1458, 1266, 873, 789, 693.

NMR (CDCl$_3$) δ: 1.24(9H, s), 2.19(3H, s), 3.04 (2H, dd, J=6.6 Hz, 1.5 Hz), 3.47(2H, s), 5.10 (2H, s), 5.64(1H, dt, J=15.8 Hz, 1.5 Hz), 6.08(1H, dt, J=15.8 Hz, 6.6 Hz), 6.88(1H, dd, J=8.1 Hz, 1.8 Hz), 6.92(1H, d, J=7.8 Hz), 7.00 (1H, t, J=1.8 Hz), 7.23(1H, t, J=7.8 Hz), 7.42–7.44(2H, m), 7.53–7.56(1H, m), 7.65–7.66 (1H, m), 8.10(1H, d, J=0.6 Hz), 8.76(1H, d, J=0.6 Hz).

EXAMPLE 147

(E)-N-(6,6-dimethyl-2-hepten-4-ynyl)-N-ethyl-3-[3-(5-thiazolyl)benzyloxy]benzylamine (compound 168)

IR$\nu_{max}^{neat}$ cm$^{-1}$: 2972, 1588, 1490, 1456, 1364, 1264, 1152, 1046, 874, 788.

NMR (CDCl$_3$) δ: 0.96(3H, t, J=7.0 Hz), 1.19(9H, s), 2.46(2H, q, J=7.0 Hz), 3.04(2H, d, J=6.0 Hz), 3.50(2H, s), 5.06(2H, s), 5.60(1H, d, J=15.8 Hz), 6.02(1H, dt, J=15.8 Hz, 6.0 Hz), 6.82(1H, dd, J=8.1 Hz, 2.1 Hz), 6.89(1H, d, J=8.0 Hz), 6.98(1H, br.s), 7.18(1H, t, J=8.0 Hz), 7.38–7.41(2H, m), 7.48–7.52(1H, m), 7.62 (1H, s), 8.05(1H, d, J=0.6 Hz), 8.71(1H, d, J=0.6 Hz).

EXAMPLE 148

(E)-N-(6,6-dimethyl-2-hepten-4-ynyl)-N-propyl-3-[3-(5-thiazolyl)benzyloxy)benzylamine (compound 169)

IR$\nu_{max}^{neat}$ cm$^{-1}$: 2968, 1490, 1458, 1364, 1264, 1152, 872, 788, 694.

NMR (CDCl$_3$) δ: 0.85(3H, t, J=7.4 Hz), 1.24(9H, s), 1.46–1.51(2H, m), 2.37(2H, t, J=7.1 Hz), 3.07 (2H, dd, J=6.4 Hz, 1.3 Hz), 3.53(2H, s), 5.10 (2H, s), 5.63(1H, dd, J=15.9 Hz, 1.3 Hz), 6.04 (1H, dt, J=15.9 Hz, 6.4 Hz), 6.86(1H, dd, J=7.8 Hz, 1.8 Hz), 6.92(1H, d, J=7.4 Hz), 7.20 (1H, s), 7.22(1H, t, J=7.8 Hz), 7.43–7.44 (2H, m), 7.53–7.55(1H, m), 7.66(1H, br.s), 8.10(1H, s), 8.76(1H, s).

EXAMPLE 149

Production of
(E)-N-(6,6-dimethyl-2-hepten-4-ynyl)-N-methyl-3-[3-(3-pyrrolyl)benzyloxy]benzylamine (compound 170)

Methyl isocyanoacetate (280 microliters) and 400 microliters of 1,8-diazabicyclo5.4.0]undeca-7-ene (DBU) were added to 20 ml of tetrahydrofuran, and with stirring at 45° to 50° C., a tetrahydrofuran solution (5 ml) of 500 mg of (E)-N-(6,6-dimethyl-2-hepten-4-ynyl)-N-methyl-3-(3-formylbenzyloxy)benzylamine was added, and the mixture was stirred at the above temperature for 5 hours. The reaction mixture was allowed to cool and neutralized with acetic acid. The solvent was evaporated under reduced pressure and ethyl acetate and water was added to the residue to extract it. The organic layer was separated, dried over anhydrous magnesium sulfate. The desiccant was separated by filtration, and the solvent was evaporated. Then, the residue was purified by silica gel column chromatography [Wakogel C-200, 30 g, eluting solvent: hexane/ethyl acetate:5/1] to give 140 mg (yield 20%) of (E)-N-(6,6-dimethyl-2-hepten-4-ynyl)-N-methyl-3-[3-(2,4-dimethoxycarbonyl-3-pyrrolyl)benzyloxy)benzylamine as a pale yellow oil.

The resulting pyrrolyl compound (32 mg) was added to a mixture of 2 g of potassium hydroxide and 6 ml of water. The mixture was heated under reflux for 6 hours with stirring. After cooling, ethyl ether was added to the reaction mixture to extract it. The extract was dried over anhydrous magnesium sulfate, and the solvent was evaporated. The residue was purified by silica gel column chromatography [Wakogel C-200, 30 g; eluting solvent: hexane/ethyl acetate=10/1→2/1] to give 12.4 mg (yield 50%) of the captioned compound as a pale yellow oil.

IR$\nu_{max}^{neat}$ cm$^{-1}$: 3440, 2972, 2928, 2872, 1610, 1490, 1454, 1364, 1266, 1034, 778.

NMR (CDCl$_3$) δ: 1.24(9H, s), 2.18(3H, s), 3.03 (2H, dd, J=6.6 Hz, 1.5 Hz), 3.47(2H, s), 5.08 (2H, s), 5.64(1H, dt, J=15.8 Hz, 1.5 Hz), 6.09 (1H, dt, J=15.8 Hz, 6.6 Hz), 6.54–6.57(1H, m), 6.82–6.92(3H, m), 6.99–7.01(1H, m), 7.10–7.13 (1H, m), 7.22(1H, t, J=7.6 Hz), 7.23–7.28 (1H, m), 7.35(1H, t, J=7.4 Hz), 7.49(1H, dt, J=7.4 Hz, 1.7 Hz), 7.59–7.61(1H, m), 8.20–8.40 (1H, br).

EXAMPLE 150

Production of
(E)-N-(6,6-dimethyl-2-hepten-4-ynyl)-N-methyl-3-[3-(1,3,4-oxadiazol-2-yl)benzyloxy]benzylamine (compound 171)

173 mg of (E)-N-(6,6-dimethyl-2-hepten-4-ynyl)-N-methyl-3-(3-methoxycarbonylbenzyloxy)benzylamine was dissolved in 3 ml of ethanol, and 100 mg of 98% hydrazine hydrate was added. The mixture was heated under reflux for 3 hours. After the reaction mixture was evaporated under reduced pressure, water and ethyl acetate were added to the residue to extract it. The organic layer was separated and dried over anhydrous sodium sulfate. The desiccant was separated by filtration and the solvent was evaporated. The residual carbohydrazide was added to 4 ml of trimethyl orthoformate and the mixture was heated under reflux for 8 hours. After evaporating the excess trimethyl orthoformate, the residue was extracted with a mixture of ethyl acetate and water. The organic layer was separated and dried over anhydrous sodium sulfate. The desiccant was separated by filtration and the solvent was evaporated under reduced pressure. The residue was purified by silica gel column chromatography Wakogel C-200, 30 g; eluting solvent: hexane/ethyl acetate=2/1] and medium-pressure liquid chromatography column: Lobar column, size A, Lichroprep Si 60 (E. Merck Co.); eluting solvent: hexane/ethyl acetate=3/1→2/1) to give 18 mg (yield 10%) of the captioned compound as a colorless oil.

IR$\nu_{max}^{neat}$ cm$^{-1}$: 2974, 1590, 1491, 1455, 1368, 1266, 1152, 960, 726.

NMR (CDCl$_3$) δ: 1.24(9H, s), 2.19(3H, s), 3.04 (1H, dd, J=6.5 Hz, 1.5 Hz), 3.47(2H, s), 5.15 (2H, s), 5.65(1H, dt, J=15.8 Hz, 1.5 Hz), 6.08 (1H, dt, J=15.8 Hz, 6.5 Hz), 6.85–6.90(1H, m), 6.90–6.94(1H, m), 7.00(1H, br.s), 7.24(1H, t, J=7.8 Hz), 7.55(1H, t, J=7.6 Hz), 7.63–7.67 (1H, m), 8.05(1H, dt, J=6.3 Hz, 1.5 Hz), 8.18 (1H, br.s), 8.49(1H, s).

EXAMPLE 151

Production of (E),
(E)-N-(6,6-dimethyl-2-hepten-4-ynyl)-N-methyl-3-[2-[3-(3-thienyl)phenyl]ethenyl]benzylamine hydrochloride (compound 172)

95 mg of (E)-3-2-[3-(3-thienyl)phenyl]ethenyl]benzyl chloride was dissolved in 2 ml of dimethylformamide. To the solution were added 58 mg of (E)-N-methyl-6,6-dimethyl-2-hepten-4-ynylamine hydrochloride and 126 mg of potassium carbonate. The mixture was stirred overnight at room temperature. The reaction mixture was evaporated under reduced pressure, and ethyl ether and water were added to the residue. The organic layer was separated and dried over anhydrous sodium sulfate. The desiccant was separated by filtration, and the solvent was evaporated. The residue was purified by silica gel column chromatography [Wakogel C-200, 15 g;

eluting solvent: hexane→hexane/ethyl acetate=10/1] to give 88 mg (yield 67%) of a free base of the captioned compound as a colorless oil.

The free base obtained as above was treated with a hydrogen chloride-methanol solution and recrystallized from a mixture of chloroform and hexane to give the captioned hydrochloride, m. p. 132°-133° C.

IR$\nu^{KBr}_{max}$ cm$^{-1}$: 3430, 2968, 2482, 1464, 966, 777, 699.

NMR (CDCl) δ: 1.25(9H, s), 2.61(3H, s), 3.56–3.61 (2H, m), 4.05–4.10(2H, m), 5.84(1H, d, J=15.9 Hz), 6.27(1H, dt, J=15.9 Hz, 7.3 Hz), 7.12–7.29(2H, m), 7.37–7.53(8H, m), 7.58 (1H, dt, J=7.4 Hz, 1.9 Hz), 7.74(1H, br.s), 7.79(1H, br.s).

Compounds of Examples 152 to 166 were obtained by the same method as in Example 151 except using the corresponding benzyl chloride, bromide or methanesulfonate derivatives and 2-hepten-4-ynylamine hydrochlorides instead of the starting compound (E)-3-[2-[3-(3-thienyl)phenyl]ethenyl]benzyl chloride and (E)-N-methyl-6,6-dimethyl-2-hepten-4-ynylamine hydrochloride.

EXAMPLE 152

(E),(E)-N-(6,6-dimethyl-2-hepten-4-ynyl)-N-ethyl-3-[2-[3-(3-thienyl)phenyl]ethenyl]benzylamine hydrochloride (compound 173)

m.p. 174°-176° C.

IR$\nu_{max}^{KBr}$ cm$^{-1}$: 3436, 2968, 966, 777, 699.

NMR (CDCl$_3$) δ: 1.25(9H, s), 1.40–1.46(3H, m), 2.98–3.01(2H, m), 3.57–3.62(2H, m), 4.07–4.09 (2H, m), 5.83(1H, d, J=15.6 Hz), 6.25(1H, dt, J=15.6 Hz, 7.3 Hz), 7.12–7.25(2H, m), 7.30–7.53 (9H, m), 7.56(1H, d, J=7.5 Hz), 7.74–7.75(1H, m), 7.86(1H, br.s).

EXAMPLE 153

(E),(E)-N-(6,6-dimethyl-2-hepten-4-ynyl)-N-propyl-3-[2-[3-(3-thienyl)phenyl]ethenyl]benzylamine (compound 174)

IR$\nu_{max}^{neat}$ cm$^{-1}$: 2968, 2806, 1605, 963, 774, 696.

NMR (CDCl$_3$) δ: 0.89(3H, t, J=7.2 Hz), 1.24(9H, s), 1.47–1.57(2H, m), 2.41(2H, t, J=7.2 Hz), 3.11 (2H, d, J=6.4 Hz), 3.58(2H, s), 5.66(1H, d, J=15.8 Hz), 6.11(1H, dt, J=15.8 Hz, 6.4 Hz), 7.16(2H, s), 7.22–7.26(1H, m), 7.30(1H, t, J=7.2 Hz), 7.36–7.51(8H, m), 7.73–7.74(1H, m).

EXAMPLE 154

(E),(E)-N-ethyl-N-(6-methoxy-6-methyl-2-hepten-4-ynyl)-3-[2-[3-(3-thienyl)phenyl]ethenyl]benzylamine (compound 175)

IR$\nu_{max}^{neat}$ cm$^{-1}$: 2980, 2932, 2818, 1605, 1251, 1170, 1149, 1074, 774, 699.

NMR (CDCl$_3$) δ: 1.08(3H, t, J=7.1 Hz), 1.46(6H, s), 2.55(2H, q, J=7.1 Hz), 3.15(2H, dd, J=6.4 Hz, 1.2 Hz), 3.36(3H, s), 3.59(2H, s), 5.71(1H, dt, J=15.9 Hz, 1.2 Hz), 6.20(1H, dt, J=15.9 Hz, 6.4 Hz), 7.16(2H, s), 7.20–7.25(2H, m), 7.31 (1H, t, J=7.5 Hz), 7.35–7.55(7H, m), 7.74(1H, t, J=2.3 Hz).

EXAMPLE 155

(E),(E)-N)(6,6-dimethyl-2-hepten-4-ynyl)-N-methyl-3-[2-[3-(1-pyrrolyl)phenyl]ethenyl]benzylamine (compound 176)

IR$\nu_{max}^{neat}$ cm$^{-1}$: 2968, 1605, 1506, 1341, 1071, 963, 756, 723, 696.

NMR (CDCl$_3$) δ: 1.24(9H, s), 2.22(3H, s), 3.08(2H, dd, J=6.6 Hz, 1.5 Hz), 3.51(2H, s), 5.67(1H, dt, J=15.9 Hz, 1.5 Hz), 6.12(1H, dt, J=15.9 Hz, 6.6 Hz), 6.37(2H, t, J=2.1 Hz), 7.13(2H, t, J=2.1 Hz), 7.15(2H, s), 7.20–7.34(3H, m), 7.37–7.44(3H, m), 7.49–7.54(2H, m).

EXAMPLE 156

(E),(E)-N-(6,6-dimethyl-2-hepten-4-ynyl)-N-ethyl-3-[2-[3-(1-pyrrolyl)phenyl]ethenyl]benzylamine (compound 177)

IR$\nu_{max}^{neat}$ cm$^{-1}$: 2968, 2926, 1608, 1587, 1506, 1341, 1071, 963, 723.

NMR (CDCl$_3$) δ: 1.07(3H, t, J=6.8 Hz), 1.24(9H, s), 2.54(2H, q, J=6.8 Hz), 3.14(2H, dd, J=6.5 Hz, 1.5 Hz), 3.60(2H, s), 5.67(1H, dt, J=15.9 Hz, 1.5 Hz), 6.10(1H, dt, J=15.9 Hz, 6.5 Hz), 6.37 (2H, t, J=2.2 Hz), 7.13(2H, t, J=2.2 Hz), 7.12–7.16(2H, m), 7.25–7.34(3H, m), 7.38–7.44 (3H, m), 7.50(1H, s), 7.52–7.54(1H, m).

EXAMPLE 157

(E),(E)-N-ethyl-N-(6-methoxy-6-methyl-2-hepten-4-ynyl)-3-2-[3-(1-pyrrolyl)phenyl]ethenyl]benzylamine (compound 178)

IR$\nu_{max}^{neat}$ cm$^{-1}$: 1605, 1506, 1341, 1170, 1149, 1074, 960, 789, 723, 696.

NMR (CDCl$_3$) δ: 1.09(3H, t, J=6.9 Hz), 1.46(6H, s), 2.56(2H, q, J=6.9 Hz), 3.15(2H, dd, J=6.5 Hz, 1.5 Hz), 3.35(3H, s), 3.61(2H, s), 5.73(1H, dt, J=15.9 Hz, 1.5 Hz), 6.20(1H, dt, J=15.9 Hz, 6.5 Hz), 6.37(2H, t, J=2.7 Hz), 7.12–7.16 (4H, m), 7.25–7.35(3H, m), 7.38–7.45(3H, m), 7.50–7.54(2H, m).

EXAMPLE 158

(E),(E)-N-(6,6-dimethyl-2-hepten-4-ynyl)-N-ethyl-3-[2-[3-(3-pyridyl)phenyl]ethenyl]benzylamine (compound 179)

IR$\nu_{max}^{neat}$ cm$^{-1}$: 3016, 2974, 1605, 1473, 1365, 1266, 1215, 963, 759, 711.

NMR (CDCl$_3$) δ: 1.07(3H, t, J=7.1 Hz), 1.24(9H, s), 2.55(2H, q, J=7.1 Hz), 3.13(1H, dd, J=6.7 Hz, 1.5 Hz), 3.60(2H, s), 5.70(1H, dt, J=15.9 Hz, 1.5 Hz), 6.10(1H, dt, J=15.9 Hz, 6.7 Hz), 7.19 (2H, s), 7.23–7.59(8H, m), 7.71(1H, br.s), 7.89–7.94(1H, m), 8.61(1H, dd, J=4.8 Hz, 1.6 Hz), 8.89(1H, d, J=1.6 Hz).

EXAMPLE 159

(E),(E)-N-(6,6-dimethyl-2-hepten-4-ynyl)-N-ethyl-3-[2-[3-(5-oxazolyl)phenyl]ethenyl)benzylamine (compound 180)

IR$\nu_{max}^{neat}$ cm$^{-1}$: 2968, 2926, 1263, 1107, 960, 798, 756, 696.

NMR (CDCl$_3$) δ: 1.07(3H, t, J=7.0 Hz), 1.24(9H, s), 2.51–2.58(2H, m), 3.12–3.14(2H, m), 3.58–3.62 (2H, m), 5.68(1H, d, J=15.7 Hz), 6.10(1H, dt, J=15.7 Hz, 6.1 Hz), 7.15–7.57(10H, m), 7.81 (1H, t, J=1.5 Hz), 7.94(1H, s).

EXAMPLE 160

(E),(E)-N-ethyl-N-(6-methoxy-6-methyl-2-hepten-4-ynyl)-3-[2-[3-(5-oxazolyl)phenyl]ethenyl]benzylamine (compound 181)

IR$\nu_{max}^{neat}$ cm$^{-1}$: 3128, 2984, 2936, 2820, 1604, 1582, 1506, 968.

NMR (CDCl$_3$) δ: 1.08(3H, t, J=7.0 Hz), 1.46(6H, s), 2.56(2H, q, J=7.0 Hz), 3.15(2H, d, J=6.3 Hz), 3.36(3H, s), 3.60(2H, s), 5.71(1H, dt, J=15.8 Hz, 1.5 Hz), 6.21(1H, dt, J=15.8 Hz, 6.3 Hz), 7.13(1H, d, J=16.1 Hz), 7.14(1H, d, J=16.1 Hz), 7.32(1H, t, J=7.5 Hz), 7.41(1H, s), 7.42-7.45(2H, m), 7.49-7.50(2H, m), 7.51-7.52 (1H, m), 7.55(1H, dt, J=7.5 Hz, 1.6 Hz), 7.81 (1H, t, J=1.6 Hz), 7.94(1H, s).

EXAMPLE 161

(E),(E)-N-(6,6-dimethyl-2-hepten-4-ynyl)-N-propyl-3-[2-[3-(1-pyrrolyl)phenyl]ethenyl]benzylamine (compound 182)

IR$\nu_{max}^{neat}$ cm$^{-1}$: 968, 1608, 1506, 1341, 1071, 960, 723, 696.

NMR (CDCl$_3$) δ: 0.89(3H, t, J=7.3 Hz), 1.24(9H, s), 1.48-1.60(2H, m), 2.42(2H, t, J=7.3 Hz), 3.12 (2H, d, J=6.2 Hz), 3.58(2H, s), 5.66(1H, d, J=15.8 Hz), 6.10(1H, dt, J=15.8 Hz, 6.2 Hz), 6.37(2H, t, J=2.2 Hz), 7.14(2H, t, J=2.2 Hz), 7.13-7.15(2H, m), 7.22-7.34(3H, m), 7.38-7.42 (3H, m), 7.48-7.52(1H, m), 7.52-7.54(1H, m).

EXAMPLE 162

(E),(E)-N-(6,6-dimethyl-2-hepten-4-ynyl)-N-ethyl-3-[2-[3-(1-imidazolyl)phenyl]ethenyl]benzylamine (compound (183)

IR$\nu_{max}^{neat}$ cm$^{-1}$: 2972, 2864, 1608, 1588, 1504, 1308, 1060, 962.

NMR (CDCl$_3$) δ: 1.10(3H, t, J=7.2 Hz), 1.25(9H, s), 2.57(2H, q, J=7.2 Hz), 3.18(2H, dd, J=6.3 Hz, 1.5 Hz), 3.61(2H, s), 5.64(1H, dt, J=15.9 Hz, 1.5 Hz), 6.06(1H, dt, J=15.9 Hz, 6.3 Hz), 7.14 (1H, d, J=16.0 Hz), 7.19(1H, d, J=16.0 Hz), 7.21-7.58(9H, m), 7.67-7.74(1H, m), 7.91 (1H, br.s).

EXAMPLE 163

(E),(E)-N-(6,6-dimethyl-2-hepten-4-ynyl)-N-methyl-2-[2-[3-(3-thienyl)phenyl]ethenyl]-4-pyridylmethylamine (compound 184)

IR$\nu_{max}^{neat}$ cm$^{-1}$: 1602, 1479, 1458, 1365, 1263, 1203, 975, 852, 774.

NMR (CDCl$_3$) δ: 1.24(9H, s), 2.34(3H, s), 3.10(2H, dd, J=7.0 Hz, 1.6 Hz), 3.52(2H, s), 5.68(1H, dt, J=15.8 Hz, 1.6 Hz), 6.10(1H, dt, J=15.8 Hz, 7.0 Hz), 7.14(1H, d, J=5.6 Hz), 7.23(1H, d, J=16.4 Hz), 7.41-7.48(4H, m), 7.49-7.55(3H, m), 7.68(1H, d, J=16.4 Hz), 7.81(1H, t, J=1.8 Hz), 8.54(1H, d, J=4.7 Hz).

EXAMPLE 164

(E)-N-(6,6-dimethyl-2-hepten-4-ynyl)-N-methyl-3-[2-[3-(3-thienyl)phenyl]ethenyl]benzylamine (compound 185)

IR$\nu_{max}^{neat}$ cm$^{-1}$: 2968, 1458, 1365, 963, 774, 699.

NMR (CDCl$_3$) δ: 1.24(9H, s), 2.16(3H, s), 2.95 (4H, s), 3.02(2H, dd, J=6.6 Hz, 1.5 Hz), 3.45 (2H, s), 5.63(1H, dt, J=15.9 Hz, 1.5 Hz), 6.08 (1H, dt, J=15.9 Hz, 6.6 Hz), 7.07-7.25(5H, m), 7.27-7.52(6H, m).

EXAMPLE 165

(E)-N-(6,6-dimethyl-2-hepten-4-ynyl)-N-ethyl-3-[2-[3-(1-pyrrolyl)phenyl)ethyl]benzylamine (compound 186)

IR$\nu_{max}^{neat}$ cm$^{-1}$: 2968, 2928, 2864, 2796, 1610, 1594, 1506, 726.

NMR (CDCl$_3$) δ: 1.03(3H, t, J=7.1 Hz), 1.24(9H, s), 2.48(2H, q, J=7.1 Hz), 2.95(4H, s), 3.06(2H, dd, J=6.2 Hz, 2.3 Hz), 3.53(2H, s), 5.62(1H, dt, J=15.8 Hz, 2.3 Hz), 6.06(1H, dt, J=15.8 Hz, 6.2 Hz), 6.33(2H, t, J=2.2 Hz), 7.04(2H, t, J=2.2 Hz), 7.04-7.08(2H, m), 7.13-7.17(3H, m), 7.19-7.23(2H, m), 7.31(1H, t, J=7.8 Hz).

EXAMPLE 166

(E)-N-(6,6-dimethyl-2-hepten-4-ynyl)-N-ethyl-3-[2-[3-(3-pyridyl)phenyl]ethyl]benzylamine (compound 187)

IR$\nu_{max}^{neat}$ cm$^{-1}$: 2968, 293Z, 2866, 1473, 1458, 1365, 789, 705.

NMR (CDCl$_3$) δ: 1.02(3H, t, J=7.3 Hz), 1.24(9H, s), 2.50(2H, q, J=7.3 Hz), 2.96-2.99(4H, m), 3.01 (1H, d, J=6.4 Hz), 3.54(1H, s), 5.63(1H, d, J=16.2 Hz), 6.08(1H, dd, J=16.2 Hz, 6.4 Hz), 7.06-7.11(1H, m), 7.15-7.27(4H, m), 7.32-7.42 (4H, m), 7.83(1H, dt, J=8.4 Hz, 1.8 Hz), 8.60 (1H, br.s), 8.80(1H, br.s).

EXAMPLE 167

Production of (E),(E)-N-(6,6-dimethyl-2-hepten-4-ynyl)-N-ethyl-5-[2-[3-(3-thienyl)phenyl]ethenyl]furfurylamine (compound 188)

18 mg of (E)-N-(6,6-dimethyl-2-hepten-4-ynyl)-N-ethyl-5-formylfurfurylamine and 19 mg of dimethyl-3-(3-thienyl)benzylphosphonate [synthesized by condensation between 3-(3-thienyl)benzyl bromide and trimethyl phosphite] were dissolved in dimethylformamide, and 2.6 mg of 60% oily sodium hydride was added. The mixture was stirred overnight at room temperature. The reaction mixture was concentrated under reduced pressure. The residue was purified by preparative thin-layer chromatography [thin layer plate: Kieselgel 60F$_{254}$, Art. 5715 (E. Merck Co.); developing solvent: hexane/ethyl acetate=3/1] to give 15 mg (yield 55%) of the captioned compound as a pale yellow oil.

IR$\nu_{max}^{neat}$ cm$^{-1}$: 2968, 1602, 1458, 1365, 1266, 1020, 960, 774.

NMR (CDCl$_3$) δ: 1.16(3H, t, J=7.0 Hz), 1.24(9H, s), 2.58-2.68(2H, m), 3.25(2H, d, J=6.8 Hz), 3.77 (2H, s), 5.73(1H, d, J=15.9 Hz), 6.13(1H, dt, J=15.9 Hz, 6.8 Hz), 6.25-6.35(2H, m), 6.90(1H, d, J=16.4 Hz), 7.04(1H, d, J=16.4 Hz), 7.32-7.52 (6H, m), 7.67(1H, br.s).

Compounds of Examples 168 and 169 were obtained by performing the same reaction as in Example 167 except that the corresponding formyl derivatives were used instead of the starting (E)-N-(6,6-dimethyl-2-hepten-4-ynyl)-N-ethyl-5-formylfurfurylamine.

EXAMPLE 168

(E),(E)-N-(6,6-dimethyl-2-hepten-4-ynyl)-N-methyl-4-[2-[3-(3-thienyl)phenyl]ethenyl]-2-pyridylmethylamine (compound 189)

IR$\nu_{max}^{neat}$ cm$^{-1}$: 2968, 2868, 1602, 1450, 1266, 966, 777.

NMR (CDCl$_3$) δ: 1.24(9H, s), 2.35(3H, s), 3.20-3.27 (2H, m), 3.74-3.79(2H, m), 5.72(1H, d, J=15.7 Hz), 6.18(1H, dt, J=15.7 Hz, 6.6 Hz), 7.19(1H, d, J=16.4 Hz), 7.19-7.63(9H, m), 7.76 (1H, m), 8.52(1H, d, J=5.3 Hz).

EXAMPLE 169

(E),(E)-N-(6,6-dimethyl-2-hepten-4-ynyl)-N-ethyl-3-[2-[3-(3-thienyl)phenyl]ethenyl]-5-isoxazolylmethylamine (compound 190)

IR$\nu_{max}^{neat}$ cm$^{-1}$: 2968, 2926, 1440, 1365, 963, 852, 774.

NMR (CDCl$_3$) δ: 0.88(3H, t, J=7.1 Hz), 1.25(9H, s), 2.53–2.68(2H, m), 3.17–3.28(2H, m), 3.81 (1H, s), 5.71(1H, d, J=15.9 Hz), 6.08(1H, dt, J=15.9 Hz, 6.5 Hz), 6.40–6.48(1H, m), 7.15–7.25 (2H, m), 7.38–7.53(5H, m), 7.56(1H, dt, J=7.1 Hz, 2.1 Hz), 7.73(1H, s).

EXAMPLE 170

Production of (E)-N-(6,6-dimethyl-2-octen-4-ynyl))-N-ethyl-3-[3-(3-thienyl)benzyloxy]benzylamine (compound 191)

50 mg of N-ethyl-3-3-(3-thienyl)benzyloxy]benzylamine hydrochloride was dissolved in 1.5 ml of dimethylformamide, and 30 mg of 1-bromo-6,6-dimethyl-2-octen-4-yne (a mixture of the E-form and the Z-form in a ratio of about 4:1) and 65 mg of sodium carbonate were added. The mixture was stirred overnight at room temperature. The reaction mixture was diluted with water and then extracted with ethyl ether. The extract was washed with a saturated aqueous solution of sodium chloride and dried over anhydrous sodium sulfate. The desiccant was separated by filtration, and then the solvent was evaporated. The residue was purified by medium-pressure liquid chromatography [column: Lobar column, size A, Lichroprep Si 60 (E. Merck Co.); eluting solvent: hexane/ethyl acetate=7/1] to give 39 mg (yield 63%) of the captioned compound as a colorless oil.

IR$\nu_{max}^{neat}$ cm$^{-1}$: 2968, 2926, 2800, 1584, 1491, 1458, 1260, 774.

NMR (CDCl$_3$) δ: 0.97(3H, t, J=7.3 Hz), 1.00–1.10 (3H, m), 1.18(6H, s), 1.44(2H, q, J=7.3 Hz), 2.45–2.60(2H, m), 3.05–3.15(2H, m), 3.50–3.60 (2H, m), 5.11(2H, s), 5.65(1H, d, J=15.9 Hz), 6.07(1H, dt, J=15.9 Hz, 6.4 Hz), 6.85–6.90 (1H, m), 6.90–6.95(1H, m), 7.01–7.06(1H, m), 7.22(1H, t, J=8.0 Hz), 7.35–7.45(4H, m), 7.47 (1H, dd, J=2.3 Hz, 1.8 Hz), 7.55(1H, dt, J=7.0 Hz, 1.8 Hz), 7.66–7.69(1H, m).

EXAMPLE 171

Production of (E)-N-(6,6-dimethyl-2-hepten-4-ynyl)-N-methyl-4-hydroxy-3-[3-(3-thienyl)benzyloxy]benzylamine hydrochloride (compound 192)

A dimethylformamide solution (1 ml) of 32 mg of 3-(3-thienyl)benzyl bromide was added to a tetrahydrofuran solution (1.5 ml) of phenolate prepared from 40 mg of (E)-N-(6,6-dimethyl-2-hepten-4-ynyl)-N-methyl-3-hydroxy-4-methoxymethyloxybenzylamine and 5 mg of 60% oily sodium hydride. The mixture was stirred at room temperature for 2 hours. Ethyl ether was added to the reaction mixture, and the insoluble inorganic salts were separated by filtration. The filtrate was concentrated under reduced pressure. The residue was dissolved in a mixture of 1 ml of 10% hydrogen chloride-methanol and 1 ml of tetrahydrofuran, and the solution was left to stand at room temperature for 2 hours. The reaction mixture was concentrated under reduced pressure, and a 5% aqueous solution of sodium hydrogen carbonate and ethyl ether were added to the residue to extract it. The organic layer was separated and dried over anhydrous magnesium sulfate. The desiccant was separated by filtration and the solvent was evaporated. The residue was purified by silica gel column chromatography [Wakogel C-200, 5 g; eluting solvent: hexane/ethyl acetate=3/1] to give 31 mg (yield 56%) of a free base of the captioned compound as a colorless oil. The free base was treated with a hydrogen chloride-methanol solution and recrystallized from a mixture of ethyl ether and isopropyl ether to give the captioned hydrochloride, m.p. 88°–90° C.

IR$\nu_{max}^{KBr}$ cm$^{-1}$: 2968, 1521, 1464, 1446, 1281, 777.

NMR (CDCl$_3$) δ: 1.25(3H, s), 3.39–3.54(1H, m), 3.59–3.74(1H, m), 3.83–4.00(1H, m), 4.01–4.20 (1H, m), 5.31(2H, s), 5.81(1H, d, J=15.6 Hz), 5.91(1H, br.s), 6.21(1H, dt, J=15.6 Hz, 7.7 Hz), 6.80(1H, d, J=7.8 Hz), 6.91(1H, d, J=7.8 Hz), 7.38–7.48(4H, m), 7.50–7.55(1H, m), 7.56–7.62(1H, m), 7.75(1H, s), 7.82(1H, s).

Compounds of Examples 172 and 173 were obtained by performing the same reaction as in Example 171 except that instead of the starting compounds (E)-N-(6,6-dimethyl-2-hepten-4-ynyl)-N-methyl-3-hydroxy-4-methoxymethyloxybenzylamine and/or 3-(3-thienyl)-benzyl bromide, the corresponding methoxymethyloxybenzylamine derivatives and/or 3-(5-oxazolyl)benzyl methanesulfonate were used.

EXAMPLE 172

(E)-N-(6,6-dimethyl-2-hepten-4-ynyl)-N-ethyl-2-hydroxy-3-[3-(5-oxazolyl)benzyloxy]benzylamine (compound 193)

IR$\nu_{max}^{neat}$ cm$^{-1}$: 2968, 1476, 1365, 1245, 1107, 1035, 954, 789, 750, 693.

NMR (CDCl$_3$) δ: 1.13(3H, t, J=7.0 Hz) 1.23(9H, s), 2.63(2H, q, J=7.0 Hz), 3.20(2H, d, J=7.0 Hz), 3.78(2H, s), 5.18(2H, s), 5.62(1H, d, J=15.7 Hz), 6.08(1H, dt, J=15.7 Hz, 7.0 Hz), 6.59–6.64(1H, m), 6.67(1H, t, J=8.0 Hz), 6.84 (1H, dd, J=8.0 Hz, 1.8 Hz), 7.37(1H, s), 7.38–7.50(2H, m), 7.60(1H, dt, J=7.0 Hz, 1.8 Hz), 7.77(1H, s), 7.91(1H, s).

EXAMPLE 173

(E)-N-(6,6-dimethyl-2-hepten-4-ynyl)-N-methyl-4-hydroxy-3-[3-(5-oxazolyl)benzyloxy]benzylamine (compound 194)

IR$\nu_{max}^{neat}$ cm$^{-1}$: 2968, 1518, 1461, 1365, 1275, 1200, 1119, 795, 759.

NMR (CDCl$_3$) δ: 1.24(9H, s), 2.19(3H, s), 2.96–3.12 (2H, m), 3.44(2H, s), 5.16(2H, s), 5.65(1H, d, J=16.1 Hz), 6.08(1H, dt, J=16.1 Hz, 6.7 Hz), 6.80(1H, dt, J=8.0 Hz, 1.7 Hz), 6.89(1H, d, J=8.0 Hz), 7.02(1H, br.s), 7.39(1H, s), 7.39–7.42(1H, m), 7.48(1H, t, J=7.6 Hz), 7.65 (1H, dt, J=7.6 Hz, 1.6 Hz), 7.73(1H, s), 7.93 (1H, s).

EXAMPLE 174

Production of (E)-N-(6,6-dimethyl-2-hepten-4-ynyl)-N-ethyl-3-[3-(3-thienyl)benzylamino)benzylamine (compound 195)

90 mg of (E)-N-(6,6-dimethyl-2-hepten-4-ynyl)-N-ethyl-3-aminobenzylamine and 63 mg of 3-(3-thienyl)-benzaldehyde were dissolved in 2.5 ml of anhydrous methanol, and the solution was stirred overnight at room temperature in the presence of molecular sieves 3A. The molecular sieves were separated by filtration from the reaction mixture. Then, 12.5 mg of sodium borohydride was added, and the mixture was further stirred for 30 minutes at room temperature. The solvent was evaporated under reduced pressure. The residue was dissolved in a mixture of methylene chloride and water. The organic layer was separated, and dried over anhydrous magnesium sulfate. The desiccant was separated by filtration, and the solvent was evaporated. The residue was purified by silica gel column chromatography [Wakogel C-200, 5 g; eluting solvent: hexane/ethyl acetate=10/1→5/1] to give 80 mg (yield 55%) of the captioned compound as a pale yellow oil.

IR$\nu_{max}^{neat}$ cm$^{-1}$: 2968, 2926, 1608, 1491, 774.

NMR (CDCl$_3$) δ: 1.01(3H, t, J=7.1 Hz), 1.24(9H, s), 2.49(2H, q, J=7.1 Hz), 3.08(2H, dd, J=6.4 Hz, 1.5 Hz), 3.48(2H, s), 4.37(2H, s), 5.63(1H, dt, J=15.9 Hz, 1.5 Hz), 6.06(1H, dt, J=15.9 Hz, 6.4 Hz), 6.51–6.56(1H, m), 6.66–6.69(1H, m), 7.11(1H, t, J=8.0 Hz), 7.31(1H, dt, J=7.8 Hz, 1.7 Hz), 7.35–7.40(3H, m), 7.45(1H, t, J=2.2 Hz), 7.51(1H, dt, J=7.8 Hz, 1.7 Hz), 7.61(1H, br.s).

Compounds of Examples 175 to 180 were obtained by performing the same reaction as in Example 174 except that instead of the starting compound (E)-N-(6,6-dimethyl-2-hepten-4-ynyl)-N-ethyl-3-aminobenzylamine and/or 3-(3-thienyl)benzaldehyde, the corresponding 3-aminobenzylamine derivatives and/or 3-substituted benzaldehyde derivatives were used.

EXAMPLE 175

(E)-N-(6,6-dimethyl-2-hepten-4-ynyl)-N-methyl-3-[3-(3-thienyl)benzylamino]benzylamine (compound 196)

IR$\nu_{max}^{neat}$ cm$^{-1}$: 2968, 1608, 1491, 1458, 1365, 774.

NMR (CDCl$_3$) δ: 1.24(9H, s), 2.18(3H, s), 3.02(2H, dd, J=6.5 Hz, 1.4 Hz), 3.42(2H, s), 4.37(2H, s), 5.63(1H, dt, J=15.8 Hz, 1.4 Hz), 6.07(1H, dt, J=15.8 Hz, 6.5 Hz), 6.52–6.56(1H, m), 6.65–6.68 (2H, m), 7.11(1H, t, J=7.9 Hz), 7.30(1H, dt, J=7.5 Hz, 1.4 Hz), 7.35–7.40(3H, m), 7.45(1H, t, J=2.1 Hz), 7.51(1H, dt, J=7.5 Hz, 1.7 Hz), 7.61 (1H, br.s).

EXAMPLE 176

(E)-N-(6,6-dimethyl-2-hepten-4-ynyl)-N-ethyl-3-[3-(1-pyrrolyl)benzylamino]benzylamine (compound 197)

IR$\nu_{max}^{neat}$ cm$^{-1}$: 2968, 1608, 1506, 1338, 1071, 783, 726.

NMR (CDCl$_3$) δ: 1.00(3H, t, J=7.1 Hz), 1.24(9H, s), 2.47(2H, q, J=7.1 Hz), 3.07(2H, dd, J=6.5 Hz, 1.5 Hz), 3.48(2H, s), 4.39(2H, s), 5.62(1H, dt, J=15.8 Hz, 1.5 Hz), 6.05(1H, dt, J=15.8 Hz, 6.5 Hz), 6.33(2H, t, J=2.2 Hz), 6.49–6.53(1H, m), 6.66–6.69(2H, m), 7.08(2H, t, J=2.2 Hz), 7.10 (1H, t, J=8.1 Hz), 7.24–7.32(2H, m), 7.36–7.42 (2H, m).

EXAMPLE 177

(E)-N-(6,6-dimethyl-2-hepten-4-ynyl)-N-methyl-3-[3-(5-oxazolyl)benzylamino)benzylamine (compound 198)

IR$\nu_{max}^{neat}$ cm$^{-1}$: 2974, 1611, 1506, 1494, 1458, 1107, 954, 696.

NMR (CDCl$_3$) δ: 1.20(9H, s), 2.14(3H, s), 3.05(2H, dd, J=6.6 Hz, 1.5 Hz), 3.42(2H, s), 4.38(2H, s), 5.59(1H, dt, J=15.9 Hz, 1.5 Hz), 6.03(1H, dt, J=15.9 Hz, 6.6 Hz), 6.52(1H, dt, J=8.0 Hz, 1.0 Hz), 6.67–6.69(2H, m), 7.11(1H, t, J=8.0 Hz), 7.35–7.42(3H, m), 7.57(1H, dt, J=7.4 Hz, 1.6 Hz), 7.68(1H, br.s), 7.91(1H, s).

EXAMPLE 178

(E)-N-(6,6-dimethyl-2-hepten-4-ynyl)-N-ethyl-3-[3-(5-oxazolyl)benzylamino]benzylamine (compound 199)

IR$\nu_{max}^{neat}$ cm$^{-1}$: 2968, 2926, 1611, 1506, 1494, 1476, 1266, 1107, 954, 789, 759, 696.

NMR (CDCl$_3$) δ: 1.00(3H, t, J=7.1 Hz), 1.24(9H, s), 2.48(2H, q, J=7.1 Hz), 3.07(2H, dd, J=6.4 Hz, 1.5 Hz), 3.48(2H, s), 4.38(2H, s), 5.62(1H, dt, J=15.9 Hz, 1.5 Hz), 6.05(1H, dt, J=15.9 Hz, 6.4 Hz), 6.50–6.54(1H, m), 6.67–6.69(2H, m), 7.11(1H, t, J=7.9 Hz), 7.36(1H, s), 7.37–7.44(2H, m), 7.57 (1H, dt, J=7.2 Hz, 1.7 Hz), 7.68(1H, br.s), 7.91 (1H, s).

EXAMPLE 179

(E)-N-ethyl-N-(6-methoxy-6-methyl-2-hepten-4-ynyl)-3-[3-(3-thienyl)benzylamino]benzylamine (compound 200)

IR$\nu_{max}^{CHCl_3}$ cm$^{-1}$: 3412, 3100, 2980, 2932, 2818, 1608, 1491, 1473, 1365.

NMR (CDCl$_3$) δ: 1.04(3H, t, J=7.0 Hz), 1.46(6H, s), 2.50(2H, q, J=7.0 Hz), 3.13(2H, d, J=6.0 Hz), 3.52(2H, s), 4.37(2H, s), 5.67(1H, d, J=16.2 Hz), 6.16(1H, dt, J=16.2 Hz, 6.0 Hz), 6.52–6.57(1H, m), 6.66–6.72(2H, m), 7.12(1H, t, J=7.8 Hz), 7.29–7.40(4H, m), 7.45(1H, t, J=2.2 Hz), 7.51 (1H, dt, J=7.5 Hz, 2.1 Hz), 7.61(1H, br.s).

EXAMPLE 180

(E)-N-(6,6-dimethyl-2-hepten-4-ynyl)-N-propyl-2-[3-(3-thienyl)benzylamino]-4-pyridylmethylamine (compound 201)

IR$\nu_{max}^{neat}$ cm$^{-1}$: 2968, 1611, 1569, 1515, 1464, 1368, 1269, 774.

NMR (CDCl$_3$) δ: 0.81(3H, t, J=7.3 Hz), 1.24(9H, s), 1.40(2H, sex, J=7.3 Hz), 2.32(2H, t, J=7.3 Hz), 3.03(2H, dd, J=6.4 Hz, 1.4 Hz), 3.42(3H, s), 4.53(2H, s), 5.59(1H, dt, J=15.9 Hz, 1.4 Hz), 5.99(1H, dt, J=15.9 Hz, 6.4 Hz), 6.48(1H, d, J=1.6 Hz), 6.58(1H, dd, J=5.4 Hz, 1.6 Hz), 7.27–7.31(1H, m), 7.34–7.40(3H, m), 7.45 (1H, t, J=1.8 Hz), 7.50(1H, dt, J=7.6 Hz, 1.7 Hz), 7.59(1H, br.s), 7.96(1H, dt, J=7.6 Hz, 1.7 Hz).

EXAMPLE 181

Production of (E)-N-(6,6-dimethyl-2-hepten-4-ynyl)-N-ethyl-3-[N'-methyl-3-(3-thienyl)benzylamino]benzylamine (compound 202)

100 mg of the (E)-N-(6,6-dimethyl-2-hepten-4-ynyl)-N-ethyl-3-[3-(3-thienyl)benzylamino]benzylamine obtained in Example 175 was dissolved in 3 ml of acetonitrile. 0.1 ml of a 35% aqueous solution of formaldehyde and 22.7 mg of sodium cyanoborohydride were added, and the mixture was stirred at room temperature for 30 minutes. The reaction mixture was evaporated under reduced pressure. The residue was dissolved in a mixture of ethyl acetate and water. The organic layer was separated, and dried over anhydrous magnesium sulfate. The desiccant was separated by filtration, and the solvent was evaporated. The residue was purified by silica gel column chromatography [Wakogel C-200, 5 g; eluting solvent: hexane/ethyl acetate=10/1→6/1] to give 55 mg (yield 53%) of the captioned compound as a pale yellow crystalline solid, m.p. 51°–52° C.

IR$\nu_{max}^{neat}$ cm$^{-1}$: 2974, 2926, 1605, 1500, 1368, 1218, 762.

NMR (CDCl$_3$) δ: 0.99(3H, t, J=7.0 Hz), 1.23(9H, s), 2.47(2H, q, J=7.0 Hz), 3.02(3H, s), 3.06(1H, dd, J=6.3 Hz, 1.4 Hz), 3.51(2H, s), 4.56(2H, s), 5.61(1H, dt, J=15.8 Hz, 1.4 Hz), 6.05(1H, dt, J=15.8 Hz, 6.3 Hz), 6.63–6.71(2H, m), 6.78–6.79 (1H, m), 7.12–7.19(2H, m), 7.31–7.38(3H, m), 7.41(1H, dd, J=2.7 Hz, 1.5 Hz), 7.46–7.49(2H, m).

EXAMPLE 182

Production of
(E),(E)-N-(6,6-dimethyl-2-hepten-4-ynyl)-N-ethyl-5-[2-[3-(3-thienyl)phenyl]ethenyl]-(1,3,4-oxadiazol-2-yl)methylamine (compound 203)

57 mg of (E)-N-(6,6-dimethyl-2-hepten-4-ynyl)-N-ethylglycylhydrazide [synthesized by condensing (E)-N-ethyl-6,6-dimethyl-2-hepten-4-ynylamine and methyl bromoacetate in the presence of sodium hydrogen carbonate, and then reacting the product with hydrazine] and 20 mg of sodium hydrogen carbonate were added to 1 ml of dioxane. To the mixture was added a dioxane solution (1 ml) of 3-(3-thienyl)cinnamoyl chloride which had been prepared from 50 mg of 3-(3-thienyl)-cinnamic acid [synthesized by condensing 3-(3-thienyl)-benzaldehyde and malonic acid under heat in the presence of piperidine/pyridine] and 0.3 ml of of thionyl chloride. The mixture was stirred at room temperature for 30 minutes. The inorganic salts were separated by filtration, and the solvent evaporated under reduced pressure. The residue was dissolved in 0.8 ml of phosphorus oxychloride, and the solution stirred at 65° C. for 16 hours. The reaction mixture was poured into ice water, and sodium hydrogen carbonate was added to neutralize it. The solution was then extracted with ethyl acetate. The extract was dried over anhydrous magnesium sulfate, and the solvent was evaporated. The residue was purified by silica gel column chromatography [Wakogel C-200, 10 g; eluting solvent: hexane/ethyl acetate=3/1] to give 37 mg (yield 36%) of the captioned compound as a colorless oil.

IR $\nu_{max}^{neat}$ cm$^{-1}$: 2972, 1648, 1364, 1266, 964, 854, 778.

NMR (CDCl$_3$) δ : 1.13(3H, t, J=7.1Hz), 1.24(9H, s), 2.65(2H, q, J=7.1Hz), 3.26(2H, dd, J=6.8Hz, 1.5Hz), 3.95(2H, s), 5.73(1H, dt, J=15.9Hz, 1.5Hz), 6.07(1H, dt, J=15.9Hz, 6.8Hz), 7.09 (1H, d, J=16.3Hz), 7.39–7.50(4H, m), 7.51 (1H, dd, J=3.1Hz, 1.7Hz), 7.60(1H, d, J=16.3Hz), 7.62(1H, dt, J=7.4Hz, 1.8Hz), 7.76(1H, t, J=1.8Hz).

EXAMPLE 183

Production of
(E)-N-(6,6-dimethyl-2-hepten-4-ynyl)-N-ethyl-3-[3-(1-pyrrolyl)benzoylamino]benzylamine (compound 204)

83 mg of (E)-N-(6,6-dimethyl-2-hepten-4-ynyl)-N-ethyl-3-aminobenzylamine and 100 mg of 3-(1-pyrrolyl)benzoic acid were dissolved in a mixture of 1 ml of methylene chloride and 2 ml of tetrahydrofuran, and 92 mg of N,N'-dicyclohexylcarbodiimide (DCC) was added. The mixture was stirred at room temperature for 3 hours. The reaction mixture was evaporated under reduced pressure, and the residue was dissolved in methylene chloride. The insoluble material was separated by filtration, and washed successively with a 5% aqueous solution of sodium hydrogen carbonate, 5% hydrochloric acid and a saturated aqueous solution of sodium chloride. It was dried over anhydrousسodium sulfate, and the solvent was evaporated. The residue was purified by silica gel column chromatography [Wakogel C-200, 20 g; eluting solvent: hexane/-ethyl acetate =10/1 → 3/1] to give 98 mg (yield 61%) of the captioned compound as a pale yellow oil.

IR $\nu_{max}^{neat}$ cm$^{-1}$: 2968, 1653, 1593, 1554, 1503, 1443, 1341, 723.

NMR (CDCl$_3$) δ : 1.05(3H, t, J=7.1Hz), 1.23(9H, s), 2.52(2H, q, J=7.1Hz), 3.10(2H, dd, J=6.7Hz, 1.6Hz), 3.56(2H, s), 5.65(1H, dt, J=15.8Hz, 1.6Hz), 6.08(1H, dt, J=15.8Hz, 6.7Hz), 6.37 (2H, t, J=2.5Hz), 7.11–7.15(3H, m), 7.31(1H, t, J=7.8Hz), 7.48–7.58(3H, m), 7.62–7.70 (2H, m), 7.91–7.94(2H, m).

EXAMPLE 184

Production of
(E)-N-(6,6-dimethyl-2-hepten-4-ynyl)N-methyl-3-3-(1,3,4-triazol-1-yl)benzyloxy]benzylamine (compound 205)

430 mg of ethyl 3-(1,3,4-triazol-1-yl)benzoate [synthesized substantially in accordance with the method described in J. Med. Chem., 5, 383 (1962)] was dissolved in a mixture of 20 ml of tetrahydrofuran and 20 ml of dioxane, and 100 mg of lithium aluminium hydride was added. The mixture was stirred at room temperature for 2 hours. The reaction mixture was concentrated under reduced pressure, and the residue was distributed between ethyl acetate and water. The organic layer was separated and dried over anhydrous sodium sulfate. The desiccant was separated by filtration, and the solvent evaporated. The residue was purified by silica gel column chromatography [Wakogel C-200, 20 g; eluting solvent: chloroform/methanol=20/1] to give 240 mg (yield 69%) of 1(3-hydroxymethylphenyl)-1,3,4-triazole.

220 mg of the resulting alcohol compound was dissolved in 20 ml of chloroform, and 2 ml of thionyl chloride was added. The mixture was stirred at room temperature for 2 hours. The reaction mixture was concentrated under reduced pressure and distributed between chloroform and water. The organic layer was separated, and washed with a 5% aqueous solution of sodium hydrogen carbonate and a saturated aqueous solution of sodium chloride. After drying over anhydrous magnesium sulfate, the solvent was evaporated under reduced pressure to give 143 mg (yield 59%) of 1-(3-chloromethylphenyl)-1,3,4-triazole.

38 mg of the resulting chloromethyl compound was dissolved in 2 ml of dimethylformamide, and the solution was added to a tetrahydrofuran solution (2 ml) of phenolate prepared in advance from 60 mg of (E)-N(6,6-dimethyl-2-hepten-4-ynyl)-N-methyl-3-hydroxybenzylamine and 14 mg of 60% oily sodium hydride. The mixture was stirred at room temperature for 5 hours. Ethyl ether and water were added to the reaction mixture to separate it. The separated organic layer was collected, and dried over anhydrous magnesium sulfate. The solvent was evaporated under reduced pressure. The residue was purified by medium-pressure liquid chromatography column: Lobar column, size A, Lichroprep Si 60 (E. Merck Co.]; eluting solvent: hexane/ethyl acetate=1/1 → 1/5) to give 48 mg (yield 59%) of the captioned compound as a pale yellow oil.

IR $\nu_{max}^{neat}$ cm$^{-1}$: 2968, 1599, 1518, 1491, 1452, 1368, 1269, 1152, 1092, 1032, 786, 762.

NMR (CDCl$_3$) δ : 1.24(9H, s), 2.19(3H, s), 3.03(2H, dd, J=6.6Hz, 1.5Hz), 3.48(2H, s), 5.15(2H, s), 5.64(1H, dt, J=15.3Hz, 1.5Hz), 6.05(1H, dt, J=15.3Hz, 6.6Hz), 6.87(1H, ddd, J=7.8Hz, 2.7Hz, 1.2Hz), 6.93(1H, d, J=7.8Hz), 6.99–7.02 (1H, m), 7.24(1H, t, J=7.8Hz), 7.35(1H, dt, J=6.9Hz, 2.4Hz), 7.50–7.59(3H, m), 8.50(2H, s).

EXAMPLE 185

Production of (E)-N-(6,6-dimethyl-2-hepten-4-ynyl)-N-ethyl-3-[3-(3-thienyl)benzylthio]benzylamine (compound 206)

10 mg of 3-3-(3-thienyl)benzylthio]benzaldehyde was dissolved in 1 ml of ethanol, and 1.8 mg of sodium borohydride was added. The mixture was stirred at room temperature for 30 minutes. The solvent was evaporated under reduced pressure, and ethyl ether and water were added to the residue to extract it. The organic layer was separated, and dried over anhydrous magnesium sulfate. The desiccant was separated by filtration, and the solvent was evaporated. The residue was dissolved in 1 ml of ethyl acetate, and 4.4 mg of methanesulfonyl chloride and 5.9 mg of triethylamine were added. The mixture was stirred at room temperature for 10 minutes. The precipitated triethylamine hydrochloride was separated by filtration, and the solvent was evaporated. The residue was dissolved in 1 ml of dimethylformamide, and (E)-N-ethyl-6,6-dimethyl-2-hepten-4-ynylamine hydrochloride and 10 mg of potassium carbonate were added. The mixture was stirred overnight at room temperature. The reaction mixture was concentrated under reduced pressure, and the residue was dissolved in ethyl ether. The insoluble material was separated by filtration, and the solvent was evaporated under reduced pressure. The residue was purified by preparative thinlayer chromatography thin-layer plate: Kieselgel 60F$_{254}$, Art. 5744 (E. Merck Co.); developing solvent: hexane/ethyl acetate=5/1] to give 7.5 mg (yield 51%) of the captioned compound as a colorless oil.

IR $v_{max}^{neat}$ cm$^{-1}$: 1478, 1363, 1265, 844, 777.

NMR (CDCl$_3$) δ : 1.00(3H, t, J=7.1Hz), 1.24(9H, s), 2.44(2H, q, J=7.1Hz), 3.03(2H, d, J=6.5Hz), 3.49(2H, s), 4.15(2H, s), 5.62(1H, d, J=15.9Hz), 6.04(1H, dt, J=15.9Hz, 6.5Hz), 7.13-7.42(8H, m), 7.45(1H, t, J=1.7Hz), 7.46-7.51(2H, m).

Production of (E),(E)-N-(6,6-dimethyl-2-hepten-4-ynyl)-N-ethyl-3-[2-[3-(5-thiazolyl)phenyl]ethenyl]benzylamine (compound 207)

116 mg of methyl (E)-3-[2-[3-(5-thiazolyl)phenyl]ethenyl]benzoate [synthesized by condensing methyl (E)-3-[2-(3-bromophenyl)ethenyl]benzoate obtained by the condensation of dimethyl 3-methoxycarbonylbenzylphosphonate with 3-bromobenzaldehyde, with 5-trimethylstannylthiazole: see "Synthesis" 757 (1986)] was dissolved in 3 ml of tetrahydrofuran, and under ice cooling 14 mg of lithium aluminium hydride was added. The mixture was stirred for 30 minutes. The reaction mixture was poured into water, and ethyl ether was added to extract it. The extract was dried over anhydrous magnesium sulfate. The desiccant was separated by filtration, and the solvent was evaporated. The residue was dissolved in a mixture of 3 ml of ethyl acetate and 3 ml of methylene chloride, and 31 microliters of methanesulfonyl chloride and 70 microliters of triethylamine were added. The mixture was stirred at room temperature for 30 minutes. The triethylamine hydrochloride was separated by filtration, and the solvent evaporated under reduced pressure. The residue was dissolved in 3 ml of dimethylformamide, and 81 mg of (E)-N-ethyl-6,6-dimethyl-2-hepten-4-ynylamine hydrochloride and 42 mg of sodium carbonate were added. The mixture was stirred at room temperature for 3 hours. The reaction mixture was concentrated under reduced pressure, and ethyl ether and water were added to the residue to extract it. The organic layer separated was collected and dried over anhydrous magnesium sulfate. The desiccant was separated by filtration, and the solvent evaporated. The residue was purified by medium-pressure liquid chromatography [column: Lobar column, size A, Lichroprep Si 60 (E. Merck Co.); eluting solvent: hexane/ethyl acetate=8/1 → 6/1] to give 63 mg (yield 36%) of the captioned compound as a cololess oil.

IR $v_{max}^{neat}$ cm$^{-1}$: 2968. 2872, 1605, 1458, 1392, 1365, 1266, 963, 876, 795.

NMR (CDCl$_3$) δ : 1.07(3H, t, J=7.1Hz), 1.24(9H, s), 2.54(2H, q, J=7.1Hz), 3.11(1H, d, J=6.7Hz), 3.59(2H, s), 5.67(1H, d, J=15.9Hz), 6.11(1H, dt, J=15.9Hz, 6.7Hz), 7.15(2H, s), 7.29-7.57 (7H, m), 7.69(1H, dd, J=3.6Hz, 1.7Hz), 8.12 (1H, s), 8.77(1H, s).

EXAMPLE 187

Production of (E)-N-(6,6-dimethyl-2-hepten-4-ynyl)-N-methyl-3-3-(3-tetrahydrothienyl)benzyloxy]benzylamine (compound 208)

25 mg of 3-(3-tetrahydrothienyl)benzyl alcohol was dissolved in 5 ml of ethyl ether, and 15 microliters of methanesulfonyl chloride and 30 microliters of triethylamine were added. Under ice cooling, the mixture was stirred for 1 hour. The triethylamine hydrochloride that precipitated was separated by filtration, and the solvent evaporated. The residue was dissolved in 1 ml of dimethylformamide, and the solution was added to 10 ml of a dimethylformamide solution of phenolate prepared in advance from 100 mg of (E)-N-(6,6-dimethyl-2-hepten-4-ynyl)-N-methyl-3-hydroxybenzylamine and 30 mg of 60% oily sodium hydride. The mixture was stirred at room temperature for 3 hours. Water and ethyl ether were added to the reaction mixture to dilute it. The organic layer was separated and dried over magnesium sulfate. The desiccant was separated by filtration, and the solvent evaporated. The residue was purified by medium-pressure liquid chromatography column: Lobar column, size A, Lichroprep Si 60 (E. Merck Co.); eluting solvent: hexane/ethyl acetate=20/1 → 10/1] to give 42 mg (yield 75%) of the captioned compound as a colorless oil.

IR $v_{max}^{neat}$ cm$^{-1}$: 1446, 1365, 1272, 1152, 1026, 885, 786, 693.

NMR (CDCl$_3$) δ: 1.24(9H, s), 2.07(1H, ddt, J=12.2Hz, 10.6Hz, 8.5Hz), 2.19(3H, s), 2.42(1H, dq, J=12.2Hz, 4.6Hz), 2.88-3.01(3H, m), 3.04(2H, dd, J=6.6Hz, 1.5Hz), 3.17(1H, dd, J=10.2Hz, 6.7Hz), 3.29-3.41(1H, m), 3.47(2H, s), 5.04 (2H, s), 5.64(1H, dt, J=15.8Hz, 1.5Hz), 6.07 (1H, dt, J=15.8Hz, 6.6Hz), 6.86(1H, ddd, J=8.2Hz, 2.6Hz, 1.4Hz), 6.91(1H, d, J=7.5Hz), 6.99(1H, br.s), 7.19-7.35(4H, m), 7.37(1H, br.s). Compounds of Examples 188 and 189 were obtained by performing the same reaction as in Example 187 except that instead of the starting 3-(3-tetrahydrothienyl)benzyl alcohol and (E)-N-(6,6-dimethyl-2-hepten-4-ynyl)-N-methyl-3-hydroxybenzylamine, the corresponding benzyl alcohol derivativee and (E)-N-(6,6-dimethyl-2-hepten-4-ynyl)-N-ethyl-3-hydroxybenzylamine were used.

EXAMPLE 188

(E)-N-(6,6-dimethyl-2-hepten-4-ynyl)-N-ethyl-3-[3-3,4-dihydro-2H-thiopyran-5-yl)benzyloxy1benzylamine (compound 209)

IR $\nu_{max}^{neat}$ cm$^{-1}$: 2968, 2926, 2866, 1599, 1491, 1455, 1263, 777.

NMR (CDCl$_3$) δ : 1.03(3H, t, J=7.1Hz), 1.24(9H, s), 2.14–2.23(1H, m), 2.50(2H, q, J=7.1Hz), 2.46–2.58(2H, m), 2.88–2.93(2H, m), 3.09(2H d, J=6.5Hz), 3.54(2H, s), 5.04(2H, s), 5.64 (1H, dt, J=15.9Hz, 1.5Hz), 6.06(1H, dt, J=15.9Hz, 6.5Hz), 6.45(1H, s), 6.85(1H, dd, J=8.4Hz, 2.0Hz), 6.92(1H, d, J=7.2Hz), 7.00 (1H, br.s), 7.19–7.36(4H, m), 7.39(1H, br.s).

EXAMPLE 189

(E)-N-(6,6-dimethyl-2-hepten-4-ynyl)-N-ethyl-3-[3-(5,6-dihydro-2H-thiopyran-3-yl)benzyloxy]benzylamine (compound 210)

IR $\nu_{max}^{neat}$ cm$^{-1}$: 3034, 2968, 2926, 1740, 1602, 1491, 1458, 1263.

NMR (CDCl$_3$) δ : 1.04(3H, t, J=7.1Hz), 1.24(9H, s), 2.45–2.59(4H, m), 2.77(2H, t, J=5.7Hz), 3.09 (2H, d, J=6.5Hz), 3.50(2H, dd, J=3.9Hz, 2.1Hz), 3.55(2H, br.s), 5.05(2H, s), 5.65 (1H, d, J=15.9Hz), 6.07(1H, dt, J=15.9Hz, 6.5Hz), 6.11–6.17(1H, m), 6.83–6.89(1H, m), 6.92(1H, d, J=7.5Hz), 7.01(1H, br.s), ( 7.19–7.36(4H, m), 7.40(1H, br.s).

EXAMPLE 190

Production of (E)-N-(6,6-dimethyl-2-hepten-4-ynyl)-N-ethyl-3-[3-(3-thienyl)phenoxymethyl]benzylamine hydrochloride (compound 211)

104 mg of 3-[3-(3-thienyl)phenoxymethyl]benzyl alcohol was dissolved in 1 ml of ethyl acetate, and 45 microliters of methanesulfonyl chloride and 88 microliters of triethylamine were added with ice cooling and stirring. The reaction mixture was stirred for 1 hour. The precipitate was removed by filtration, and the organic layer was separated, then dried over anhydrous magnesium sulfate. The desiccant was separated by filtration, and the solvent was evaporated to give 3-[3-(3-thienyl)phenoxymethyl)benzyl methanesulfonate as a pale yellow oil.

The resulting sulfonated compound was dissolved in 2 ml of dimethylformamide, and 71 mg of (E)-N-ethyl-6,6-dimethyl-2-hepten-4-ynylamine hydrochloride and 37 mg of potassium carbonate were added. The reaction mixture was stirred overnight. The reaction solution was extracted with water and ethyl acetate. The organic layer was separated, washed with a saturated aqueous solution of sodium chloride, and dried over anhydrous sodium sulfate. The desiccant was separated by filtration, and the solvent was evaporated. The residue was purified by medium-pressure liquid chromatography [column: Lobar column, size A, Lichroprep Si 60 (E. Merck Co.); eluting solvent: hexane/ ethyl acetate=20/1] to give 61 mg (yield 40%) of the captioned compound as a colorless oil.

The free base obtained as above was treated with a hydrogen chloride-methanol solution and recrystallized from ethyl ether to give the captioned hydrochloride, m.p. 125°–127° C.

IR $\nu_{max}^{KBr}$ cm$^{-1}$: 2974, 1605, 1455, 1278, 1218, 1185, 777.

NMR (CDCl$_3$) δ : 1.24(9H, s), 1.25(3H, s), 2.76–2.77 (2H, m), 3.33–3.37(2H, m), 3.37–3.89(2H, m), 5.14(2H, s), 5.72(1H, d, J=15.8Hz), 6.12–6.22 (1H, m), 6.85–6.93(1H, m), 7.18–7.25(3H, m), 7.31(1H, t, J=7.9Hz), 7.36–7.39(3H, m), 7.41–7.47(3H, m).

Compounds of Examples 191 to 204 below were obtained by performing the same reaction as in Example 190 except that instead of the starting compounds in Example 90, 3-[3-(3-thienyl)phenoxymethyl]benzyl alcohol and (E)-N-ethyl-6,6-dimethyl-2-hepten-4-ynylamine hydrochloride, the corresponding benzyl alcohol derivatives and various 2-hepten-4-ynylamine hydrochlorides were used.

EXAMPLE 191

(E)-N-(6,6-dimethyl-2-hepten-4-ynyl)-N-methyl-3-[3-(3-thienyl)phenoxymethyl]benzylamine (compound 212)

IR $\nu_{max}^{neat}$ cm$^{-1}$: 2974, 2872, 1605, 1584, 1365, 1218, 771.

NMR (CDCl$_3$) δ : 1.24(9H, s), 2.19(3H, s), 3.05 (2H, dd, J=6.6Hz, 1.5Hz), 3.51(2H, s), 5.10 (2H, s), 5.64(1H, dt, J=15.9Hz, 1.5Hz), 6.08 (1H, dt, J=15.9Hz, 6.6Hz), 6.91(1H, ddd, J=8.2Hz, 2.6Hz, 1.2Hz), 7.18–7.22(2H, m), 7.27–7.38(6H, m), 7.40–7.42(1H, m), 7.43–7.45 (1H, m).

EXAMPLE 192

(E)-N-(6,6-dimethyl-2-hepten-4-ynyl)-N-propyl-3-[3-(3-thienyl)phenoxymethyl]benzylamine hydrochloride (compound 213)

m.p.: 160°–165° C.

IR $\nu_{max}^{KBr}$ cm$^{-1}$: 2974, 1605, 1584, 1455, 1287, 1182, 774.

NMR (CDCl$_3$) δ : 0.92(3H, t, J=7.4Hz), 1.25(9H, s), 1.88–1.92(2H, m), 2.80–2.84(2H, m), 3.45–3.75 (2H, m), 4.12–4.15(2H, m), 5.77(1H, d, J=15.8Hz), 6.23(1H, dt, J=15.8Hz, 7.5Hz), 6.89(1H, ddd, J=7.9Hz, 2.5Hz, 1.2Hz), 7.19–7.22(2H, m), 7.28–7.40(3H, m), 7.45–7.56(3H, m), 7.68(1H, d, J=6.5Hz), 7.71–7.73(1H, m).

EXAMPLE 193

(E)-N-ethyl-N-(6-methoxy-6-methyl-2-hepten-4-ynyl)-3-[3-(3-thienyl)phenoxymethyl]benzylamine (compound 214)

IR $\nu_{max}^{neat}$ cm$^{-1}$: 2980, 2938, 1605, 1584, 1365, 1251, 1173, 1074, 771.

NMR (CDCl$_3$) δ : 1.04(3H, t, J=7.1Hz), 1.46(6H, s), 2.52 (2H, q, J=7.1Hz), 3.11(2H, dd, J=6.3Hz, 1.4Hz), 3.35(3H, s), 3.60(2H, s), 5.11(2H, s), 5.68 (1H, dt, J=15.9Hz, 1.4Hz), 6.15(1H, dt, J=15.9Hz, 6.3Hz), 6.92(1H, ddd, J=8.0Hz, 2.3Hz, 0.9Hz), 7.18–7.22(2H, m), 7.26–7.31 (2H, m), 7.32–7.35(2H, m), 7.36–7.38(2H, m), 7.40–7.45(2H, m).

EXAMPLE 194

(E)-N-(6,6-dimethyl-2-hepten-4-ynyl)-N-ethyl-3-(3-thienyl)phenylthiomethyl]benzylamine hydrochloride (compound 215)

IR $\nu_{max}^{KBr}$ cm$^{-1}$: 2974, 2926, 2608, 2500, 1593, 1458, 1431, 777.

NMR (CDCl$_3$) δ : 1.25(9H, s), 1.29–1.41(3H, m), 2.73–2.98(2H, m), 3.30–3.60(2H, m), 3.90–4.15 (2H, m), 4.17(2H, s), 5.73(1H, d, J=16.1Hz), 6.12–6.26(1H, m), 7.20–7.49(10H, m), 7.55–7.64 (1H, m).

EXAMPLE 195

(E)-N-ethyl-N-(6-methoxy-6-methyl-2-hepten-4-ynyl)-3-[3-(3-thienyl)phenylthiomethyl]benzylamine (compound 216)

IR $\nu_{max}^{neat}$ cm$^{-1}$: 2980, 2938, 2818, 1593, 1380, 1251, 1206, 1173.

NMR (CDCl$_3$) δ : 1.00(3H, t, J=7.1Hz), 1.46(6H, s), 2.46 (2H, q, J=7.1Hz), 3.05(2H, dd, J=6.4Hz, 1.4Hz), 3.36(3H, s), 3.51(2H, s), 4.14(2H, s), 5.65 (1H, dt, J=15.8Hz, 1.4Hz), 6.13(1H, dt, J=15.8Hz, 6.4Hz), 7.18-7.28(6H, m), 7.30 (1H, dd, J=4.5Hz, 1.5Hz), 7.35-7.42(3H, m), 7.47-7.50(1H, m).

EXAMPLE 196

(E)-N-(6,6-dimethyl-2-hepten-4-ynyl)-N-ethyl-3-[3-(5-oxazolyl)phenylthiomethyl]benzylamine (compound 217)

IR $\nu_{max}^{neat}$ cm$^{-1}$: 2974, 2872, 2806, 1503, 1458, 1107, 948.

NMR (CDCl$_3$) δ : 1.00(3H, t, J=7.1Hz), 1.24(9H, s), 2.45 (2H, q, J=7.1Hz), 3.03(2H, dd, J=6.6Hz, 1.5Hz), 3.51(2H, s), 4.15(2H, s), 5.61(1H, dt, J=15.9Hz, 1.5Hz), 6.03(1H, dt, J=15.9Hz, 6.6Hz), 7.13-7.35(7H, m), 7.45 (1H, dt, J=7.0Hz, 1.7Hz), 7.55-7.57(1H, m), 7.90(1H, s).

EXAMPLE 197

(E)-N-(6-methoxy-6-methyl-2-hepten-4-ynyl)-N-propyl-3-[3-(3-thienyl)benzyloxy]benzylamine (compound 218)

IR $\nu_{max}^{neat}$ cm$^{-1}$: 2938, 1596, 1455, 1380, 1257, 1149, 1074, 774.

NMR (CDCl$_3$) δ : 0.86(3H, t, J=7.4Hz), 1.46(6H, s), 1.49-1.52(2H, m), 2.37(2H, t, J=7.4Hz), 3.10 (2H, dd, J=6.4Hz, 1.8Hz), 3.35(3H, s), 3.53 (2H, s), 5.10(2H, s), 5.65(1H, dt, J=15.9Hz, 1.8Hz), 6.15(1H, dt, J=15.9Hz, 6.4Hz), 6.86 (1H, dd, J=7.6Hz, 2.7Hz), 6.90(1H, d, J=7.6Hz), 7.22(1H, t, J=7.6Hz), 7.36-7.44(4H, m), 7.47 (1H, dd, J=2.8Hz, 1.7Hz), 7.55(1H, dt, J=7.3Hz 1.7Hz), 7.66-7.68(1H, m).

EXAMPLE 198

(E)-N-ethyl-N-(6-methoxy-6-methyl-2-hepten-4-ynyl)-3-[3-(3-thienyl)benzylthio]benzylamine (compound 219)

IR $\nu_{max}^{neat}$ cm$^{-1}$: 2986, 2938, 2818, 1380, 1365, 1251, 1149, 1074.

NMR (CDCl$_3$) δ : 1.00(3H, t, J=7.1Hz), 1.46(6H, s), 2.45(2H, q, J=7.1Hz), 3.04(2H, dd, J=6.4Hz, 1.8Hz), 3.35(3H, s), 3.48(2H, s), 4.14(2H, s), 5.65(1H, dt, J=15.9Hz, 1.8Hz), 6.11(1H, dt, J=15.9Hz, 6.4Hz), 7.13-7.17(1H, m), 7.19-7.24 (3H, m), 7.28-7.34(4H, m), 7.38(1H, dd, J=3.0Hz, 1.5Hz), 7.44-7.80(2H, m).

EXAMPLE 199

(E)-N-(6,6-dimethyl-2-hepten-4-ynyl)-N-ethyl-3-[3-(1-pyrrolyl)benzylthio]benzylamine (compound 220)

IR $\nu_{max}^{neat}$ cm$^{-1}$: 2968, 1596, 1506, 1341, 1071, 723.

NMR (CDCl$_3$) δ : 0.99(3H, t, J=7.1Hz), 1.24(9H, s), 2.45 (2H, q, J=7.1Hz), 3.03(2H, dd, J=6.4Hz, 1.5Hz), 3.48(2H, s), 4.06(2H, s), 5.61(1H, dt, J=15.9Hz, 1.5Hz), 6.02(1H, dt, J=15.9Hz, 6.4Hz), 6.32(2H, t, J=2.2Hz), 7.02(2H, t, J=2.2Hz), 7.12-7.22(4H, m), 7.23-7.37(4H, m).

EXAMPLE 200

(E)-N-(6,6-dimethyl-2-hepten-4-ynyl)-N-ethyl-3-[3-(5-oxazolyl)benzylthio]benzylamine (compound 221)

IR $\nu_{max}^{neat}$ cm$^{-1}$: 2974, 2932, 2872, 2806, 1476, 1107, 957, 693, 646.

NMR (CDCl$_3$) δ : 0.99(3H, t, J=7.1Hz), 1.24(9H, s), 2.44(2H, q, J=7.1Hz), 3.03(2H, dd, J=6.3Hz, 1.4Hz), 3.47(2H, s), 4.13(2H, s), 5.61(1H, dt, J=15.9Hz, 1.4Hz), 6.02(1H, dt, J=15.9Hz, 6.3Hz), 7.11-7.21(3H, m), 7.24-7.30(2H, m), 7.31(1H, s), 7.33-7.36(1H, m), 7.52(1H, dt, J=7.9Hz, 1.4Hz), 7.54-7.56(1H, m), 7.90(1H, s).

EXAMPLE 201

(E)-N-(6,6-dimethyl-2-hepten-4-ynyl)-N-ethyl-3-[4-(3-thienyl)-2-thienylmethylthio]benzylamine (compound 222)

IR $\nu_{max}^{neat}$ cm$^{-1}$: 2974, 2932, 1476, 1458, 1365, 1203, 1179, 783.

NMR (CDCl$_3$) δ : 0.99(3H, t, J=7.5Hz), 1.24(9H, s), 2.45(2H, q, J=7.5Hz), 3.03(2H, dd, J=6.3Hz, 1.4Hz), 3.49(2H, s), 4.30(2H, s), 5.60(1H, dt, J=15.9Hz, 1.4Hz), 6.03(1H, dt, J=15.9Hz, 6.3Hz), 7.07-7.09(1H, m), 7.14-7.19(1H, m), 7.20(1H, d, J=1.2Hz), 7.21-7.25(2H, m), 7.24 (1H, dd, J=6.0Hz, 1.5Hz), 7.27(1H, dd, J=3.0Hz, 1.5Hz), 7.31(1H, dd, J=6.0Hz, 3.0Hz), 7.32-7.35(1H, m).

EXAMPLE 202

(E)-N-ethyl-N-(6-methoxy-6-methyl-2-hepten-4-ynyl)-3-[4-(3-thienyl)-2-thienylmethylthio]benzylamine (compound 223)

IR $\nu_{max}^{neat}$ cm$^{-1}$: 2980, 2938, 2818, 1473, 1362, 1248, 1206, 1173, 1149, 783.

NMR (CDCl$_3$) δ : 1.00(3H, t, J=7.1Hz), 1.46(6H, s), 2.46(2H, q, J=7.1Hz), 3.05(2H, dd, J=6.4Hz, 1.8Hz), 3.35(3H, s), 3.50(2H, s), 4.30(2H, s), 5.65(1H, dt, J=15.9Hz, 1.8Hz), 6.12(1H, dt, J=15.9Hz, 6.4Hz), 7.07-7.09(1H, m), 7.15-7.34 (8H, m).

EXAMPLE 203

(E)-N-(6,6-dimethyl-2-hepten-4-ynyl)-N-ethyl-2-[3-(3-thienyl)benzylthio]-4-thiazolylmethylamine (compound 224)

IR $\nu_{max}^{neat}$ cm$^{-1}$: 2974, 2932, 1413, 1029, 777.

NMR (CDCl$_3$) δ : 1.05(3H, t, J=7.1Hz), 1.24(9H, s), 2.25 (2H, q, J=7.1Hz), 3.15(2H, dd, J=6.3Hz, 1.5Hz), 3.73(2H, s), 4.43(2H, s), 5.65(1H, dt, J=15.9Hz, 1.5Hz), 6.07(1H, dt, J=15.9Hz, 6.3Hz), 7.00(1H, s), 7.26-7.40(4H, m), 7.44 (1H, dd, J=2.6Hz, 1.5Hz), 7.49(1H, dt, J=7.4Hz, 1.7Hz), 7.59(1H, t, J=1.7Hz).

EXAMPLE 204

(E)-N-ethyl-N-(6-methoxy-6-methyl-2-hepten-4-ynyl)-3-[2-3-(3-thienyl)phenyl]ethyl]benzylamine (compound 225)

IR $\nu_{max}^{neat}$ cm$^{-1}$: 2980, 2938, 1458, 1365, 1251, 1149, 1077, 774.

NMR (CDCl$_3$) δ : 1.03(3H, t, J=7.1Hz), 1.46(6H, s), 2.45(2H, q, J=7.1Hz), 2.95(4H, s), 3.08(2H, dd, J=6.3Hz, 1.4Hz), 3.35(3H, s), 3.53(2H, s), 5.66(1H, dt, J=15.8Hz, 1.4Hz), 6.15(1H, dt, J=15.8Hz, 6.3Hz), 7.05-7.17(4H, m), 7.23(1H, t, J=7.3Hz), 7.30(1H, t, J=7.3Hz), 7.37-7.39 (2H, m), 7.39-7.41(1H, m), 7.41-7.43(1H, m).

EXAMPLE 205

Production of (E)-N-(6,6-dimethyl-2-hepten-4-ynyl)-N-ethyl-3-[4-(3-thienyl)-2-thienylthiomethyl]benzylamine (compound 226)

34 mg of 3-[4-(3-thienyl)2-thienylthiomethyl]benzaldehyde was dissolved in 1 ml of ethanol, and 1 ml of a 43% tetrahydrofuran solution of ethylamine was added. After the solution was stirred for 2 hours, 6 mg of sodium borohydride was added, and the mixture was stirred for 30 minutes at room temperature. The solvent was evaporated, and water and ethyl ether were added to the residue to extract it. The organic layer was separated, washed with a saturated aqueous solution of sodium chloride, and dried over anhydrous magnesium sulfate. The desiccant was separated by filtration, and the solvent was evaporated. The residue was dissolved in 1 ml of dimethylformamide, and 5 mg of 1-bromo-6,6-dimethyl-2-hepten-4-yne and 5 mg of potassium carbonate were added. The mixture was stirred overnight at room temperature. The solvent was evaporated, and water and ethyl acetate were added to the residue to extract it. The organic layer was separated, washed with a saturated aqueous solution of sodium chloride, and dried over anhydrous magnesium sulfate. The desiccant was separated by filtration, and the solvent was evaporated. The residue was purified by medium-pressure liquid chromatography [column: Lobar column, size A, Lichroprep Si 60F (E. Merck Co.); eluting solvent: hexane/ethyl acetate=10/1] to give 3 mg (yield 6%) of the captioned compound as a colorless oil.

IR $\nu_{max}^{neat}$ cm$^{-1}$: 2968, 2926, 1188, 963, 783.

NMR (CDCl$_3$) δ : 0.98(3H, t, J=7.1Hz), 1.24(9H, s), 2.43(2H, q, J=7.1Hz), 3.01(2H, dd, J=6.5Hz, 1.5Hz), 3.48(2H, s), 3.98(2H, s), 5.60(1H, dt, J=15.9Hz, 1.5Hz), 6.03(1H, dt, J=15.9Hz, 6.5Hz), 7.08-7.13(3H, m). 7.18-7.29(4H, m), 7.20-7.25 (2H, m).

EXAMPLE 206

Production of (E)-N-ethyl-N-(6-methoxy-6-methyl-2-hepten-4-ynyl)-3-[3-(3-thienyl)benzylamino]benzylamine (compound 227)

65 mg of (E)-N-ethyl-N-(6-methoxy-6-methyl-2-hepten-4-ynyl)-3-aminobenzylamine and 43 mg of 3-(3thienyl)benzaldehyde were dissolved in 2 ml of methanol, and the solution was stirred overnight at room temperature. With stirring under ice cooling, 12.9 mg of sodium borohydride was added, and stirred for 1 hour at room temperature. The solvent was evaporated under reduced pressure, and the residue was dissolved in ethyl acetate and water. The organic layer was separated, and dried over anhydrous magnesium sulfate. The desiccant was separated by filtration, and the solvent was evaporated. The residue was purified by silica gel column chromatography Wakogel C-200, 5 g; eluting solvent: methylene chloride/ methanol=60/1] to give 87 mg (yield 84%) of the captioned compound as a pale yellow oil.

IR $\nu_{max}^{neat}$ cm$^{-1}$: 3400, 2980, 1611, 1206, 1074, 771.

NMR (CDCl$_3$) δ : 1.02(3H, t, J=7.0Hz), 1.46(6H, s), 2.49(2H, q, J=7.0Hz), 3.09(2H, dd, J=6.4Hz, 1.8Hz), 3.35(3H, s), 3.49(2H, s), 4.05(1H, br.s), 4.37(2H, s), 5.67(1H, dt, J=15.8Hz, 1.8Hz), 6.15(1H, dt, J=15.8Hz, 6.4Hz), 6.54 (1H, ddd, J=7.9Hz, 2.7Hz, 1.0Hz), 6.65-6.70 (2H, m), 7.11(1H, t, J=7.9Hz), 7.30(1H, dt, J=7.8Hz, 2.3Hz), 7.37(1H, t, J=7.8Hz), 7.38 (2H, d, J=2.2Hz), 7.45(1H, t, J=2.2Hz), 7.51 (1H, dt, J=7.8Hz, 2.3Hz), 7.60-7.62(1H, m).

EXAMPLE 207

Production of (E)-N-(6,6-dimethyl-2-hepten-4-ynyl)-N-ethyl-3-[5-(3-thienyl)-3-thienylmethyloxy]benzylamine (compound 228)

118 mg of 5-(3-thienyl)-3-thienylmethanol was dissolved in 3 ml of chloroform, and 58 microliters of thionyl chloride was added under ice cooling, then the mixture was stirred for 40 minutes under ice cooling. A 5% aqueous solution of sodium hydrogen carbonate and chloroform were added to extract it. The organic layer was separated, and dried over anhydrous magnesium sulfate. The desiccant was separated by filtration. The residue, 5-(3-thienyl)-3-thienylmethyl chloride, was dissolved in 2 ml of dimethylformamide, and the resulting solution was added to 5 ml of a tetrahydrofuran solution of phenolate, prepared from 163 mg of (E)-N-(6,6-di-methyl-2-hepten-4-ynyl)-N-ethyl-3-hydroxybenzylamine and 28 mg of 60% oily sodium hydride, and the mixture was stirred overnight at room temperature. Water and ethyl acetate were added to extract it. The organic layer was separated, and dried over anhydrous magnesium sulfate. The desiccant was separated by filtration, and the solvent was evaporated. The residue was purified by mediumpressure liquid chromatography column: Lobar column, size B, Lichroprep Si 60F (E. Merck Co.); eluting solvent: hexane/ethyl acetate=12/1] to give 190 mg (yield 40%) of the captioned compound as a colorless oil.

IR $\nu_{max}^{neat}$ cm$^{-1}$: 2974, 1590, 1458, 1218, 756.

NMR (CDCl$_3$) δ : 1.03(3H, t, J=7.0Hz), 1.24(9H, s), 2.50(2H, q, J=7.0Hz), 3.09(1H, dd, J=6.3Hz, 1.5Hz), 3.54(2H, s), 5.03(2H, s), 5.64(1H, dt, J=15.9Hz, 1.5Hz), 6.07(1H, dt, J=15.9Hz, 6.3Hz), 6.85(1H, dd, J=7.5Hz, 2.5Hz), 6.92 (1H, d, J=7.5Hz), 6.99-7.01(1H, m), 7.18-7.24 (3H, m), 7.30(1H, dd, J=4.8Hz, 1.5Hz), 7.34 (1H, dd, J=4.8Hz, 3.0Hz), 7.38(1H, dd, J=3.0Hz, 1.5Hz).

Compounds of Examples 208 to 212 below were obtained by performing the same reaction as in Example 207 except that instead of the starting compound in Example 107, 5-(3-thienyl)-3-thienylmethanol, the various alcohol derivatives therefor were used.

EXAMPLE 208

(E)-N-(6,6-dimethyl-2-hepten-4-ynyl)-N-ethyl-3-5-(3-thienyl)-3-pyridylmethyloxy]benzylamine (compound 229)

IR $\nu_{max}^{neat}$ cm$^{-1}$: 2974, 1599, 1455, 1263, 783.

NMR (CDCl$_3$) δ : 1.03(3H, t, J=7.0Hz), 1.23(9H, s), 2.50(2H, q, J=7.0Hz), 3.09(1H, dd, J=6.3Hz, 1.5Hz), 3.55(2H, s), 5.13(2H, s), 5.67(1H, dt, J=15.9Hz, 1.5Hz), 6.07(1H, dt, J=15.9Hz, 6.3Hz), 6.87(1H, dd, J=7.8Hz, 2.8Hz), 6.95 (1H, d, J=7.8Hz), 7.02-7.04(1H, m), 7.23 (1H, t, J=7.8Hz), 7.42(1H, dd, J=4.8Hz, 1.2Hz), 7.45(1H, dd, J=4.8Hz, 2.9Hz), 7.56(1H, dd, J=2.9Hz, 1.2Hz), 7.97(1H, t, J=2.0Hz), 8.60 (1H, d, J=2.0Hz), 8.83(1H, d, J=2.0Hz).

EXAMPLE 209

(E)-N-(6,6-dimethyl-2-hepten-4-ynyl)-N-ethyl-3-5-(3-thienyl)-3-furylmethyloxy]benzylamine (compound 230)

IR $\nu_{max}^{neat}$ cm$^{-1}$: 2968, 2926, 1584, 1491, 1455, 1368, 1152, 1020, 693.

NMR (CDCl$_3$) δ : 1.04(3H, t, J=7.1Hz), 1.23(9H, s), 2.51(2H, q, J=7.1Hz), 3.10(2H, dd, J=6.3Hz, 1.4Hz), 3.54(2H, s), 5.03(2H, s), 5.65(1H, dt, J=15.9Hz, 1.4Hz), 6.07(1H, dt, J=15.9Hz, 6.3Hz), 6.44(1H, d, J=3.5Hz), 6.47(1H, d, J=3.5Hz), 6.87(1H, dd, J=8.0Hz, 2.7Hz), 6.93 (1H, d, J=7.6Hz), 7.02-7.04(1H, m), 7.22 (1H, t, J=8.1Hz), 7.32(2H, d, J=2.5Hz), 7.49 (1H, dd, J=2.0Hz, 1.5Hz).

EXAMPLE 210

(E)-N-(6,6-dimethyl-2-hepten-4-ynyl)-N-ethyl-3-2-(3-thienyl)-4-thiazolylmethyloxy]benzylamine (compound 231)

IR $\nu_{max}^{neat}$ cm$^{-1}$: 2974, 1458, 1365, 1263, 1155, 786.

NMR (CDCl$_3$) δ : 1.03(3H, t, J=7.5Hz), 1.24(9H, s), 2.50(2H, q, J=7.5Hz), 3.09(2H, dd, J=6.3Hz, 1.9Hz), 3.54(2H, s), 5.24(2H, s), 5.63(1H, dt, J=15.9Hz, 1.9Hz), 6.07(1H, dt, J=15.9Hz, 6.3Hz), 6.70(1H, dd, J=7.9Hz, 2.8Hz), 6.93 (1H, d, J=8.1Hz), 7.03-7.05(1H, m), 7.22 (1H, t, J=7.9Hz), 7.25-7.26(1H, m), 7.38 (1H, dd, J=5.2Hz, 2.8Hz), 7.56(1H, dd, J=5.2Hz, 1.6Hz), 7.86(1H, dd, J=2.8Hz, 1.9Hz).

EXAMPLE 211

(E)-N-(6,6-dimethyl-2-hepten-4-ynyl)-N-ethyl-3-3-(3-thienyl)-5-isothiazolylmethyloxy]benzylamine (compound 232)

IR $\nu_{max}^{neat}$ cm$^{-1}$: 2974, 1590, 1491, 1449, 1365, 1263, 789.

NMR (CDCl$_3$) δ : 1.03(3H, t, J=7.5Hz), 1.24(9H, s), 2.50(2H, q, J=7.5Hz), 3.09(1H, dd, J=6.8Hz, 1.9Hz), 3.54(2H, s), 5.34(2H, s), 5.62(1H, dt, J=15.9Hz, 1.9Hz), 6.06(1H, dt, J=15.9Hz, 6.8Hz), 6.85(1H, dd, J=7.5Hz, 2.4Hz), 6.95 (1H, d, J=7.5Hz), 7.01-7.03(1H, m), 7.23 (1H, t, J=7.5Hz), 7.37(1H, dd, J=5.4Hz, 3.0Hz), 7.45(1H, t, J=1.2Hz), 7.61(1H, dd, J=5.4Hz, 1.2Hz), 7.76(1H, dd, J=3.0Hz, 1.2Hz).

EXAMPLE 212

(E)-N-(6,6-dimethyl-2-hepten-4-ynyl)-N-ethyl-3-[4-(5-oxazolyl)-2-thienylmethyloxy]benzylamine (compound 233)

IR $\nu_{max}^{neat}$ cm$^{-1}$: 2974, 1590, 1491, 1455, 1365, 1260, 963.

NMR (CDCl$_3$) δ : 1.03(3H, t, J=7.2Hz), 1.24(9H, s), 2.50(2H, q, J=7.2Hz), 3.09(2H, dd, J=6.3Hz, 1.5Hz), 3.54(2H, s), 5.64(1H, dt, J=15.9Hz, 1.5Hz), 6.07(1H, dt, J=15.9Hz, 6.3Hz), 6.85 (1H, ddd, J=8.0Hz, 2.1Hz, 1.0Hz), 6.94(1H, d, (1H, t, J=8.0Hz), 7.30-7.33(1H, m), 7.52(1H, d, J=1.5Hz), 7.85(1H, s).

EXAMPLE 213

Production of
(E)-N-(6,6-dimethyl-2-hepten-4-ynyl-N-ethyl-3-3-(3-tetrahydrothiopyranyl)benzyloxy]benzylamine (compound 234)

64 mg of 3-(tetrahydrothiopyranyl)benzyl alcohol was dissolved in 1 ml of ethyl acetate, and 85 microliters of triethylamine and 31 microliters of methanesulfonyl chloride were added. The mixture was stirred for 30 minutes. The precipitate was separated by filtration. The organic layer was separated, washed with a saturated aqueous solution of sodium chloride, and dried over anhydrous magnesium sulfate. The desiccant was separated by filtration, and the solvent was evaporated. The residue, 3-(3-tetrahydrothiopyranyl)benzyl methanesulfonate, was dissolved in 1 ml of dimethylformamide. The solution was added to 1 ml of a tetrahydrofuran solution of phenolate, prepared from 100 mg of (E)-N-(6,6-dimethyl-2-hepten-4-ynyl)-N-ethyl-3-hydroxybenzylamine and 18 mg of 60% oily sodium hydride, and the mixture was stirred for 2 hours at room temperature. Water and ethyl acetate were added to extract it. The organic layer was separated, washed with a saturated aqueous solution of sodium chloride, and dried over anhydrous magnesium sulfate. The desiccant was separated by filtration, and the solvent was evaporated. The residue was purified by medium-pressure liquid chromatography column: Lobar column, size A, Lichroprep si 60F (E. Merck Co.); eluting solvent: hexane/ethyl acetate =20/1 → 10/1] to give 60 mg (yield 85%) of the captioned compound as a colorless oil.

IR $\nu_{max}^{neat}$ cm$^{-1}$: 2968, 2926, 1600, 1460, 700.

NMR (CDCl$_3$) δ : 1.03(3H, t, J=7.1Hz), 1.24(9H, s), 1.51-1.67(1H, m), 1.78-2.23(3H, m), 2.50 (2H, q, J=7.1Hz), 2.52-3.10(5H, m), 3.08 (2H, d, J=6.5Hz), 3.54(2H, s), 5.03(2H, s), 5.64(1H, d, J=15.9Hz), 6.06(1H, dt, J=15.9Hz, 6.5Hz), 6.83-6.89(1H, m), 6.92(1H, d, J=7.2Hz), 6.99-7.01(1H, m), 7.15(1H, dt, J=6.9Hz, 1.8Hz), 7.22(1H, t, J=7.2Hz), 7.26-7.36(3H, m).

Compound of Example 214 was obtained by performing the same reaction as in Example 213 except that instead of the starting compound in Example 213, 3-(3-tetrahydrothiopyranyl)benzyl alcohol, 3-(5,6-dihydro2H -thiopyran-4-yl)benzyl alcohol was used.

EXAMPLE 214

(E)-N-(6,6-dimethyl-2-hepten-4-ynyl)-N-ethyl-3-(5,6-dihydro-2H-thiopyran-4-yl)benzyloxy]benzylamine (compound 235)

IR $\nu_{max}^{neat}$ cm$^{-1}$: 2974, 1584, 1491, 1365, 1200, 1044, 960, 783, 696.

NMR (CDCl$_3$) δ : 1.03(3H, t, J=7.1Hz), 1.24(9H, s), 2.50(2H, q, J=7.1Hz), 2.67-2.74(2H, m), 2.89 (2H, t, J=5.7Hz), 3.08(2H, dd, J=6.4Hz, 1.2Hz), 3.34(2H, dt, J=4.4Hz, 2.2Hz), 3.53(2H, s), 5.05(2H, s), 5.64(1H, dt, J=15.9Hz, 1.2Hz), 6.06(1H, dt, J=15.9Hz, 6.4Hz), 6.19(1H, tt, J=4.4Hz, 2.2Hz), 6.85(1H, dd, J=8.3Hz, 2.0Hz), 6.91(1H, d, J=7.6Hz), 6.99-7.01(1H, m), 7.21 (1H, t, J=7.6Hz), 7.27-7.36(3H, m), 7.40-7.42 (1H, m).

EXAMPLE 215

Production of
(E),(E)-N-(6,6-dimethyl-2-hepten-4-ynyl)-N-ethyl-3-[2-[3-(2,3-dihydro-4-thienyl)phenyl]ethenyl]benzylamine (compound 236)

40 mg of (E)-3-[2-[3-(2,3-dihydro-4-thienyl)phenyl]ethenyl]benzyl alcohol was dissolved in 2 ml of methylene chloride, and 60 microliters of triethylamine and 20 microliters of methanesulfonyl chloride were added with stirring under ice cooling. The mixture was stirred for 1 hour at room temperature. Water was added to extract it. The organic layer was separated, and dried over anhydrous magnesium sulfate. The desiccant was separated by filtration, and the solvent was evaporated.

The residue, (E)-3-[2-3-(2,3-dihydro-4-thienyl)phenyl]ethenyl]benzyl methanesulfonate, was dissolved in 1 ml of dimethylformamide, and 27 mg of (E)-N-ethyl-6,6-dimethyl2-hepten-4-ynylamine hydrochloride and 94 mg of potassium carbonate were added thereto. The mixture was stirred overnight at room temperature. The solvent was evaporated, and water and ethyl acetate were added to the residue to extract it. The organic layer was separated, washed with a saturated aqueous solution of sodium chloride, and dried over anhydrous magnesium sulfate. The desiccant was separated by filtration, and the solvent was evaporated. The residue was purified by silica gel column chromatography Wakogel C-200, 5 g; eluting solvent: benzene/ethyl acetate =40/1 → 15/1] to give 15 mg (yield 25%) of the captioned compound as a colorless oil.

IR $\nu_{max}^{neat}$ cm$^{-1}$: 2972, 1600, 1466, 1264, 758.

NMR (CDCl$_3$) δ : 1.06(3H, t, J=7.1Hz), 1.24(9H, s), 2.54(2H, q, J=7.1Hz), 3.12(2H, dd, J=6.3Hz, 1.3Hz), 3.15-3.22(2H, m), 3.38-3.44(2H, m), 3.58(2H, s), 5.66(1H, dt, J=15.9Hz, 1.6Hz), 6.10(1H, dt, J=15.9Hz, 6.3Hz), 6.62(1H, t, J=2.1Hz), 7.10(2H, s), 7.21-7.41(6H, m), 7.45-7.48(2H, m).

Compounds of Examples 216 to 219 below were obtained by performing the same reaction as in Example 215 except that instead of the starting compounds in Example 115, (E)-3-[2-[3-(2,3-dihydro-4-thienyl)-phenyl]ethenyl]benzyl alcohol and (E)-N-ethyl-6,6-dimethyl2-hepten-4-ynylamine hydrochloride, the corresponding alcohol derivatives and the hydrochlorides of various 2-hepten-4-ynylamine derivatives were used.

EXAMPLE 216

(E),(E)-N-(6,6-dimethyl-2-hepten-4-ynyl)-N-ethyl-5-[2-3-(3-thienyl)phenyl]ethenyl)-2-thienyl-methylamine (compound 237)

IR $\nu_{max}^{neat}$ cm$^{-1}$: 2974, 2932, 1365, 954, 795, 774.

NMR (CDCl$_3$) δ : 1.08(3H, t, J=7.1Hz), 1.25(9H, s), 2.57(2H, q, J=7.1Hz), 3.16(2H, dd, J=6.7Hz, 1.5Hz), 3.76(2H, s), 5.69(1H, dt, J=15.9Hz, 1.5Hz), 6.09(1H, dt, J=15.9Hz, 6.7Hz), 6.78 (1H, d, J=3.6Hz), 6.89(1H, d, J=16.1Hz), 6.90 (1H, d, J=3.6Hz), 7.22(1H, d, J=16.1Hz), 7.35-7.50(6H, m), 7.64-7.66(1H, m).

EXAMPLE 217

(E),(E)-N-(6,6-dimethyl-2-hepten-4-ynyl)-N-methyl-3-[2-[3-(5-thiazolyl)phenyl)ethenyl)benzylamine (compound 238)

IR $\nu_{max}^{neat}$ cm$^{-1}$: 2974, 1458, 1365, 1266, 960, 876, 795.

NMR (CDCl$_3$) δ : 1.24(9H, s), 2.22(3H, s), 3.08 (1H, dd, J=6.5Hz, 1.5Hz), 3.52(2H, s), 5.67 (1H, dt, J=15.9Hz, 1.5Hz), 6.11(1H, dt, J=15.9Hz, 6.5Hz), 7.16(2H, s), 7.23(1H, d, J=7.6Hz), 7.32(1H, t, J=7.6Hz), 7.40-7.52 (5H, m), 7.69(1H, t, J=1.8Hz), 8.13(1H, s), 8.77(1H, s).

EXAMPLE 218

(E),(E)-N-(6,6-dimethyl-2-hepten-4-ynyl)-N-propyl-3-[2-[3-(5-thiazolyl)phenyl)ethenyl]benzylamine (compound 239)

IR $\nu_{max}^{neat}$ cm$^{-1}$: 2974, 1365, 1266, 963, 876, 795.

NMR (CDCl$_3$) δ : 0.89(3H, t, J=7.3Hz), 1.24(9H, s), 1.48-1.60(2H, m), 2.41(3H, t, J=7.3Hz), 3.12(1H, dd, J=6.3Hz, 1.5Hz), 3.58(2H, s), 5.64(1H, dt, J=15.8Hz, 1.5Hz), 6.10(1H, dt, J=15.8Hz, 6.3Hz), 7.15(2H, d, J=2.2Hz), 7.26-7.27(1H, m), 7.31(1H, t, J=7.6Hz), 7.40-7.53(5H, m), 7.70(1H, t, J=1.8Hz), 8.13(1H, s), 8.78(1H, s).

EXAMPLE 219

(E),(E)-N-(6,6-dimethyl-2-hepten-4-ynyl)-N-ethyl-4-2-[3-(3-thienyl)phenyl]ethenyl]-2-thienylmethylamine (compound 240)

IR $\nu_{max}^{neat}$ cm$^{-1}$: 2974, 2932, 1365, 960, 849, 774.

NMR (CDCl$_3$) δ : 1.11(3H, t, J=7.1Hz), 1.25(9H, s), 2.57(2H, q, J=7.1Hz), 3.17(2H, dd, J=6.3Hz, 1.5Hz), 3.78(2H, s), 5.69(1H, dt, J=15.9Hz, 1.5Hz), 6.09(1H, dt, J=15.9Hz, 6.3Hz), 6.93 (1H, d, J=16.4Hz), 7.09(1H, d, J=16.4Hz), 7.15-7.18(2H, m), 7.36-7.43(4H, m), 7.45-7.50 (2H, m), 7.66-7.68(1H, m).

EXAMPLE 220

Production of (E),(E)-N-(6,6-dimethyl-2-hepten-4-ynyl)-N-ethyl-3-2-4-(3-thienyl)-2-thienyl)ethenyl]benzylamine (compound 241)

40 mg of (E)-3-2-[4-(3-thienyl)-2-thienyl]ethenyl]benzyl chloride was dissolved in 1 ml of dimethylformamide, and 31 mg of (E)-N-ethyl-6,6-dimethyl-2-hepten-4-ynylamine hydrochloride and 52 mg of potassium carbonate were added. The mixture was stirred overnight. The solvent was evaporated, and water and ethyl acetate were added to the residue to extract it. The organic layer was separated, washed with a saturated aqueous solution of sodium chloride, and dried over anhydrous magnesium sulfate. The desiccant was separated by filtration, and the solvent was evaporated. The residue was purified by medium-pressure liquid chromatography [column: Lobar column, size A, Lichroprep Si 60F (E. Merck Co.); eluting solvent: hexane/ethyl acetate =30/1 → 15/1] to give 44 mg (yield 76%) of the captioned compound, m.p. 100°-102° C., as a crystalline powder.

IR $\nu_{max}^{neat}$ cm$^{-1}$: 3466, 2974, 1104, 957, 741.

NMR (CDCl$_3$) δ : 1.06(3H, t, J=7.1Hz), 1.24(9H, s), 2.53(2H, q, J=7.1Hz), 3.12(2H, dd, J=6.3Hz, 1.5Hz), 3.57(2H, s), 5.66(1H, dt, J=15.9Hz, 1.5Hz), 6.10(1H, dt, J=15.9Hz, 6.3Hz), 6.95 (1H, d, J=16.1Hz), 7.19-7.38(9H, m), 7.42-7.45(1H, m).

Compounds of Examples 221 to 223 below were obtained by performing the same reaction as in Example 220 except that instead of the starting compound in Example 220, (E)-N-ethyl-6,6-dimethyl-2-hepten-4-ynylamine hydrochloride, the corresponding amine derivatives were used.

EXAMPLE 221

(E),(E)-N-(6,6-dimethyl-2-hepten-4-ynyl)-N-methyl-3-[2-[4-(3-thienyl)-2-thienyl]ethenyl]benzylamine (compound 242)

IR $\nu_{max}^{neat}$ cm$^{-1}$: 3442, 2974, 1458, 1365, 954, 825, 744.

NMR (CDCl$_3$) δ : 1.24(9H, s), 2.21(3H, s), 3.08(2H, dd, J=6.6Hz, 1.5Hz), 3.50(2H, s), 5.67(1H, dt, J=15.9Hz, 1.5Hz), 6.11(1H, dt, J=15.9Hz, 6.6Hz), 6.95(1H, d, J=16.0Hz), 7.18-7.38 (9H, m), 7.42-7.46(1H, m).

EXAMPLE 222

(E),(E)-N-(6,6-dimethyl-2-hepten-4-ynyl)-N-propyl-3-[2-[4-(3-thienyl)-2-thienyl]ethenyl]benzylamine (compound 243)

IR $\nu_{max}^{neat}$ cm$^{-1}$: 2968, 1458, 1365, 1203, 954, 744.

NMR (CDCl$_3$) δ : 0.88(3H, t, J=7.4Hz), 1.24(9H, s), 1.47–1.54(2H, m), 2.39(2H, q, J=7.4Hz), 3.11(2H, dd, J=6.3Hz, 1.1Hz), 3.56(2H, s), 5.65(1H, dt, J=15.9Hz, 1.1Hz), 6.10(1H, dt, J=15.9Hz, 6.3Hz), 7.95(1H, d, J=16.6z), 7.19–7.38(9H, m), 7.43–7.45(1H, m).

EXAMPLE 223

(E)-N-(6-methoxy-6-methyl-2-hepten-4-ynyl)-N-propyl-3-[2-[3-(3-thienyl)phenyl]ethenyl]benzylamine (compound 244)

IR $\nu_{max}^{neat}$ cm$^{-1}$: 2938, 1605, 1365, 1251, 1149, 1074, 963, 774.

NMR (CDCl$_3$) δ : 0.90(3H, t, J=7.3Hz), 1.46(6H, s), 1.48–1.60(2H, m), 2.41(2H, t, J=7.3Hz), 3.14 (2H, dd, J=6.3Hz, 1.4Hz), 3.35(3H, s), 3.59 (2H, s), 5.70(1H, dt, J=15.8Hz, 1.4Hz), 6.20 (1H, dt, J=15.8Hz, 6.3Hz), 7.15(2H, s), 7.20–7.23(1H, m), 7.31(1H, t, J=7.6Hz), 7.36–7.50(8H, m), 7.73(1H, t, J=1.4Hz).

EXAMPLE 224

Production of (E),(E)-N-(6,6-dimethyl-2-hepten-4-ynyl)-N-ethyl-5-[2-3-(3-thienyl)phenyl]ethenyl]-3-thienylmethylamine (compound 245)

228 m9 of 2,4-thiophenedicarboxaldehyde 2-ethylene acetal was dissolved in 3 ml of ethanol, and 57 mg of sodium borohydride was added. The mixture was stirred for 30 minutes at room temperature. The solvent was evaporated, and water and ethyl ether were added to the residue to extract it. The organic layer was separated, and dried over anhydrous magnesium sulfate. The desiccant was separated, and the solvent was evaporated. The residue was purified by silica gel column chromatography Wakogel C-200, 10 g; eluting solvent: hexane/ethyl acetate =1/1] to give 130 mg of 4-hydroxymethyl-2-thiophenecarboxaldehyde ethylene acetal as a colorless oil.

The resulting alcohol compound (127 mg) was dissolved in 4 ml of chloroform, and 121 mg of thionyl chloride was added. The mixture was stirred for 1 hour at room temperature. A saturated aqueous solution of sodium hydrogen carbonate was added to extract it. The organic layer was separated, and dried over anhydrous magnesium sulfate. The desiccant was separated by filtration, and the solvent was evaporated. The residue was dissolved in 2 ml of dimethylformamide, and 140 mg of (E)-N-ethyl-6,6-dimethyl-2-hepten-4-ynylamine hydrochloride and 144 mg of potassium carbonate were added. The mixture was stirred overnight at room temperature. The solvent was evaporated. The residue was worked up in a customary manner, and purified by medium-pressure liquid chromatography [column: Lobar column, size B, Lichroprep Si 60F (E. Merck Co.); eluting solvent: hexane/ethyl acetate =5/1] to give 108 mg of (E)-N-(6,6-dimethyl-2-hepten-4-ynyl)-N-ethyl-2-formyl-4-thienylmethylamine as a colorless oil.

46 mg of the resulting formyl compound and 43 mg of 3-(3-thienyl)benzylethylphosphonate were dissolved in 1.5 ml of dimethylformamide, and 6 mg of 60% oily sodium hydride was added. The mixture was stirred for 1 hour at room temperature. Water and ethyl ether were added to extract it. The organic layer was separated, and dried over anhydrous magnesium sulfate. The desiccant was separated by filtration, and the solvent was evaporated. The residue was purified by medium-pressure liquid chromatography column: Lobar column, size B, Lichroprep Si 60F (E. Merck Co.); eluting solvent: hexane/ethyl acetate =8/1] to give 51 mg (yield 77%) of the captioned compound as a colorless oil.

IR $\nu_{max}^{neat}$ cm$^{-1}$: 2974, 2932, 1365, 954, 852, 771.

NMR (CDCl$_3$) δ : 1.06(3H, t, J=7.1Hz), 1.24(9H, s), 2.52(2H, q, J=7.1Hz), 3.11(2H, dd, J=6.5Hz, 1.4Hz), 3.54(2H, s), 5.66(1H, dt, J=15.9Hz, 25 1.4Hz), 6.08(1H, dt, J=15.9Hz, 6.5Hz), 6.94 (1H, d, J=16.1Hz), 6.96(1H, s), 7.04–7.05 (1H, m), 7.23(1H, d, J=16.1Hz), 7.35–7.43 (4H, m), 7.45–7.50(2H, m), 7.66(1H, br.s).

EXAMPLE 225

Production of (E),(E)-N-(6,6-dimethyl-2-hepten-4-ynyl)-N-methyl-5-[2-[3-(3-thienyl)phenyl]ethenyl]-(1,3,4-oxadiazol-2-yl)methylamine hydrochloride (compound 245)

2.56 g of (E)-N-(6,6-dimethyl-2-hepten-4-ynyl)-N-methylglycylhydrazine [synthesized by condensing (E)-N-methyl-6,6-dimethyl-2-hepten-4-ynylamine with ethyl bromoacetate in the presence of sodium hydrogen carbonate, and subsequently reacting with hydrazine] and 16.6 g of sodium hydrogen carbonate were added to 25 ml of dioxane. To the resulting mixture, a dioxane solution of 3-(3-thienyl)cinnamoyl chloride prepared in advance from 3-(3-thienyl)cinnamic acid synthesized by heat condensation of 3-(3-thienyl)benzaldehyde with malonic acid in the presence of piperidine and pyridine] and 6 ml of thionyl chloride were added. The reaction mixture was stirred for 30 minutes at room temperature. The inorganic salt was separated by filtration, and the solvent was evaporated under reduced pressure. The residue was dissolved in 30 ml of phosphorus oxychloride, and stirred for 12 hours at 60° C. The reaction solution was poured onto ice-water, and neutralized with sodium hydrogen carbonate. Ethyl acetate was added to the solution to extract it. The extract was dried over anhydrous magnesium sulfate, and the solvent was evaporated. The residue was purified by medium-pressure liquid chromatography [column: Lobar column, size C, Lichroprep Si 60F (E. Merck Co.); eluting solvent: hexane/ethyl acetate = −2/1] to give 3.7 g (yield 81%) of the free base of the captioned compound as a colorless oil.

The resulting free base was treated with a methanol solution of hydrogen chloride, and recrystallized from ethyl acetate to give the hydrochloride of the captioned compound, m.p. 144°–145° C.

IR $\nu_{max}^{KBr}$ cm$^{-1}$: 2974, 2872, 2458, 1644, 1533, 1464, 1365, 1266, 966, 777.

NMR (CDCl$_3$) δ : 1.24(9H, s), 2.91(3H, s), 3.87 (2H, d, J=7.5Hz), 4.52(2H, s), 5.97(1H, d, J=15.6Hz), 6.30(1H, dt, J=15.6Hz, 7.5Hz), 7.10(1H, d, J=16.5Hz), 7.40–7.54(5H, m), 7.65(1H, dt, J=6.9Hz, 1.8Hz), 7.72(1H, d, J=16.5Hz), 7.77–7.79(1H, m).

Compound of Example 226 was obtained by performing the same reaction as in Example 225 except that instead of the starting compound in Example 225, (E)-N-(6,6-dimethyl-2-hepten-4-ynyl)-N-methylglycylhydrazine, (E)-N-(6,6-dimethyl-2-hepten-4-ynyl)-N-propylglycylhydrazine was used.

EXAMPLE 226

(E)-N-(6,6-dimethyl-2-hepten-4-ynyl)-N-propyl-5-[2-[3-(3-thienyl)phenyl]ethenyl]-(1,3,4-oxadiazol-2-yl)methylamine (compound 247)

m.p. 50.5°-52° C.

IR $\nu_{max}^{KBr}$ cm$^{-1}$: 2968, 2872, 2824, 1647, 1536, 1458, 1365, 1266, 966, 852, 777.

NMR (CDCl$_3$) δ : 0.91(3H, t, J=7.3Hz), 1.24(9H, s), 1.50-1.57(2H, m), 2.49-2.54(2H, m), 3.25 (2H, dd, J=6.6Hz, 1.4Hz), 3.94(2H, s), 5.73 (1H, dt, J=15.9Hz, 1.4Hz), 6.06(1H, dt, J=15.9Hz, 6.6Hz), 7.08(1H, d, J=16.3Hz), 7.26-7.51(5H, m), 7.59(1H, d, J=16.3Hz), 7.60-7.63(1H, m), 7.75-7.76(1H, m).

EXAMPLE 227

Production of
(E)-N-(6,6-dimethyl-2-hepten-4-ynyl)-N-ethyl-3-[4-(3-thienyl)-2-thienylmethyloxy]benzylamine hydrochloride (compound 248)

100 mg of 2-hydroxymethyl-4-(3-thienyl)thiophene was suspended in 5 ml of chloroform, and with stirring under ice cooling, 2 microliters of dimethylformamide and 80 microliters of thionyl chloride were added. The mixture was stirred for 30 minutes, and neutralized with a saturated aqueous solution of sodium hydrogen carbonate under ice cooling. The organic layer was separated, washed with a saturated aqueous solution of sodium chloride, and dried over anhydrous magnesium sulfate. The desiccant was separated by filtration, and the chloroform was evaporated to give 2-chloromethyl-4-(3-thienyl)thiophene as a yellow powder.

3 ml of a dimethylformamide solution of the resulting chloromethyl compound was added to a solution of phenolate [prepared by dissolving 165 mg of (E)-N-(6,6-dimethyl-2-hepten-4-ynyl)-N-ethyl-3-hydroxybenzylamine in 3 ml of anhydrous tetrahydrofuran, adding 26 mg of 60% oily sodium hydride under ice cooling, and then stirring for 10 minutes], and stirred for 3 hours at room temperature. 20 ml of water and 30 ml of ethyl acetate were added to extract it. The organic layer was separated, washed with a saturated aqueous solution of sodium chloride, and dried over anhydrous magnesium sulfate. The solvent was evaporated. The residue was purified by medium-pressure liquid chromatography [column: Lobar column, size B, Lichroprep Si 60F (E. Merck Co.); eluting solvent: hexane/ethyl acetate =20/1 → 10/1], followed by recrystallization from methanol to give 179 mg of the free base of the captioned compound (yield 78%, m.p. 68°-69° C.) as white needles. The resulting free base was treated with a methanol solution of hydrogen chloride, followed by recrystallization from ethyl acetate to give the hydrochloride of the captioned compound, m.p. 128°-129° C.

IR $\nu_{max}^{KBr}$ cm$^{-1}$: 2974, 2926, 2608, 1602, 1458, 1266, 1179, 786.

NMR (CDCl$_3$) δ : 1.25(9H, s), 1.34-1.41(3H, m), 2.90-3.05(2H, m), 3.45-3.60(2H, m), 4.00-4.08 (2H, m), 5.35(2H, s), 5.78(1H, dt, J=15.9Hz, 2.1Hz), 6.18(1H, dt, J=15.9Hz, 6.9Hz), 7.00-7.10(2H, m), 7.15-7.40(5H, m), 7.49-7.65 (2H, m).

EXAMPLE 228

Production of
(E)-N-(6,6-dimethyl-2-hepten-4-ynyl)-N-ethyl-3-[4-(3-thienyl)-2-thienylmethyloxy]benzylamine maleate (compound 249)

100 mg of (E)-N-(6,6-dimethyl-2-hepten-4-ynyl)-N-ethyl-3-[4-(3-thienyl)-2-thienylmethyloxy]benzylamine obtained in Example 227 was dissolved in 1 ml of methylene chloride, and a methylene chloride solution (1 ml) of 26 mg of maleic acid was added. The solvent was evaporated. The residue was recrystallized from ethyl ether to give 115 mg (yield 90%) of the maleate of the captioned compound, m.p. 100°-102° C.

IR $\nu_{max}^{KBr}$ cm$^{-1}$:1 3466, 2974, 1584, 1497, 1389, 1371, 1266, 1185, 786.

NMR (CDCl$_3$) δ : 1.26(9H, s), 1.30(3H, t, J=4.1Hz), 3.02(2H, q, J=4.1Hz), 3.62(2H, br.s), 4.09 (2H, s), 5.23(2H, s), 5.82(1H, d, J=15.6Hz), 5.95(1H, dt, J=15.6Hz, 7.3Hz), 6.99(1H, d, J=7.5Hz), 7.25(1H, dd, J=7.5Hz, 2.1Hz), 7.12-7.16(1H, m), 7.29-7.39(6H, m).

Compounds of Examples 229 to 233 were obtained by performing the same reaction as in Example 227 except that instead of the starting compound in Example 227, (E)-N-(6,6-dimethyl-2-hepten-4-ynyl)-N-ethyl-3-hydroxybenzylamine, the corresponding various 3-hydroxybenzylamine derivatives were used.

EXAMPLE 229

(E)-N-(6,6-dimethyl-2-hepten-4-ynyl)-N-methyl-3-[4-(3-thienyl)-2-thienylmethyloxy]benzylamine (compound 250)

IR $\nu_{max}^{neat}$ cm$^{-1}$: 2974, 2788, 1584, 1488, 1455, 1269, 1026, 783.

NMR (CDCl$_3$) δ : 1.24(9H, s), 1.60(3H, s), 3.04(2H, dd, J=6.6Hz, 1.5Hz), 3.47(2H, s), 5.22(2H, s), 5.65(1H, dt, J=15.9Hz, 1.5Hz), 6.01(1H, dt, J=15.9Hz, 6.6Hz), 6.85-6.94(2H, m), 6.99-7.01 (1H, m), 7.23(1H, t, J=7.8Hz), 7.29-7.36 (5H, m).

EXAMPLE 230

(E)-N-(6,6-dimethyl-2-hepten-4-ynyl)-N-propyl-3-4-(3-thienyl)-2-thienylmethyloxy]benzylamine (compound 251)

IR $\nu_{max}^{neat}$ cm$^{-1}$: 2968, 2872, 1584, 1455, 1263, 1029, 783.

NMR (CDCl$_3$) δ : 0.86(3H, t, J=7.3Hz), 1.24(9H, s), 1.46-1.52(2H, m), 2.36-2.40(2H, m), 3.07(2H, dd, J=6.3Hz, 1.4Hz), 3.53(2H, s), 5.21(2H, s), 5.63(1H, dt, J=15.9Hz, 1.4Hz), 6.06(1H, dt, J=15.9Hz, 6.3Hz), 6.86(1H, ddd, J=7.8Hz, 2.6Hz, 0.9Hz), 6.93(1H, d, J=7.8Hz), 7.01-7.03(1H, m), 7.21(1H, t, J=7.8Hz), 7.28-7.35(5H, m).

EXAMPLE 231

(E)-N-(6-methoxy-6-methyl-2-hepten-4-ynyl)-N-methyl-3-[4-(3-thienyl)-2-thienylmethyloxy]benzylamine (compound 252)

IR $\nu_{max}^{neat}$ cm$^{-1}$: 2986, 1455, 1365, 1251, 1170, 1152, 1074, 1023, 783.

NMR (CDCl$_3$) δ : 1.46(6H, s), 2.20(3H, s), 3.06 (2H, dd, J=7.8Hz, 1.5Hz), 3.35(3H, s), 3.48 (2H, s), 5.22(2H, s), 5.69(1H, dt, J=15.8Hz, 1.5Hz), 6.18(1H, dt, J=15.8Hz, 7.8Hz), 6.87-6.94 (2H, m), 6.99-7.01(1H, m), 7.21-7.36(6H, m).

EXAMPLE 232

(E)-N-ethyl-N-(6 6-methyl-2-hepten-4-ynyl)-3-[4-(3-thienyl)-2-thienylmethyloxy)benzylamine (compound 253)

IR $\nu_{max}{}^{neat}$ cm$^{-1}$: 1455, 1377, 1365, 1254, 1173, 1149, 1074, 1032, 837, 783.

NMR (CDCl$_3$) δ : 1.04(3H, t, J=7.1Hz), 1.46(6H, s), 2.50(2H, q, J=7.1Hz), 3.10(2H, dd, J=6.4Hz, 1.4Hz), 3.35(3H, s), 3.54(2H, s), 5.22(2H, s), 5.69(1H, dt, J=15.8Hz, 1.4Hz), 6.16(1H, dt, J=15.8Hz, 6.4Hz), 6.86(1H, ddd, J=7.9Hz, 2.7Hz, 1.0Hz), 6.93(1H, d, J=7.9Hz), 7.00-7.10(1H, m), 7.23(1H, t, J=7.9Hz), 7.29(1H, dd, J=4.6Hz, 1.3Hz), 7.33-7.39(4H, m).

EXAMPLE 233

(E)-N-(6-methoxy-6-methyl-2-hepten-4-ynyl)-N-propyl-3-[4-(3-thienyl)-2-thienylmethyloxy)benzylamine (compound 254)

IR $\nu_{max}{}^{neat}$ cm$^{-1}$: 1455, 1365, 1254, 1173, 1152, 1077, 1032, 783.

NMR (CDCl$_3$) δ : 0.87(3H, t, J=7.3Hz), 1.39-1.58 (2H, m), 2.38(2H, t, J=7.3Hz), 3.09(2H, dd, J=6.4Hz, 1.4Hz), 3.35(3H, s), 3.54(2H, s), 5.22(2H, s), 5.68(1H, dt, J=15.9Hz, 1.4Hz), 6.16(1H, dt, J=15.9Hz, 6.4Hz), 6.87(1H, dd, J=7.9Hz, 2.9Hz), 6.93(1H, d, J=7.9Hz), 7.00-7.03(1H, m), 7.22(1H, t, J=7.9Hz), 7.30(1H, dd, J=4.5Hz, 1.4Hz), 7.32-7.36 (4H, m).

Compounds of Examples 234 to 236 were obtained by performing the same reaction as in Example 103 except that instead of the starting compounds in Example 103, the corresponding 3-hydroxybenzylamine derivatives and 3-heterocyclylbenzyl methanesulfonyl derivatives were used.

EXAMPLE 234

(E)-N-butyl-N-(6,6-dimethyl-2-hepten-4-ynyl)-3-[3-(3-thienyl)benzyloxy]benzylamine (compound 255)

IR $\nu_{max}{}^{neat}$ cm$^{-1}$: 2968, 1599, 1458, 1260, 771, 693.

NMR (CDCl$_3$) δ : 0.87(3H, t, J=6.8Hz), 1.24(9H, s), 1.23-1.37(2H, m), 1.39-1.51(2H, m), 2.40(2H, t, J=7.2Hz), 3.06(2H, d, J=6.0Hz), 3.52(2H, s), 5.10(2H, s), 5.62(1H, dt, J=15.9Hz, 2.0Hz), 6.06(1H, dt, J=15.9Hz, 6.0Hz), 6.88(1H, dd, J=7.8Hz, 2.1Hz), 6.91(1H, d, J=7.8Hz), 6.98-7.40(1H, m), 7.21(1H, t, J=7.8Hz), 7.31-7.44(3H, m), 7.47(1H, dd, J=2.8Hz, 1.7Hz), 7.55(1H, dt, J=7.8Hz, 1.7Hz), 7.65-7.70(1H, m).

EXAMPLE 235

(E)-N-ethyl-N-(6-ethoxy-6-methyl-2-hepten-4-ynyl)-3-[3-(3-thienyl)benzyloxy]benzylamine (compound 256)

IR $\nu_{max}{}^{neat}$ cm$^{-1}$: 2980, 2932, 2806, 1596, 1491, 1452, 1383, 1362, 1260, 1158, 1110, 1071.

NMR (CDCl$_3$) δ : 1.03(3H, t, J=7.0Hz), 1.20(3H, t, J=7.1Hz), 1.47(6H, s), 2.50(2H, q, J=7.0Hz), 3.10(2H, dd, J=6.4Hz, 1.8Hz), 3.54(2H, s), 3.60(2H, q, J=7.1Hz), 5.10(2H, s), 5.66(1H, dt, J=15.8Hz, 1.8Hz), 6.14(1H, dt, J=15.8Hz, 6.4Hz), 6.87(1H, dd, J=8.0Hz, 2.7Hz), 6.92(1H, d, J=7.6Hz), 7.00-7.02(1H, m), 7.22(1H, t, J=7.6Hz), 7.34-7.44(4H, m), 7.47(1H, dd, J=2.5Hz, 2.0Hz), 7.55(1H, dt, J=7.6Hz, 1.4Hz), 7.66-7.68(1H, m).

EXAMPLE 236

(E)-N-ethyl-N-(6,6-dimethyl-2-hepten-4-ynyl)-3-[3-(5-methyl-3-thienyl)benzyloxy]benzylamine (compound 257)

IR $\nu_{max}{}^{KBr}$ cm$^{-1}$: 3448, 2972, 2612, 1606, 1456, 1268, 1036, 792, 696.

NMR (CDCl$_3$) δ : 1.25(9H, s), 1.42(3H, t, J=7.1Hz), 2.52(3H, d, J=1.4Hz), 2.95-3.05(2H, m), 3.47-3.66(2H, m), 4.07(2H, d, J=4.5Hz), 5.21 (2H, s), 5.80(1H, d, J=15.6Hz), 6.20(1H, dt, J=15.6Hz, 7.6Hz), 7.05(1H, dd, J=8.3Hz, 1.4Hz), 7.07-7.09(1H, m), 7.10-7.20(1H, m), 7.23(1H, d, J=1.7Hz), 7.33(1H, t, J=8.3Hz), 7.36 (1H, d, J=1.7Hz), 7.37-7.39(1H, m), 7.48-7.54 (2H, m), 7.67-7.69(1H, m).

EXAMPLE 237

Production of (E)-N-ethyl-N-(6,6-dimethyl-2-hepten-4-ynyl)-3-[3-(3-thienyl)benzyloxy]-5-isoxazolylmethylamine (compound 258)

The captioned compound was obtained by performing the same reaction as in Example 190 except that instead of the starting compound in Example 190, 3-[3-(3-thienyl)phenoxymethyl]benzyl alcohol, 3-[3-(3-thienyl)benzyloxy]-5-isoxazolylmethyl alcohol was used.

IR $\nu_{max}{}^{neat}$ cm$^{-1}$: 1 2974, 1620, 1506, 1461, 1362, 774.

NMR (CDCl$_3$) δ : 1.08(3H, t, J=7.2Hz), 1.24(9H, s), 2.55(2H, q, J=7.2Hz), 3.16(2H, d, J=5.9Hz), 3.67(2H, s), 5.29(2H, s), 5.67(1H, d, J=15.5Hz), 5.83(1H, s), 6.02(1H, dt, J=15.5Hz, 5.9Hz), 7.36(1H, dt, J=7.5Hz, 1.5Hz), 7.39-7.46 (3H, m), 7.48(1H, dd, J=2.5Hz, 2.1Hz), 7.58 (1H, dt, J=7.5Hz, 1.5Hz), 7.66-7.68(1H, m).

EXAMPLE 238

Tablets, capsules and granules containing (E)-N-(6,6-dimethyl-2-hepten-4-ynyl)-N-propyl-3-(2-methylbenzyloxy)benzylamine hydrochloride (compound 45) as an active ingredient (1) Tablets (25 mg/tablet)

Twenty-five parts of compound 45, 70 parts of lactose, 30 parts of corn starch, 23 parts of crystalline cellulose and 2 parts of magnesium stearate were uniformly mixed, and tableted by a conventional method to give tablets containing 25 mg of the active ingredient per tablet.

(2) Capsules (25 mg/capsule)

Twenty-five parts of compound 45, 125 parts of lactose, 45 parts of corn starch and 5 parts of magnesium stearate were uniformly mixed, and then 200 mg of the mixture was filled into each of hard gelatin capsules (No. 2) to give capsules containing 25 mg of the active ingredient per capsule.

(3) Granules (50 mg/g)

Fifty parts of compound 45, 700 parts of lactose and 230 parts of corn starch were uniformly mixed, and then kneaded with a paste preapred from 20 parts of hydroxypropylcellulose and purified water. The kneaded mixture was granulated by a conventional method to give granules containing 50 mg of the active ingredient per gram.

EXAMPLE 239

Production of a Powder Containing the Compound of Example 119 as an Active Ingredient 25 parts of the compound (hydrochloride) of Example 119 was dissolved in a mixture of 500 parts of ethanol and 500 parts of chloroform, and 75 parts of polyvinyl pyrrolidone K-30 was added. The mixture was evaporated to dryness under reduced pressure by a conventional method. The residual solid was pulverized to a fine powder, and uniformly mixed with 250 parts of lactose, 145 parts of corn starch and 5 parts of magnesium stearate to form a powder containing 25 mg of the active ingredient per 500 mg.

EXAMPLE 240

Production of Capsules Containing the Compound of Example 119 as an Active Ingredient 25 parts of the compound (hydrochloride) of Example 119 was dissolved in a mixture of 500 parts of ethanol and 500 parts of chloroform, and 72.5 parts of polyvinyl pyrrolidone K-30 and 2.5 parts of Tween 60 were added. The mixture was evaporated to dryness under reduced pressure by a conventional method. The residual solid was pulverized to a fine powder, and uniformly mixed with 50 parts of lactose, 45 parts of corn starch and 5 parts of magnesium stearate. The powder was filled in hard gelatin capsules in an amount of 200 mg per capsule to give capsules containing 25 mg of the active ingredient per capsule.

EXAMPLE 241

Production of Capsules Containing the Compound of Example 119 as an Active Ingredient 25 parts of the compound (hydrochloride) of Example 119 was suspended in 1000 parts of water, and 150 parts of beta-cyclodextrin was added. The mixture was stirred at room temperature for 12 hours. 1000 parts of water was further added, and the mixture was stirred for an additional 3 hours at room temperature. The mixture was lyophilized by a conventional method, and the resulting cotton-like solid was lightly pulverized. The particles were filled in hard gelatin capsules in an amount of 70 mg per capsule to form capsules containing 10 mg of the active ingredient per capsule.

General methods of synthesizing the starting compounds used in the above Examples will be described below.

REFERENTIAL EXAMPLE 1

Production of 3-benzyloxybenzylamine hydrochloride

Three hundred milligrams of 3-benzyloxybenzaldehyde was dissolved in 15% ammonia/ethanol, and the solution was stirred for 3 hours. Then, 100 mg of sodium borohydride was added, and the mixture was stirred for 1 hour. The reaction mixture was distilled under reduced pressure, and 20 ml of water and 20 ml of ethyl ether were added. The organic layer was separated, washed with a saturated aqueous sodium chloride solution and dried over anhydrous sodium sulfate. The desiccant was removed by filtration, and the solvent was evaporated. The residue was recrystallized from a mixture of tetrahydrofuran and ethyl ether containing hydrogen chloride to give 140 mg (yield 40%) of the captioned compound as colorless scales having a melting point of 155° to 159° C.

REFERENTIAL EXAMPLE 2

Production of N-methyl-3-benzyloxybenzylamine hydrochloride 15.0 g of m-hydroxybenzaldehyde was dissolved in 200 ml of ethanol, and 25.0 g of potassium carbonate and 32 g of benzyl bromide were added. With stirring, the mixture was heated under reflux for 6 hours. After the reaction, the insoluble inorganic salts were removed by filtration. The filtrate was evaporated under reduced pressure, and purified by silica gel column chromatography [Wakogel C-200, 150 g; hexane/chloroform=1/1] and then recrystallized from hexane to give 21.1 g (yield 81.1%) of 3-benzyloxybenzaldehyde having a melting point of 56° to 57° C.

The resulting benzyloxy compound (7.23 g) was dissolved in 40 ml of a 40% methanol solution of monomethylamine, and 2.4 g of sodium borohydride was added. The mixture was stirred at room temperature for 3 hours. The reaction mixture was concentrated under reduced pressure, and the residue was dissolved in a mixture of 100 ml of water and 100 ml of ethyl ether. The organic layer was separated and then dried over anhydrous sodium sulfate. The desiccant was removed by filtration, and then the solvent was evaporated. The residue was recrystallized from a mixture of methanol and ethyl ether containing hydrogen chloride to give 7.68 g (yield 85.5%) of the captioned compound as colorless needles having a melting point of 127° to 129° C.

The N-methylbenzylamine derivatives used in Examples 4 to 18 can be synthesized by a similar method.

REFERENTIAL EXAMPLE 3

Production of N-isopropyl-3-benzyloxybenzylamine hydrochloride

Three hundred grams of 3-benzyloxybenzaldehyde was dissolved in 10 ml of ethanol, and 84 mg of isopropylamine was added. The mixture was stirred at room temperature for 3 hours. Then, 100 mg of sodium cyanoborohydride was added, and the mixture was stirred for 1 hour. Water (20 ml) and 20 ml of ethyl ether were added, and the organic layer was separated. The organic layer was dried over anhydrous magnesium sulfate, and the dessiccant was removed by filtration. The solvent was evaporated, and the residue was recrystallized from a mixture of tetrahydrofuran and ethyl ether containing hydrogen chloride to give 320 mg (yield 78%) of the captioned compound as colorless scales having a melting point of 150° to 151° C.

The N-substituted benzylamine derivatives used in Examples 19 to 30 can be synthesized by a similar method.

REFERENTIAL EXAMPLE 4

Production of 3-benzyloxy-4-fluorobenzyl bromide 54 mg of 4-fluoro-3-hydroxybenzaldehyde was dissolved in 2 ml of 2-propanol, and 73 mg of benzyl chloride, 80 mg of potassium carbonate and 5 mg of sodium iodide were added to the solution. The mixture was heated under reflux for 7 hours with stirring. The reaction mixture was diluted with ethyl ether, and the inorganic salts were removed by filtration. The filtrate was evaporated under reduced pressure, and purified by silica gel column chromatography (Wakogel C-200, 5 g; eluting solvent: hexane/ethyl acetate=20/1), and then recrystallized from chloroform/hexane to give 77 mg of 3-benzyloxy-4-fluorobenzaldehyde as colorless needles having a melting point of 68° to 69° C.

The benzyloxy compound obtained above (71 mg) was dissolved in 15 ml of ethanol, and 22 mg of sodium borohydride was added. The mixture was stirred at room temperature for 30 minutes. The reaction mixture was concentrated under reduced pressure, and ethyl ether and water were added. The organic layer was separated, washed with water and then dried over anhydrous magnesium sulfate. The desiccant was removed by filtration, the filtrate was evaporated under reduced pressure. The residue was dissolved in 1.5 ml of methylene chloride, and then 41 microliters of phosphorus tribromide was added. The mixture was stirred at room temperature for 30 minutes. Water and methylene chloride were added to the reaction mixture. The organic layer was separated, washed with water and dried over anhydrous magnesium sulfate. The desiccant was removed by filtration, and the filtrate was concentrated under reduced pressure. The residue was purified by silica gel column chromatography (Wakogel, C-200, 5 g; eluting solvent: hexane/ethyl acetate=20/1) to give 68 mg (yield 25%) of the captioned compound as colorless crystals having a melting point of 81° to 82° C.

REFERENTIAL EXAMPLE 5

Production of 3-benzyloxy-5-methylbenzyl bromide 420 mg of benzyl 3-benzyloxy-5-methylbenzoate obtained by benzylating 3-hydroxy-5-methylbenzoic acid was dissolved in 10 ml of tetrahydrofuran, and 72 mg of lithium aluminum hydride was added. The mixture was stirred under ice cooling for 1.5 hours. Acetone was added to the reaction mixture to decompose the excess of the reducing agent. Water and ethyl ether were added, and the organic layer was separated, and dried over anhydrous magnesium sulfate. The desiccant was removed by filtration, and the filtrate was evaporated under reduced pressure to give a mixture of 3-benzyloxy-5-methylbenzyl alcohol and benzyl alcohol.

The mixture was dissolved in 10 ml of methylene chloride, and 0.23 ml of phosphorus tribromide was added. The mixture was stirred at room temperature for 30 minutes. Water and methylene chloride were added to the reaction mixture. The organic layer was separated and dried over anhydrous sodium sulfate. The desiccant was removed by filtration, and the filtrate was concentrated under reduced pressure, and purified by medium-pressure liquid chromatography [column: Lobar column, size A, Lichroprep Si 60 (a product of E. Merck Co.); eluting solvent: hexane/ethyl acetate=100/1] to give 137 mg (yield 37.2%) of the captioned compound as a colorless oil.

When 3-benzyloxy-4-hydroxybenzoic acid is used as a starting material and similarly reduced and brominated, 3-benzyloxy-4-hydroxybenzyl bromide used in Example 33 can be obtained.

REFERENTIAL EXAMPLE 6

Production of 3-(2-methoxybenzyloxy)benzyl methanesulfonate 530 mg of 3-(2-methoxybenzyloxy)benzyl alcohol obtained by reducing 3-(2-methoxybenzyloxy)benzaldehyde with sodium borohydride in ethanol was dissolved in 8 ml of methylene chloride. The solution was stirred at −5° to 0° C., 0.20 ml of methanesulfonyl chloride and 0.65 ml of triethylamine were added. The mixture was stirred at this temperature for 5 minutes. The reaction mixture was diluted with methylene chloride, washed with a saturated aqueous solution of sodium hydrogen carbonate, and dried over anhydrous magnesium sulfate. The solvent was evaporated to give 660 mg (yield 95.3%) of the captioned compound as a colorless oil.

By a similar method, the benzyl methanesulfonates used in Examples 35 to 46 can be synthesized.

REFERENTIAL EXAMPLE 7

Production of (E)-N-(6,6-dimethyl-2-hepten-4-ynyl)-N-methyl-3-hydroxybenzylamine 10.0 g of 3-hydroxybenzaldehyde and 9.55 g of a 40% methanol solution of methylamine were mixed, and then the solvent was evaporated. The resulting Schiff base was dissolved in 50 ml of ethanol, and with stirring under ice cooling, 10.0 g of sodium borohydride was added. The mixture was stirred overnight at room temperature. The solvent was evaporated under reduced pressure, and the residue was extracted with ethyl acetate and a saturated aqueous sodium chloride solution. The organic layer was separated, and dried over anhydrous sodium sulfate. The solvent was evaporated, and the residue was purified by silica gel column chromatography [Wakogel C-100, 100 g; eluting solvent: methylene chloride/methanol=10/1→5/1to give 8.88 g (yield 79%) of N-methyl-3-hydroxybenzylamine as pale yellow crystals having a melting point of 138° to 140° C.

The resulting N-methylamine compound (8.88 g) and 18.0 g of potassium carbonate were added to 30 ml of dimethylformamide, and with stirring at room temperature, a dimethylformamide solution (10 ml) of 13.0 g of 1-bromo-6,6-dimethyl-2-hepten-4-yne (a mixture of the E- and Z-forms in a ratio of about 3:1) was added. The mixture was stirred overnight at room temperature. After the reaction, the solvent was evaporated. The residue was extracted with ethyl acetate and a saturated aqueous sodium chloride solution. The organic layer was separated, and dried over anhydrous magnesium sulfate. The desiccant was removed by filtration, and the solvent was evaporated. The residue was purified by silica gel column chromatography (Wakogel C-200, 300 g; the eluting solvent: hexane/ethyl acetate=10/1) to give 7.94 g (overall yield 39%) of the captioned compound as pale yellow crystals.

When the same reaction as above is carried out using ethylamine or propylamine instead of methylamine, (E)-N-(6,6-dimethyl-2-hepten-4-ynyl)-N-ethyl-3-hydoxybenzylamine used in Examples 101 to 103 or (E)-N-(6,6-dimethyl-2-hepten-4-ynyl)-N-propyl-3-hydroxybenzylamine used in Examples 104 and 105 is obtained.

REFERENTIAL EXAMPLE 8

Production of ethyl 3-(beta-phenethyl)benzoate 863 mg of 3-ethoxycarbonylbenzyltriphenyl phosphonium bromide was suspended in 20 ml of anhydrous tetrahydrofuran, and with stirring under cooling at −30° C., 1.6 ml of 1.53M hexane solution of butyl lithium was added dropwise. After the dropwise addition, the mixture was stirred at room temperature for 1 hour. The reaction mixture was poured into water, and then extracted with ethyl acetate. The extract was washed with a saturated aqueous sodium chloride solution and dried over anhydrous sodium sulfate. The desiccant was removed by filtration and the solvent was evaporated. The residue was purified by silica gel column chromatography (Wakogel C-200, 50 g; eluting solvent: toluene) to give 260 mg (yield 52%) of a mixture of ethyl (E)- and (Z)-3-styrylbenzoates. Two hundred milligrams of the stilbene compound obtained above was dissolved in 2 ml of ethanol, and hydrogenated at room temperature under atmospheric pressure for 5 hours in the presence of 10 mg of a 10% palladium-carbon catalyst. The catalyst was separated by filtration, and then the filtrate was evaporated under reduced pressure to give 200 mg (yield 99%) of the captioned compound as a colorless oil.

REFERENTIAL EXAMPLE 9

Production of (E)-3-styrylbenzyl bromide

The mixture of ethyl (E)- and (Z)-3-styrylbenzoates obtained in Referential Example 8 was reduced by using lithium aluminum hydride in anhydrous tetrahydrofuran to give a mixture of (E)- and (Z)-3-styrylbenzyl alcohols. The mixture was separated and purified by medium-pressure liquid chromatography [column: Lobar column, size A, Lichroprep Si 60 (a product of E. Merck Co.); eluting solvent: hexane/ethyl acetate=5/1] to obtain (E)-3-styrylbenzyl alcohol (colorless crystals; m.p. 87-88° C.) and (Z)-3-styrylbenzyl alcohol (colorless oil).

(E)-3-styrylbenzyl alcohol obtained above (105 mg) was dissolved in 5 ml of chloroform, and 80 microliters of phosphorus tribromide was added, and the mixture was stirred for 40 minutes. The reaction mixture was poured into ice water, and extracted with chloroform. The extract was dried over anhydrous sodium sulfate. The desiccant was removed by filtration, and the filtrate was evaporated under reduced pressure to give 133 mg (yield 93.8%) of the captioned compound.

By a similar method, (Z)-3-styrylbenzyl bromide, (E)-3-(o-methylstyryl)benzyl bromide, and (E)-3-[2-(1-naphthyl)vinyl]benzyl bromide are obtained.

REFERENTIAL EXAMPLE 10

Production of 3-benzylaminobenzyl alcohol hydrochloride 334 mg of 3-aminobenzaldehyde dimethyl acetal was dissolved in 10 ml of anhydrous benzene, and 212 mg of benzaldehyde and 2 g of molecular sieve 4A (a product of Nippon Chromato Kogyo Co., Ltd.) were added. The mixture was stirred at room temperature for 4 hours. The molecular sieve was removed by filtration, and the filtrate was evaporated under reduced pressure. The residue was dissolved in 20 ml of methanol, and 100 mg of sodium borohydride was added. The mixture was stirred for 2 hours. The reaction mixture was diluted with water, and extracted with ethyl ether. The extract was dried over anhydrous sodium sulfate, and the solvent was evaporated. The residue was recrystallized from hexane to give 451 mg (yield 87.7%) of 3-benzylaminobenzaldehyde dimethyl acetal having a melting point of 55° to 56° C.

The resulting acetal (257 mg) was added to 10 ml of 1N HCl, and the mixture was heated at 80° C. for 10 minutes. The reaction mixture was evaporated under reduced pressure. The residue was dissolved in 25 ml of 20% hydrous methanol. With stirring, 200 mg of sodium borohydride was added. The mixture was stirred at room temperature for 1 hour. The reaction mixture was alkalified with sodium carbonate, and extracted with ethyl ether. The extract was dried over anhydrous sodium sulfate and evaporated under reduced pressure. The residue was purified by silica gel column chromatography (Wakogel C-200, 20 g; eluting solvent: hexane/ethyl acetate=5/1), and then treated with HCl-methanol to give 222 mg (yield 89%) of the captioned compound having a melting point of 136° to 137° C.

REFERENTIAL EXAMPLE 11

Production of 3-(2-phenylethynyl)benzyl bromide 213 mg of 3-acetoxymethylstilbene was dissolved in 4 ml of ethyl ether, and 148 mg of bromine was added. The mixture was stirred at room temperature for 2 hours. The crystals were collected by filtration, and dried to give 253 mg (yield 73%) of 1,2-dibromo-2-phenyl-(3-acetoxyphenyl)ethane having a melting point of 156° to 157° C.

The resulting dibromo compound (250 mg) was dissolved in 1 ml of ethanol, and 360 mg of potassium hydroxide was added. The mixture was heated under reflux for 8 hours. The reaction mixture was diluted with water, and then extracted with ethyl ether. The extract was concentrated under reduced pressure, and the residue was purified by medium-pressure liquid chromatography column: Lobar column, size B, Lichroprep Si 60 (a product of E. Merck Co.); eluting solvent: hexane/ethyl acetate=3/1] to give 120 mg (yield 95%) of 3-(2-phenylethynyl)benzyl alcohol as a colorless oil.

The resulting acetylene compound (116 mg) was dissolved in 1 ml of chloroform, and 0.1 ml of phosphorus tribromide was added. The mixture was stirred at room temperature for 1 hour. Water and chloroform were added to the reaction mixture. The organic layer was separated, washed with a saturated aqueous solution of sodium hydrogen carbonate and water, and then dried over anhydrous sodium sulfate. The desiccant was removed by filtration, and the filtrate was evaporated under reduced pressure to give 150 mg (yield 99%) of the captioned compound as a colorless oil.

REFERENTIAL EXAMPLE 12

Production of N-methyl-3-benzyloxy-alpha-phenethylamine 1.0 g of 3-benzyloxybenzaldehyde was dissolved in 10 ml of a 40% methanol solution of methylamine, and after 1 hour, the solution was concentrated to dryness under reduced pressure. The residue was dissolved in 20 ml of anhydrous ethyl ether, and 12 ml of a 0.89M ethyl ether solution of methyl lithium was added. The mixture was heated under reflux with stirring for 3 hours. The reaction mixture was allowed to cool, and poured into 20 ml of ice water. The organic layer was then separated and dried over anhydrous magnesium sulfate. The desiccant was removed by filtration, and the filtrate was evaporated under reduced pressure to give 800 mg (yield 70%) of the captioned compound as a colorless oil.

REFERENTIAL EXAMPLE 13

Production of 3-anilinomethylbenzyl alcohol hydrochloride 1.34 g of isophthalaldehyde was dissolved in 20 ml of anhydrous benzene, and 0.93 g of aniline and 10 g of molecular sieve 4A (a product of Nippon Chromato Kogyo Co., Ltd.) were added. The mixture was stirred at room temperature for 4 hours. The molecular sieve was removed by filtration, and the filtrate was evaporated under reduce pressure. The residue was dissolved in 10 ml of methanol, and then 0.5 g of sodium borohydride was added. The mixture was stirred for 3 hours. The reaction mixture was diluted with water, and extracted with ethyl acetate. The extract was dried over anhydrous sodium sulfate, and the solvent was evaporated. The residue was purified by silica gel column chromatography (Wakogel C-200, 50 g; eluting solvent: hexane/ethyl acetate=3/1) and treated with HCl-methanol to give 1.21 g (yield 48.4%) of the captioned compound having a melting point of 124° to 126° C.

REFERENTIAL EXAMPLE 14

Production of N-methyl-3-benzoylaminobenzylamine hydrochloride 1.06 g of 3-aminobenzaldehyde dimethyl acetal was dissolved in a mixture of 5 ml of toluene and 10 ml of water containing 0.8 g of sodium hydroxide, and 5 ml of a toluene solution of 1.3 g of benzoyl chloride was added. The mixture was stirred at room temperature for 2 hours. The organic layer was separated, and evaporated under reduced pressure. The residue was dissolved in a mixture of 10 ml of methanol and 10 ml of 10% hydrochloric acid, and heated at 90° C. for 30 minutes. Water (20 ml) was added to the reaction mixture to allow it to cool. There was obtained 1.16 g (yield 87.3%) of 3-benzoylaminobenzaldehyde as colorless needles having a melting point of 122° to 123° C.

The above aldehyde (314 mg) was dissolved in 5 ml of a 40% methanol solution of methylamine, and the solution was left to stand at room temperature. Sodium borohydride (110 mg) was added, and the mixture was stirred for 2 hours. The reaction mixture was diluted with water and concentrated under reduced pressure to remove methanol. Ethyl ether was added to the residue to extract the product. The ether layer was washed with a saturated aqueous sodium chloride solution and dried over anhydrous sodium sulfate. The solvent was evaporated, and the residue was treated with HCl/methanol to give 305 mg (yield 79.1%) of the captioned compound as colorless needles having a melting point of 213° to 214° C.

When a similar reaction is carried out by using 3-(N-phenylcarbamoyl)benzaldehyde obtained by condensation of 3-formylbenzoyl chloride and aniline, N-methyl-3-(N-phenylcarbamoyl)benzylamine hydrochloride can be synthesized.

REFERENTIAL EXAMPLE 15

Production of N-methyl-3-furfuryloxybenzylamine hydrochloride

Two grams of furfuryl alcohol was dissolved in 20 ml of anhydrous ethyl ether, and 3 ml of an anhydrous ethyl ether solution containing 2 g of phosphorus tribromide was added. The mixture was stirred for 30 minutes under ice cooling. The reaction mixture was washed with a 30% aqueous solution of sodium hydroxide, and dried over granular sodium hydroxide. The solution was then added to a previously prepared solution of 3-hydroxybenzaldehyde sodium salt (obtained by dissolving 2.44 g of 3-hydroxybenzaldehyde and 0.8 g of 60% oily sodium hydride in a mixture of 5 ml of anhydrous dimethylformamide and 10 ml of anhydrous ethyl ether), and the mixture was stirred at room temperature for 1 hour. To the reaction mixture were added isopropyl ether and water. The organic layer was separated, washed with a 10% aqueous solution of sodium hydroxide, and then dried over anhydrous sodium sulfate. The desiccant was removed by filtration, and the solvent was evaporated. The residue was purified by silica gel column chromatography (Wakogel C-200, 100 g; eluting solvent: hexane/ethyl acetate=3/1) to give 3-furfuryloxybenzaldehyde as a pale yellow oil.

The resulting furfuryloxy compound (0.5 g) was reductively aminated in the same method as in Referential Example 2 to give 0.38 g (yield 60%) of the captioned compound as a crystalline powder having a melting point of 144° to 146° C.

REFERENTIAL EXAMPLE 16

Production of 2-benzyloxy-6-chloromethylpyridine 0.80 g of 6-chloro-2-picoline 1-oxide was added to an alcoholate solution prepared from 0.33 g of 60% oily sodium hydride, 0.69 ml of benzyl alcohol and 5 ml of dimethyl sulfoxide. The mixture was stirred overnight at room temperature. 1N-HCl (1.7 ml) was added to the reaction mixture and then water and chloroform were added. The organic layer was separated, and dried over anhydrous sodium sulfate. The desiccant was removed by filtration, and the filtrate was evaporated under reduced pressure. The residue was purified by silica gel column chromatography (Wakogel C-200, 100 g; eluting solvent: chloroform/methanol=80/1→40/1) to give 0.64 g (yield 54%) of 6-benzyloxy-2-picoline 1-oxide.

The resulting benzyloxy compound (0.42 g) was dissolved in 12.5 ml of acetic anhydride. The mixture was heated under reflux for 1 hour, and then concentrated under reduced pressure. Water and chloroform were added to the residue to extract the product. The organic layer was separated, and dried over anhydrous magnesium sulfate. The desiccant was removed by filtration, and the filtrate was evaporated under reduced pressure, and the residue was purified by silica gel column chromatography (Wakogel C-200, 40 g; eluting solvent: hexane/ethyl acetate=4/1) to give 0.26 g (yield 51%) of 2-acetoxymethyl-6-benzyloxypyridine.

The above acetoxymethyl compound (151 mg) was dissolved in 6 ml of ethanol, and 195 microliters of a 40% aqueous solution of sodium hydroxide was added. The mixture was stirred overnight at room temperature. After the reaction, the solvent was evaporated under reduced pressure. Water and chloroform were added to the residue to extract the product. The organic layer was separated and dried over anhydrous magnesium sulfate. The desiccant was removed by filtration, and the filtrate was evaporated under reduced pressure. The residue was dissolved in 3 ml of chloroform, and 90 microliters of thionyl chloride was added. The mixture was stirred overnight at room temperature. The reaction mixture was extracted with a saturated aqueous solution of sodium hydrogen carbonate and chloroform. The organic layer was separated, dried over anhydrous magnesium sulfate, and concentrated to dryness under reduced pressure. The residue was purified by silica gel column chromatography (Wakogel C-100, 10 g; eluting solvent: hexane/ethyl acetate=3/1) to give 100 mg (yield 69%) of the captioned compound as a pale yellow oil.

By a similar method to above, the chloromethylpyridine derivatives used in Examples 93 to 95 can be synthesized.

REFERENTIAL EXAMPLE 17

Production of (E)-3-chloromethyl-5-styrylpyrazole 228 mg of (E)-5-styrylpyrazole-3-carboxylic acid Ann., 453, 151 (1927)) was dissolved in 5 ml of anhydrous tetrahydrofuran and 68 mg of lithium aluminum hydride was added by portions. The mixture was stirred at room temperature for 1 hour. Hydrous ethyl ether was added to decompose the excess of the reducing agent, and then the mixture was extracted with a 10% aqueous solution of citric acid and ethyl acetate. The organic layer was separated and evaporated under reduced pressure. The residue was washed with ethyl ether, dissolved in 1 ml of 10% HCl/methanol, and again evaporated under reduced pressure. The residue was washed with ethyl ether and filtered to give 96 mg (yield 38%) of (E)-3-hydroxymethyl-5-styrylpyrazole hydrochloride.

90 mg of the hydrochloride was dissolved in 3 ml of chloroform, and 0.5 ml of thionyl chloride was added. The mixture was heated at 50° C. for 20 hours. The reaction mixture was evaporated under reduced pressure. The residue was washed with ethyl acetate and filtered to give 60 mg (yield 82%) of the captioned compound as a colorless crystalline powder.

REFERENTIAL EXAMPLE 18

Production of (E)- and (Z)-2-hydroxymethyl-5-styrylfurans 389 mg of benzyltriphenylphosphonium chloride was suspended in 5 ml of anhydrous tetrahydrofuran, and in a nitrogen atmosphere, 0.75 ml of a 1.59M hexane solution of n-butyl lithium at −30° C. was added. The mixture was stirred at this temperature for 30 minutes. One milliliters of a tetrahydrofuran solution of 5-hydroxymethylfurfural (126 mg) was added to the resulting solution. The mixture was heated to room temperature, and 6 ml of methylene chloride was added. The mixture was stirred overnight. After the reaction, water and chloroform were added to the reaction mixture. The organic layer was separated and dried over anhydrous magnesium sulfate. The desiccant was removed by filtration, and the filtrate was evaporated under reduced pressure. The residue was coarsely purified by silica gel column chromatography (Wakogel C-200, 5 g; eluting solvent: hexane/ethyl acetate=3/1), and again purified by high-performance liquid chromatography (column: Senshu Pack, silica gel-5301N; eluting solvent: hexane/ethyl acetate=3/1) to give 103 mg (yield 51%) of the E-form and 58 mg (yield 29%) of the Z-form of the captioned compounds as pale yellow oils.

REFERENTIAL EXAMPLE 19

Production of a mixture of of (E)- and (Z)-2-hydroxymethyl-4-styrylthiazoles

Diethyl thiazole-2,4-dicarboxylate (1.5 g) was suspended in 15 ml of ethanol, and at −10° C., 3 ml of an ethanol solution of 0.16 g of sodium borohydride and 0.58 g of calcium chloride was added. The mixture was stirred at this temperature for 2 hours. Acetone was added to decompose the excess of the reducing agent, and then the solvent was evaporated under reduced pressure. Dilute sulfuric acid was added to the residue, and insoluble calcium sulfate was separated by filtration. The filtrate was adjusted to pH 10 with an aqueous solution of potassium carbonate, and then extracted with chloroform. The chloroform layer was dried over anhydrous magnesium sulfate, and then further concentrated under reduced pressure. The residue was treated with isopropyl ether to give 0.78 g (yield 64%) of ethyl 2-hydroxymethylthiazole-4-carboxylate as a colorless crystalline powder.

The resulting hydroxymethyl ester (0.78 g) was dissolved in 40 ml of chloroform, and 25 g of active manganese dioxide was added. The mixture was stirred at room temperature for 5 days. The precipitate was removed by filtration, and the filtrate was evaporated under reduced pressure to give 0.67 g (yield 87%) of ethyl 2-formylthiazole-4-carboxylate as colorless needles.

The resulting formyl compound (150 mg) was added to a phosphoran solution prepared in advance from 351 mg of benzyltriphenylphosphonium bromide, 56.9 mg of powdery sodium methoxide and 0.8 ml of methanol, and the mixture was stirred at room temperature for 2.5 hours. The insoluble precipitate was removed by filtration. The filtrate was evaporated under reduced pressure, and the residue was extracted by adding water and methylene chloride. The organic layer was separated, and dried over anhydrous magnesium sulfate. The desiccant was separated by filtration. The filtrate was evaporated under reduced pressure, and the residue was purified by silica gel column chromatography (Wakogel C-200, 24 g; eluting solvent: hexane/ethyl acetate=5/1). The resulting mixture of ethyl (E)- and (Z)-2-styrylthiazole-4-carboxylates was dissolved in 4 ml of ethanol. To the solution was added at -5° C., 1.2 ml of an ethanol solution of 29 mg of sodium borohydride and 100 mg of calcium chloride. The temperature of the mixture was returned to room temperature, and it was stirred overnight at this temperature. Acetone was added to decompose the excess of the reducing agent, and then the solvent was evaporated under reduced pressure. Dilute sulfuric acid was added to the residue, and insoluble calcium sulfate was removed by filtration. Then, potassium carbonate was added to the filtrate to adjust its pH to 10. The solution was concentrated under reduced pressure, and the residue was purified by silica gel column chromatography (Wakogel C-200, 15 g; eluting solvent: hexane/ethyl acetate=2/1→1/1) to give 80 mg (yield 63%) of the captioned mixture as a pale yellow oil.

REFERENTIAL EXAMPLE 20

Production of (E)-2-hydroxymethyl-5-styryloxazole 150 mg of ethyl (E)-5-styryloxazole-2carboxylate Yakugaku Zasshi, vol. 91, page 425 (1971)) was suspended in 15 ml of ethanol, and at −10° C., 5 ml of an ethanol solution of 35 mg of sodium borohydride and 123 mg of calcium chloride was added, and the mixture was stirred at room temperature for 3 hours. The reaction mixture was concentrated under reduced pressure, and water and ethyl ether were added to the residue to perform extraction. The organic layer was separated, and then dried over anhydrous magnesium sulfate. The desiccant was removed by filtration and the filtrate was concentrated under reduced pressure to give 120 mg (yield 97%) of the captioned compound as a colorless oil.

REFERENTIAL EXAMPLE 21

Production of 3-isopropenylbenzyl methanesulfonate

Methyl 3-formylbenzoate (0.67 g) was dissolved in 10 ml of methanol, and 0.74 g of methyl orthoformate and 8 mg of p-toluenesulfonic acid were added. The mixture was stirred at room temperature for 10 hours. Sodium methoxide was added to the reaction mixture to make it basic, and then the solvent was evaporated. The residue was dissolved in ethyl acetate, and washed with a 5% aqueous solution of sodium hydrogen carbonate. The solvent was then evaporated to give 0.75 g of methyl 3-formylbenzoate dimethyl acetal.

0.6 g of the acetal obtained above was dissolved in 12 ml of anhydrous tetrahydrofuran, and with stirring at -20° C., 3.6 ml of a 2N hexane solution of methyl magnesium bromide was added, and the mixture was stirred for 2 hours. A saturated aqueous solution of ammonium chloride was added to the reaction mixture to terminate the reaction. Ethyl acetate was added to the reaction mixture to perform extraction. The extract was worked up in a customary manner to give 0.48 g of crude 3-(1-hydroxy-1-methylethyl)benzaldehyde dimethyl acetal.

0.4 g of the alcohol compound obtained above was dissolved in 8 ml of purified methylene chloride, and with stirring under ice cooling, 0.24 g of methanesulfonyl chloride and 0.38 g of triethylamine were added. The mixture was stirred at room temperature for 2 hours. The reaction mixture was evaporatd under reduced pressure and then extracted by adding ethyl ether and water. The extract was worked up in a customary manner to give 0.35 g of crude 3-isopropenylbenzaldehyde dimethyl acetal as a pale yellow oil.

0.30 g of the isopropenyl compound obtained above was dissolved in 3 ml of 50% hydrous trifluoroacetic acid, and the solution was left to stand for 1 hour at room temperature. The solvent was evaporated, and methylene chloride and water were added to the residue to perform extraction, and the extract was worked up in a customary manner to give 0.28 g of crude 3-isopropenylbenzaldehyde.

0.25 g of the resulting aldehyde compound was dissolved in 5 ml of ethanol, and 80 mg of sodium borohydride was added. The mixture was stirred at room temperature for 1 hour. The reaction mixture was concentrated under reduced pressure, and extracted by adding ethyl ether and water. The extract was worked up in a customary manner, and the product was purified by medium-pressure liquid chromatography [column: Lobar column, size A, Lichroprep Si 60F (a product of E. Merck Co.); eluting solvent: hexane/ethyl acetate=10/1→5/1] to give 0.07 g (overall yield from 3-formylbenzoic acid 23%) of 3-isopropenylbenzyl alcohol as a colorless oil.

50 mg of the resulting alcohol compound was dissolved in 1 ml of chloroform, and with stirring under ice cooling, 43 mg of methanesulfonyl chloride and 69 mg of triethylamine were added. The mixture was stirred at the above temperature for 2 hours. The reaction mixture was distilled under reduced pressure, and the residue was extracted by adding ethyl ether and a saturated aqueous sodium chloride solution. The extract was worked up in a customary manner to give 75 mg of the captioned compound as a pale yellow oil.

REFERENTIAL EXAMPLE 22

Production of 3-(3-methyl-2-butenyl)benzyl bromide

Magnesium metal (1.2 g) was added to 2 ml of tetrahydrofuran. With stirring at room temperature, 20 ml of a solution of 2.0 g of 3-bromobenzaldehyde dimethyl acetal in a 1:1 mixture of tetrahydrofuran and ethyl ether was added dropwise over the course of 1 hour. With stirring under ice cooling, 15 ml of a tetrahydrofuran solution of 2.25 g of 3-methyl-2-butenyl bromide was added to the resulting solution. The temperature of the mixture was returned to room temperature, and then it was stirred for 1 hour. A saturated aqueous solution of ammonium chloride was added to the reaction mixture to terminate the reaction. Ethyl ether was added, and the reaction mixture was treated in a customary manner to give 1.71 g (yield 90%) of 3-(3-methyl-2-butenyl)benzaldehyde dimethyl acetal as a colorless oil.

250 mg of the acetal compound obtained above was dissolved in a mixture of 20 ml of tetrahydrofuran and 5 ml of water, and 1 ml of 35% hydrochloric acid was added. The mixture was stirred at 50° C. for 1 hour. The reaction mixture was diluted with water and ethyl ether, and worked up in a customary manner to give 188 mg (yield 45%) of 3-(3-methyl-2-butenyl)benzaldehyde.

170 mg of the aldehyde compound was dissolved in 20 ml of ethanol, and 100 mg of sodium borohydride was added. The mixture was stirred at room temperature for 1 hour. Water and ethyl ether were added to the reaction mixture to dilute it, and it was then worked up in a customary manner to give 158 mg (yield 92%) of 3-(3-methyl-2-butenyl)benzyl alcohol.

130 mg of the resulting alcohol compound was dissolved in 20 ml of ethyl ether, and 2 ml of pyridine and 270 mg of phosphorus tribromide were added. The mixture was stirred for 1 hour under ice cooling. The reaction mixture was poured into ice water, and ethyl ether was added. The mixture was worked up in a customary manner to give 109 mg (yield 62%) of the captioned compound as a pale yellow oil.

The 3-(2-methyl-1-propenyl)benzyl bromide and -(2-methyl-2-propenyl)benzyl bromide used in Examples 53 and 54 can be formed by substantially the same methods as in Referential Examples 21 and 22.

REFERENTIAL EXAMPLE 23

Production of 2-(2-furyl)benzyl chloride

Ethyl 3-(2-furyl)benzoate J. Chem. Soc., (B), 1971, 2305] was dissolved in 5 ml of anhydrous ethyl ether, and with stirring under ice cooling, 23 mg of lithium aluminum hydride was added. The mixture was stirred for 40 minutes. After the reaction, the reaction mixture was extracted by adding water and ethyl ether. The extract was worked up in a customary manner to give 170 mg (yield 83%) of 3-(2-furyl)benzyl alcohol.

160 mg of the resulting alcohol compound was dissolved in 3 ml of anhydrous ethyl ether. Thionyl chloride (73 microliters) was added, and under ice cooling, the mixture was stirred for 3 hours. After the reaction, the reaction mixture was washed with a saturated aqueous solution of sodium chloride and 5% sodium hydrogen carbonate to give an ethyl ether solution of the captioned compound. It was used directly in the reaction of Example 58.

REFERENTIAL EXAMPLE 24

Production of 3-(2-oxazolyl)benzyl bromide 200 mg of 3-(2-ozazolyl)toluene synthesized in accordance with the method described in Angew. Chem., 75, 165 (1963)] was dissolved in 5 ml of carbon tetrachloride, and 231 mg of N-bromosuccinimide and a catalytic amount of benzoyl peroxide were added. The mixture was refluxed with stirring for 2 hours. The insoluble material was removed after the reaction, and the solvent was evaporated to give the captioned compound.

By a similar method, 3-(2-thiazolyl)benzyl bromide used in Example 60 can be synthesized.

REFERENTIAL EXAMPLE 25

Production of 3-(1-pyrrolyl)benzyl methanesulfonate

Ethyl m-aminobenzoate (1.6 g) was dissolved in 10 ml of glacial acetic acid, and 1.3 g of 2,5-dimethoxytetrahydrofuran was added. The mixture was refluxed for 2 hours, and the solvent was evaporated. The residue was dissolved in a mixture of ethyl acetate and water. The organic layer was separated, and then worked up in a customary manner. Finally, recrystallization from hexane gave 1.7 g (yield 82%) of ethyl 3-(1-pyrrolyl)benzoate as colorless needles having a melting point of 64° to 65° C. The resulting pyrrolyl compound (1.1 g) was dissolved in 30 ml of ethyl ether, and with stirring under ice cooling, 0.2 g of lithium aluminum hydride was added. The mixture was stirred for 1 hour. The reaction mixture was extracted by adding water and ethyl ether. The extract was worked up in a customary manner. Recrystallization from a mixture of ethyl acetate and hexane gave 0.80 g (yield 91%) of 3-(1-pyrrolyl)benzyl alcohol as colorless needles having a melting point of 66° to 68° C.

170 mg of the resulting alcohol compound was dissolved in 10 ml of methylene chloride, and 120 mg of methanesulfonyl chloride and 150 mg of triethylamine were added. The mixture was stirred for 1 hour under ice cooling. The reaction mixture was washed with water, and dried over anhydrous magnesium sulfate. The solvent was evaporated to give 230 mg (yield 92%) of the captioned compound as a pale yellow oil.

By a similar method, 3-(5-oxazolyl)benzyl methanesulfonate used in Examples 61, 102 and 105 can be synthesized [see Chem. Pharm Bull., 27, 793 (1979); Tetrahedron Lett., 1972, 2369].

REFERENTIAL EXAMPLE 26

Production of (E)-N-(6,6-dimethyl-2-hepten-4-ynyl)-N-methyl-3-hydroxybenzylamine 10.0 g of 3-hydroxybenzaldehyde and 9.55 g of a 40% methanol solution of methylamine were mixed, and then the solvent was evaporated. The resulting Schiff base was dissolved in 50 ml of ethanol, and with stirring under ice cooling, 10.0 g of sodium borohydride was added. The mixture was stirred overnight at room temperature. The solvent was evaporated under reduced pressure, and ethyl acetate and a saturated aqueous solution of sodium chloride were added to extract it. The organic layer was separated, and dried over anhydrous sodium sulfate. The solvent was evaporated, and the residue was purified by silica gel column chromatography Wakogel C-100, 100 g; eluting solvent: methylene chloride/methanol=10/1→5/1) to give 8.88 g (yield A%) of N-methyl-3-hydroxybenzylamine as pale yellow crystals, m.p. 138°-140° C.

The resulting N-methylamine compound (8.88 g) and 18.0 g of potassium carbonate were added to 30 ml of dimethylformamide. With stirring at room temperature, a dimethylformamide solution (10 ml) of 13.0 g of 1-bromo-6,6-dimethyl-2-hepten-4-yne (a mixture of the E-form and the Z-form in a ratio of about 3:1) was added. The mixture was stirred overnight at room temperature. residue was extracted with a mixture of ethyl acetate and a saturated aqueous solution of sodium chloride. The organic layer was separated and dried over anhydrous magnesium sulfate. The desiccant was separated by filtration, and the solvent was evaporated. The residue was purified by silica gel column chromatography [Wakogel C-200, 300 g; eluting solvent hexane/ethyl acetate=10/1] to give 7.94 g (total yield 39%) of the captioned compound as pale yellow crystals, m.p. 76°-77° C.

The 3-hydroxybenzylamine derivatives used in Examples 26 to 48, such as (E)-N-(6,6-dimethyl-2-hepten-4-ynyl)-N-ethyl-3-hydroxybenzylamine, (E)-N-(6,6-dimethyl-2-hepten-4-ynyl)-N-propyl-3-hydroxybenzylamine or (E)-N-ethyl-N-(6-methoxy-6-methyl-2-hepten-4-ynyl)-3-hydroxybenzylamine, were obtained by performing the same reaction as in Referential Example 26 except that in place of the starting methylamine-methanol solution, a methanol solution of ethylamine or propylamine was used and as required, 1-bromo-6-methoxy-6-methyl-2-hepten-4-yne was used instead of 1-bromo-6,6-dimethyl-2-hepten-4-yne was used.

REFERENTIAL EXAMPLE 27

Production of 3-(2-furyl)benzyl chloride

Ethyl 3-(2-furyl)benzoate [J. Chem. Soc., (B), 1971, 2305 was dissolved in 5 ml of anhydrous ethyl ether. With stirring under ice cooling, 23 mg of lithium aluminium hydride was added The mixture was stirred for 40 minutes. After the reaction, water and ethyl ether were added to extract the reaction mixture The extract was worked up in a customary manner to give 170 mg (yield 83%) of 3-(2-furyl)benzyl alcohol.

REFERENTIAL EXAMPLE 28

Production of 3-(1-pyrrolyl)benzylmethanesulfonate 1.6 g of ethyl m-aminobenzoate was dissolved in 10 ml of glacial acetic acid, and 1.3 g of 2,5-dimethoxytetrahydrofuran was added. The mixture was heated under reflux for 2 hours The solvent was evaporated, and the residue was dissolved in ethyl acetate and water. The organic layer was separated and worked up in a customary manner, and finally recrystallized from hexane to give 1.7 g (yield 82%) of purified ethyl 3-(1-pyrrolyl)-benzoate as colorless needles, m.p. 64°-65° C.

1.1 g of the resulting pyrrolyl compound was dissolved in 30 ml of ethyl ether, and with stirring under ice cooling, 0.2 g of lithium aluminium hydride was added. The mixture was stirred for 1 hour. Water and ethyl ether were added to the reaction mixture to extract it. The extract was worked up in a customary manner and then recrystallized from a mixture of ethyl acetate and hexane to give 0.80 g (yield 91%) of 3-(1-pyrrolyl)benzyl alcohol as colorless needles, m.p. 66°-68° C.

170 mg of the resulting alcohol compound was dissolved in 10 ml of methylene chloride, and 120 mg of methanesulfonyl chloride and 150 mg of triethylamine were added. The mixture was stirred under ice cooling for 1 hour. The reaction mixture was washed with water, and dried over anhydrous magnesium sulfate. Evaporation of the solvent gave 230 mg (yield 92%) of the captioned compound as a pale yellow oil.

REFERENTIAL EXAMPLE 29

Production of 3-(3-thienyl)benzylmethanesulfonate 790 mg of magnesium was suspended in 1 ml of anhydrous tetrahydrofuran, and a minute amount of 1,2-dibromoethane was added After determining the occurrence of bubbling, a tetrahydrofuran solution (12 ml) of g of 3-bromobenzaldehyde dimethyl acetal was added dropwise at room temperature over 1.5 hours with stirring. The mixture was stirred at 45° to 55° C. for 30 minutes, and then 80 mg of bis(diphenylphosphino)ethane nickel (II) chloride and a tetrahydrofuran solution (6 ml) of 3-bromothiophene were added. The mixture was stirred at room temperature for 3 hours. A saturated aqueous solution of ammonium chloride was added to the reaction mixture, and the insoluble material was separated by filtration. Ethyl acetate was added to extract the reaction mixture The extract was treated in a customary manner and purified by silica gel column chromatography Wakogel C-100, 70 g; eluting solvent: hexane/ethyl acetate=50/1→10/1) to give 1.35 g (yield 27%) of 3-(3-thienyl)benzaldehyde dimethyl acetate, m.p. 45°-46° C.

The resulting thienyl compound (1.35 g) was dissolved in a mixture of 4 ml of 1N hydrochloric acid and 8 ml of tetrahydrofuran. The solution was stirred at room temperature for 1 hour, and the solvent was evaporated under reduced pressure. The residue was extracted with ethyl acetate and water. The extract was worked up in a customary manner to give 1.05 g (yield 96%) of 3-(3-thienyl)benzaldehyde, m.p. 44°-45° C.

1.05 g of the resulting aldehyde compound was dissolved in 15 ml of ethanol, and 250 mg of sodium borohydride was added. The mixture was stirred at room temperature for 30 minutes. The reaction mixture was concentrated under reduced pressure, and the residue was extracted with ethyl acetate and water. The extract was worked up in a customary manner and purified by silica gel column chromatography Wakogel C-100, 20 g; eluting solvent: hexane/ethyl acetate=5/1) to give 960 mg (yield 86%) of 3-(3-thienyl)benzyl alcohol, m.p. 89°-90° C.

300 mg of the resulting alcohol compound was dissolved in 7 ml of ethyl acetate, and to its solution, with stirring under ice cooling, 320 mg of triethylamine and an ethyl acetate solution (1 ml) of 270 mg of methanesulfonyl chloride were added. The mixture was stirred at room temperature for 30 minutes. The precipitated salt was separated by filtration, and the reaction mixture was washed with a saturated aqueous solution of sodium hydrogen carbonate, and dried over anhydrous magnesium sulfate. The solvent was evaporated under reduced pressure to give the captioned compound as a pale yellow powder.

When the starting 3-bromothiophene is replaced by the corresponding bromine-substituted heterocyclic derivative in Referential Example 29, a 3-(3-furyl)benzyl derivative, a 3-(2-thienyl)benzyl derivative, a 3-(2-pyridyl)benzyl derivative, a 3-(3-pyridyl)benzyl derivative and a 3-(4-pyridyl)benzyl derivative are obtained.

REFERENTIAL EXAMPLE 30

Production of 5-(3-methylphenyl)isoxazol 1.56 g of 3-ethynyltoluene was dissolved in 20 ml of ethyl ether, and with stirring at −70° C., 8.5 ml of 1.5M n-butyllithium-hexane solution and 1.2 ml of ethyl formate were added. The mixture was stirred at the same temperature for 20 minutes. The reaction mixture was poured into ice water, and the organic layer was separated. The solvent was evaporated to give 900 mg (yield 47%) of 3-(3-methylphenyl)-2-propynaldehyde as a colorless oil.

130 mg of the resulting aldehyde was dissolved in 20 ml of ethanol, and 5 ml of an aqueous solution of 70 mg of hydroxylamine hydrochloride was added. The solvent was evaporated under reduced pressure. The residue was purified by medium-pressure liquid chromatography column: Lobar column, size A, Lichroprep Si 60 (E. Merck Co.); eluting solvent: hexane/ethyl acetate=-10/1] to give 122 mg (yield 85%) of 3-(3-methylphenyl)-2-propynaldehyde oxime as a pale yellow oil.

122 mg of the resulting oxime compound was dissolved in 20 ml of ethanol, and one drop of a 1N aqueous solution of sodium hydroxide was added. The solution was left to stand for 3 minutes, and three drops of 1N HCl was added to terminate the reaction. The solvent was evaporated under reduced pressure. The residue was extracted with a mixture of water and ethyl ether. The organic layer was separated, and the solvent was evaporated to give 106 mg (yield 87%) of the captioned compound as a pale yellow oil.

REFERENTIAL EXAMPLE 31

Production of 1-(3-hydroxymethylphenyl)imidazole 230 mg of 1-(3-ethoxycarbonylphenyl)imidazole see J. Am. Chem. Soc., 79, 4922 (1957)1 was dissolved in ml of ethyl ether, and 50 mg of lithium aluminium hydride was added. The mixture was stirred at room temperature for 2 hours. The reaction mixture was poured into ice water. The organic layer was separated and dried over anhydrous magnesium sulfate. The desiccant was separated by filtration. The solvent was evaporated and then the residue was purified by silica gel column chromatography Wakogel C-200, 20 g; eluting solvent: chloroform/methanol=20/1) to give 160 mg (yield 92%) of the captioned compound as a colorless oil.

REFERENTIAL EXAMPLE 32

Production of 3-(2-oxazolyl)benzyl bromide 200 mg of 2-(3-methylphenyl)oxazole synthesized substantially in accordance with the method described in Ang. Chem., 75, 165 (1963) was dissolved in 5 ml of carbon tetrachloride, and 231 mg of N-bromosuccinimide and a catalytic amount of benzoyl peroxide were added. The mixture was refluxed for 2 hours with stirring. After the reaction, the insoluble material was separated by filtration, and the solvent was evaporated under reduced pressure to give the captioned compound.

By a similar method, 3-(2-thiazolyl)benzyl bromide can be synthesized.

REFERENTIAL EXAMPLE 33

Production of 3-(5-oxazolyl)benzyl alcohol 400 mg of 3-(hydroxymethyl)benzaldehyde (produced by reducing isophthalaldehyde with an equimolar sodium borohydride), 574 mg of p-toluenesulfonylmethyl isocyanide and 406 mg of potassium carbonate were added to 10 ml of methanol. With stirring, the mixture was heated under reflux for 1 hour. The reaction mixture was concentrated under reduced pressure, and the residue was extracted with ethyl acetate and water. The extract was worked up in a customary manner, and purified by silica gel column chromatography Wakogel C-200, 50 g; eluting solvent: hexane/ethyl acetate=1/1) to give 375 mg (yield 73%) of the captioned compound as a white powder.

When the above alcohol compound is mesylated by the same method as in Referential Example 28, 3-(5ox-azolyl)benzylmethanesulfonate is obtained as a colorless oil.

REFERENTIAL EXAMPLE 34

Production of 3-(4-isoxazolyl)benzyl bromide 185 mg of 4-(3-methylphenyl)isoxazole [see J. Heterocyclic Chem., 11, 51 (1974); and J. Chem. Soc., Perkin II, 1121 (1977)] was dissolved in 8 ml of carbon tetrachloride, and 206 mg of N-bromosuccinimide and a catalytic amount of benzoyl peroxide were added. The mixture was refluxed with stirring for 3 hours. The insoluble material was separated by filtration and the solvent was evaporated. The residue was purified by silica gel column chromatography Wakogel C-200, 30 g; eluting solvent: hexane/ethyl acetate=10/1 to give 210 mg (yield 76%) of the captioned compound as a colorless powder.

When the same reaction as in Referential Example 34 is carried out except using 4-(3-methylphenyl)isothiazole [see J. prakt. Chem., 318, 507 (1976)1, 5-(3-methylphenyl)isothiazole [see J. prakt. Chem., 318, 507 (1976)], 5-(3-methylphenyl)pyrimidine see J. Heterocyclic Chem., 11, 55 (1974); Heterocycles, 19, 1080 (1982)], or 1-(3-methylphenyl)-1,2,4-triazole see J. Org. Chem., 21, 1037 (1956), and Japanese Laid-Open Patent Publication No. 4173/1976] instead of the starting 4-(3-methylphenyl)isoxazole, 3-(4-isothiazolyl)benzyl bromide, 3-(5-isothiazolyl)benzyl bromide, 3-(5-pyrimidyl)-benzyl bromide or 3-(1,2,4-triazol-1-yl)benzylbromide are obtained.

REFERENTIAL EXAMPLE 35

Production of 3-(2,3-dihydro-4-thienyl)benzyl alcohol and 3-(2,5-dihydro-3-thienyl)benzyl alcohol A tetrahydrofuran solution (10 ml) of tetrahydrothiophen-3-one was added dropwise with stirring under ice cooling to a tetrahydrofuran solution (15 ml) of a Grignard reagent prepared from 2.31 g of 3-bromobenzaldehyde dimethyl acetal and 0.36 g of metallic magnesium. After the addition, the mixture was stirred at room temperature for 1 hour. The reaction mixture was poured into ice water, and ethyl ether was added to extract the product. The extract was worked up in a customary manner to give 1.20 g (yield 47%) of a crude product of 3-(3-hydroxytetrahydro-3-thienyl)benzaldehyde dimethyl acetal.

1.20 g of the resulting alcohol compound was dissolved in a mixture of 20 ml of tetrahydrofuran and 3 ml of 10% HCl. After standing for 2 hours at room temperature, ethyl ether and water were added to the solution to dilute it. The organic layer was separated, and the solvent was evaporated under reduced pressure. The residue was dissolved in 20 ml of methylene chloride, and 1.0 ml of methanesulfonyl chloride and 2.0 ml of triethylamine were added. The mixture was stirred under ice cooling for 30 minutes. The reaction mixture was poured into ice water, and the organic layer was separated and the solvent was evaporated to dryness under reduced pressure. The residue was dissolved in 10 ml of ethanol, and 0.2 g of sodium borohydride was added. The solution was stirred at room temperature for 1 hour. The reaction mixture was concentrated under reduced pressure, and ethyl ether and water were added to the residue to extract it. The extract was worked up in a customary manner, and the product was purified by medium-pressure liquid chromatography [Lobar column, size B, Lichroprep Si 60 (E. Merck & Co.); eluting solvent: hexane→ hexane/ethyl acetate 10/1] to give 0.45 g (yield 50%) of 3-(2,3-dihydro-4-thienyl)benzyl alcohol and 0.20 g (yield 22%) of 3-(2,5-dihydro-3-thienyl)benzyl alcohol.

REFERENTIAL EXAMPLE 36

Production of 3-(1-pyrrolidinyl)benzyl alcohol 0.25 g of N-(3-ethoxycarbonylphenyl)succinimide [synthesized by heat condensing ethyl m-aminobenzoate with succinic anhydride in acetic acid] was dissolved in 5 ml of anhydrous tetrahydrofuran, and with stirring under ice cooling, 0.17 g of lithium aluminium hydride was added. The mixture was maintained at room temperature for 30 minutes, and then heated under reflux for 4 hours. After the reaction, ethyl acetate and water were added. The organic layer was separated, and then worked up in a customary manner and purified by medium-pressure liquid chromatography [Lobar column, size B, Lichroprep Si 60 (E. Merck & Co.); eluting solvent: hexane/ethyl acetate=10/1) to give 84 mg (yield 47%) of the captioned compound as a colorless oil.

When the resulting alcohol compound is mesylated by the same method as in Referential Example 29, 3-(1-pyrrolidinyl)benzyl methanesulfonate is obtained as a colorless oil.

REFERENTIAL EXAMPLE 37

Production of 5-(3-thienyl)thienylmethyl alcohol 5 g of 3-bromothiophene was dissolved in 35 ml of anhydrous ethyl ether, and with stirring under cooling at −70° to −65° C., 19 ml of a 15% n-butyllithium-hexane solution and 10.5 g of tributyltin chloride were added. The mixture was stirred at the above temperature for 1 hour and then at room temperature for 1 hour. The reaction mixture was washed with a saturated aqueous solution of sodium hydrogen carbonate, and then the solvent was evaporated. The residue was purified by distillation under reduced pressure to give 8.5 g (yield 74%) of tributyl(3-thienyl)tin, b.p. 150°-158° C./2 mmHg.

1.19 g of the above tin compound and 0.56 g of 5-bromothiophene-2-carbaldehyde were dissolved in 3 ml of toluene, and 20 mg of tetrakis(triphenylphosphine)-palladium was added. The mixture was heated with stirring under reflux for 7 hours. The reaction mixture was washed with a 10% aqueous solution of potassium fluoride and a 5% aqueous solution of potassium carbonate. The solvent was evaporated, and the residue was purified by silica gel column chromatography Wakogel C-200, 50 g; eluting solvent: hexane/ethyl acetate=10/1 to give 0.36 g (yield 63%) of 5-(3-thienyl)thiophene-2-carbaldehyde.

144 mg of the resulting aldehyde compound was reduced with 15.6 mg of lithium aluminium hydride in 4 ml of tetrahydrofuran, and then worked up in a customary manner to give 134 mg (yield 92%) of the captioned compound as a colorless oil.

REFERENTIAL EXAMPLE 38

Production of 2-(5-oxazolyl)-4-pyridinemethanol 1.07 g of dimethyl pyridine-2,4-dicarboxylate was dissolved in 20 ml of toluene, and with stirring under cooling at −80° to −70° C., 6.04 ml of a 1M toluene solution of diisobutylaluminium hydride was added dropwise over 2.5 hours, and the mixture was stirred at this temperature for 1 hour. The reaction mixture was poured into ice water, and ethyl ether was added. The organic layer was separated, worked up in a customary manner, and then purified by medium-pressure liquid chromatography Lobar column, size B, Lichroprep Si 60 (E. Merck Co.); eluting solvent: hexane/ethyl acetate=4/1→3/1) to give 0.27 g (yield 30%) of methyl 2-formylisonicotinate as a colorless crystalline powder.

203 mg of the resulting formyl compound was dissolved in 8 ml of methanol, and 240 mg of p-toluenesulfonylmethyl isocyanide and 170 mg of potassium carbonate were added. The mixture was heated under reflux for 10 minutes. The reaction mixture was evaporated to dryness under reduced pressure. The residue was extracted with methylene chloride and water. The organic layer was worked up in a customary manner to give 224 mg (yield 91%) of methyl 2-(5-oxazolyl)isonicotinate as a pale yellow powder.

102 mg of the resulting oxazolyl compound was dissolved in 2 ml of anhydrous tetrahydrofuran, and with stirring under ice cooling, 14 mg of lithium aluminium hydride was added. The mixture was stirred at this temperature for 30 minutes. The reaction mixture was poured into ice water, and methylene chloride was added to extract it. The extract was worked up in a customary manner and purified by silica gel column chromatography [Wakogel C-200, 5.5 g; eluting solvent: methylene chloride/methanol=50/1→20/1] to give 49.5 mg (yield 56%) of the captioned compound as a pale yellow crystalline powder.

REFERENTIAL EXAMPLE 39

Production of 5-(5-oxazolyl)-3-pyridinemethanol 1.67 g of dimethyl pyridine-3,5-dicarboxylate was dissolved in 30 ml of anhydrous tetrahydrofuran, and with stirring under ice cooling, 162 mg of lithium aluminium hydride was added. The mixture was stirred at this temperature for 30 minutes. The reaction mixture was poured into ice water, and ethyl ether was added to extract it. The extract was worked up in a customary manner to give crude methyl 5-hydroxymethylnicotinate. The crude product was dissolved in 20 ml of methylene chloride, and 2.2 g of pyridinium chlorochromate was added. The mixture was stirred overnight at room temperature. The reaction mixture was poured into ice water. The organic layer was separated, worked up in a customary manner, and purified by silica gel column chromatography Wakogel C-200, 80 g; eluting solvent: chloroform/methanol=20/1) to give 0.37 g (yield 26%) of 5 methyl 5-formylnicotinate, m.p. 96°–97° C.

110 mg of the resulting formyl compound was used as a starting material, and subjected to oxazolylation and reduction as in Referential Example 38 to give 77 mg (yield 64%) of the captioned compound as a colorless oil.

When the same reaction as in Referential Example 39 is carried out using dimethyl pyridine-2,6-dicarboxylate instead of the starting dimethyl pyridine-3,5-dicarboxylate, 6-(5-oxazolyl)-2-pyridinemethanol is obtained.

REFERENTIAL EXAMPLE 40

Production of 5-(5-hydroxymethyl-2-furyl)oxazole 300 mg of 5-formylfurfuryl alcohol see Japanese Laid-Open Patent Publication No. 154758/1979 was dissolved in 10 ml of methanol, and 502 mg of p-toluenesulfonylmethyl isocyanide and 329 mg of potassium carbonate were added. The mixture was heated under reflux for 1 hour. The reaction mixture was concentrated under reduced pressure, and the residue was dissolved in a mixture of water and ethyl acetate. The organic layer was separated, and dried over anhydrous magnesium sulfate. The desiccant was separated by filtration, and the solvent was evaporated under reduced pressure. The residue was purified by silica gel column chromatography Wakogel C-200, 45 g; eluting solvent: hexane/ethyl acetate=3/2→1/1] to give 260 mg (yield 66%) of the captioned compound as a pale yellow crystalline powder.

REFERENTIAL EXAMPLE 41

Production of 4-hydroxymethyl-2-(5-oxazolyl)thiazole 1.5 g of diethyl thiazole-2,4-dicarboxylate was suspended in 15 ml of ethanol, and at −10° C., 0.16 g of sodium borohydride and 3 ml of an ethanol solution of 0.58 g of calcium chloride were added. The mixture was stirred at the above temperature for 2 hours. Acetone was added to decompose the excess of the reducing agent, and the solvent was evaporated under reduced pressure. Dilute sulfuric acid was added to the residue, and insoluble calcium sulfate was separated by filtration. The filtrate was adjusted to pH 10 with an aqueous solution of potassium carbonate, and then extracted with chloroform. The chloroform layer was dried over anhydrous magnesium sulfate and evaporated to dryness under reduced pressure. The residue was treated with isopropyl ether to give 0.78 g (yield 64%) of ethyl 2-hydroxymethylthiazole-4-carboxylate as a colorless crystalline powder.

0.78 g of the resulting hydroxymethyl compound was dissolved in 40 ml of chloroform, and 25 g of active manganese dioxide was added. The mixture was stirred at room temperature for 5 days. The precipitate was separated by filtration, and the filtrate was evaporated to dryness under reduced pressure to give 0.67 g (yield 87%) of ethyl 2-formylthiazole-4-carboxylate as colorless needles.

60 mg of ethyl 2-(5-oxazolyl)thiazxole-4-carboxylate prepared by reacting 80 mg of the resulting formyl compound, 91 mg of p-toluenesulfonylmethyl isocyanide and 60 mg of potassium carbonate as in Referential Example 13 was dissolved in 3 ml of ethanol. To the solution were added 6.6 mg of sodium borohydride and 24 mg of calcium chloride. The mixture was stirred at room temperature for 1 hour. The reaction mixture was concentrated under reduced pressure, and 10% sulfuric acid was added to the residue. The resulting precipitate was separated by filtration, and potassium carbonate was added to the filtrate to adjust its pH to 10. Chloroform was added to extract the product. The extract was dried over anhydrous magnesium sulfate, and the solvent was evaporated. The residue was purified by preparative thin-layer chromatography thin-layer plate: Kieselgel 60F254, Art. 5744 (E. Merck Co.); developing solvent: hexane/ethyl acetate=1/4] to give 20 mg (yield 25%) of the captioned compound as a white crystalline powder.

REFERENTIAL EXAMPLE 42

Production of 5-(5-hydroxymethyl-3-furyl)oxazole 408 mg of dimethyl furan-3,5-dicarboxylate [see J. Chem. Soc., Perkin I, 1130 (1973)] was dissolved in 4 ml of anhydrous tetrahydrofuran, and 59 mg of lithium aluminium hydride was added. The mixture was stirred overnight at room temperature. The reaction mixture was poured into water, and ethyl acetate was added to extract it. The extract was worked up in a customary manner and purified by silica gel column chromatography [Wakogel C-200, 20 g; eluting solvent: hexane/ethyl acetate=2/1] to give 44 mg (yield 13%) of methyl 5-hydroxymethylfuran-3-carboxylate as a colorless oil.

44 mg of the resulting alcohol compound was dissolved in 2 ml of chloroform, and 60 mg of pyridinium chlorochromate was added. The mixture was stirred overnight at room temperature. The reaction mixture was poured into ice water, and the organic layer was separated, worked up in a customary manner, and purified by silica gel column chromatography [Wakogel C-200, 2 g; eluting solvent: hexane/ethyl acetate=3/1] to give 28 mg of a purified formyl compound. It was dissolved in 2 ml of methanol, and 35 mg of p-toluenesulfonylmethylisocyanide and 25 mg of potassium carbonate were added. The mixture was refluxed for 30 minutes, and worked up in a customary manner to give 30 mg of methyl 5-(5-oxazolyl)furan-3-carboxylate. The resulting compound was dissolved in 2 ml of tetrahydrofuran, and with ice cooling, 6 mg of lithium aluminium hydride was added. The mixture was stirred at the above temperature for 30 minutes. The reaction mixture was poured into ice water, and ethyl ether was added to extract it. The extract was worked up in a customary manner to give 22 mg (yield 48%) of the captioned compound as a pale yellow oil.

REFERENTIAL EXAMPLE 43

Production of 6-methyl-3-(1-pyrrolyl)benzyl alcohol 158 mg of methyl 3-amino-6-methylbenzoate was dissolved in 3 ml of acetic acid, and 139 mg of 2,5-dimethoxytetrahydrofuran was added. The mixture was heated under reflux for 1 hour. The reaction mixture was evaporated to dryness under reduced pressure. The residue was purified by silica gel column chromatography Wakogel C-200, 10 g; eluting solvent: hexane/ethyl acetate=10/1) to give 185 mg (yield 87%) of methyl 3-(1-pyrrolyl)-6-methylbenzoate, m.p. 56°-57° C.

180 mg of the resulting pyrrolyl compound was dissolved in 2 ml of ethyl ether, and 24 mg of lithium aluminium hydride was added. The mixture was stirred at room temperature for 30 minutes. Water and ethyl ether were added to the reaction mixture. The organic layer was separated and dried over anhydrous magnesium sulfate. The desiccant was separated by filtration, and the solvent was evaporated to give 155 mg (yield quantitative) of the captioned compound as a colorless crystalline powder, m.p. 70°-71° C.

When the same reaction as in Referential Example 18 is carried out using methyl 3-amino-2-methylbenzoate instead of the starting methyl 3-amino-6-methylbenzoate, 2-methyl-3-(1-pyrrolyl)benzyl alcohol is obtained.

REFERENTIAL EXAMPLE 44

Production of (E)-N-(6,6-dimethyl-2-hepten-4-ynyl)-N-methyl-3-(3-formylbenzyloxy)benzylamine A dimethylformamide solution (1.5 ml) of 90 mg of 3-chloromethylbenzaldehyde was added to a phenolate solution prepared from 150 mg of (E)-N-(6,6-dimethyl-2-hepten-4-ynyl)-N-methyl-3-hydroxybenzylamine, 23.2 mg of 60% oily sodium hydride and 1 ml of tetrahydrofuran. The mixture was stirred overnight at room temperature. The solvent was evaporated under reduced pressure. The residue was extracted with ethyl acetate-water, worked up in a customary manner, and purified by silica gel column chromatography [Wakogel C-200, 15 g; eluting solvent: hexane/ethyl acetate=10/1→5/1] to give 85 mg (yield 39%) of the captioned compound as a colorless oil.

When the same reaction as in Referential Example 34 is carried out using methyl 3-bromomethylbenzoate instead of the starting 3-chloromethylbenzaldehyde, (E)-N-(6,6-dimethyl-2-hepten-4-ynyl)-N-methyl-3-(3-methoxycarbonylbenzyloxy)benzylamine is obtained.

REFERENTIAL EXAMPLE 45

Production of (E)-3-[2-[3-(3-thienyl)phenyl]ethenyl]benzyl chloride:

2.40 g of 3-(3-thienyl)benzyl chloride was dissolved in 40 ml of toluene, and 3.62 g of triphenylphosphine was added. The mixture was heated under reflux for 50 hours. The reaction mixture was allowed to cool, and the precipitated crystals were collected by filtration to give 3.60 g (yield 66%) of 3-(3-thienyl)benzyltriphenylphosphonium chloride.

1.21 g of the resulting phosphonium salt was dissolved in 45 ml of ethanol, and 0.35 g of 3-formylbenzyl alcohol and 0.27 g of sodium ethoxide were added. The mixture was stirred at room temperature for 2 hours. The solvent was evaporated under reduced pressure. The residue was distributed between ethyl acetate and water, worked up in a customary manner, and purified by silica gel column chromatography [Wakogel C-300, 100 g; eluting solvent: hexane/ethyl acetate=10/1→5/1] to give 0.34 g (yield 46%) of an E-form of 3-[2-[3-(3-thienyl)-phenyl]ethenyl]benzyl alcohol and 0.34 g of its Z-form.

0.20 g of the resulting (E)-form alcohol was dissolved in 6 ml of chloroform, and 0.15 ml of thionyl chloride and one drop of dimethylformamide were added. The mixture was stirred at room temperature for 1 hour. The reaction mixture was concentrated under reduced pressure. The residue was distributed between ethyl ether and water, worked up in a customary manner, and purified by silica gel column chromatography [Wakogel C-100, 20 g; eluting solvent: hexane/ethyl acetate=20/1] to give 0.19 g (yield 87%) of the captioned compound as a colorless crystalline powder, m.p. 79°-81 ° C.

When the same reaction as in Referential Example 45 is carried out except that instead of the starting 3-(3-thienyl)benzyl chloride, the corresponding 3-substituted benzyl chloride or bromide is used, (E)-3-2-[3-(5-oxazolyl)phenyl]ethenyl]benzyl chloride, (E)-3-[2-[3-(5-thiazolyl)phenyl]ethenyl]benzyl chloride and (E)-3-[2-[3-(1-imidazolyl)phenyl]ethenyl]benzyl chloride are obtained.

REFERENTIAL EXAMPLE 46

Production of
(E)-3-[2-[3-(1-pyrrolyl)phenyl]ethenyl]benzyl alcohol 560 mg of 3-(dimethoxymethyl)benzyltriphenylphosphonium bromide synthesized by brominating 3-hydroxymethylbenzaldehyde with phosphorus tribromide, and then acetalizing the product in anhydrous methanol in the presence of p-toluenesulfonic acid, followed by reacting it with triphenylphosphine] and 180 mg of 3-(1-pyrrolyl)benzaldehyde [synthesized by oxidizing 3-(1-pyrrolyl)benzyl alcohol with pyridinium chlorochromate in chloroform]were dissolved in 20 ml of methanol. 110 mg of sodium methoxide was added, and the mixture was stirred at room temperature for 3 hours. The reaction mixture was concentrated under reduced pressure, and ethyl acetate and water were added to the residue to extract it. The organic layer was worked up in a customary manner, and purified by medium-pressure liquid chromatography [Lobar column, size B, Lichroprep Si 60 (E. Merck Co.); eluting solvent: hexane/ethyl acetate=10/1] to give 135 mg (yield 42%) of an E-form of 3-[2-[3-(1-pyrrolyl)phenyl]ethenyl]benzaldehyde dimethyl acetal and 127 mg of its Z-form.

135 mg of the resulting (E)-form acetal was dissolved in a mixture of 5 ml of tetrahydrofuran and 5 ml of 2 N HCl. The solution was stirred at room temperature for 3 hours. The solvent was then evaporated under reduced pressure. The residue was worked up in a customary manner. The resulting formyl compound was dissolved in 10 ml of ethanol, and 40 mg of sodium borohydride was added. The mixture was stirred at room temperature for 30 minutes. The reaction mixture was concentrated under reduced pressure. The residue was distributed between ethyl acetate and water, worked up in a customary manner, and purified by silica gel column chromatography [Wakogel C-100, 20 g; eluting solvent: hexane/ethyl acetate=5/1] to give 78 mg (yield 67%) of the captioned compound as a colorless crystalline powder, m.p. 108°-110 ° C.

When the same reaction as in Referential Example 46 is carried out using 3-(3-pyridyl)benzaldehyde instead of the starting 3-(1-pyrrolyl)benzaldehyde, (E)-3-[2-[3-(3-pyridyl)phenyl]ethenyl]benzyl alcohol is obtained.

REFERENTIAL EXAMPLE 47

Production of 3-[2-[3-(3-thienyl)phenyl]ethyl]benzyl alcohol 81 mg of (Z)-3-[2-[3-(3-thienyl)phenyl]ethenyl]benzyl alcohol was dissolved in 3 ml of ethanol, and in the presence of 15 mg of 10% palladium-carbon, catalytically reduced at ordinary temperature and atmospheric pressure for 15 hours. The catalyst was separated by filtration, and the solvent was evaporated to give the captioned compound as a colorless oil in a quantitative yield.

When the same reduction as in Referential Example 47 is carried out using (Z)-3-[2-[3-(1-pyrrolyl)phenyl]ethenyl]benzyl alcohol or (Z)-3-[2-[3-(3-pyridyl)phenyl]ethenyl]benzyl alcohol instead of the starting (Z)-3-[2-[3-(3-thienyl)phenyl]ethenyl]benzyl alcohol, 3-[2-[3-(1-pyrrolyl)phenyl]ethyl]benzyl alcohol and 3-[2-[3-(3-pyridyl)phenyl]ethyl]benzyl alcohol are obtained.

REFERENTIAL EXAMPLE 48

Production of
(E)-N-(6,6-dimethyl-2-hepten-4-ynyl)-N-ethyl-5-formylfurfurylamine 100 mg of 5-hydroxymethylfurfural was dissolved in 2 ml of anhydrous ethyl ether, and with stirring under ice cooling, an ethyl ether solution (1 ml) of 30 microliters of phosphorus tribromide was added. The mixture was stirred at the above temperature for 10 minutes. The reaction mixture was washed with a saturated aqueous solution of sodium hydrogen carbonate. Then, 183 mg of (E)-N-ethyl-6,6-dimethyl-2-hepten-4-ynylamine hydrochloride, 136 mg of potassium carbonate and 3 ml of dimethylformamide were added, and the mixture was stirred overnight at room temperature. The reaction mixture was concentrated under reduced pressure. The residue was distributed between ethyl ether and water, worked up in a customary manner, and purified by silica gel column chromatography to give 132 mg (yield 53%) of the captioned compound as a pale yellow oil.

REFERENTIAL EXAMPLE 49

Production of
(E)-N-(6,6-dimethyl-2-hepten-4-ynyl)-N-methyl-4-formyl-2-pyridylmethylamine 160 mg of (E)-N-(6,6-dimethyl-2-hepten-4-ynyl)-N-methyl-4-ethoxycarbonyl-2-pyridylmethylamine [synthesized by tosylating 4-ethoxycarbonyl-2-pyridinemethanol with p-toluenesulfonyl chloride and triethylamine, and thereafter condensing the tosylated product with (E)-N-methyl-6,6-dimethyl-2-hepten-4-ynylamine] was dissolved in 2 ml of toluene, and with stirring under cooling at −75° to −70 ° C., 0.56 ml of a 1 M toluene solution of diisobutyl aluminium hydride was added. The mixture was stirred at the above temperature for 40 minutes. The reaction mixture was poured into ice water, and ethyl ether was added. The organic layer was separated, worked up in a customary manner, and purified by medium-pressure liquid chromatography [Lobar column, size A, Lichroprep Si 60 (E. Merck Co.); eluting solvent: hexane/ethyl acetate=4/1] to give 15 mg (yield 11%) of the captioned compound as a pale yellow oil.

The same reaction as in Referential Example 49 is carried out except that instead of the starting (E)-N-(6,6-dimethyl-2-hepten-4-ynyl)-N-methyl-4-ethoxycarbonyl-2-pyridylmethylamine, (E)-N-(6,6-dimethyl-2-hepten-4-ynyl)-N-ethyl-3-ethoxycarbonyl-5-isoxazolylmethylamine [synthesized by brominating ethyl 5-methylisoxazole-3-carboxylate with N-bromosuccinimide and condensing the brominated product with (E)-N-ethyl-6,6-dimethyl-2-hepten-4-ynylamine] is used, (E)-N-(6,6-dimethyl-2-hepten-4-ynyl)-N-ethyl-3-formyl-5-isoxazolylamine is obtained.

REFERENTIAL EXAMPLE 50

Production of
(E)-N-(6,6-dimethyl-2-hepten-4-ynyl)-N-methyl-3-hydroxy-4-methoxymethyloxybenzylamine 3 g of 3,4-dihydroxybenzaldehyde and 0.87 g of 60% oily sodium hydride were suspended in 13 ml of tetrahydrofuran, and a dimethylformamide solution (10 ml) of 3.3 ml of methoxymethyl chloride was added. The mixture was stirred at room temperature for 1 hour. The reaction mixture was concentrated under reduced pressure. The residue was distributed between ethyl acetate and water, the organic layer was worked up in a customary manner, and then purified by silica gel column chromatography [Wakogel C-200, 150 g; eluting solvent: hexane/ethyl acetate=4/1] to give 1.78 g (yield 45%) of 3-hydroxy-4-methoxymethyloxybenzaldehyde.

360 mg of the resulting methoxymethyloxy compound was dissolved in 6 ml of a 40% methanol solution of methylamine, and 151 mg of sodium borohydride was added. The mixture was stirred for 1 hour at room temperature. The reaction mixture was concentrated under reduced pressure. The residue was distributed between ethyl acetate and water. The organic layer was separated, and the solvent was evaporated. The residue was dissolved in 10 ml of dimethylformamide, and 361 mg of 1-bromo-6,6-dimethyl-2-hepten-4-yne (a 3:1 mixture of the E-form and Z-form) and 276 mg of potassium carbonate were added. The mixture was stirred overnight at room temperature. The reaction mixture was concentrated under reduced pressure. The residue was distributed between ethyl ether and water. The organic layer was separated, worked up in a customary manner, and purified by silica gel column chromatography Wakogel C-200, 30 g; eluting solvent: hexane/ethyl acetate=3/1] to give 140 mg (yield 22%) of the captioned compound as a pale yellow oil.

When 2,3-dihydroxybenzaldehyde is used instead of the starting 3,4-dihydroxybenzaldehyde, and selectively alkylated with methoxymethyl chloride and triethylamine in chloroform to synthesize 3-hydroxy-2-methoxymethyloxybenzaldehyde and thereafter the same reaction as in Referential Example 50 is carried out, (E)-N-(6,6-dimethyl-2-hepten-4-ynyl)-N-methyl-3-hydroxy-2-methoxymethyloxybenzylamine is obtained.

REFERENTIAL EXAMPLE 51

Production of
(E)-N-(6,6-dimethyl-2-hepten-4-ynyl)-N-ethyl-3-aminobenzylamine 6.0 g of N-(3-bromomethylphenyl)phthalimide [synthesized by brominating N-(m-tolyl)phthalimide with N-bromosuccinimide in carbon tetrachloride] was dissolved in 100 ml of dimethylformamide, and 3.82 g of (E)-N-ethyl-6,6-dimethyl-2-hepten-4-ynylamine hydrochloride and 7.87 g of potassium carbonate were added. The mixture was stirred overnight at room temperature. The reaction mixture was concentrated under reduced pressure. The residue was extracted with ethyl acetate-water and the organic layer was separated, and the solvent was evaporated, and then the residue was washed with a small amount of ethyl ether to give 5.5 g (yield 72%) of (E)-N-(6,6-dimethyl-2-hepten-4-ynyl)-N-ethyl-3-phthalimidobenzylamine, m.p. 96°-98 ° C.

150 mg of the resulting benzylamine compound was dissolved in 5 ml of ethanol, and 23 mg of hydrazine was added. The mixture was stirred at room temperature for 30 minutes. The precipitate was separated by filtration, and the solvent was evaporated. The residue was distributed between methylene chloride and water. The organic layer was worked up in a customary manner and purified by silica gel column chromatography [Wakogel C-100, 5 g; eluting solvent: hexane/ethyl acetate=10/1→3/1] to give 95 mg (yield 95%) of the captioned compound as a pale yellow crystalline powder, m.p. 65°-66 ° C.

REFERENTIAL EXAMPLE 52

Production of 3-[3-(3-thienyl)benzylthio]benzaldehyde 0.3 g of sulfur was added to a tetrahydrofuran solution (20 ml) of a Grignard reagent prepared from 1.0 g of 3-bromobenzaldehyde dimethyl acetal and 0.4 g of magnesium, and the mixture was stirred at room temperature for 2 hours. 0.3 g of lithium aluminium hydride was added and the mixture was stirred at 40° C. for 3 hours. The reaction mixture was poured into ice water, and hydrochloric acid was added to acidify it. Ethyl ether was added to extract it. The extract was worked up in a customary manner, and the solvent was evaporated to give 0.36 g (yield 60%) of 3-mercaptobenzaldehyde.

60 mg of the resulting mercapto compound was dissolved in 5 ml of dimethylformamide, and 50 mg of 3-(3-thienyl)benzylbromide and 30 mg of 60% oily sodium hydride were added. The mixture was stirred at room temperature for 3 hours. The reaction mixture was poured into ice water, worked up in a customary manner, and purified by medium-pressure liquid chromatography [column: Lobar column, size A, Lichroprep Si 60 (E. Merck Co.); eluting solvent: hexane/ethyl acetate=30/1→10/1] to give 2.3 mg (yield 4%) of the captioned compound as a colorless oil.

REFERENTIAL EXAMPLE 53

Production of 3-(3-tetrahydrothienyl)benzyl alcohol 30 mg of the 3-(2,5-dihydro-3-thienyl)benzyl alcohol obtained in Referential Example 35 was dissolved in 25 ml of ethanol, and in the presence of 50 mg of 10% palladium-carbon, catalytically reduced for 8 hours under a hydrogen pressure of 3.5 kg/cm$^2$. The catalyst was separated by filtration, and the solvent was evaporated under reduced pressure to give 25 mg (yield 82%) of the captioned compound as a colorless oil.

REFERENTIAL EXAMPLE 54

Production of 3-(3,4-dihydro-2H-thiopyran-5-yl)benzyl alcohol and 3-(5,6-dihydro-2H-thiopyran-3-yl)benzyl alcohol 534 mg of 3-(tetrahydro-3-hydroxy-3-thiopyranyl)-benzaldehyde dimethyl acetal obtained by performing the same reaction as in Referential Example 35 using 3-bromobenzaldehyde dimethyl acetal and tetrahydrothiopyran-3-one as starting materials was dissolved in 5 ml of ethyl acetate, and with stirring under ice cooling, 187 microliters of methanesulfonyl chloride and 553 microliters of triethylamine were added. The mixture was stirred for 30 minutes. The triethylamine hydrochloride was separated by filtration and the solvent was evaporated. The residue was dissolved in 20 ml of benzene, and 373 mg of 90% potassium tert-butoxide was added, and the mixture was stirred at room temperature for 15 hours. Ethyl ether and water were added to the reaction mixture, and the mixture was worked up in a customary manner. The resulting 3-dihydrothiopyranylbenzaldehyde dimethyl acetal was dissolved in a mixture of 3 ml of 1 N HCl and 6 ml of tetrahydrofuran. The solution was stirred at room temperature for 3 hours. The reaction mixture was concentrated under reduced pressure, and the residue was distributed between ethyl ether and water, and worked up in a customary manner. The resulting formyl compound was dissolved in 20 ml of tetrahydrofuran, and 380 mg of lithium aluminium hydride was added. The mixture was stirred for one hour under ice cooling. The reaction mixture was poured into ice water, worked up in a customary manner and purified by silica gel column chromatography [Wakogel C-200, 20 g; eluting solvent: hexane/ethyl acetate=2/1] to give 7 mg (yield 2%) of the captioned 3-(3,4-dihydro-2H-thiopyran-5-yl)benzyl alcohol and 4 mg (yield 1%) of 3-(5,6-dihydro-2H-thiopyran-3-yl)benzyl alcohol.

REFERENTIAL EXAMPLE 55

Production of 3-[3-(3-thienyl)phenoxymethyl]benzyl alcohol 1.4 g of 3-bromomethylbenzaldehyde was dissolved in 3 ml of dimethylformamide, and the solution was added to 5 ml of a tetrahydrofuran solution of phenolate, prepared from 1.5 g of 3-bromophenol and 0.36 g of 60% oily sodium hydride. The mixture was stirred for 2 hours at room temperature. The solvent was evaporated, and water and ethyl acetate were added to the residue to extract it. The extract was worked up in a customary manner to give crude 3-(3-bromophenoxymethyl)benzaldehyde. When the same reaction as in Referential Example 12 was performed using 440 mg of the resulting aldehyde compound, 747 mg of tributyl(3-thienyl)stannane and 10 mg of tetrakis(triphenylphosphine)palladium, 341 mg (yield 77%) of 3-[3-(3-thienyl)-phenoxymethyl)benzaldehyde was obtained.

341 mg of the resulting thienyl compound was suspended in 5 ml of ethanol, and 44 mg of sodium borohydride was added. The mixture was stirred for 30 minutes at room temperature. The solvent was evaporated, and water and ethyl ether were added to the residue to extract it. The extract was worked up in a customary manner to give 288 mg (yield 83%) of the captioned compound as a white crystalline powder, m.p. 62°–63° C.

When the same reaction as in Referential Example 55 is carried out except using 3-bromothiophenol instead of the starting 3-bromophenol, 3-[3-(3-thienyl)phenylthiomethyl]benzyl alcohol is obtained.

REFERENTIAL EXAMPLE 56

Production of 3-[3-(5-oxazolyl)phenylthiomethyl)benzyl alcohol 200 mg of 3-mercaptobenzaldehyde was dissolved in 6 ml of dimethylformamide, and 291 mg of 3-hydroxymethylbenzyl bromide and 402 mg of potassium carbonate were added. The mixture was stirred for 3 hours at room temperature. The solvent was evaporated, water and ethyl ether were added to the residue to extract it. The extract was worked up in a customary manner, and purified by silica gel column chromatography [Wakogel C-200, 10 g; eluting solvent: hexane/ethyl acetate=2/1] to give 190 mg (yield 51%) of 3-[3-(hydroxymethyl)benzylthio]benzaldehyde as a pale yellow oil.

When the same reaction as in Referential Example 33 was carried out except using 172 mg of the resulting aldehyde compound, 130 mg of p-toluenesulfonylmethyl isocyanide and 92 mg of potassium carbonate, 167 mg (yield 84%) of the captioned compound wss obtained.

REFERENTIAL EXAMPLE 57

Production of 3-[3-(1-pyrrolyl)benzylthio]benzyl alcohol 47 mg of 3-(1-pyrrolyl)benzyl methanesulfonate obtained in Referential Example 28 was dissolved in 1 ml of dimethylformamide, and 36 mg of 3-mercaptobenzaldehyde and 36 mg of potassium carbonate were added. The mixture was stirred overnight at room temperature. The solvent was evaporated. The residue was worked up in a customary manner, and purified by silica gel column chromatography [Wakogel C-200, 3 g; eluting solvent: hexane/ethyl acetate=5/1] to give 34 mg (yield 58%) of 3-[3-(1pyrrolyl)benzylthio]benzaldehyde.

The resulting aldehyde compound was reduced with sodium borohydride in a customary manner to give the captioned compound as a colorless oil.

3-[3-(3-thienyl)benzyloxy]benzyl alcohol, 3-[4-(3-thienyl)-2-thienylmethylthio]benzyl alcohol, 3-[3-(5-oxazolyl)benzylthio]benzyl alcohol, 3-[3-(5-oxazolyl)-benzylthio]benzyl alcohol and 3-[3-(1-pyrrolyl) benzyloxy]benzyl alcohol are obtained by performing the same reaction as in Referential Example 57 except that instead of the starting 3-(1-pyrrolyl)benzyl methanesulfonate and/or 3-mercaptobenzaldehyde, the corresponding methanesulfonate and/or 3-hydroxybenzaldehyde are used.

REFERENTIAL EXAMPLE 58

Production of 2-[3-(3-thienyl)benzylthio]4-thiazolylmethyl alcohol

The same reaction as in Referential Example 57 is carried out except using 3-(3-thienyl)benzyl bromide [prepared by reducing 3-(3-thienyl)benzaldehyde with sodium borohydride, followed by reacting with phosphorus tribromide] and 4-carboethoxy-2-mercaptothiazole [J. Org. Chem., 25, 1337 (1960)], and the resulting ester compound is reduced with lithium aluminium hydride to give the captioned compound.

REFERENTIAL EXAMPLE 59

Production of 5-(3-thienyl)-3-thienylmethanol

The same reaction as in Referential Example 37 was carried out except using 380 mg of 5-bromo-3-thiophenecarboxylic acid ethyl ester [see J. Am. Chem. Soc., 26, 2446 (1954)], 730 mg of tributyl(3-thienyl)stannane and 10 mg of tetrakis(triphenylphosphine) palladium to give 172 mg (yield 51%) of 5-(3-thienyl)-3-thiophenecarboxylic acid ethyl ester.

172 mg of the resulting thienylthiophene derivative was dissolved in 3 ml of anhydrous tetrahydrofuran, and 28 mg of lithium aluminium hydride was added under ice cooling. The mixture was stirred for 20 minutes. Water and ethyl ether were added to extract it. The extract was worked up in a customary manner to give the captioned compound in a quantitative yield.

When the same reaction as in Referential Example 59 is carried out except using 5-bromo-3-pyridine carboxylic acid methyl ester or 5-bromo-2-furancarboxylic acid methyl ester [J. Org. Chem., 21, 517 (1956)] instead of the starting 5-bromo-3-thiophenecarboxylic acid ethyl ester, 5-(3-thienyl)-3-pyridylmethanol or 5-(3-thienyl)-2-furylmethanol is obtained.

REFERENTIAL EXAMPLE 60

Production of 2-(3-thienyl)-5-thiazolylmethanol

Using 3-thiocarbamoylthiophene as a starting material, the captioned compound is synthesized in accordance with the method described in J. Heterocyclic Chem., 23, 577 (1986).

REFERENTIAL EXAMPLE 61

Production of 3-(3-thienyl)-5-isothiazolylmethanol

Using 3-carbamoylthiophene as a starting material, the captioned compound is synthesized in accordance with the method described in J. Chem. Soc. Perkin I, 2342 (1987).

REFERENTIAL EXAMPLE 62

Production of 3-(3-tetrahydrothiopyranyl)benzyl alcohol 700 mg of 3-(tetrahydro-3-hydroxy-3-thiopyranyl)-benzaldehyde dimethyl acetal obtained in Referential Example 54 was reacted with 0.72 ml of triethylamine and 0.24 ml of methanesulfonyl chloride in 7 ml of ethyl acetate.

The resulting crude methanesulfonate compound was dissolved in 10 ml of ethyl ether, and 495 mg of lithium aluminium hydride was added to the solution. The mixture was stirred for 3 hours at room temperature, and worked up in a customary manner. After evaporating the solvent, the residue was dissolved in 10 ml of tetrahydrofuran, and 8 ml of 2 N HCl was added. The mixture was stirred for 1 hour at room temperature. Ethyl ether was added to extract it, and the organic layer was worked up in a customary manner to give 3-(3-tetrahydrothiopyranyl)benzaldehyde.

Using lithium aluminium hydride, the resulting aldehyde compound was reduced in a customary manner to give 75 mg (yield 14%) of the captioned compound as a colorless oil.

REFERENTIAL EXAMPLE 63

Production of (E)-3-[2-[3-(2,3-dihydro-4-thienyl)phenyl]ethenyl]benzyl alcohol 100 mg of 3-(2,3-dihydro-4-thienyl)benzaldehyde [obtained as an intermediate in Referential Example 35] and 157 mg of diethyl 3-carboethoxybenzylphosphonate [see Australian J. Chem., 18, 163 (1965)] were dissolved in 1 ml of dimethylformamide, and 31 mg of 60% oily sodium hydride was added. The mixture was stirred for 3 hours at room temperature. The solvent was evaporated, and water and ethyl acetate were added to the residue to extract it. The extract was worked up in a customary manner, and purified by medium-pressure liquid chromatography [column: Lobar column, size A, Lichroprep Si 60F (E. Merck Co.); eluting solvent: hexane/ethyl acetate=30/1→20/1] to give 70 mg (yield 41%) of (E)-3-[2-[3-(2,3-dihydro-4-thienyl)phenyl]ethenyl]benzoic acid ethyl ester.

The resulting ester compound was reduced in the same manner as in Referential Example 59, and purified by silica gel column chromatography [Wakogel C-200, 1 g; eluting solvent: hexane/ethyl acetate=10/1→2/1] to give 41 mg (yield 63%) of the captioned compound.

REFERENTIAL EXAMPLE 64

Production of (E)-5-[2-[3-(3-thienyl)phenyl]ethenyl]-2-thienylmethanol 12.5 g of 2-thiophenecarboxaldehyde dimethyl acetal was dissolved in 80 ml of anhydrous ethyl ether, and in an atmosphere of nitrogen, 19.7 ml of a 15% n-butyllithiumhexane solution was added at −10° C. The mixture was stirred for 2 hours at room temperature. 30 ml of ethyl ether solution containing 2.46 ml of dimethylformamide was added to the reaction solution at −40° C. with stirring. The mixture was extracted with ethyl ether. The extract was worked up in a customary manner, and purified by reduced distillation to give 3.3 g (yield 59%) of 2,5-thiophenedicarboxaldehyde 2-dimethyl acetal as a yellow oil.

Using 100 mg of the resulting aldehyde compound, 168 mg of diethyl 3-(3-thienyl)benzylphosphonate and 22 mg of 60% oil sodium hydride, the same reaction as in Referential Example 63 was carried out, and a 50% aqueous solution of trifluoroacetic acid was added to the reaction solution. The mixture was stirred for 1 hour at room temperature, neutralized by adding a saturated aqueous solution of sodium hydrogen carbonate, worked up in a customary manner, and purified by medium-pressure liquid chromatography [column: Lobar column, size B, Lichroprep Si 60F (E. Merck Co.); eluting solvent: hexane/ethyl acetate=5/1] to give 111 mg (yield 69%) of (E)-5-[2-[3-(3-thienyl)-phenyl]ethenyl]-2-thiophenecarboxaldehyde as a yellow oil.

Using sodium borohydride, the resulting aldehyde compound is reduced in a customary manner to give the captioned alcohol compound.

(E)-4-[2-[3-(3-thienyl)phenyl]ethenyl]-2-thienylmethanol is obtained by performing the same reaction as in Referential Example 64 except using 4-bromo-2-thiophenecarboxaldehyde ethylene acetal [J. Org. Chem., 41, 1320 (1976)] instead of the starting 2-thiophenecarboxaldehyde dimethyl acetal.

REFERENTIAL EXAMPLE 65

Production of 4-(5-oxazolyl)-2-thienylmethanol

Using 2,4-thiophenedicarboxaldehyde 2-dimethyl acetal and p-toluenesulfonyl isocyanide as starting materials, the same reaction as in Referential Example 33 is carried out to give 4-(5-oxazolyl)-2-thiophenecarboxaldehyde dimethyl acetal. In the same manner as in Referential Example 64, the resulting acetal is converted to the aldehyde, followed by reducing to give the captioned compound.

REFERENTIAL EXAMPLE 66

Production of (E)-3-[2-[4-(3-thienyl)-2-thienyl]ethenyl]benzyl chloride 100 mg of 4-(3-thienyl)-2-thiophenecarboxaldehyde and 250 mg of 3-chloromethylbenzyltriphenylphosphonium chloride [prepared by refluxing a xylene solution of α,α'-dichloro-m-xylene and triphenylphosphine] were suspended in 1 ml of tetrahydrofuran, and 31 mg of 60% oily sodium hydride was added under ice cooling. The mixture was stirred for 1.5 hours at room temperature, and the solvent was evaporated. The residue was neutralized with 1 N HCl, and extracted with ethyl acetate. The extract was worked up in a customary manner, purified by silica gel column chromatography [Wakogel C-300, 5 g; eluting solvent: hexane/ethyl acetate=10/1], and recrystallized from chloroform-hexane to give 80 mg (yield 49%) of the captioned compound as a pale yellow crystalline powder, m.p. 137°-138° C.

REFERENTIAL EXAMPLE 67

Production of (E)-3-[2-[3-(5-thiazolyl)phenyl]ethenyl]benzyl alcohol

When the same reaction as in Referential Example 66 was carried out using 1.0 g of 3-bromobenzaldehyde and 2.7 g of 3-carbomethoxybenzyltriphenylphosphonium bromide [prepared by refluxing a xylene solution of 3-bromomethylbenzoic acid methyl ester and triphenylphosphine] as starting materials, 1.3 g of a mixture of (E)- and (Z)-3-[2-(3-bromophenyl)ethenyl]-benzoic acid methyl ester was obtained.

1.3 g of the resulting mixture of geometrical isomers was dissolved in 6 ml of toluene, and 70 mg of iodine was added. The mixture was refluxed overnight. The solution was washed with an aqueous solution of sodium sulfite, worked up in a customary manner, and recrystallized from ethyl acetate-hexane to give 817 mg (yield 47%) of (E)-3-[2-(3-bromophenyl)ethenyl]benzoic acid methyl ester, m.p. 79°-84° C., as a yellow crystalline powder.

3-[2-[3-(5-Thiazolyl)phenyl]ethenyl]benzoic acid methyl ester, obtained by reacting the resulting bromo compound with tributyl(5-thiazolyl)stannane in the same condition as in Referential Example 37, is reduced in a customary manner, using lithium aluminium hydride, to give the captioned compound.

REFERENTIAL EXAMPLE 68

Production of 3-[4-(3-thienyl)-2-thienylthiomethyl]benzaldehyde

Using 3-(4-bromothienylthiomethyl)benzaldehyde [obtained by performing the same reaction as in Referential Example 56 using 4-bromo-2-thiophenethiol [Chem. Abst., 56, 4277 (1962)] and 3-bromomethylbenzaldehyde as starting materials], tributyl(3-thienyl)stannane and tetrakis(triphenylphosphine)palladium, the same reaction as in Referential Example 37 is carried out to give the captioned compound as a colorless oil.

REFERENTIAL EXAMPLE 69

Production of 3-[3-(3-thienyl)benzyloxy]-5-isoxazolylmethyl alcohol

The captioned compound is obtained by performing the same reaction as in Referential Example 58 except using 5-carboethoxy-3-hydroxyisoxazole [see Bull. Soc. Chim. France, II, 478 (1980)] instead of the starting 4-carboethoxy-2-mercaptothiazole in Referential Example 58.

The compounds provided by this invention inhibit biosynthesis of cholesterol by inhibiting the squalene-epoxidase of mammals, and thus lower the blood cholesterol level. Accordingly, the compounds are expected to be useful for the treatment and prevention of diseases induced by the excess of cholesterol, such as obesity, hyperlipemia, and arteriosclerosis, and heart and brain diseases incident to them.

What we claim is:

1. A substituted alkylamine derivative represented by the formula (I)

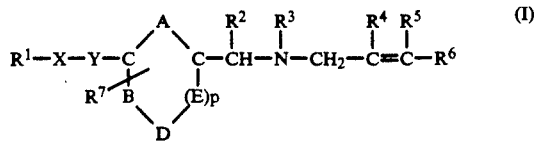

wherein
$R^1$ is selected from the group consisting of
a) a $C_{2-6}$ alkenyl group, or a $C_{2-6}$ alkenyl group substituted by a hydroxyl group, a halogen atom, a cyano group, a $C_{1-4}$ alkoxy group, an aryl group, a furyl group, an oxazolyl group or a thiazolyl group,
b) a $C_{5-7}$ cycloalkenyl group, or a $C_{5-7}$ cycloalkenyl group substituted by a hydroxyl group, a halogen atom, a cyano group, a $C_{1-4}$ alkoxy group, an aryl group, a furyl group, an oxazolyl group or a thiazolyl group,
c) a $C_{2-6}$ alkynyl group, or a $C_{2-6}$ alkynyl group substituted by a hydroxyl group, a halogen atom, a cyano group, a $C_{1-4}$ alkoxy group, an aryl group, a furyl group, an oxazolyl group or a thiazolyl group,
d) an aryl group, or an aryl group substituted by a hydroxy group, a halogen atom, a cyano group, a formyl group, a $C_{1-6}$ alkyl group, a $C_{1-2}$ halogenalkyl group, a $C_{1-2}$ hydroxyalkyl group, a $C_{2-6}$ alkenyl group, a $C_{1-4}$ alkoxy group or a $C_{3-5}$ alkenyloxy group,
e) a heterocyclic group selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, primidinyl, pyrazinyl, triazinyl, dihydrothienyl, tetrahydrothienyl, pyrrolinyl, pyrrolidinyl, oxazolinyl, oxazolidinyl, isoxazolinyl, osoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl group, said heterocyclic group being optionally substituted by a hydroxy group, a halogen atom, a cyano group, a formyl group, a $C_{1-6}$ alkyl group, a $C_{1-6}$ halogenoalkyl group, a $C_{1-6}$ hydroxyalkyl group, a $C_{2-6}$ alkenyl group, a $C_{1-4}$ alkoxy group, or a $C_{3-5}$ alkenyloxy group,
f) a fused heterocyclic group selected from the group consisting of a benzo[b]furanyl, a benzo[b]thienyl group, a benzoxazolyl group, a benzothiazolyl group, a quinolyl group and an isoquinolyl group, said fused heterocyclic group being optionally substituted by a hydroxy group, a halogen atom, a cyano group, a formyl group, a $C_{1-6}$ alkyl group, a $C_{1-2}$ halogenalkyl group a $C_{1-2}$ hydroxyalkyl group,a $C_{2-6}$ alkenyl group, a $C_{1-4}$ alkoxy group, or a $C_{3-5}$ alkenyloxy group, and
g) the group represented by the formula

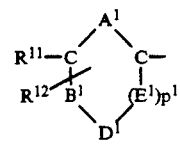

wherein
R$^{11}$ is a heterocyclic group selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, primidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4dithianyl, 1,4-dithiinyl, 1,4-oxathiinyl and thiomorpholinyl group; and R$^{12}$ is a hydrogen atom, a halogen atom, a hydroxyl group, a cyano group, a C$_{1-6}$ alkyl group or a C$_{1-4}$ alkoxy group;

p$^1$ is 0 or 1;
A$^1$ is CH, N, O or S;
B$^1$ is CH, N, O or S;
D$^1$ is CH, N, O or S;
E$^1$ is CH, N, O or S;
provided that no more than 2 of B$^1$, D$^1$ and E$^1$ can be simultaneously N, O or S;

R$^2$ is a hydrogen atom or a C$_{1-6}$ alkyl group;
R$^3$ is a hydrogen atom, a C$_{1-6}$ alkyl group, C$_{2-6}$ alkenyl group, a C$_{2-6}$ alkynyl group, or a C$_{3-6}$ cycloalkyl group;
R$^4$ and R$^5$ may be the same or different and each is a hydrogen atom, or a halogen atom;
R$^6$ is selected from the group consisting of a) a C$_{1-17}$ acyclic hydrocarbon group, or a C$_{1-17}$ acyclic hydrocarbon group substituted by a hydroxy group, a halogen atom, a C$_{3-6}$ cycloalkyl group, a C$_{1-4}$ alkoxy group, a phenyl group, or a phenyl group substituted by a halogen atom, a C$_{1-6}$ alkyl group or a C$_{1-4}$ alkoxy group,
in which said acyclic hydrocarbon group may contain 1 or 2 unsaturated bonds selected from the group consisting of double and triple bonds,
b) a C$_{3-6}$ cycloalkyl group, or a C$_{3-6}$ cycloalkyl group substituted by a hydroxy group, a halogen atom, a C$_{1-4}$ alkoxy group, a phenyl group, or a phenyl group substituted by a halogen atom, a C$_{1-6}$ alkyl group or a C$_{1-4}$ alkoxy group, and
c) a phenyl group, or a phenyl group substituted by a hydroxyl group, a halogen atom, a C$_{1-6}$ alkyl group or a C$_{1-4}$ alkoxy group;
R$^7$ is a hydrogen atom, a halogen atom, a hydroxyl group, a cyano group, a C$_{1-6}$ alkyl group or a C$_{1-4}$ alkoxy group;
p is 1;
A is CH;
B is CH;
D is CH;
E is CH;
X and Y are independently O, S, CO, CHR$^a$ or NR$^b$, or X—Y is —CH=CH— or —C≡C—, in which
R$^a$ is a hydrogen atom or a C$_{1-6}$ alkyl group; and
R$^b$ is a hydrogen atom or a C$_{1-6}$ alkyl group;
provided that, when one of X and Y is O, S or NR$^b$, the other is CO or CHR$^a$;
and, further, provided that the rings

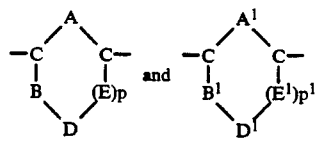

are aromatic rings,
or a non-toxic salt thereof.

2. The substituted alkylamine derivative according to claim 1, wherein X—Y is OCH$_2$, CH$_2$O, CH$_2$CH$_2$, NHCH$_2$, CH$_2$NH, SCH$_2$, CH$_2$S,

CH=CH or C≡C.

3. The substituted alkylamine derivative according to claim 1, wherein R$^1$ is the group represented by the formula

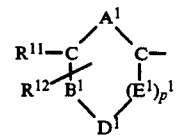

wherein
R$^{11}$ is a heterocyclic group selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl groups;

R$^{12}$ is a hydrogen atom, a halogen atom, a hydroxyl group, a cyano group, a C$_{1-6}$ alkyl group or a C$_{1-4}$ alkoxy group;
p$^1$ is 0 or 1;
A$^1$ is CH, N, O or S;
B$^1$ is CH, N, O or S;
D$^1$ is CH, N, O or S;
E$^1$ is CH, N, O or S;
provided that less than 2 of B$^1$, D$^1$ and E$^1$ can be simultaneously N, O or S;

R$^6$ is the group represented by the formula

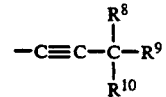

wherein
R$^8$ and R$^9$ are independently a C$_{1-6}$ alkyl group, or they represent groups which when taken together, form a C$_{3-6}$ cycloalkane together with the adjoining carbon atom;
R$^{10}$ is a hydrogen atom, a C$_{1-6}$ alkyl group or a C$_{1-4}$ alkoxy group.

4. The substituted alkylamine derivative according to claim 3, wherein X—Y is OCH$_2$, CH$_2$O, CH$_2$CH$_2$, NHCH$_2$, CH$_2$NH, SCH$_2$, CH$_2$S,

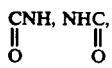

CH=CH or C≡C.

5. The substituted alkylamine derivative according to claim 3, wherein at least one of A$^1$, B$^1$, D$^1$, and E$^1$ is N, O or S; p is 0 or 1; and X—Y is OCH$_2$, CH$_2$O, CH$_2$CH$_2$, NHCH$_2$, CH$_2$NH, SCH$_2$, CH$_2$S,

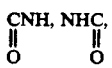

CH=CH or C≡C.

6. The substituted alkylamine derivative according to claim 3, wherein

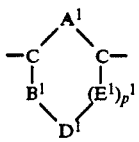

forms a thiophene, oxazole, isoxazole, thiazole, pyridine or pyrimidine ring; and X—Y is OCH$_2$, CH$_2$O, CH$_2$CH$_2$, NHCH$_2$, CH$_2$NH, SCH$_2$, CH$_2$S,

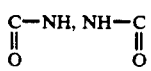

CH=CH, or C≡C.

7. The substituted alkylamine derivative according to claim 3, wherein each or both of R$^7$ and R$^{12}$ are hydrogen atoms.

8. The substituted alkylamine derivative of claim 10, wherein

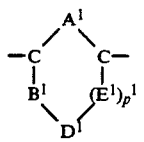

represents a thiophene ring.

9. The substituted alkylamine derivative of claim 8, wherein X—Y represents CH$_2$O.

10. (E)-N-(6,6-dimethyl-2-heptene-4-ynyl)-N-ethyl-3-[4-(3-thienyl)-2-thienyl-methyloxy]benzylamine, or a non-toxic salt thereof.

11. The compound of claim 10 in the form of its hydrochloride.

12. The substituted alkylamine derivative of claim 1, wherein R$^1$ represents a thienyl moiety substituted by a hydroxyl group, a halogen atom, a cyano group, a formyl group, a C$_{1-6}$ alkyl group, a C$_{1-6}$ halogenoalkyl group, a C$_{1-6}$ hydroxyl alkyl group, a C$_{2-6}$ alkenyl group, a C$_{1-4}$ alkoxy group, a C$_{3-5}$ alkynyloxy group, or a heterocyclic group, wherein said heterocyclic group is selected from the group consisting of a pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl, triazinyl, dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1,2-dithiolanyl, 1,3-dithiolanyl, 1,2-dithiolyl, 1,3-dithiolyl, dihydrothiopyranyl, tetrahydrothiopyranyl, 1,4-dithianyl, 1,4-dithiinyl, 1,4-oxathiinyl and thiomorpholinyl group;

with the proviso that when the thienyl group is substituted by said heterocyclic group, the heterocyclic group may also optionally be substituted by a halogen atom, a hydroxyl group, a cyano group, a C$_{1-6}$ alkyl group, or a C$_{1-4}$ alkoxy group.

13. The substituted alkylamine derivative of claim 12, wherein X—Y represents CH=CH, CH≡C, CH$_2$O or CH$_2$NH, R$^2$ represents a hydrogen atom, R$^3$ represents methyl, ethyl, propyl, allyl, propargyl, or cyclopropyl, R$^4$ and R$^5$ each represent a hydrogen atom and R$^6$ represents —CH=CH—R$^c$ or —C≡C—R$^c$, wherein R$^c$ represents a C$_{3-6}$ alkyl group, a C$_{3-6}$ alkenyl group, or C$_{3-6}$ cycloalkyl group wherein the alkyl and alkenyl groups may be substituted by a lower alkoxy group having 1 to 4 carbon atoms, and the cycloalkyl group may be substituted by an alkyl group having 1 to 4 carbon atoms.

14. A pharmaceutical preparation comprising an effective amount of a compound of general formula (I) according to claim 1 or a pharmaceutically acceptable salt thereof and a pharmaceutically acceptable carrier or diluent.

15. The pharmaceutical preparation of claim 14 comprising a squalene epoxidase inhibiting effective amount of the substituted alkylamine derivative of formula (I) wherein

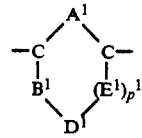

represents a thienyl group, or a pharmaceutically acceptable salt thereof.

16. The pharmaceutical preparation of claim 14 wherein the compound of general formula (I) is (E)--N-(6,6-dimethyl-2-heptene-4-ynyl)-N-ethyl-3-[4-(3-thienyl)-2-thienyl-methyloxy]benzylamine, or a non-toxic salt thereof.

17. A method of treating hypercholesterolemia, hyperlipemia or arteriosclerosis in an individual in need of such treatment which comprises administering to said individual a therapeutically effective amount of a compound of general formula (I) according to claim 1 or a pharmaceutically acceptable salt thereof.

18. The method of claim 17 wherein in said compound of general formula (I),

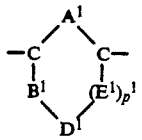

represents a thienyl group.

19. The method of claim 17 wherein said compound of general formula (I) is (E)--N-(6,6-dimethyl-2-heptene-4-ynyl)-N-ethyl-3-[4-(3-thienyl)-2-thienyl-methoxy]benzylamine, or a non-toxic salt thereof.

* * * * *